US012766148B2

(12) United States Patent
Saha et al.

(10) Patent No.: US 12,766,148 B2
(45) **Date of Patent: *Oct. 20, 2026**

(54) CANCER TREATMENTS USING COMBINATIONS OF CDK AND ERK INHIBITORS

(71) Applicant: BIOMED VALLEY DISCOVERIES, INC., Kansas City, MO (US)

(72) Inventors: Saurabh Saha, Wellesley Hills, MA (US); Dean Welsch, Parkville, MO (US); Gary DeCrescenzo, Parkville, MO (US); Jeffrey James Roix, Boston, MA (US)

(73) Assignee: Biomed Valley Discoveries, Inc., Kansas City, MO (US)

( * ) Notice: Subject to any disclaimer, the term of this patent is extended or adjusted under 35 U.S.C. 154(b) by 28 days.

This patent is subject to a terminal disclaimer.

(21) Appl. No.: 18/787,389

(22) Filed: Jul. 29, 2024

(65) Prior Publication Data

US 2024/0374604 A1 Nov. 14, 2024

Related U.S. Application Data

(60) Division of application No. 18/310,034, filed on May 1, 2023, now Pat. No. 12,076,324, which is a continuation of application No. 17/460,743, filed on Aug. 30, 2021, now Pat. No. 11,679,112, which is a continuation of application No. 16/856,849, filed on Apr. 23, 2020, now Pat. No. 11,135,225, which is a division of application No. 15/105,924, filed as application No. PCT/US2014/071747 on Dec. 19, 2014, now Pat. No. 11,013,743.

(60) Provisional application No. 61/919,597, filed on Dec. 20, 2013.

(51) Int. Cl.

| | |
|---|---|
| ***A61K 31/4439*** | (2006.01) |
| ***A61K 31/49*** | (2006.01) |
| ***A61K 31/496*** | (2006.01) |
| ***A61K 31/505*** | (2006.01) |
| ***A61K 31/506*** | (2006.01) |
| ***A61K 31/519*** | (2006.01) |
| ***A61K 45/06*** | (2006.01) |
| ***A61P 35/00*** | (2006.01) |
| ***C07D 401/04*** | (2006.01) |

(52) U.S. Cl.

CPC ........ *A61K 31/519* (2013.01); *A61K 31/4439* (2013.01); *A61K 31/506* (2013.01); *A61K 45/06* (2013.01); *C07D 401/04* (2013.01)

(58) Field of Classification Search

None

See application file for complete search history.

(56) References Cited

U.S. PATENT DOCUMENTS 7,354,939 B2 4/2008 Martinez-Botella et al.

FOREIGN PATENT DOCUMENTS

WO 2005113541 A1 12/2005

OTHER PUBLICATIONS

Brufsky A. Updates in the Management of Hormone Receptor-Positive (HR+) Advanced Breast Cancer. Journal of Managed Care Medicine. 2010;267:34. (Year: 2010).*

Flaherty. "BRAF Inhibitors and Melanoma." Cancer J. Nov. 2011-Dec 17(6):505-11.

Jing et al. "Comprehensive Predictive Biomarker Analysis for MEK Inhibitor GSK1120212." Mal Cancer Ther. Mar. 2012;11(3):720-9.

Hoeflich et al. "In vivo Antitumor Activity of MEK and Phosphatidylinositol 3-Kinase Inhibitors in Basal-Like Breast Cancer Models." Clin Cancer Res. Jul. 15, 2009;15(14):4649-64.

Serra et al. "P13K inhibition results in enhanced HER signaling and acquired ERK dependency in HER2-Dverexpressing breast cancer." Oncogene. Jun. 2, 2011;30(22):2547-57.

Hatzivassiliou, et al. "ERK Inhibition Overcomes Acquired Resistance to MEK Inhibitors," Mal Cancer Ther 2012; 11:1143-1154.

Feldmann, G., et al., Inhibiting the cyclin-dependent kinase CDK5 blocks pancreatic cancer formation and progression via suppression of Ras-Ral signaling, NIH Public Access, Cancer Research Jun. 1, 2010; 70(11); pp. 1460-4469.

International Search Report for PCT/US2014/071747 dated Apr. 1, 2015.

Hu et al. Combined inhibition of cyclin-dependent kinases (Dinaciclib) and AKT (MK-2206) or ERK (SCH772984) Jramatically blocks pancreatic tumor growth and metastases in patientderived orthotopic xenograft models. Mol Sancer Ther 12:6263, Nov. 2013.

Morris et al., Discovery of a Novel ERK Inhibitor with Activity in Models of Acquired Resistance to BRAF and MEK inhibitors, Cancer Discovery, Jul. 2013, p. 742-750.

Avruch, J et al. Ras activation of the Raf kinase: tyrosine kinase recruitment of the MAP kinase cascade. Recent Prog. Horm. Res., 2001, 127-155.

Brose et al. BRAF and RAS mutations in human lung cancer and melanoma. Cancer Res., 2002, 62, 6997-7000.

Davies et al., Mutations of the BRAF gene in human cancer. Nature, 2002, 417, 949-954.

Fransen et al., Mutation analysis of the Braf, Araf and RAF-1 genes in human colorectal adenocarcinomas. Carcinogenesis, 2004, 25, 527-533.

(Continued)

*Primary Examiner* — Nissa M Westerberg

(74) *Attorney, Agent, or Firm* — Bryan Cave Leighton Paisner LLP

(57) ABSTRACT

The present invention provides, inter alia, methods, kits, and pharmaceutical compositions for treating or ameliorating the effects of a cancer in a subject in need thereof. The method comprises administering to the subject an effective amount of (i) a first anti-cancer agent, which is BVD-523 or a pharmaceutically acceptable salt thereof and (ii) a second anti-cancer agent, which is a CDK inhibitor or a pharmaceutically acceptable salt thereof, to treat or ameliorate the effects of the cancer. Additional methods for effecting cancer cell death are also provided.

26 Claims, 116 Drawing Sheets

Specification includes a Sequence Listing.

(56) References Cited

OTHER PUBLICATIONS

Fry, D.W. et al. (2004). Specific inhibition of cyclin-dependent kinase 4/6 by PD 0332991 and associated antitumor activity in human tumor xenografts.
Garnett, M.J et al. Wildtype and mutant B-RAF activate C-RAF through distinct mechanisms involving heterodimerization. Mol. Cell, 2005, 20, 963-969.
Hocker et al., Ultraviolet radiation and melanoma: A systematic review and analysis of reported sequence variants. Hum. Mutat., 2007, 28, 578-588.
Li et al., Recent advances in the research and development of B-Raf Inhibitors. Current Medicinal Chemistry, 2010, 17:1618-1634.
Long GV, et al. Prognostic and Clinicopathologic Associations of Oncogenic BRAF in Metastatic Melanoma. J Clin Oncol. 2011.
Parry, D. et al. (2010). Dinaciclib (SCH 727965), a novel and potent cyclin-dependent kinase inhibitor. Mol Cancer Ther 9: 2344-2353.
Rushworth, L.K et al. Regulation and role of Raf-1/B-Raf heterodimerization. Mol. Cell Biol., 2006, 26, 2262-2272.
Seth et al., Concomitant mutations and splice variants in KRAS and BRAF demonstrate complex perturbation of the Ras/Raf signalling pathway in advanced colorectal cancer, Gut 2009;58:1234-1241.
Tang, L H., et al. Attenuation of the retinoblastoma pathway in pancreatic neuroendocrine tumors due to increased cdk4/cdk6. Clinical Cancer Research 18.17 (2012): 4612-4620.
Wan, et al., Mechanism of activation of the RAF-ERK signaling pathway by oncogenic mutations of B-RAF. Cell, 2004, 116, 855-867.
Weber, C.K. et al. Active Ras induces heterodimerization of cRaf and BRaf. Cancer Res., 2001, 61, 3595-3598.
Wellbrock C, Karasarides M, Marais R. The RAF proteins take centre stage. Nat Rev Mol Cell Biol. 2004; 5:875-85.
Xu et al., High prevalence of BRAF gene mutation in papillary thyroid carcinomas and thyroid tumor cell lines. Cancer Res., 2003, 63, 4561-4567.
Kwong, L N., et al. Oncogenic NRAS signaling differentially regulates survival and proliferation in melanoma. Nature medicine 18.10 (2012): 1503-1510.
Sherr, C J, et al. The RB and p53 pathways in cancer. Cancer cell 2.2 (2002): 103-112.
Shapiro, G I. Cyclin-dependent kinase pathways as targets for cancer treatment. Journal of clinical oncology 24. 11; 2006): 1770-1783.
Extended European Search Report for EP Application 24217401.9 dated Sep. 4, 2025.

* cited by examiner

CANCER TREATMENTS USING COMBINATIONS OF CDK AND ERK INHIBITORS

CROSS REFERENCE TO RELATED APPLICATIONS

This application is a divisional application of U.S. patent application Ser. No. 18/310,034, filed on May 1, 2023, which is a continuation application of U.S. patent application Ser. No. 17/460,743, filed on Aug. 30, 2021, now U.S. Pat. No. 11,679,112, which is a continuation application of U.S. patent application Ser. No. 16/856,849, filed on Apr. 23, 2020, now U.S. Pat. No. 11,135,225, which is a divisional application of U.S. patent application Ser. No. 15/105,924, filed on Jun. 17, 2016, now U.S. Pat. No. 11,013,743, which is the National Stage of International Application No. PCT/US2014/071747, filed on Dec. 19, 2014, which claims the benefit of U.S. Provisional Patent Application No. 61/919,597, filed Dec. 20, 2013. The entire contents of the above patent documents are incorporated by reference as if recited in full herein.

FIELD OF INVENTION

The present invention provides, inter alia, methods, pharmaceutical compositions and kits for treating or ameliorating the effects of a cancer in a subject using a first anti-cancer agent, which is BVD-523 or a pharmaceutically acceptable salt thereof and a second anti-cancer agent, which is a cyclin dependent kinase (CDK) inhibitor or a pharmaceutically acceptable salt thereof.

INCORPORATION BY REFERENCE OF SEQUENCE LISTING

This application contains references to amino acids and/or nucleic acid sequences that have been filed concurrently herewith as sequence listing XML file "1065272.000663-seq.xml", file size of 43,690 bytes, created on May 1, 2023. The aforementioned sequence listing is hereby incorporated by reference in its entirety pursuant to 37 C.F.R. § 1.52 (e) (5).

BACKGROUND OF THE INVENTION

Within cellular signaling networks, RAS and RAF play significant roles in the regulation of various biological processes including cell growth, proliferation, differentiation, inflammatory responses, and programmed cell death. Notably, mutations in RAS genes were the first genetic alterations identified in human cancer. Activating mutations of HRAS, NRAS, and KRAS ('RAS'), as well as BRAF are found frequently in several types of cancer.

To date, progress has been slow in developing effective, longer term treatment options for patients suffering from cancer in which one or more mutations of RAS and/or RAF are present. For example, drug resistance is a common problem with many current MAPK inhibitors used today.

In view of the foregoing, there is, inter alia, a need for new methods for treating malignancies associated with the MAPK signaling pathway of which RAS and RAF are members. The present application is directed to meeting these and other needs.

SUMMARY OF THE INVENTION

One embodiment of the present invention is a method of treating or ameliorating the effects of a cancer in a subject in need thereof. The method comprises administering to the subject an effective amount of (i) a first anti-cancer agent, which is BVD-523 or a pharmaceutically acceptable salt thereof and (ii) a second anti-cancer agent, which is a CDK inhibitor or a pharmaceutically acceptable salt thereof, to treat or ameliorate the effects of the cancer.

Another embodiment of the present invention is a method of treating or ameliorating the effects of a cancer in a subject in need thereof. The method comprises administering to the subject an effective amount of (i) a first anti-cancer agent, which is BVD-523 or a pharmaceutically acceptable salt thereof and (ii) a second anti-cancer agent, which is selected from the group consisting of dinaciclib, palbociclib, and pharmaceutically acceptable salts thereof, to treat or ameliorate the effects of the cancer.

An additional embodiment of the present invention is a method of effecting cancer cell death. The method comprises contacting the cancer cell with an effective amount of (i) a first anti-cancer agent, which is BVD-523 or a pharmaceutically acceptable salt thereof and (ii) a second anti-cancer agent, which is a CDK inhibitor or a pharmaceutically acceptable salt thereof.

Another embodiment of the present invention is a kit for treating or ameliorating the effects of a cancer in a subject in need thereof. The kit comprises an effective amount of (i) a first anti-cancer agent, which is BVD-523 or a pharmaceutically acceptable salt thereof and (ii) a second anti-cancer agent, which is a CDK inhibitor or a pharmaceutically acceptable salt thereof, packaged together with instructions for their use.

An additional embodiment of the present invention is a pharmaceutical composition for treating or ameliorating the effects of a cancer in a subject in need thereof. The pharmaceutical composition comprises a pharmaceutically acceptable diluent or carrier and an effective amount of (i) a first anti-cancer agent, which is BVD-523 or a pharmaceutically acceptable salt thereof and (ii) a second anti-cancer agent, which is a CDK inhibitor or a pharmaceutically acceptable salt thereof, wherein administration of the first and second anti-cancer agents provides a synergistic effect compared to administration of either anti-cancer agent alone.

BRIEF DESCRIPTION OF THE DRAWINGS

FIG. 3A shows a dose matrix showing inhibition (%) for the combination in A549 cells. FIG. 3S shows Loewe excess for the combination in 3P and FIG. 3T shows Bliss excess for the combination in 3P.

FIG. 4A shows a dose matrix showing inhibition (%) for the combination in A549 cells. FIG. 4S shows Loewe excess for the combination in 4P and FIG. 4T shows Bliss excess for the combination in 4P.

FIG. 5A shows a dose matrix showing inhibition (%) for the combination in A549 cells. FIG. 5S shows Loewe excess for the combination in 5P and FIG. 5T shows Bliss excess for the combination in 5P.

FIG. 6A shows a dose matrix showing inhibition (%) for the combination in A549 cells. FIG. 6S shows Loewe excess for the combination in 6P and FIG. 6T shows Bliss excess for the combination in 6P.

FIG. 7A shows a dose matrix showing inhibition (%) for the combination in A549 cells. FIG. 7S shows Loewe excess for the combination in 7P and FIG. 7T shows Bliss excess for the combination in 7P.

FIG. 8A shows a dose matrix showing inhibition (%) for the combination in A549 cells. FIG. 8S shows Loewe excess for the combination in 8P and FIG. 8T shows Bliss excess for the combination in 8P.

FIG. 10A shows a dose matrix showing inhibition (%) for the combination in A375 cells. FIG. 10B-FIG. 10C show the results of single agent proliferation assays for the combination in 10A. FIG. 10D shows Loewe excess for the combination in 10A and FIG. 10E shows Bliss excess for the combination in 10A.

DETAILED DESCRIPTION OF THE INVENTION

Figure 1:
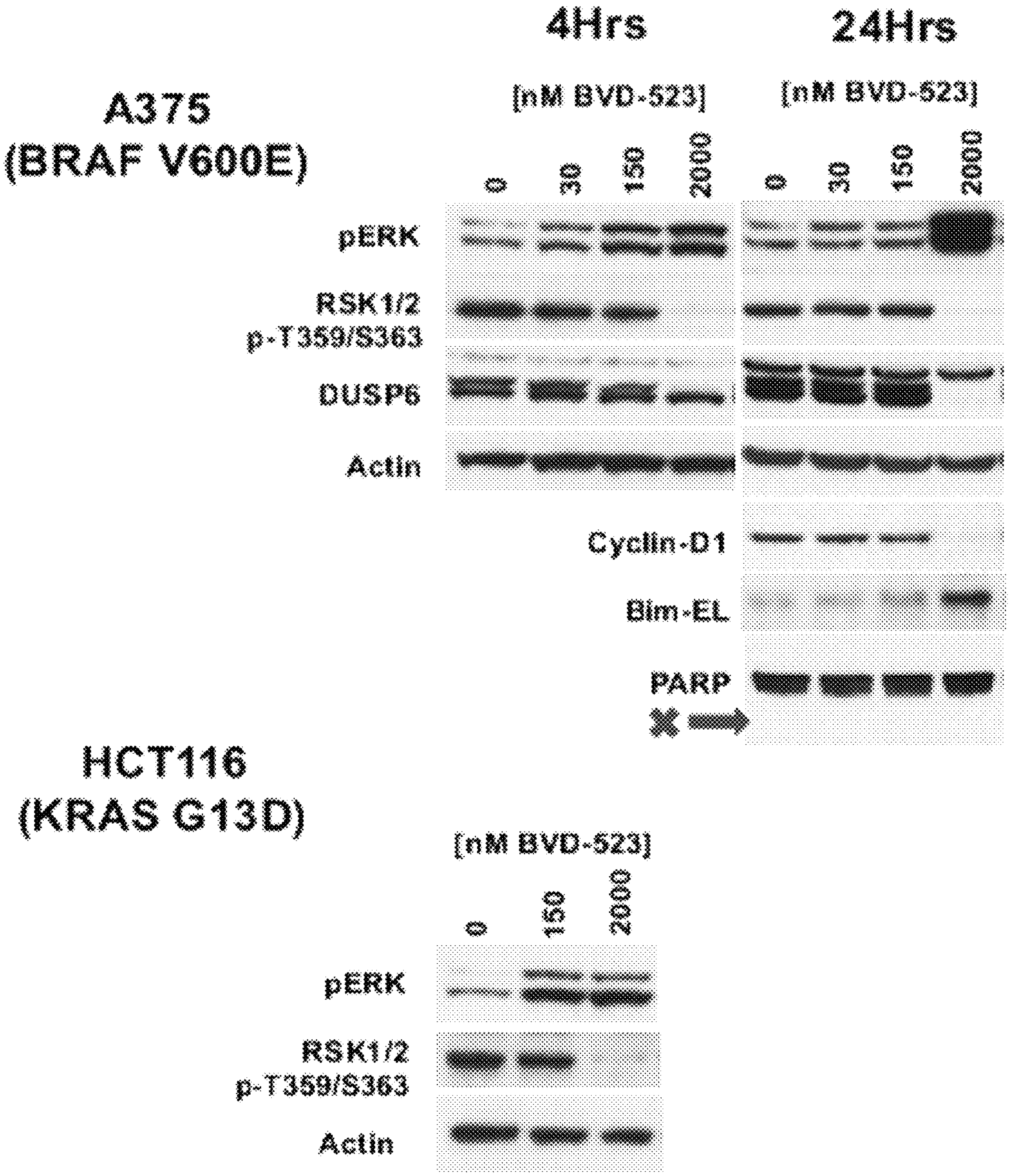
FIG. 1 shows that both direct ERK substrate phosphorylation and known effector pathways are modulated following acute and prolonged treatment with BVD-523 in vitro. Western blots were performed using a variety of antibodies to detect changes in whole-cell lysates of cancer lines exposed to BVD-523. In the A375 BRAF mutant cell line (a human melanoma cell line) and in the HCT116 KRAS mutant cell line (a human colorectal carcinoma cell line), phosphorylation of ERK-dependent residues (T359/S363) in RSK 1 and 2 proteins was reduced after 4 hours of treatment with BVD-523 at micromolar concentrations. Following 24 hours of treatment, direct substrate inhibition was maintained in BRAF mutant cell lines, and the MAPK feedback phosphatase DUSP6 was greatly reduced, suggesting durable and nearly complete MAPK pathway inhibition. Lastly, consistent with cytostatic effects of BVD-523 across multiple cell line backgrounds, the MAPK effector and G1/S-cell-cycle determinant gene cyclin-D1 was greatly reduced after 24 hours of treatment. In the A375 cell line, while the apoptosis effector and ERK substrate Bim-EL was increased following prolonged treatment, increased apoptosis was not observed, consistent with a lack of PARP cleavage, as well as other observations (not shown) that additional factors influence the capacity for BVD-523 to induce cell death.
Figure 2A:
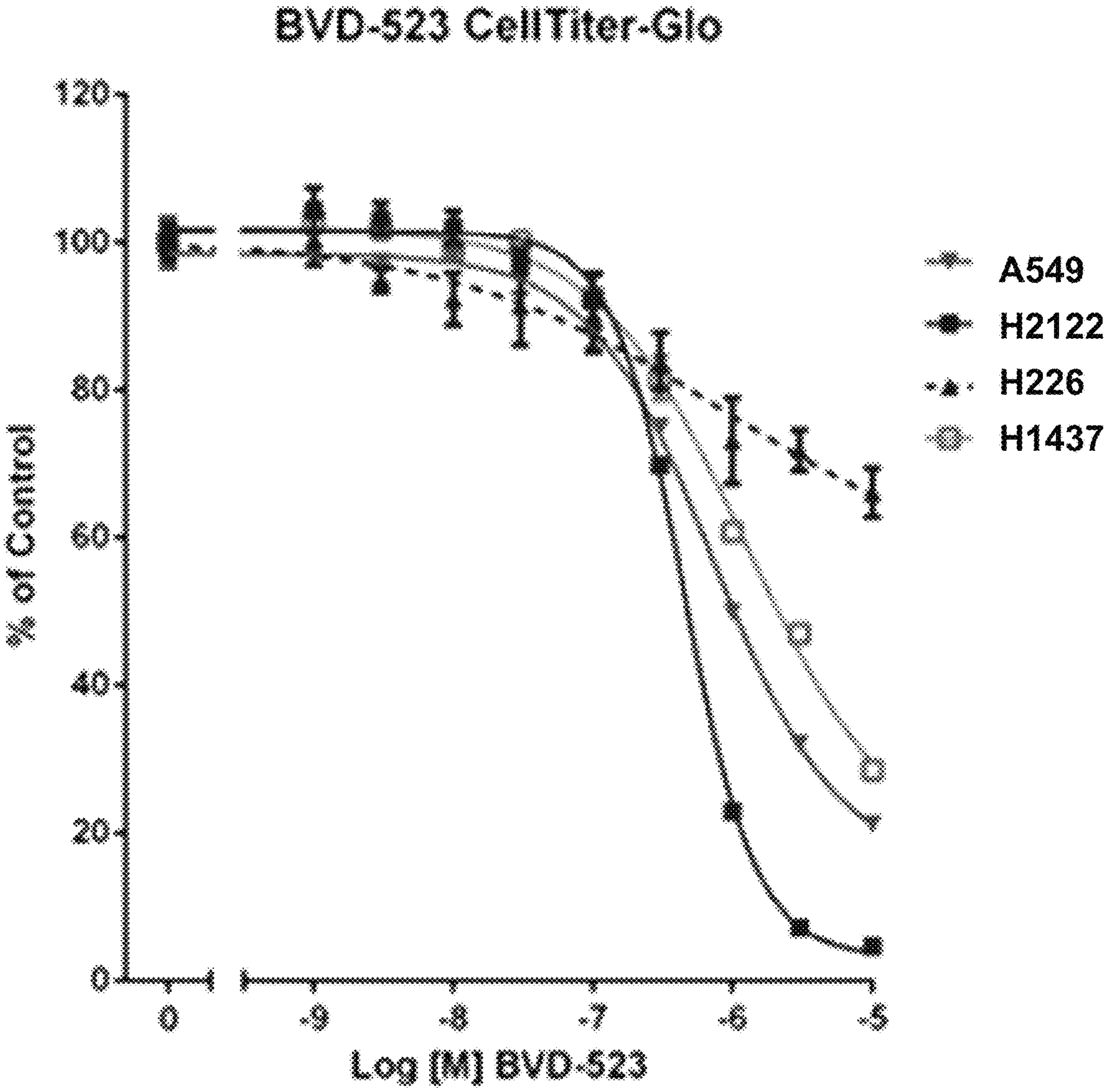
FIGS. 2A-2L show the results of single agent proliferation assays as assessed by either CELLTITER-GLO® (a homogeneous method to determine the number of viable cells in culture based on quantitation of the ATP present, which signals the presence of metabolically active cells) reagent or Hoechst staining. Proliferation results are shown for treatment with BVD-523 (FIG. 2A and FIG. 2B), SCH772984 (FIG. 2C and FIG. 2D), Trametinib (FIG. 2E and FIG. 2F), Palbociclib (FIG. 2G and FIG. 2H), LEE-011 (FIG. 2I and FIG. 2J), and Paclitaxel (FIG. 2K and FIG. 2L).
Figure 2B:
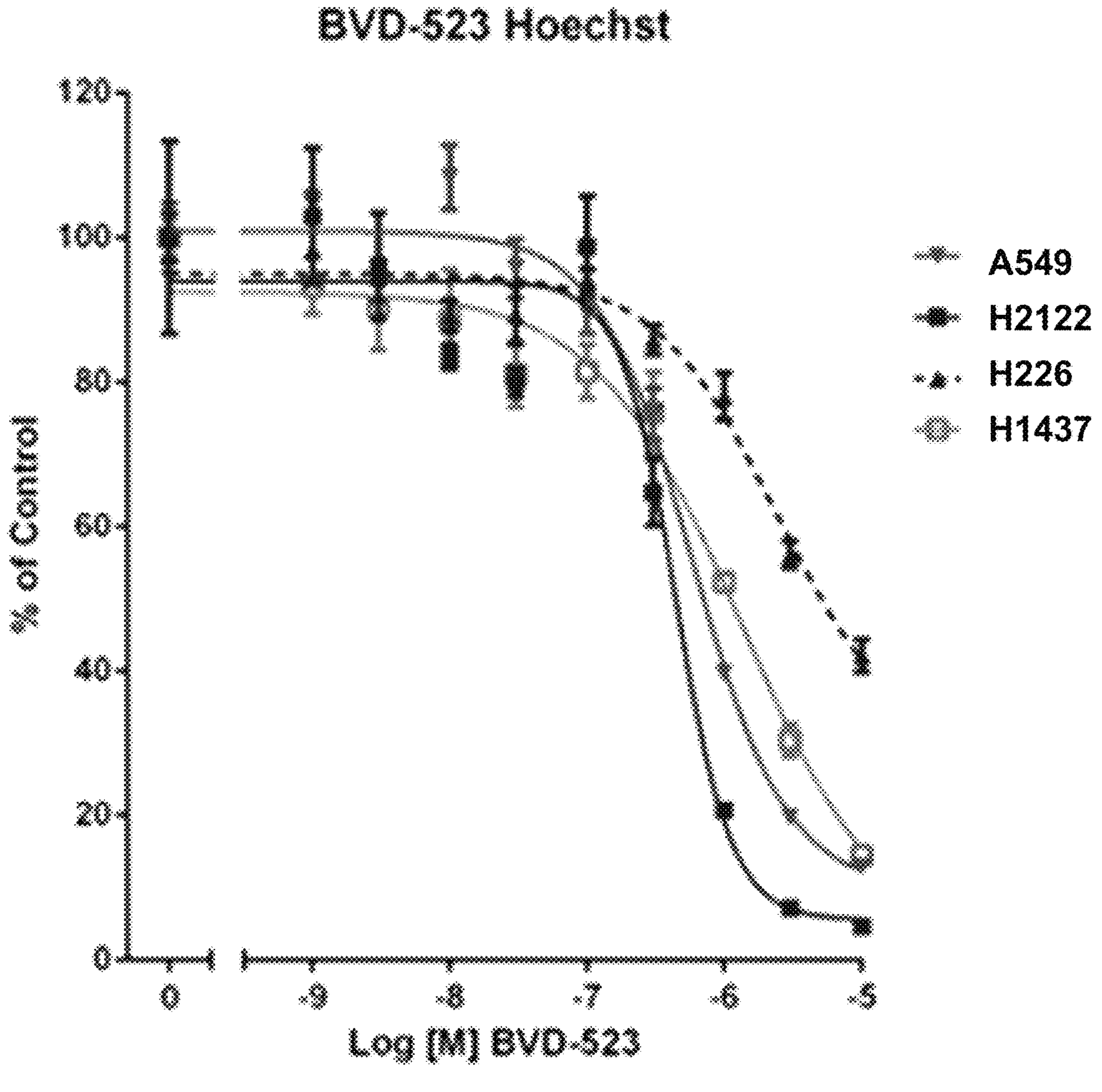
Figure 2C:
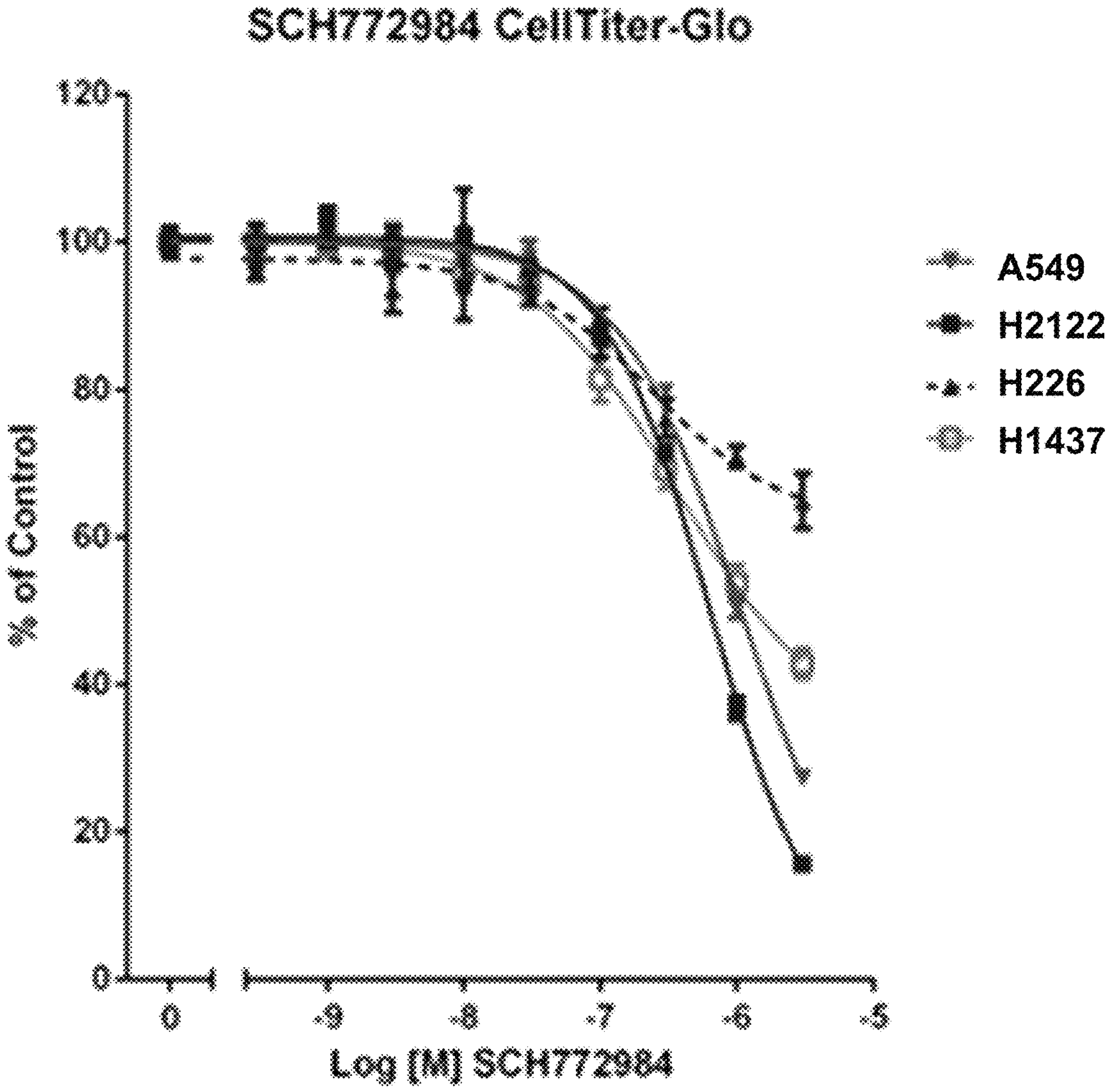
Figure 2D:
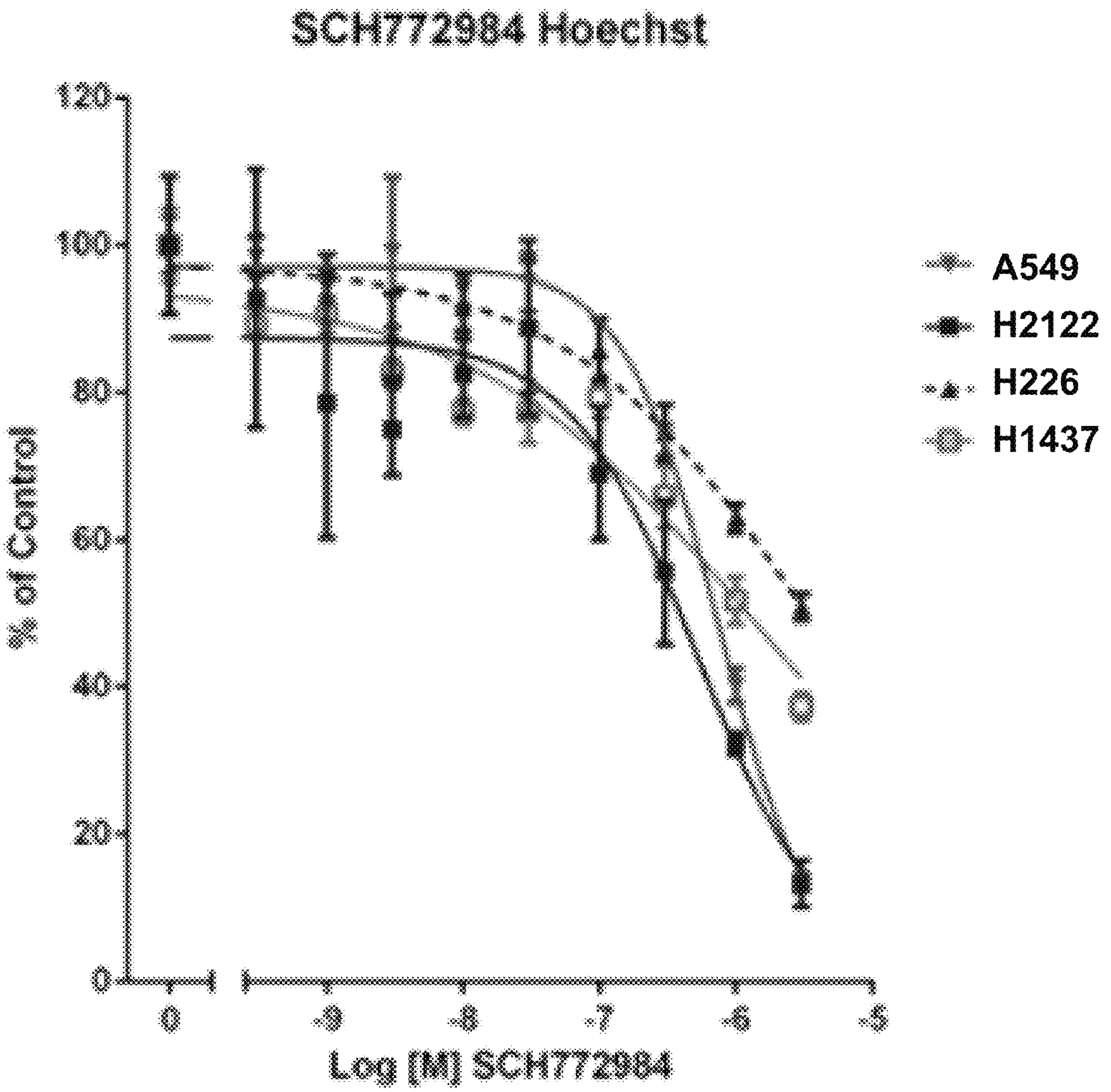
Figure 2E:
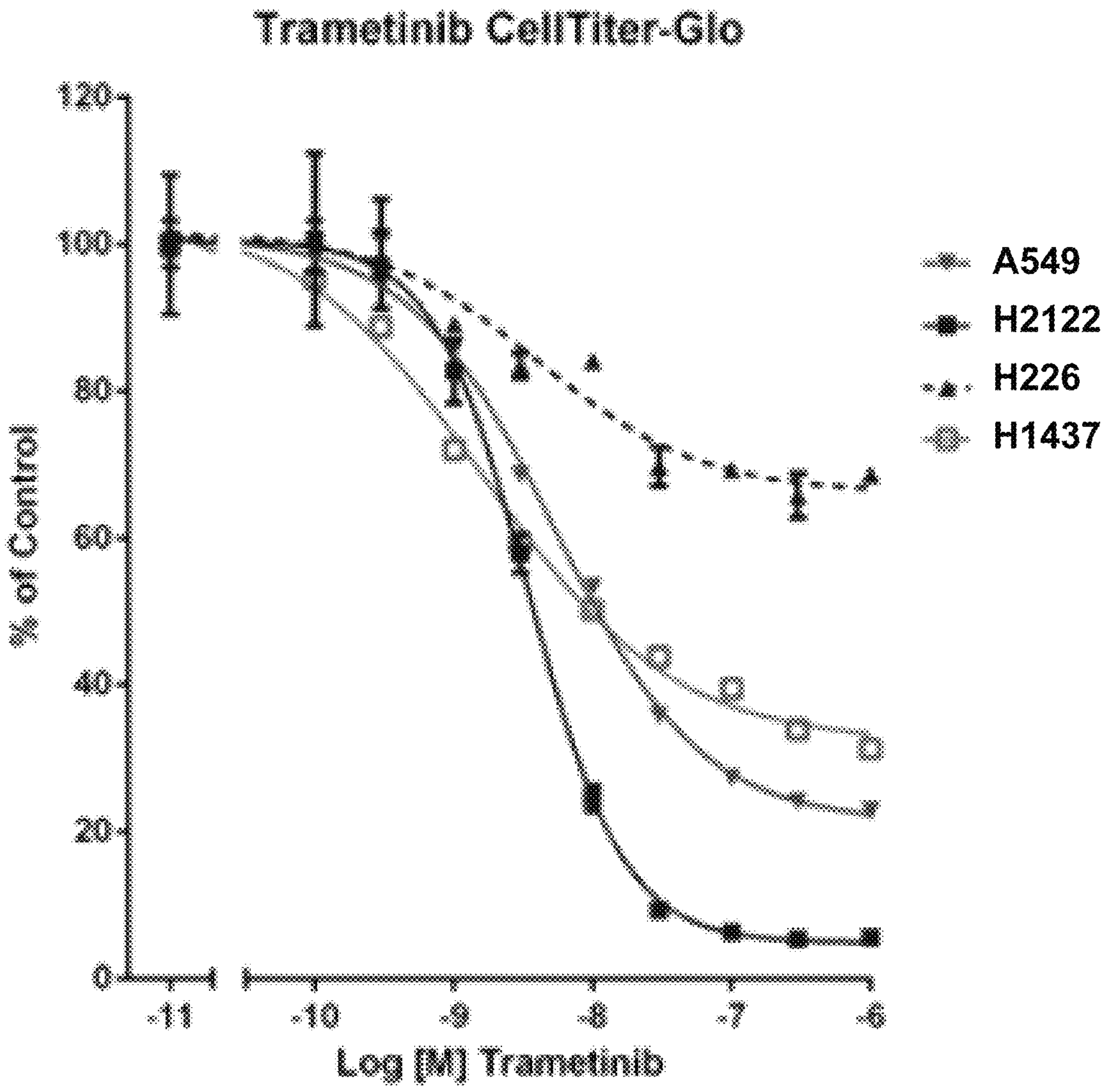
Figure 2F:
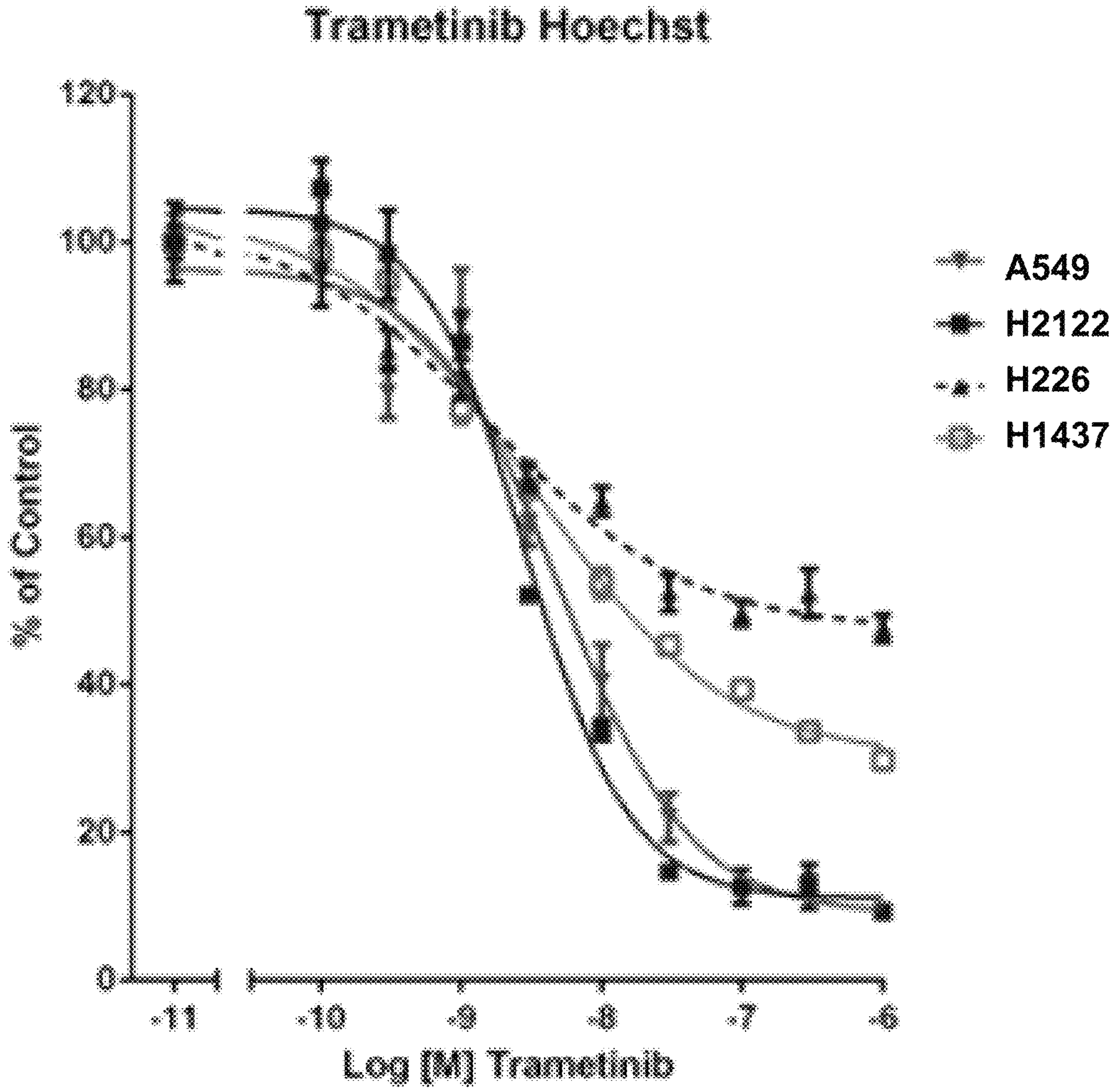
Figure 2G:
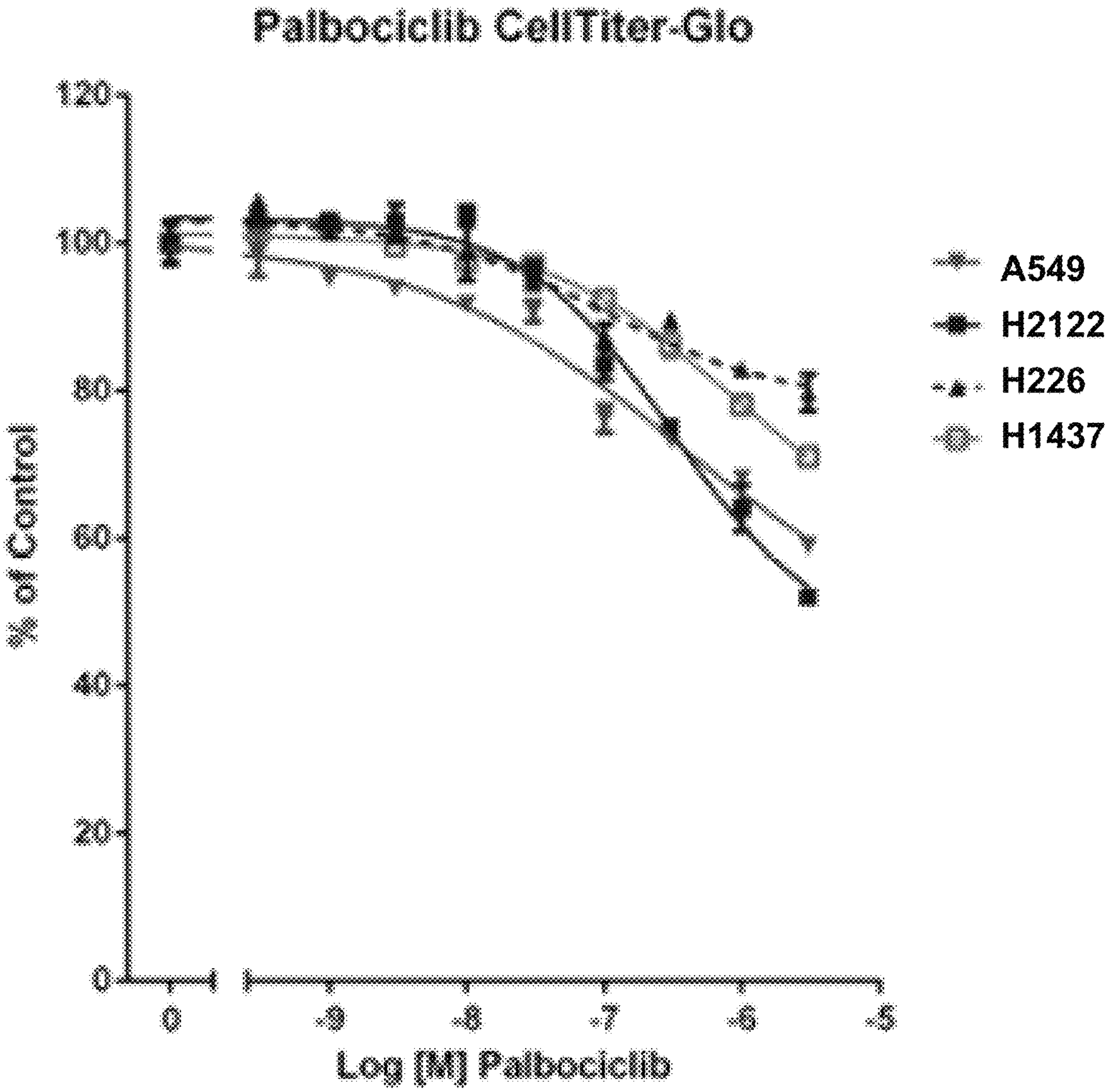
Figure 2H:
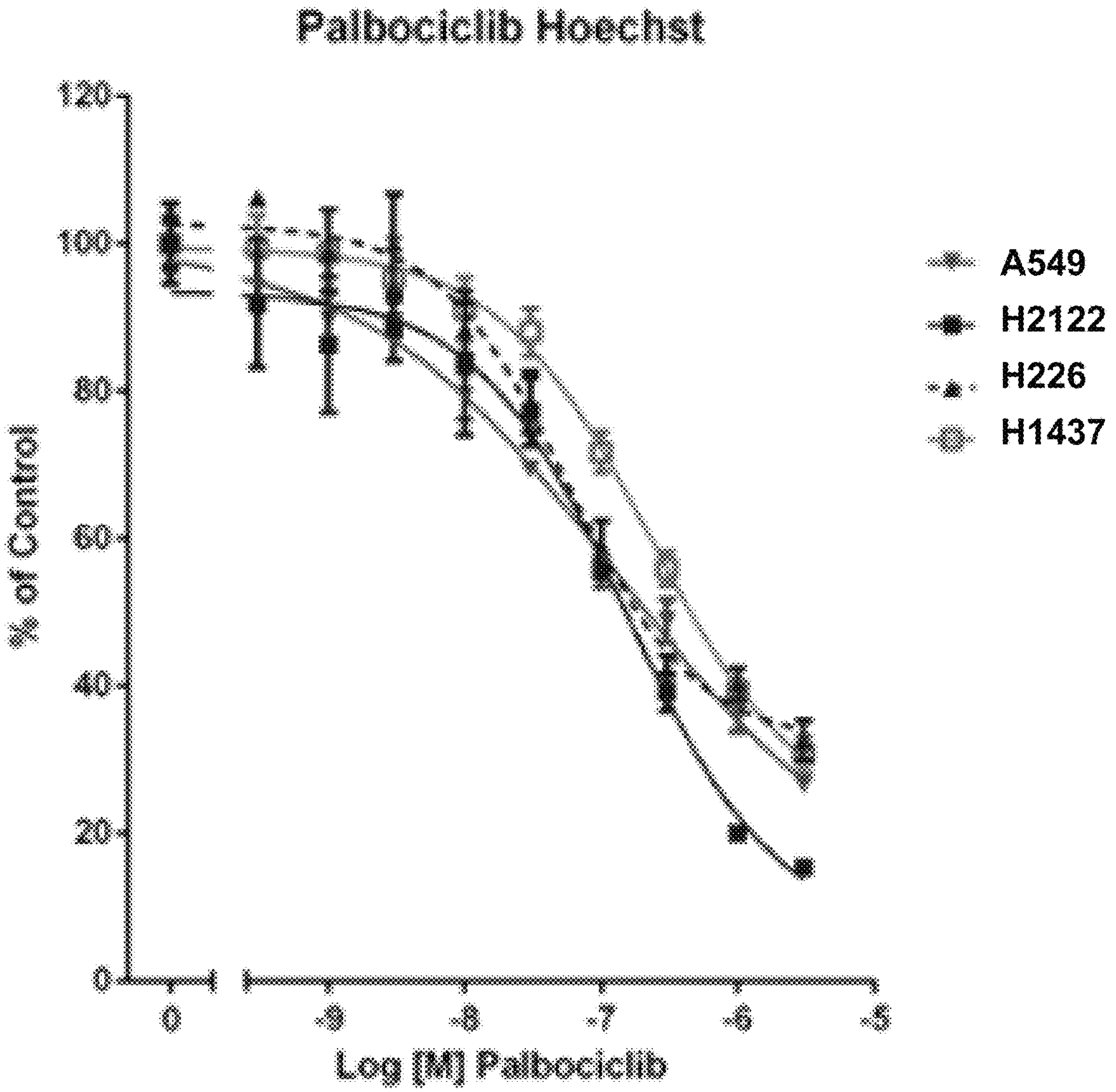
Figure 2I:
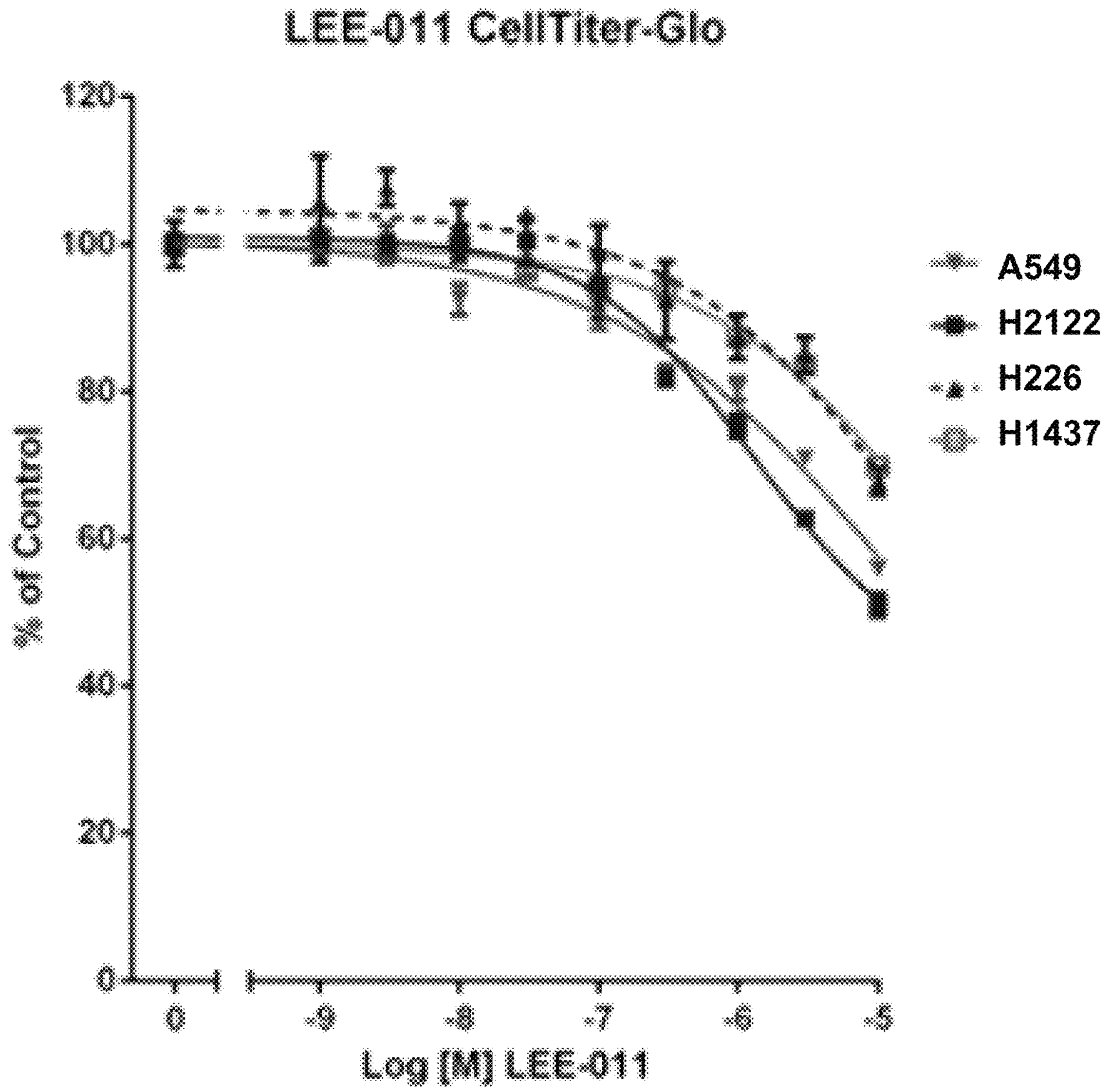
Figure 2J:
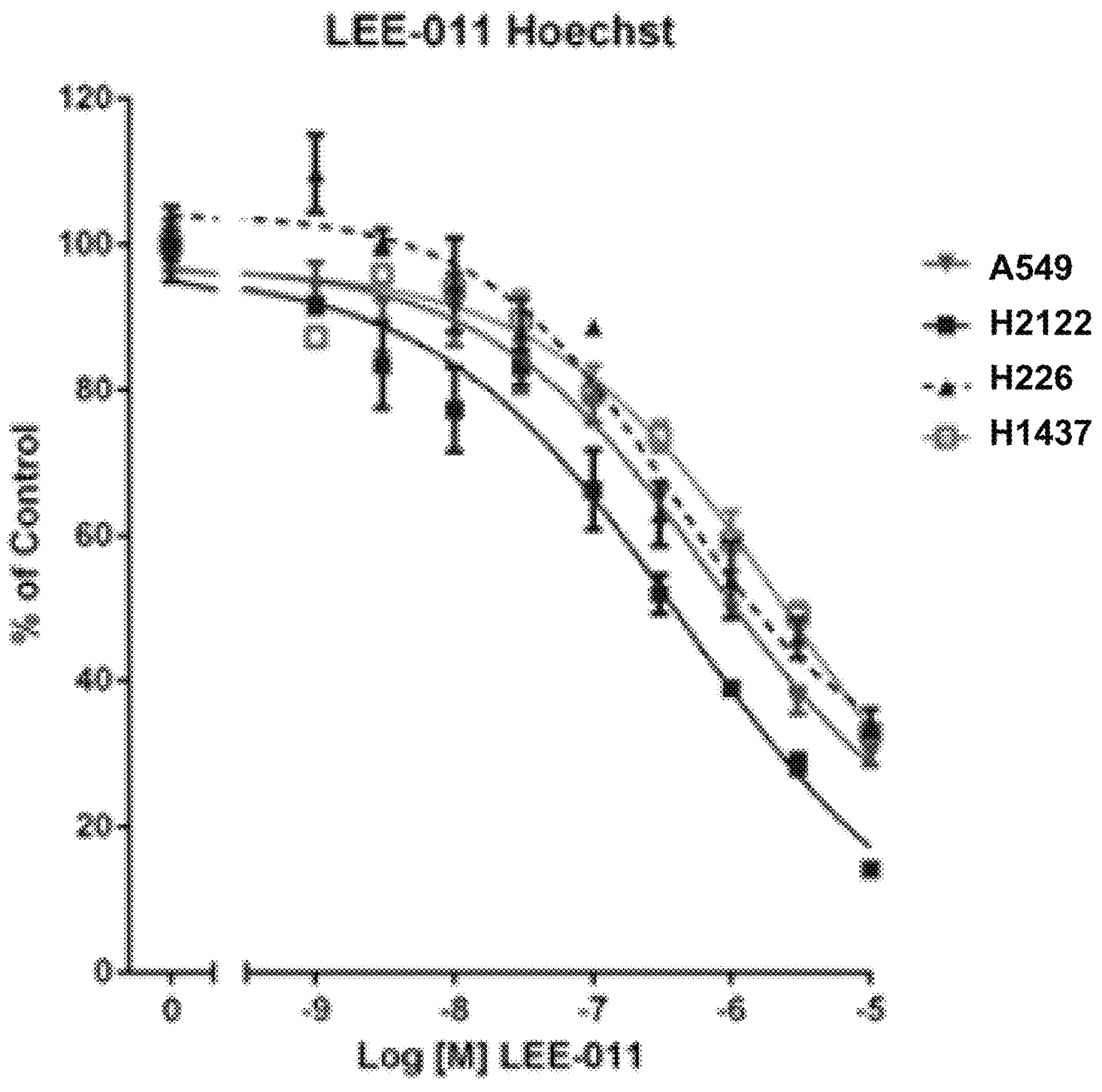
Figure 2K:
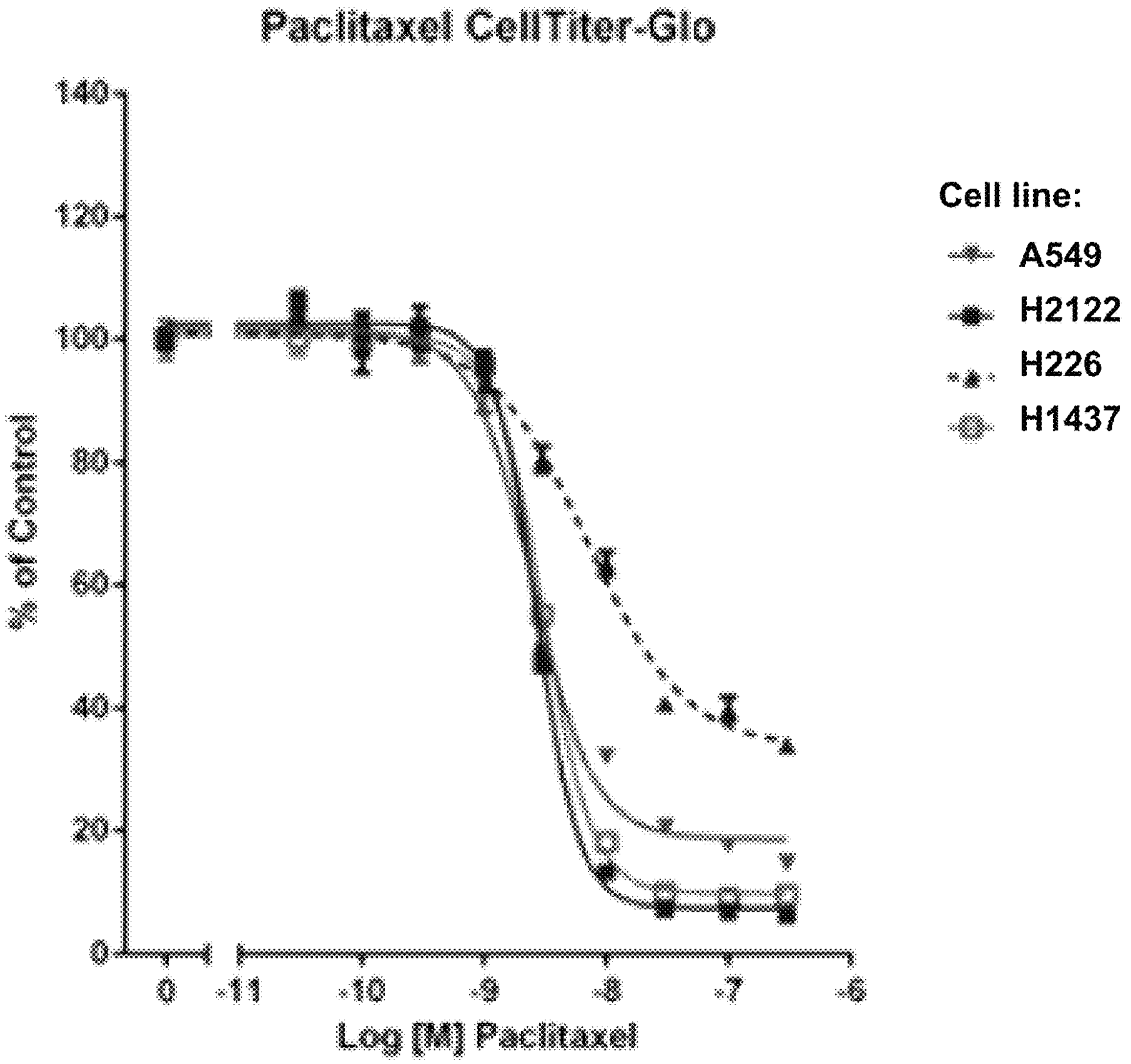
Figure 2L:
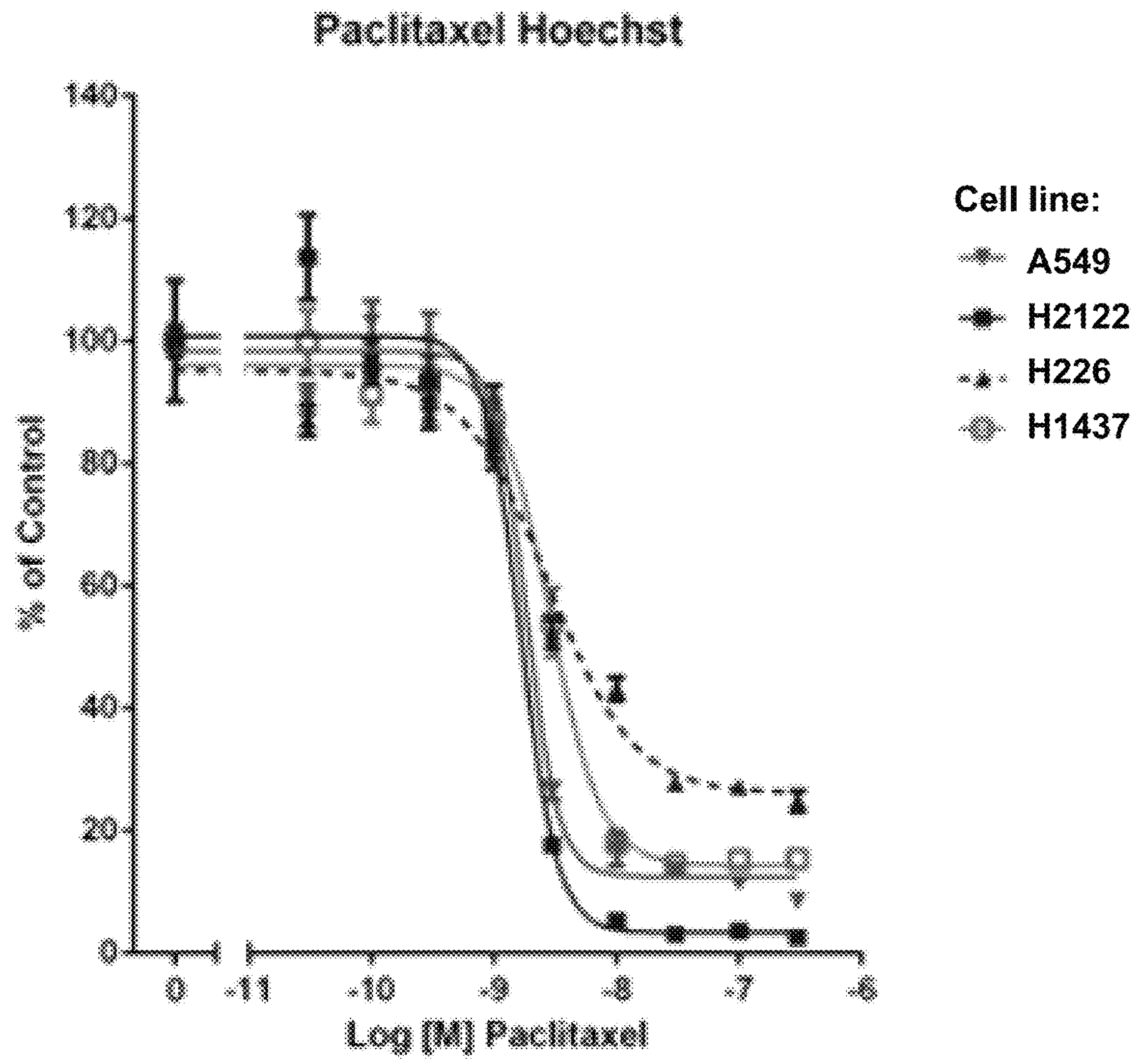
Figure 3A:
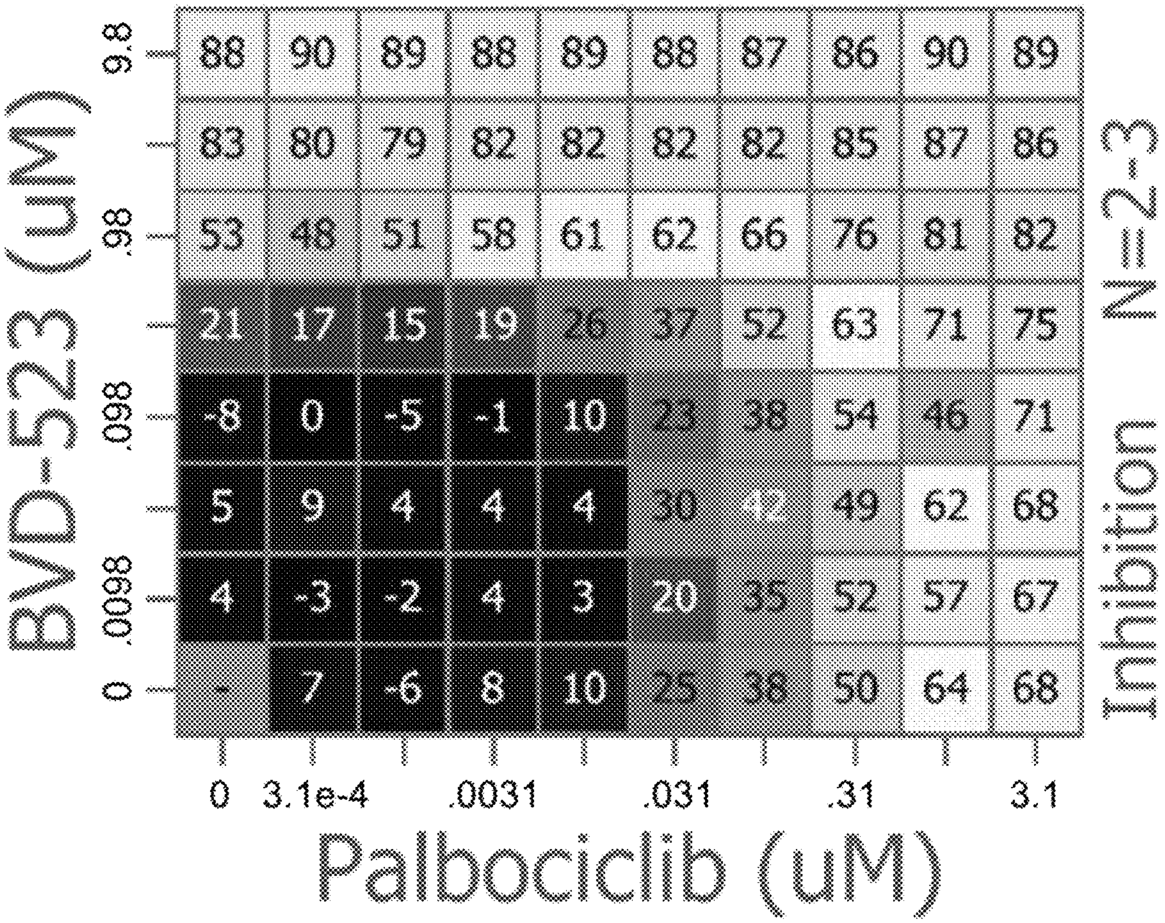
FIGS. 3A-3T show the results of the combination of BVD-523 and Palbociclib.
Figure 3B:
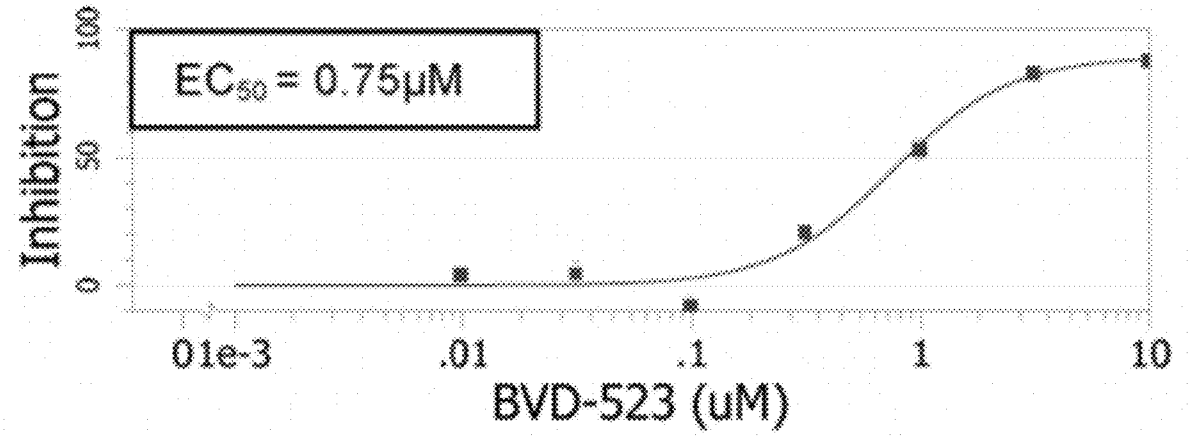
FIG. 3B-FIG. 3C show the results of single agent proliferation assays for the combination in 3A.
Figure 3C:
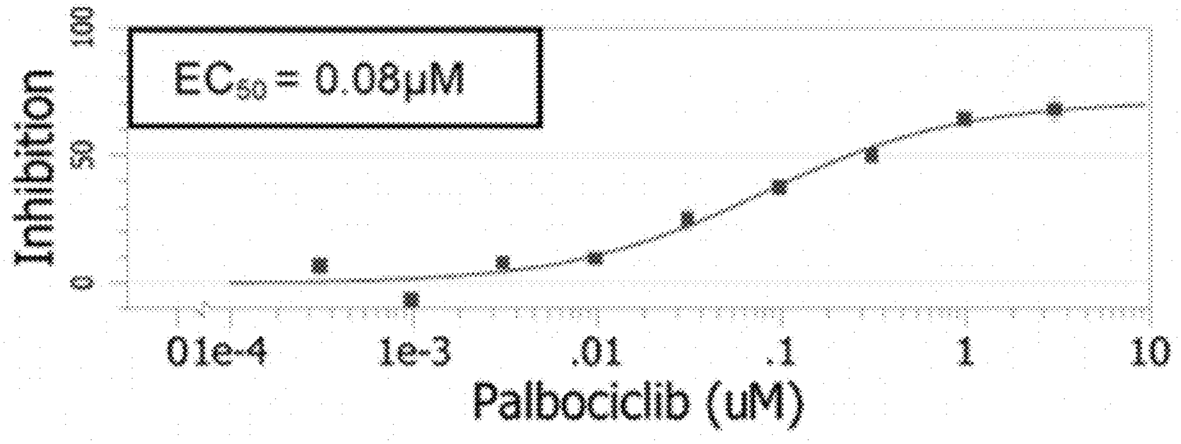
Figure 3D:
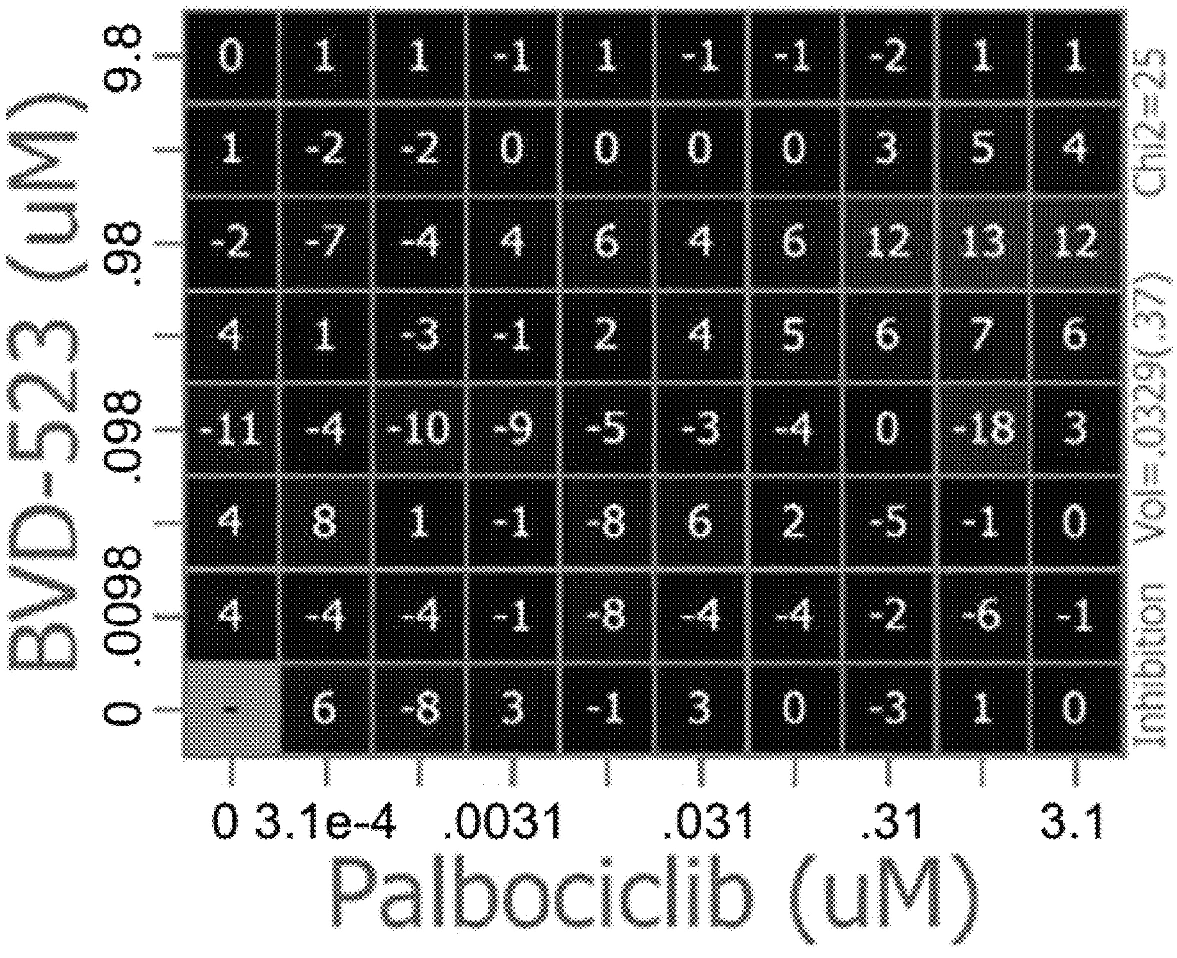
FIG. 3D shows Loewe excess for the combination in 3A and FIG. 3E shows Bliss excess for the combination in 3A.
Figure 3E:
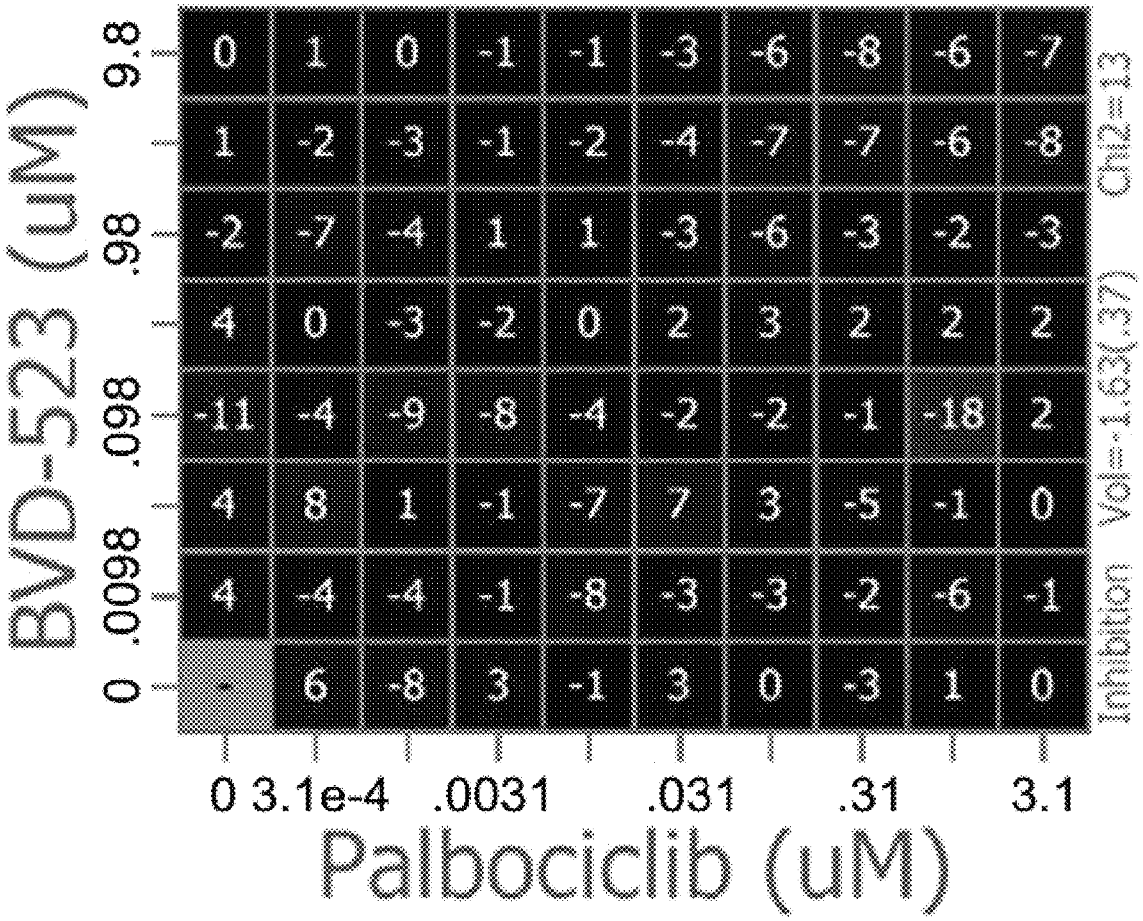
Figure 3F:
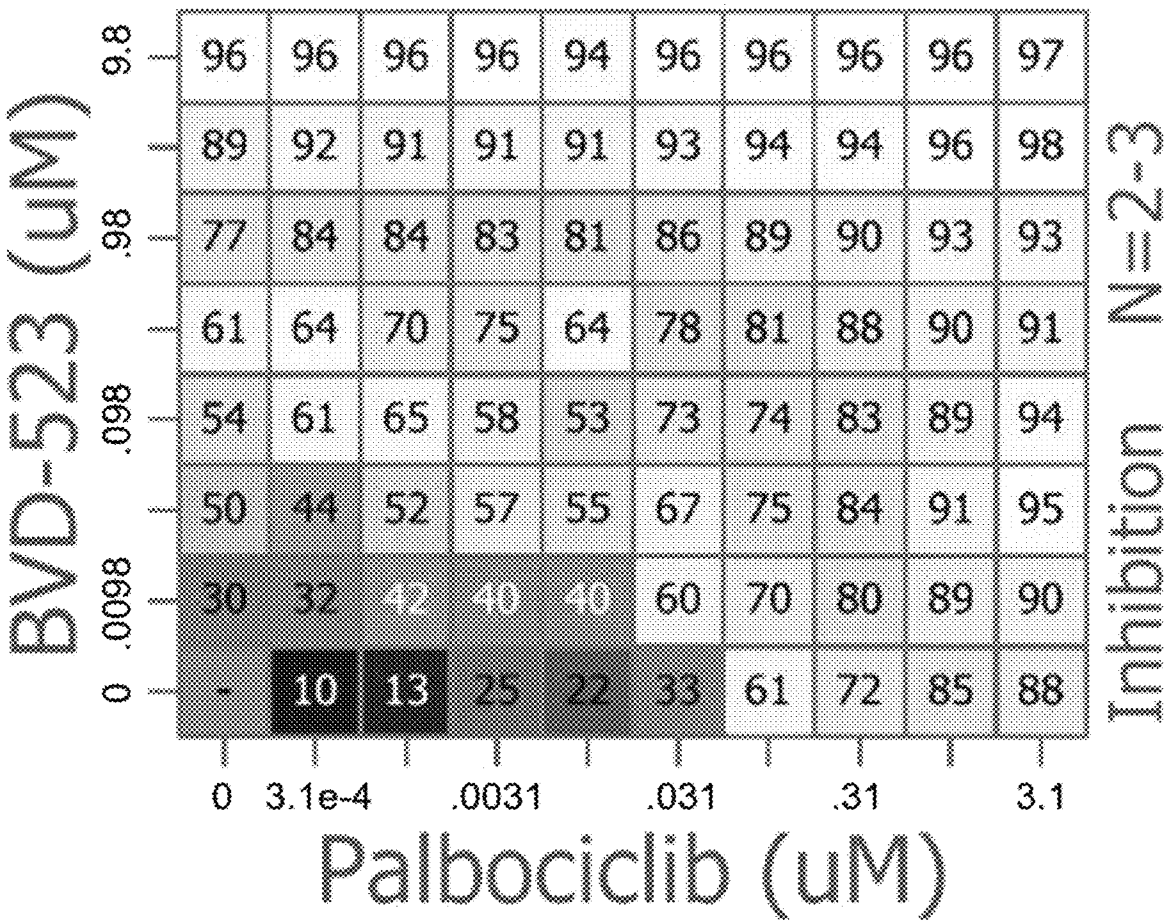
FIG. 3F shows a dose matrix showing inhibition (%) for the combination in H2122 cells.
Figure 3G:
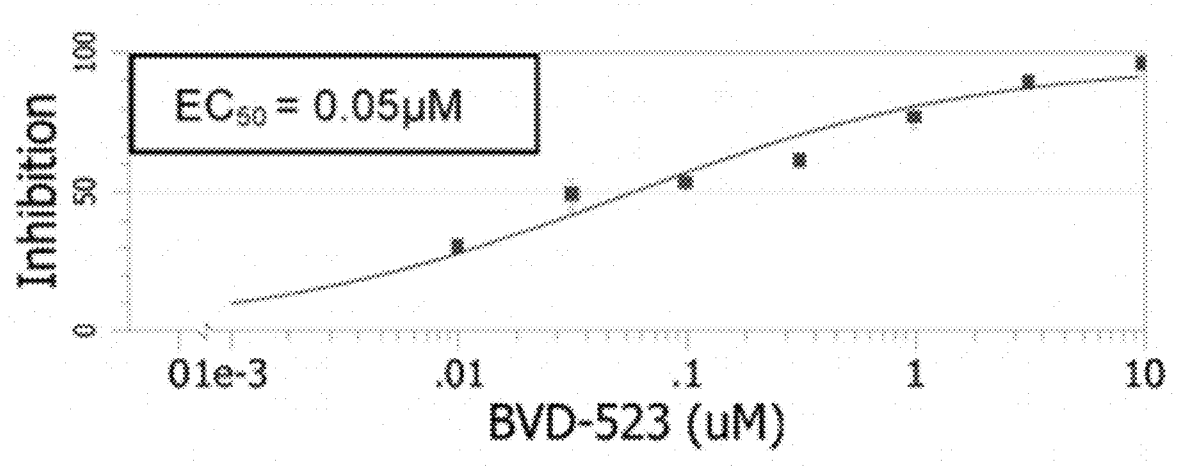
FIG. 3G-FIG. 3H show the results of single agent proliferation assays for the combination in 3F.
Figure 3H:
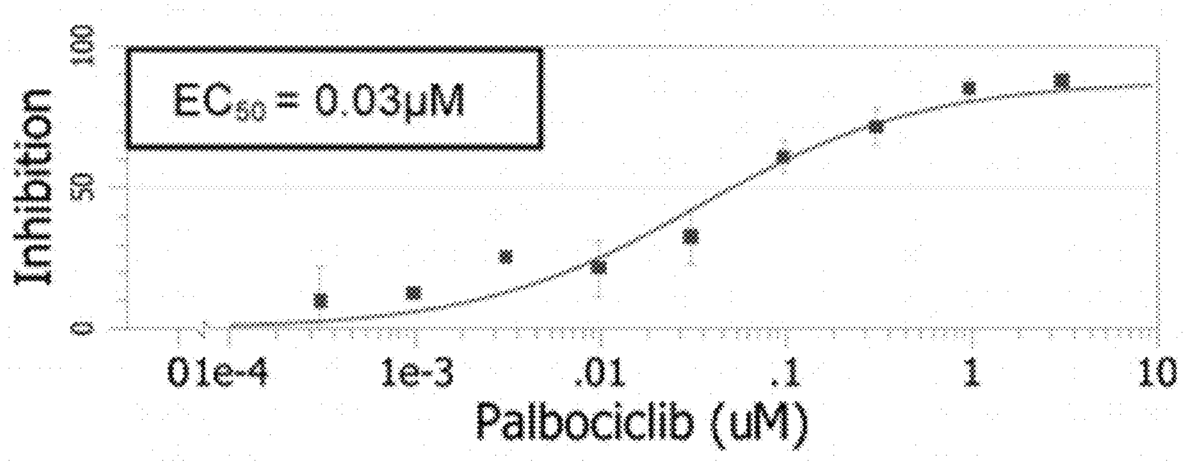
Figure 3I:
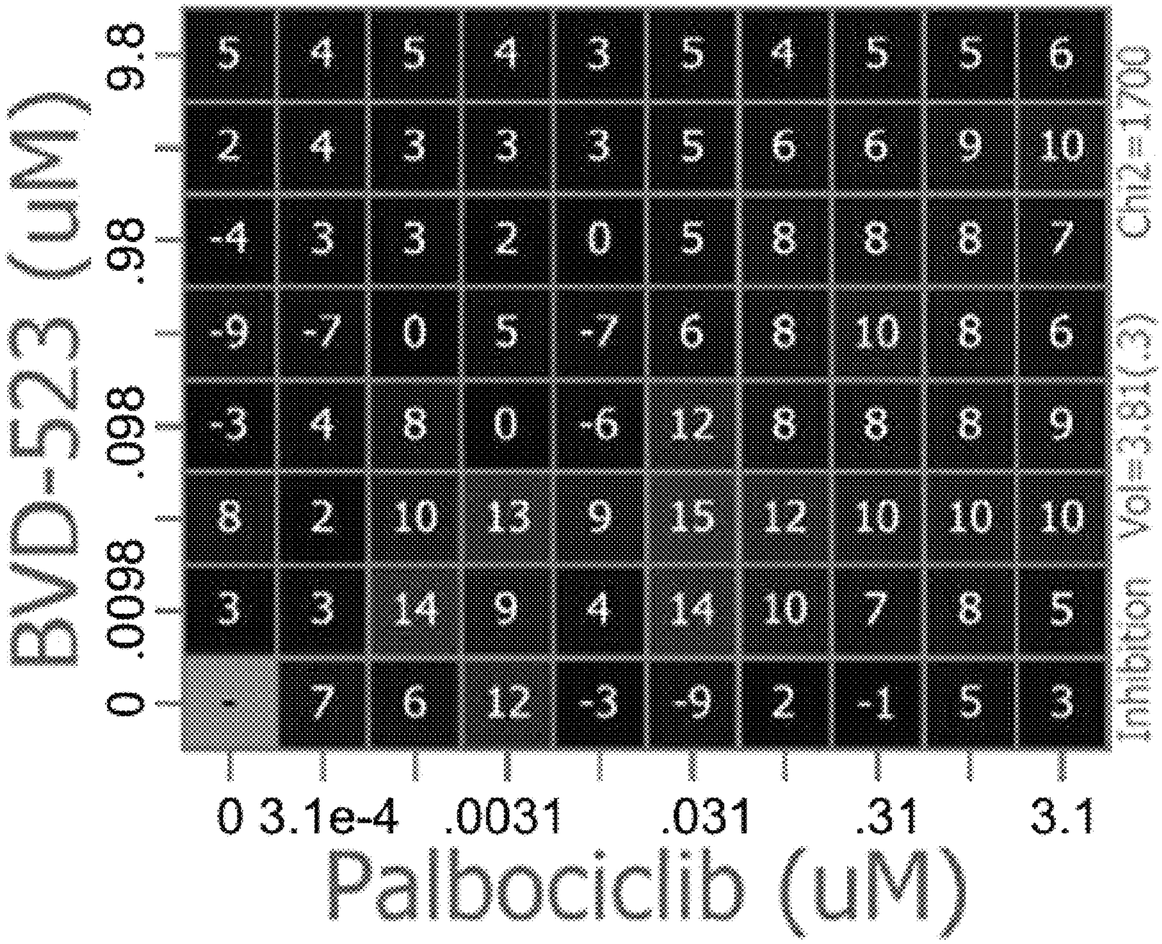
FIG. 3I shows Loewe excess for the combination in 3F and FIG. 3J shows Bliss excess for the combination in 3F.
Figure 3J:
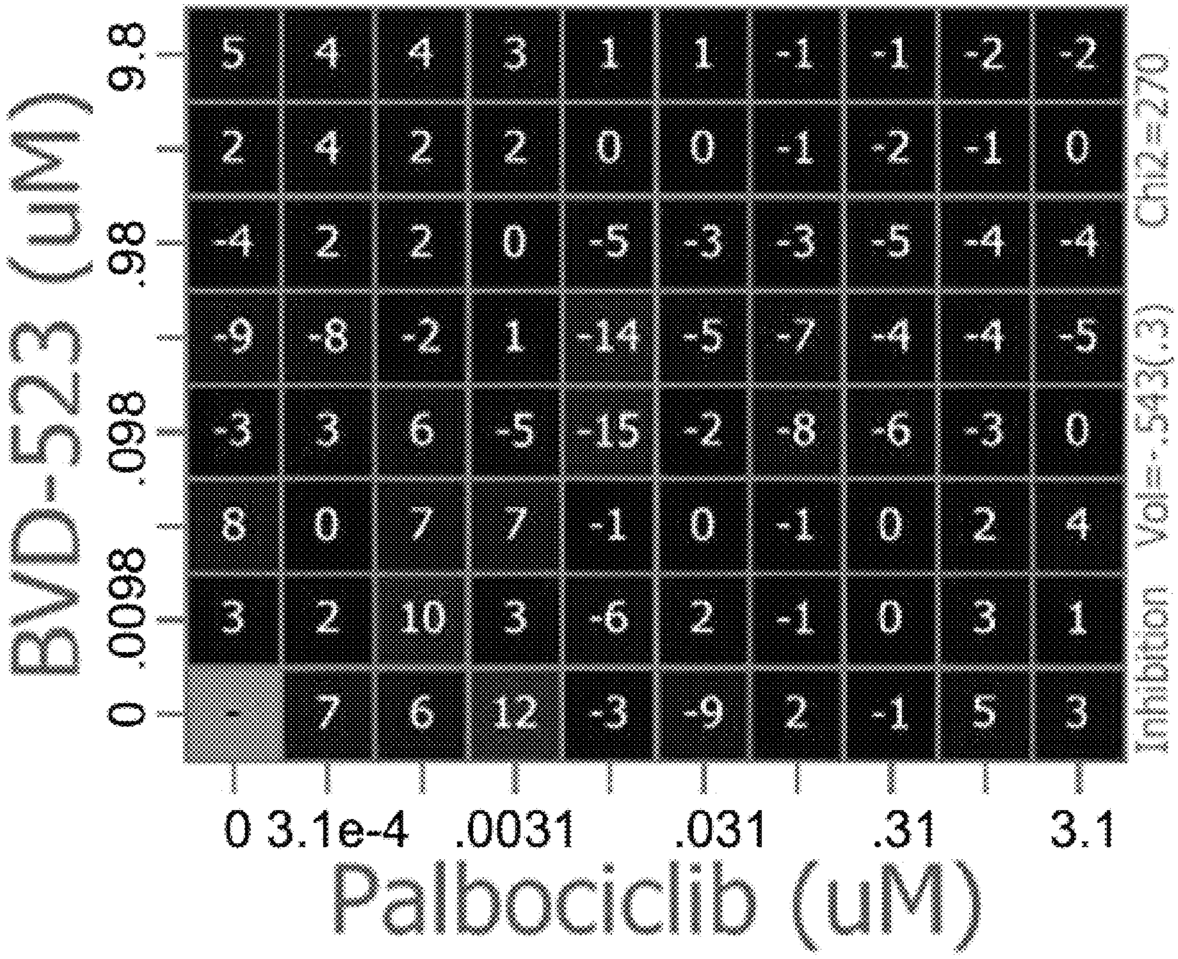
Figure 3K:
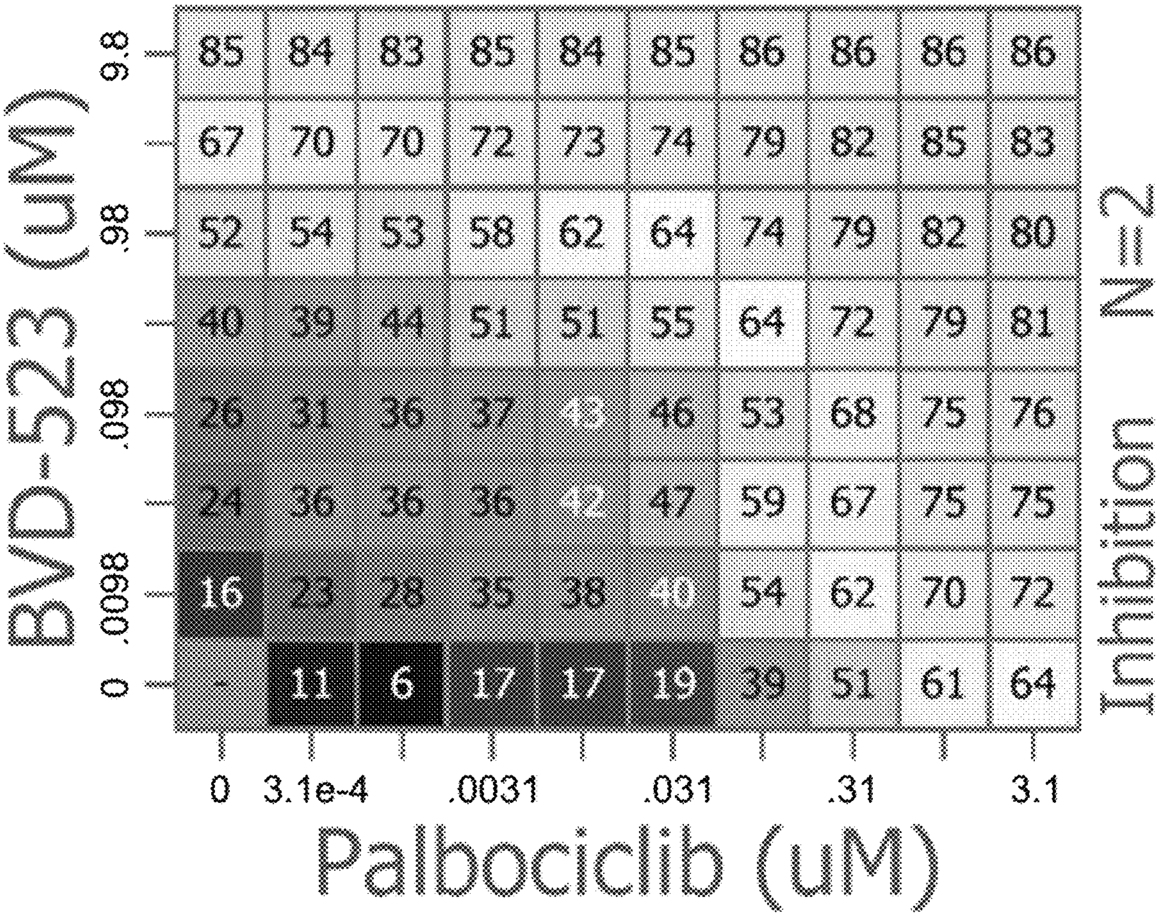
FIG. 3K shows a dose matrix showing inhibition (%) for the combination in H1437 cells.
Figure 3L:
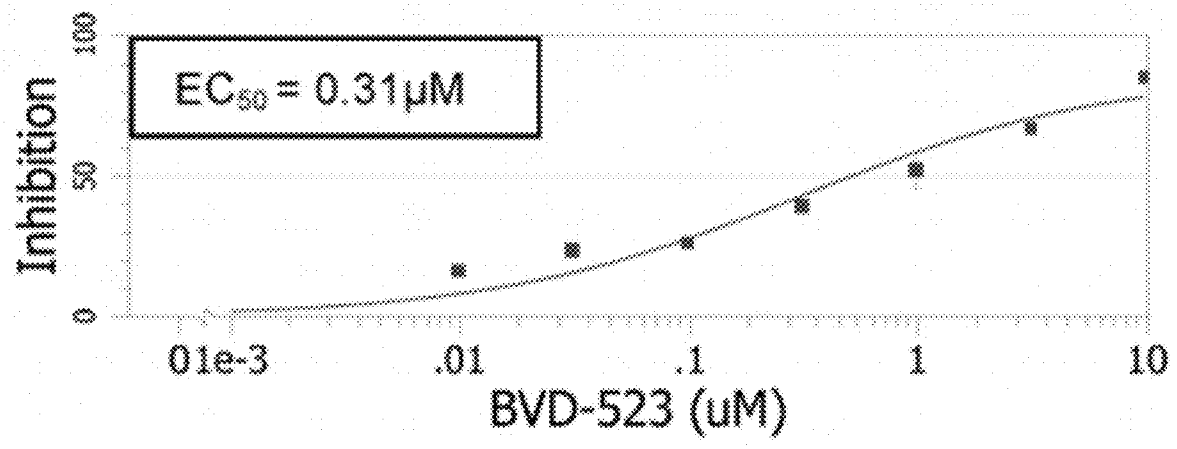
FIG. 3L-FIG. 3M show the results of single agent proliferation assays for the combination in 3K.
Figure 3M:
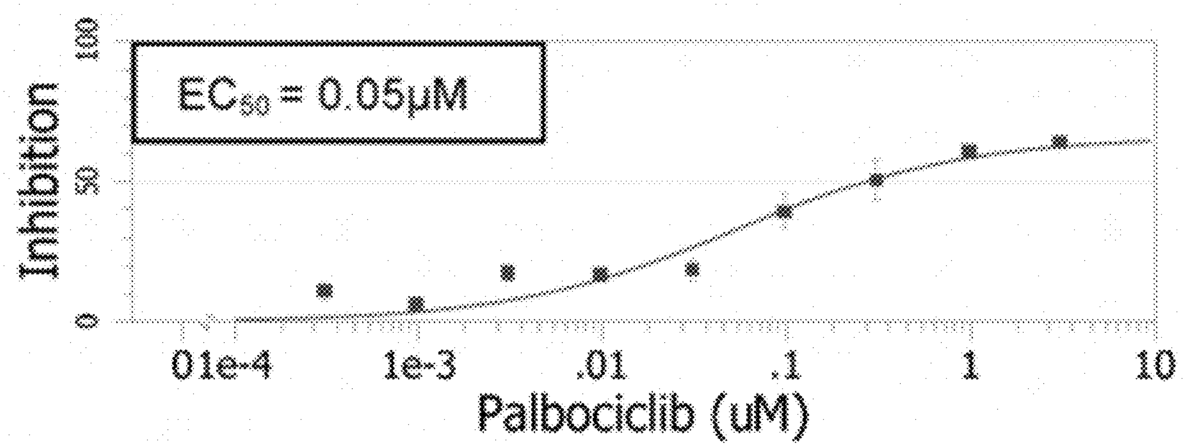
Figure 3N:
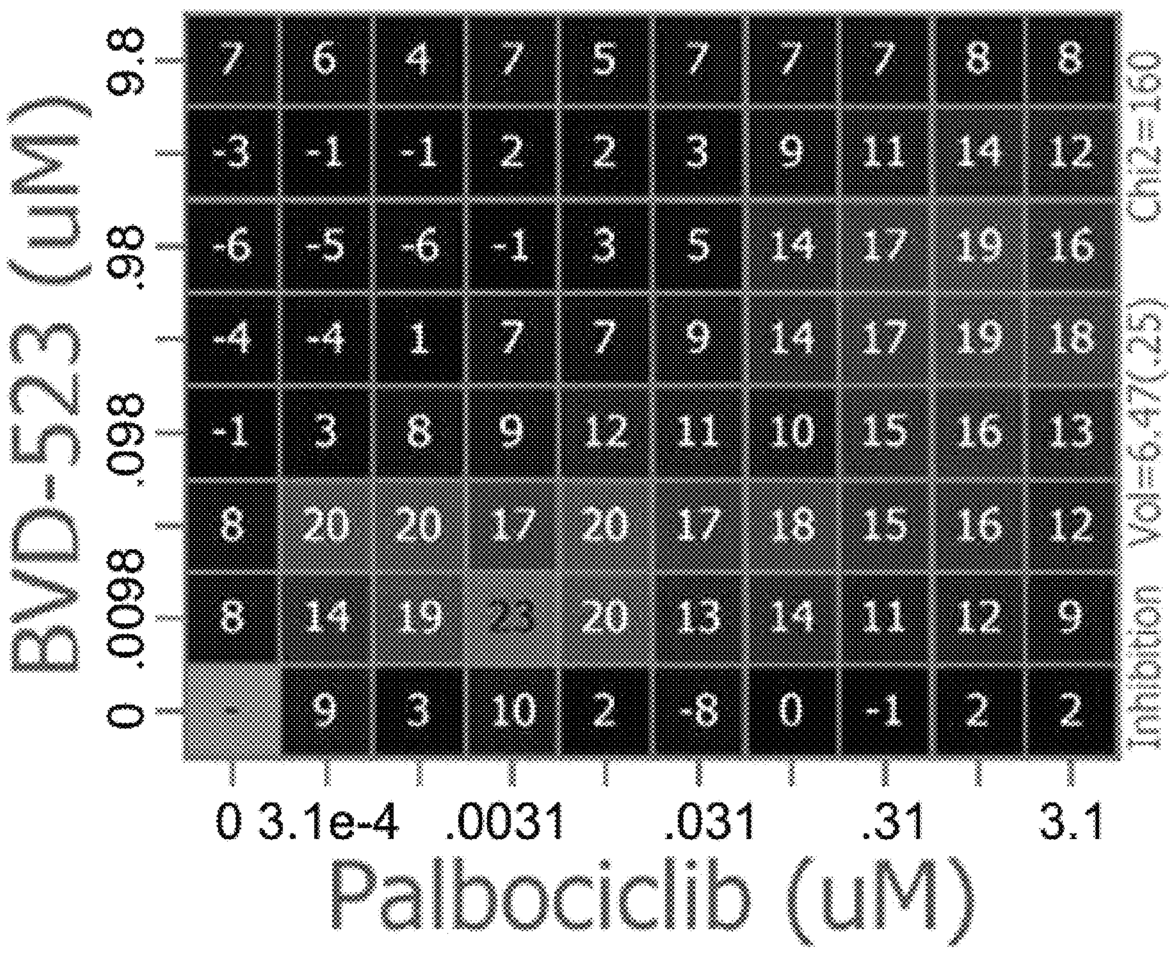
FIG. 3N shows Loewe excess for the combination in 3K and FIG. 3O shows Bliss excess for the combination in 3K.
Figure 3O:
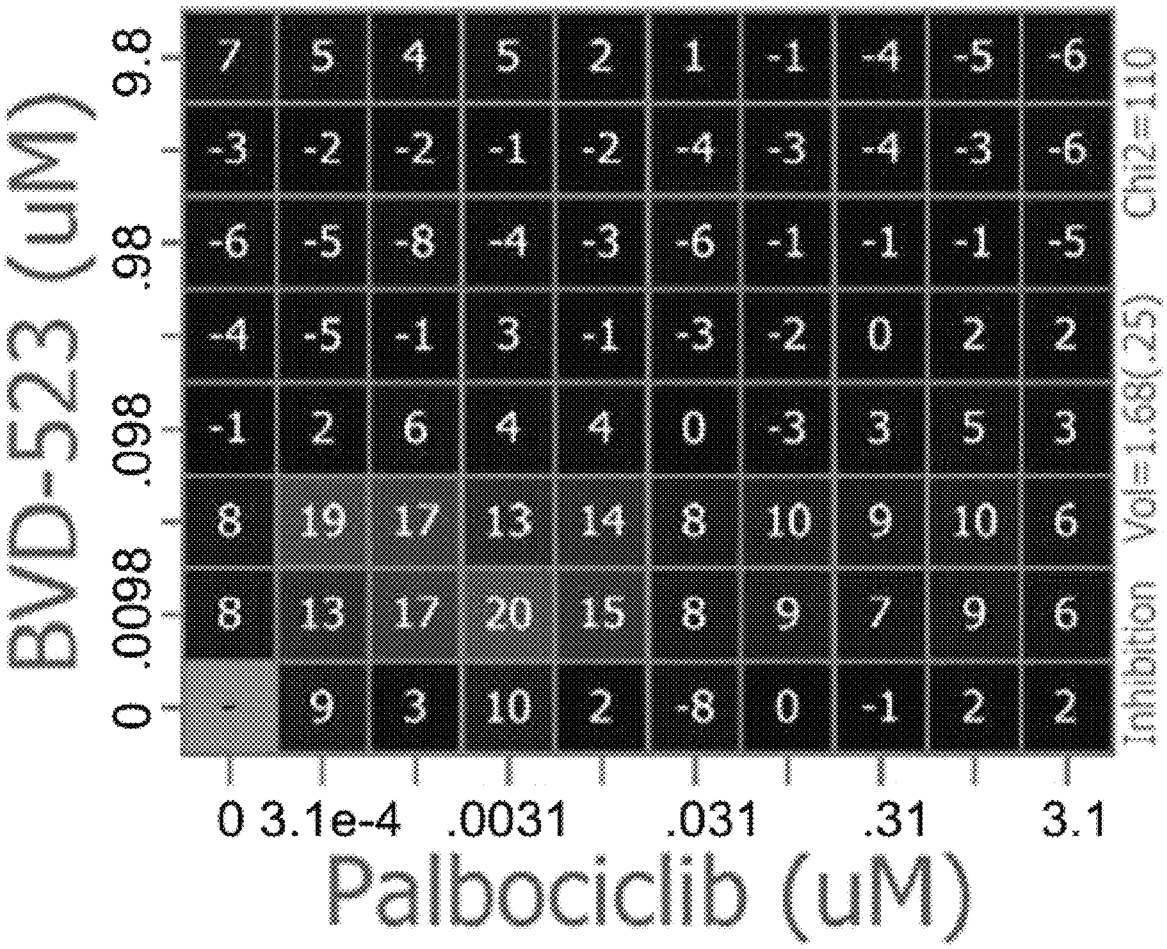
Figure 3P:
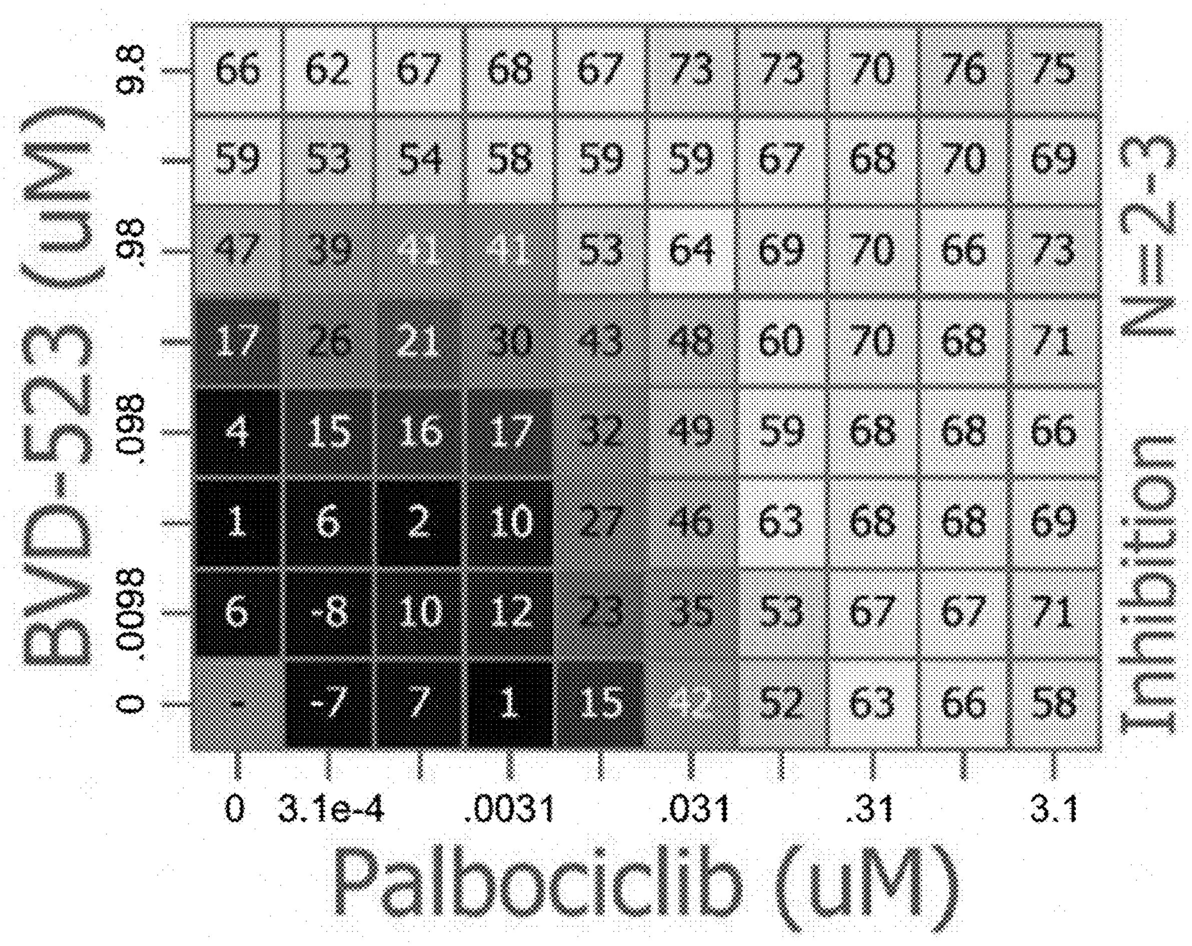
FIG. 3P shows a dose matrix showing inhibition (%) for the combination in H226 cells.
Figure 3Q:
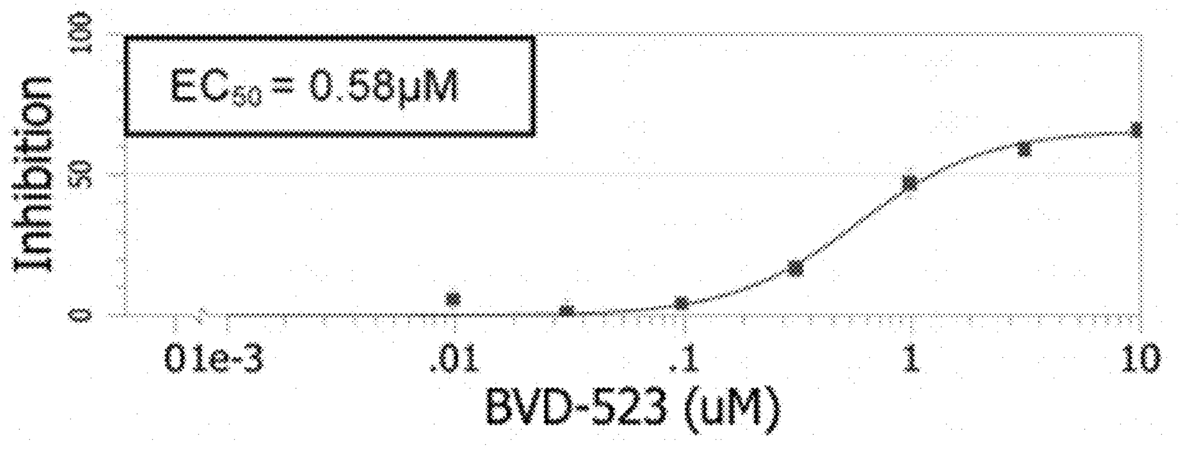
FIG. 3Q-FIG. 3R show the results of single agent proliferation assays for the combination in 3P.
Figure 3R:
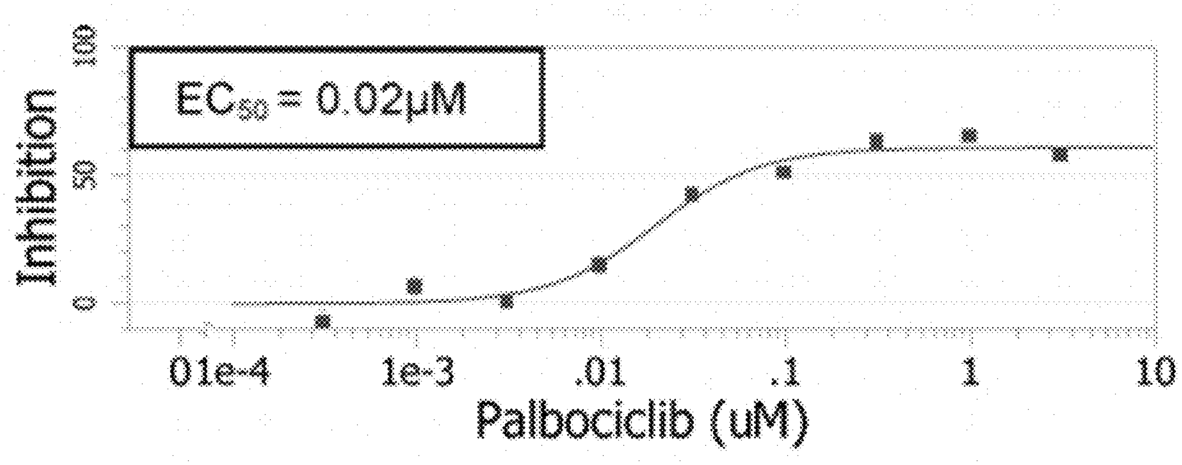
Figure 3S:
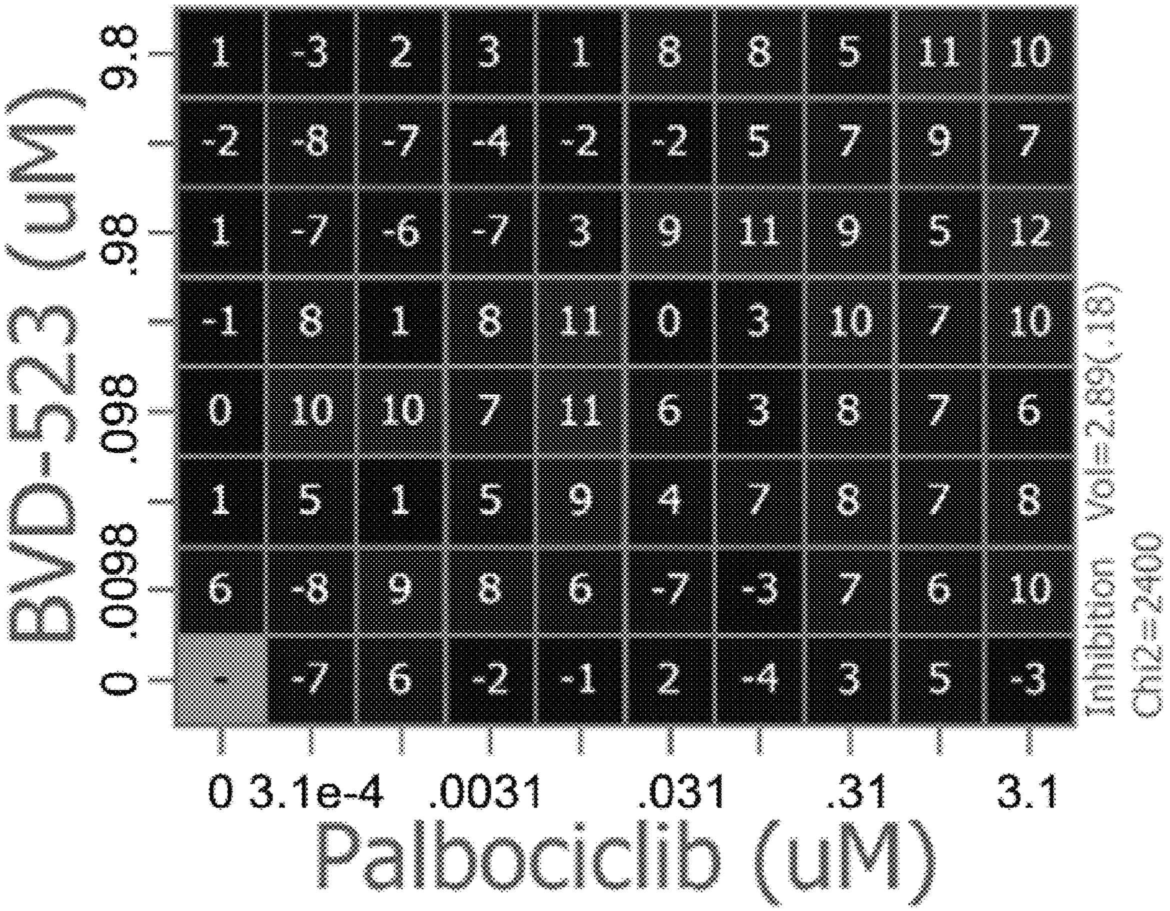
Figure 3T:
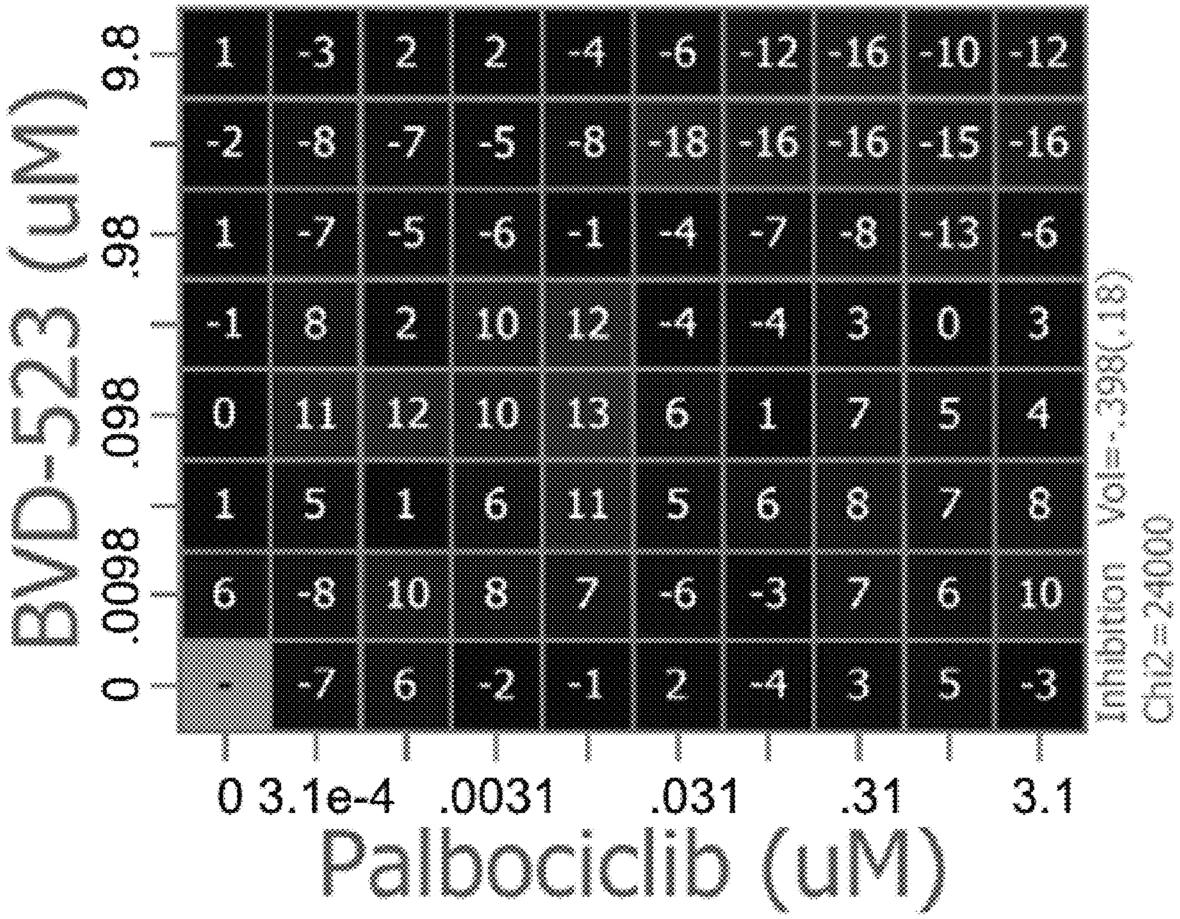
Figure 4A:
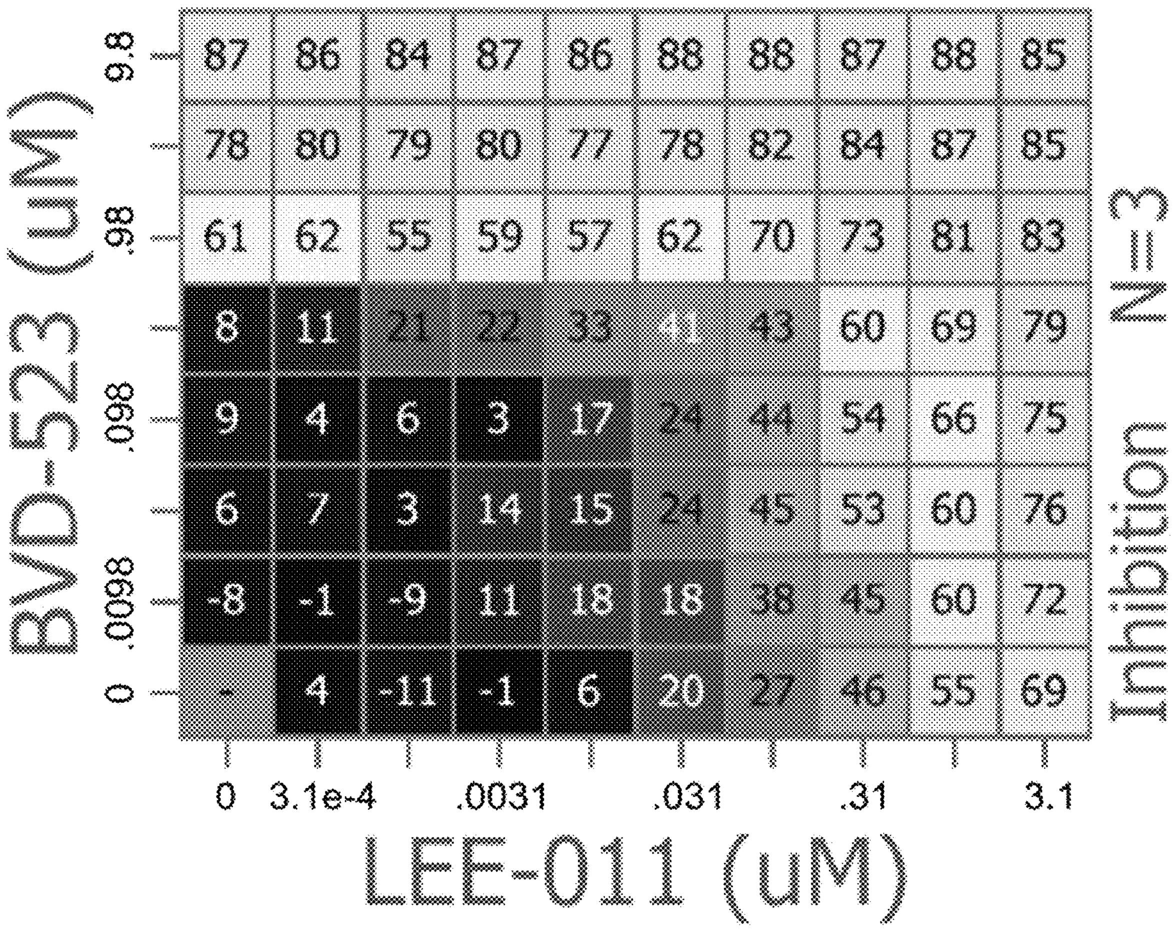
FIGS. 4A-4T show the results of the combination of BVD-523 and LEE-011.
Figure 4B:
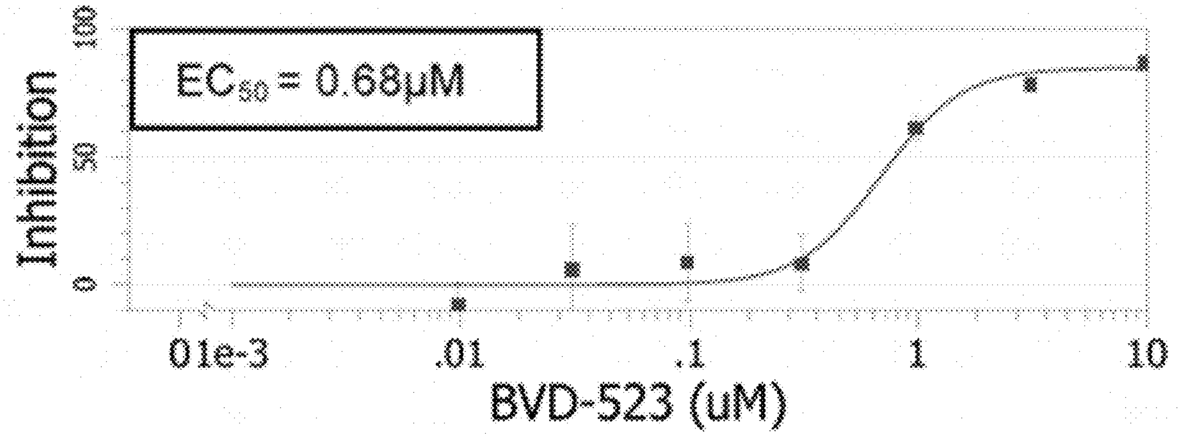
FIG. 4B-FIG. 4C show the results of single agent proliferation assays for the combination in 4A.
Figure 4C:
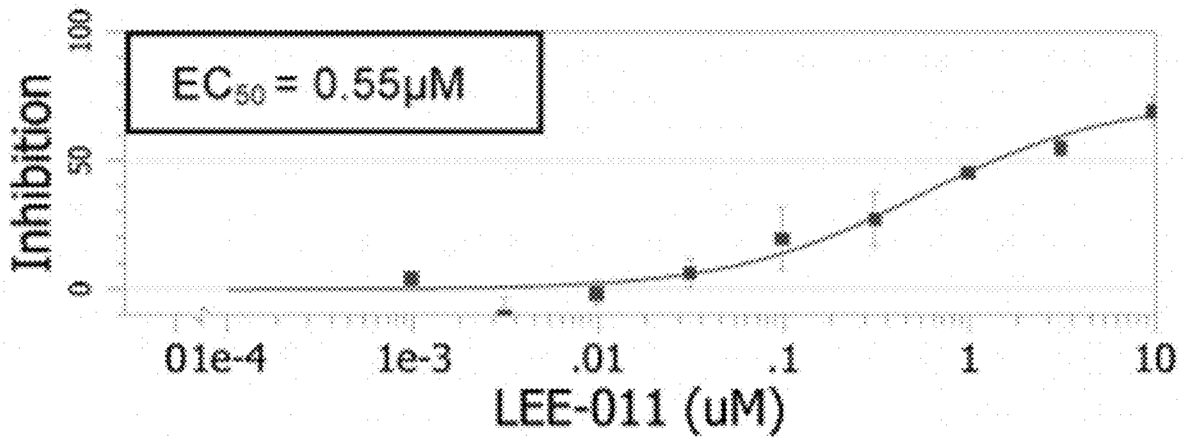
Figure 4D:
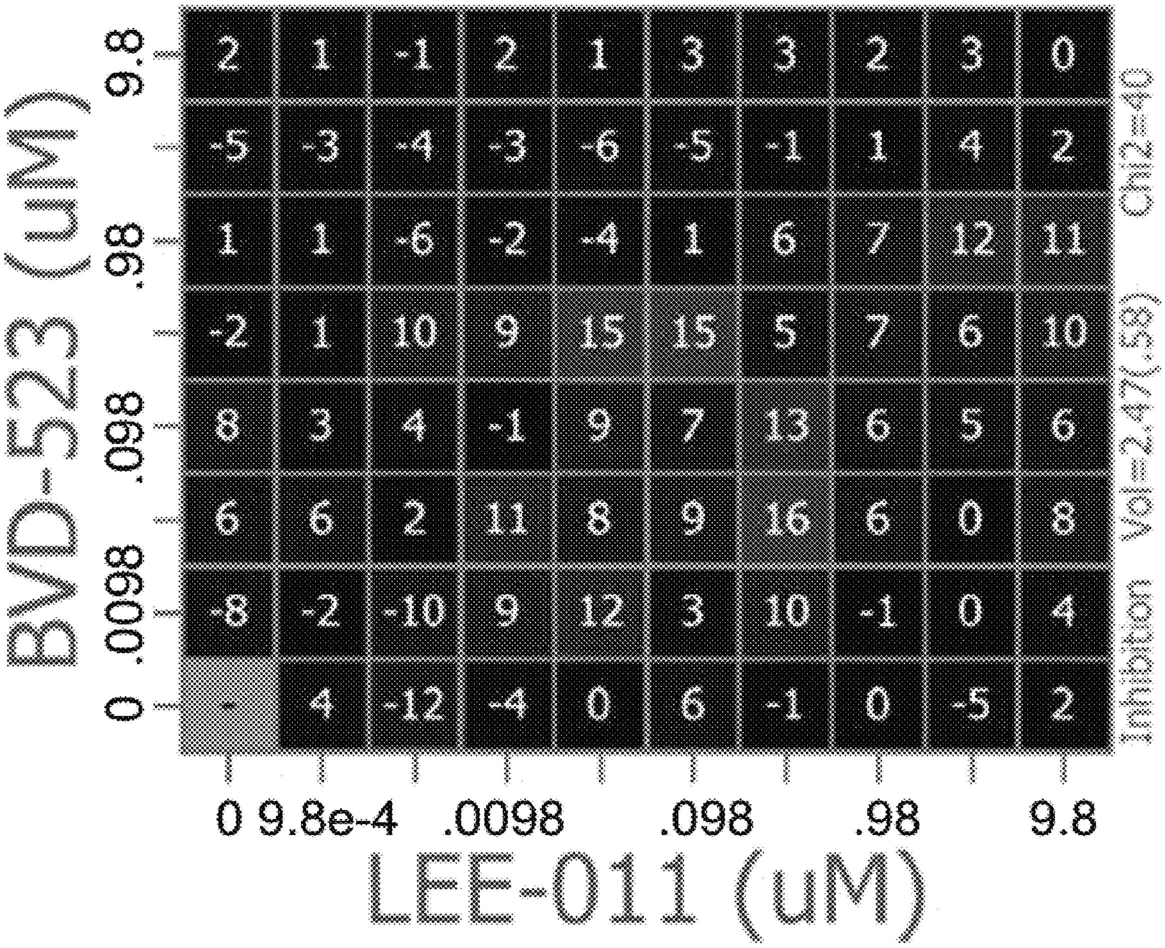
FIG. 4D shows Loewe excess for the combination in 4A and FIG. 4E shows Bliss excess for the combination in 4A.
Figure 4E:
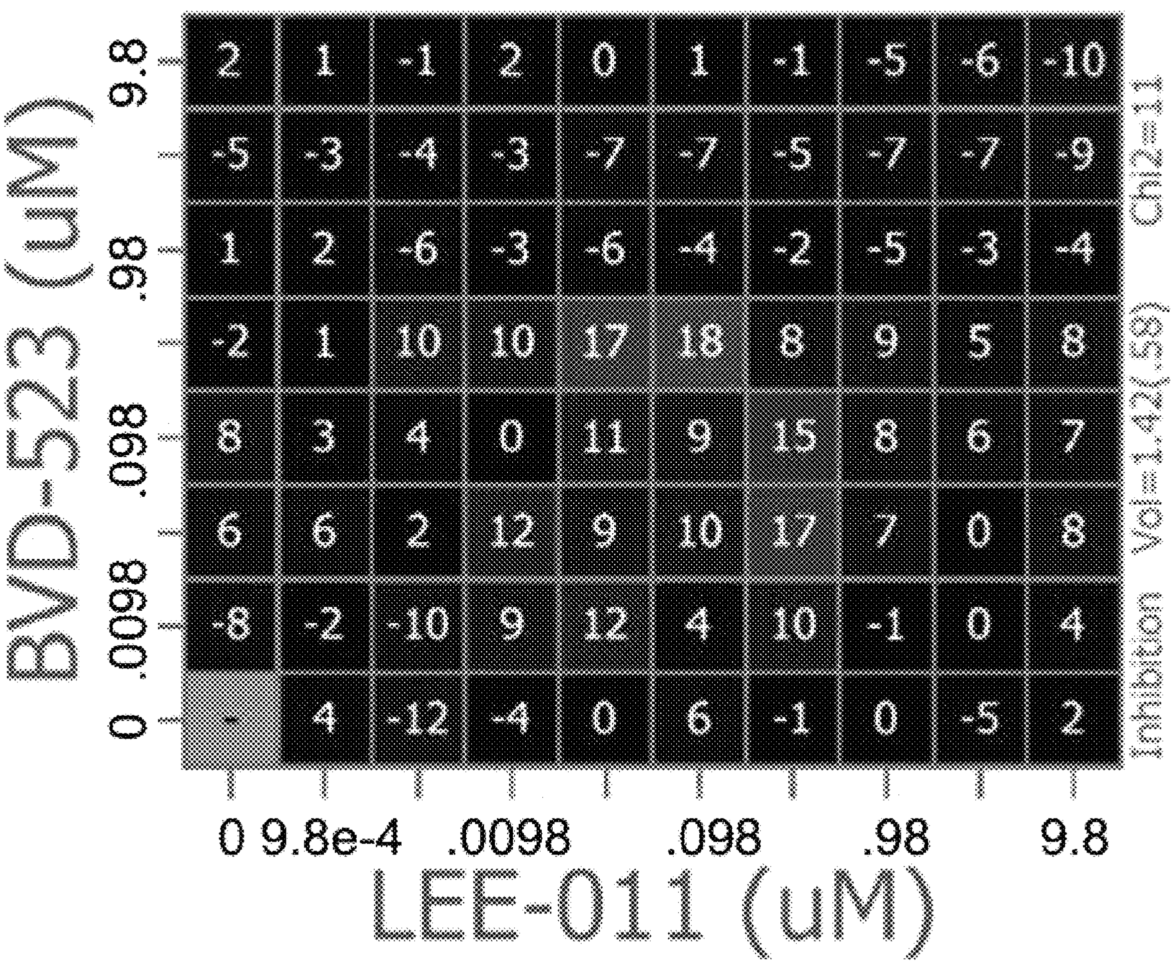
Figure 4F:
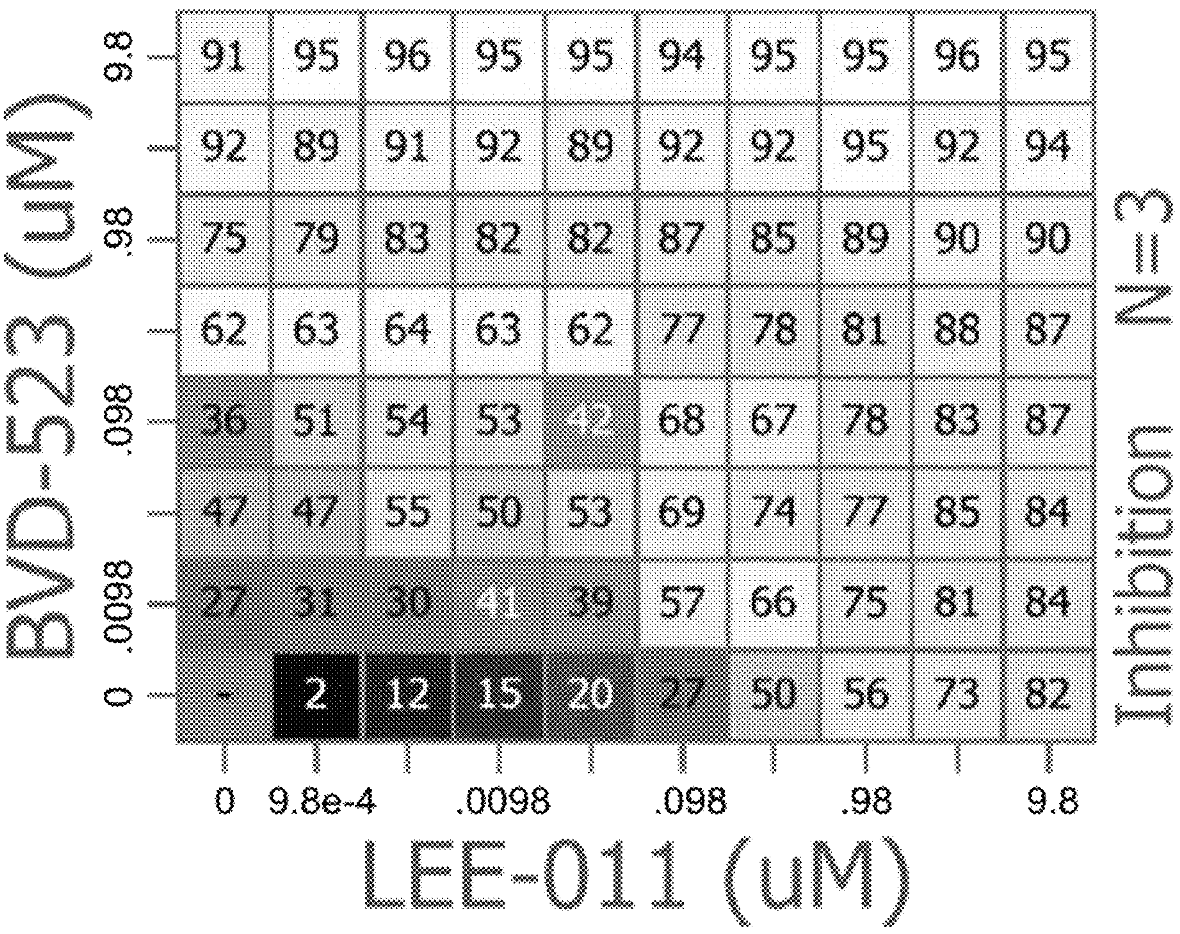
FIG. 4F shows a dose matrix showing inhibition (%) for the combination in H2122 cells.
Figure 4G:
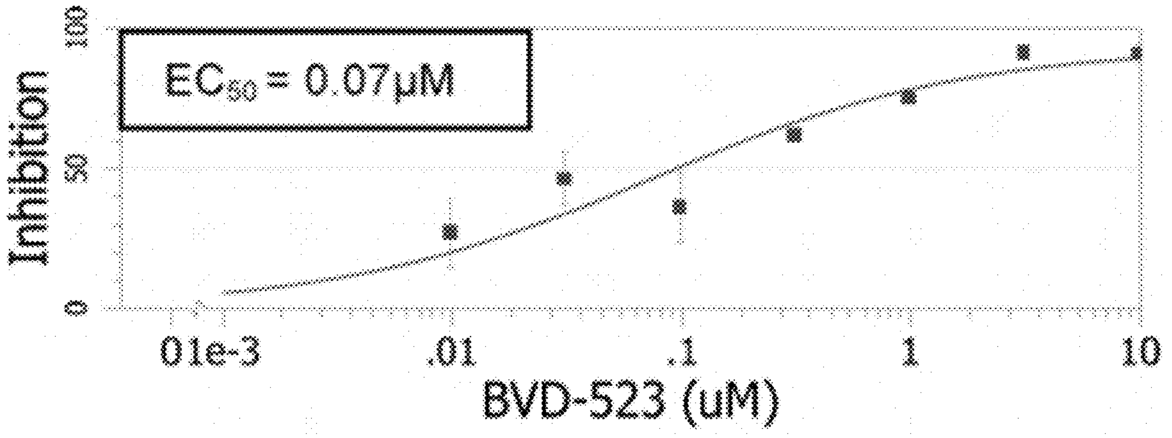
FIG. 4G-FIG. 4H show the results of single agent proliferation assays for the combination in 4F.
Figure 4H:
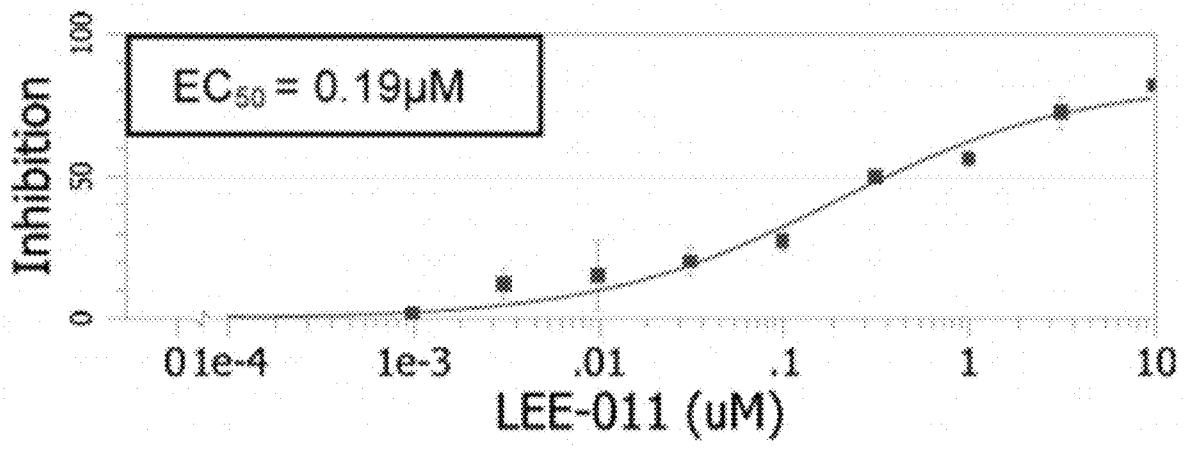
Figure 4I:
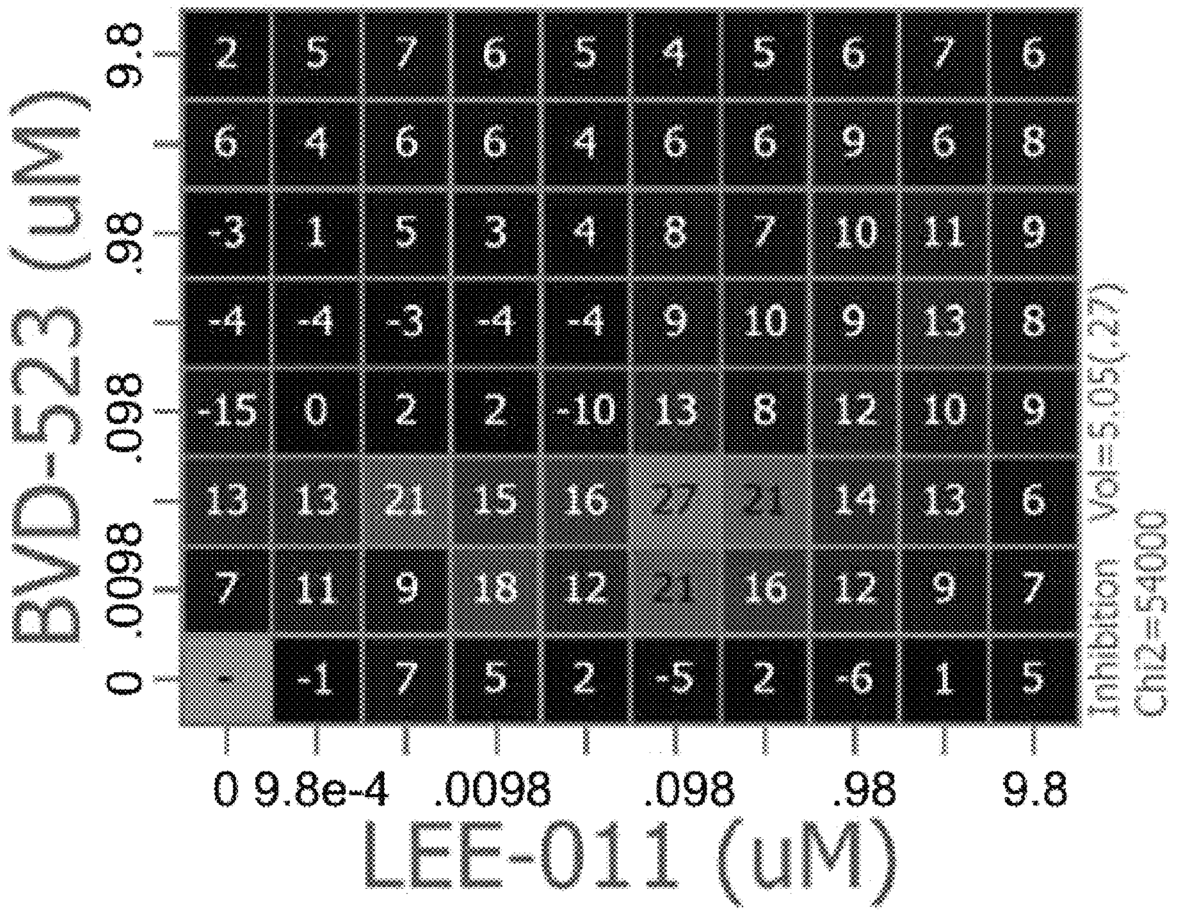
FIG. 4I shows Loewe excess for the combination in 4F and FIG. 4J shows Bliss excess for the combination in 4F.
Figure 4J:
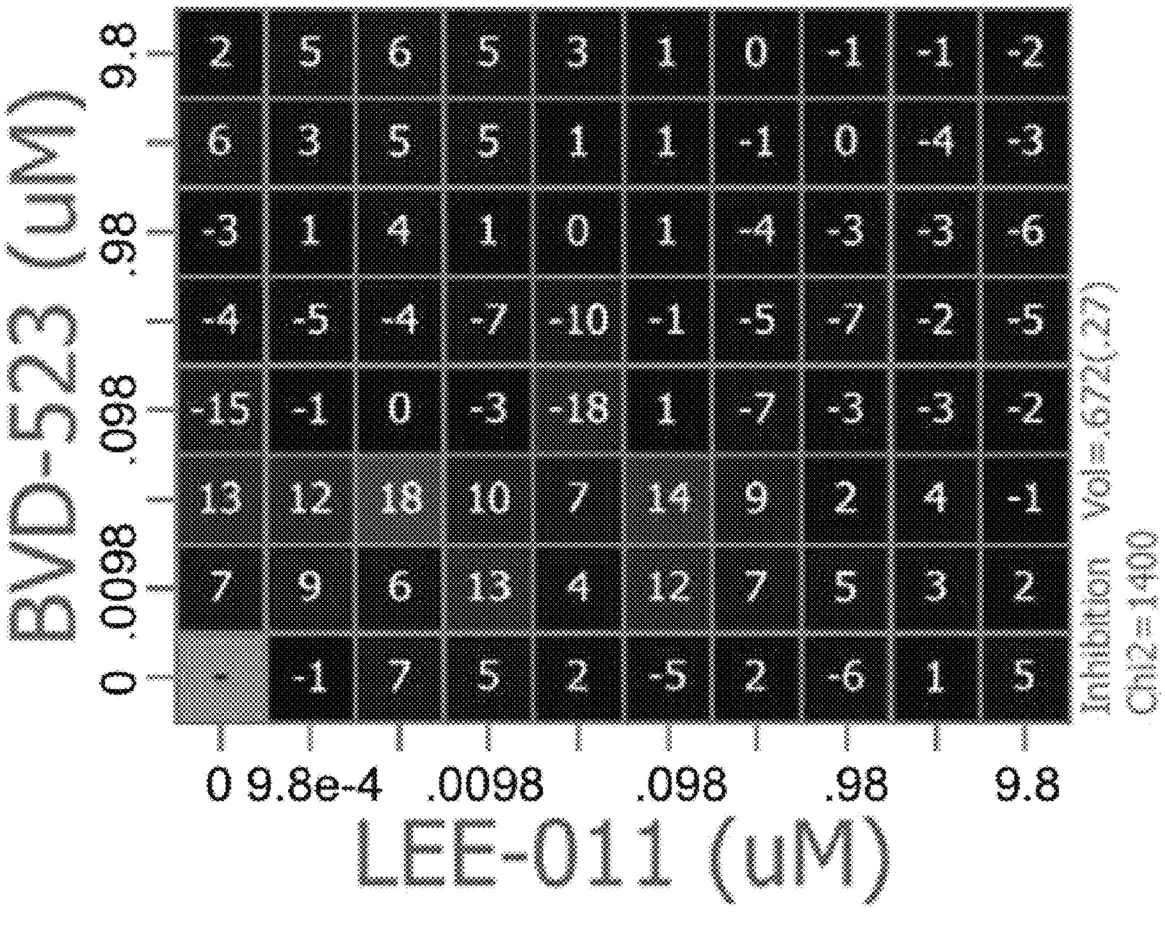
Figure 4K:
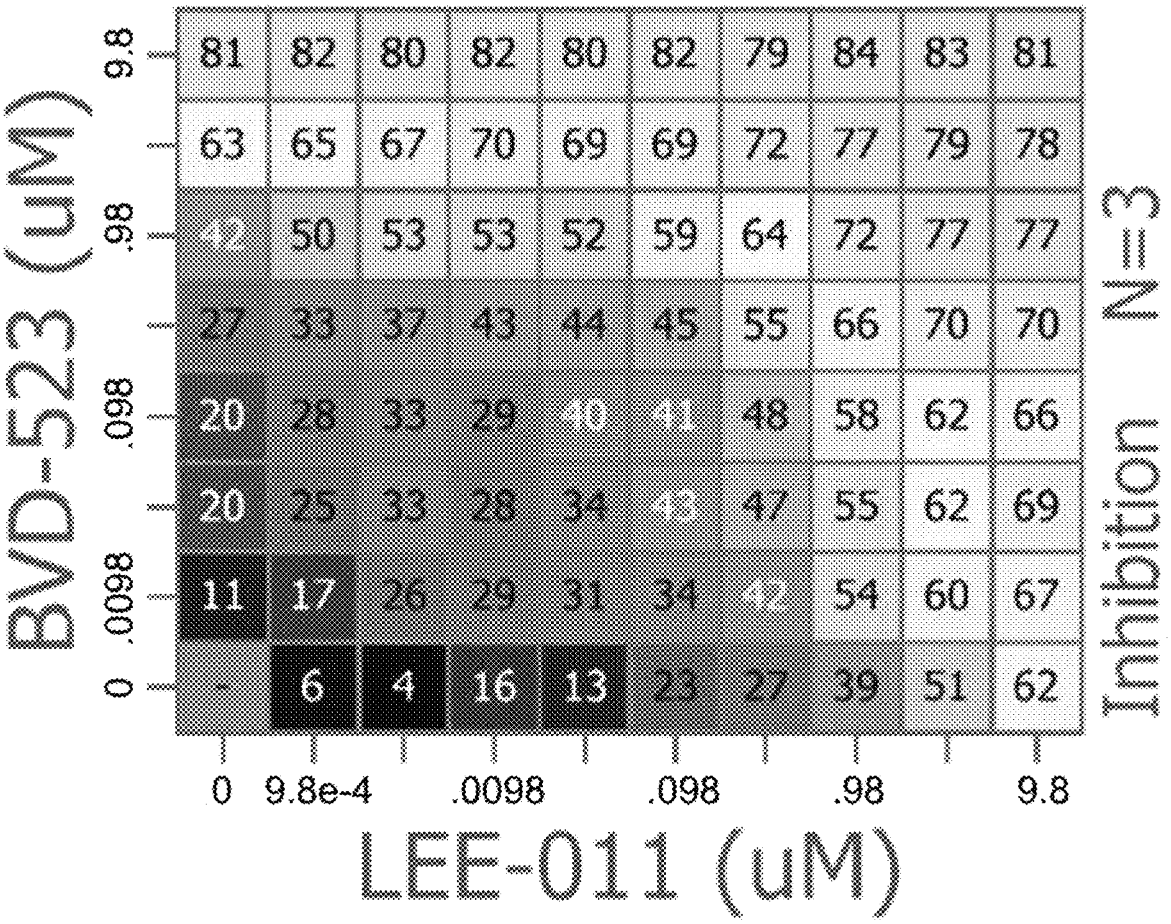
FIG. 4K shows a dose matrix showing inhibition (%) for the combination in H1437 cells.
Figure 4L:
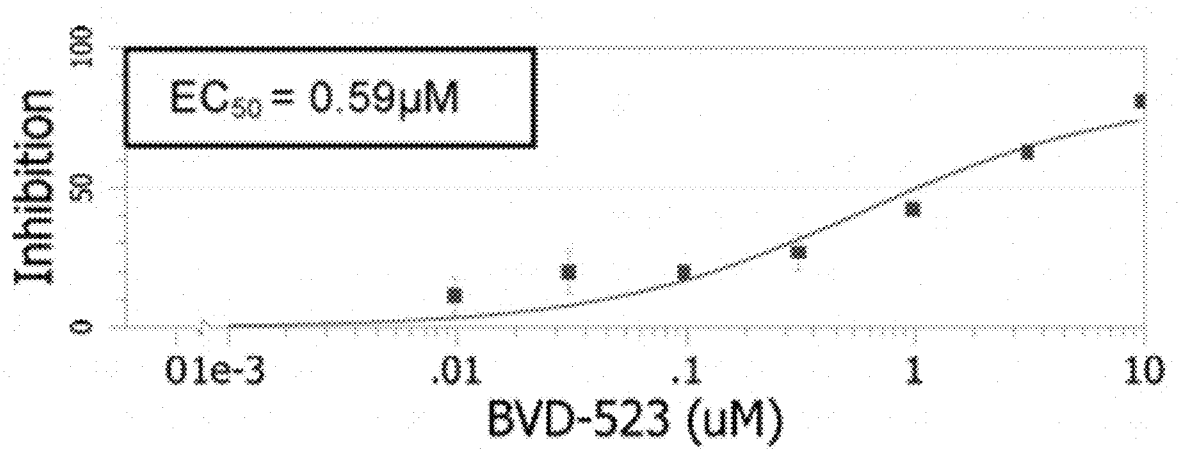
FIG. 4L-FIG. 4M show the results of single agent proliferation assays for the combination in 4K.
Figure 4M:
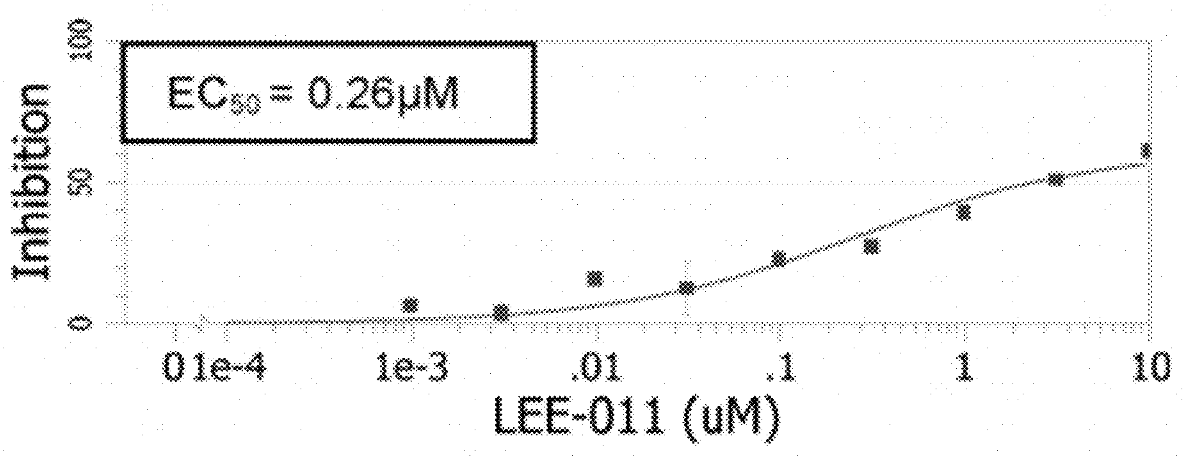
Figure 4N:
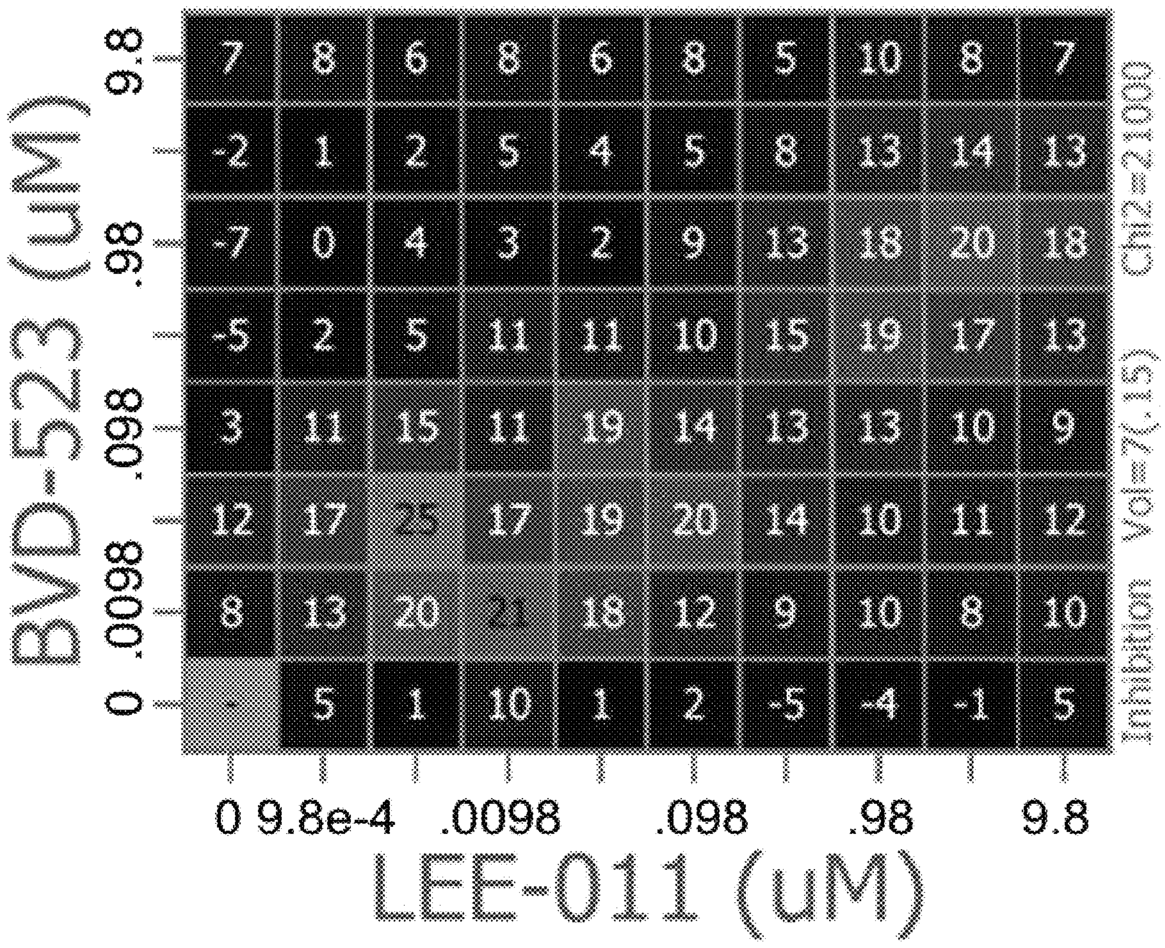
FIG. 4N shows Loewe excess for the combination in 4K and FIG. 4O shows Bliss excess for the combination in 4K.
Figure 4O:
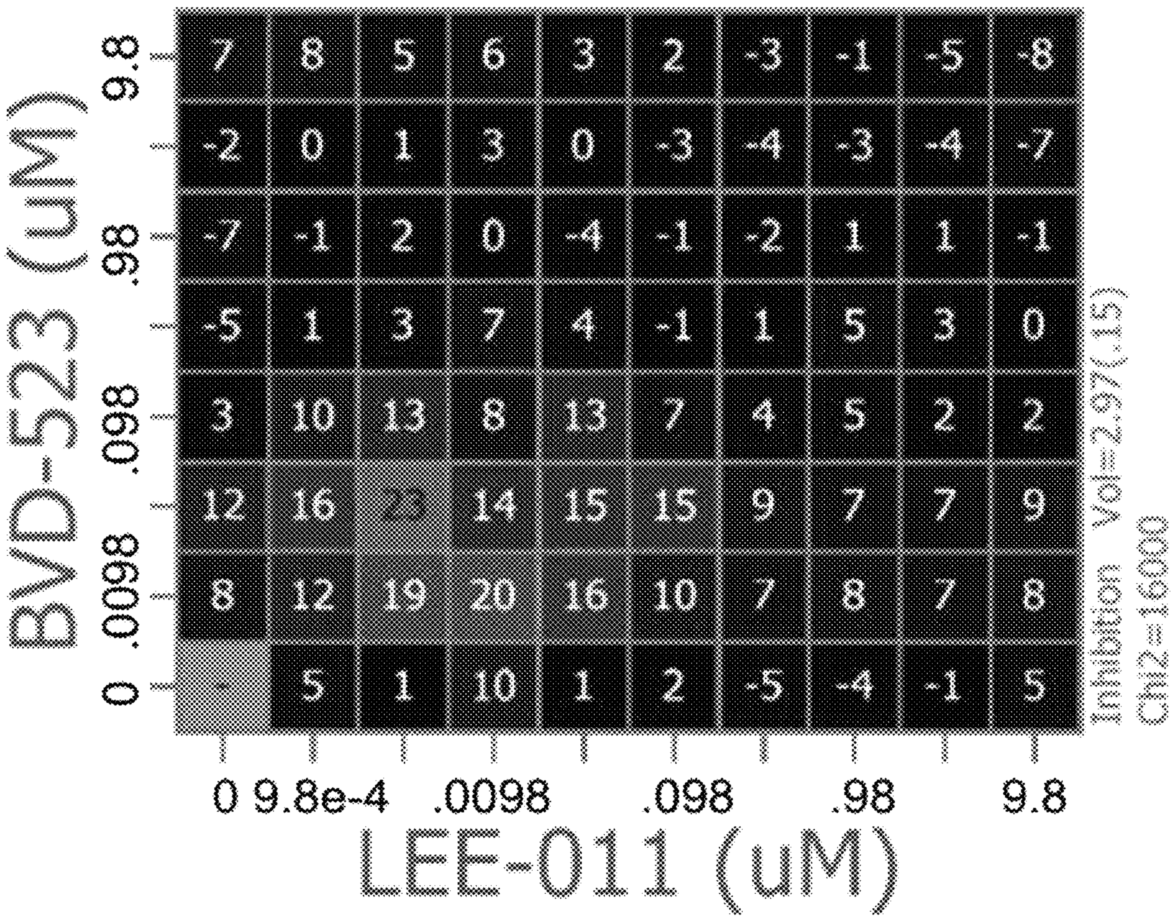
Figure 4P:
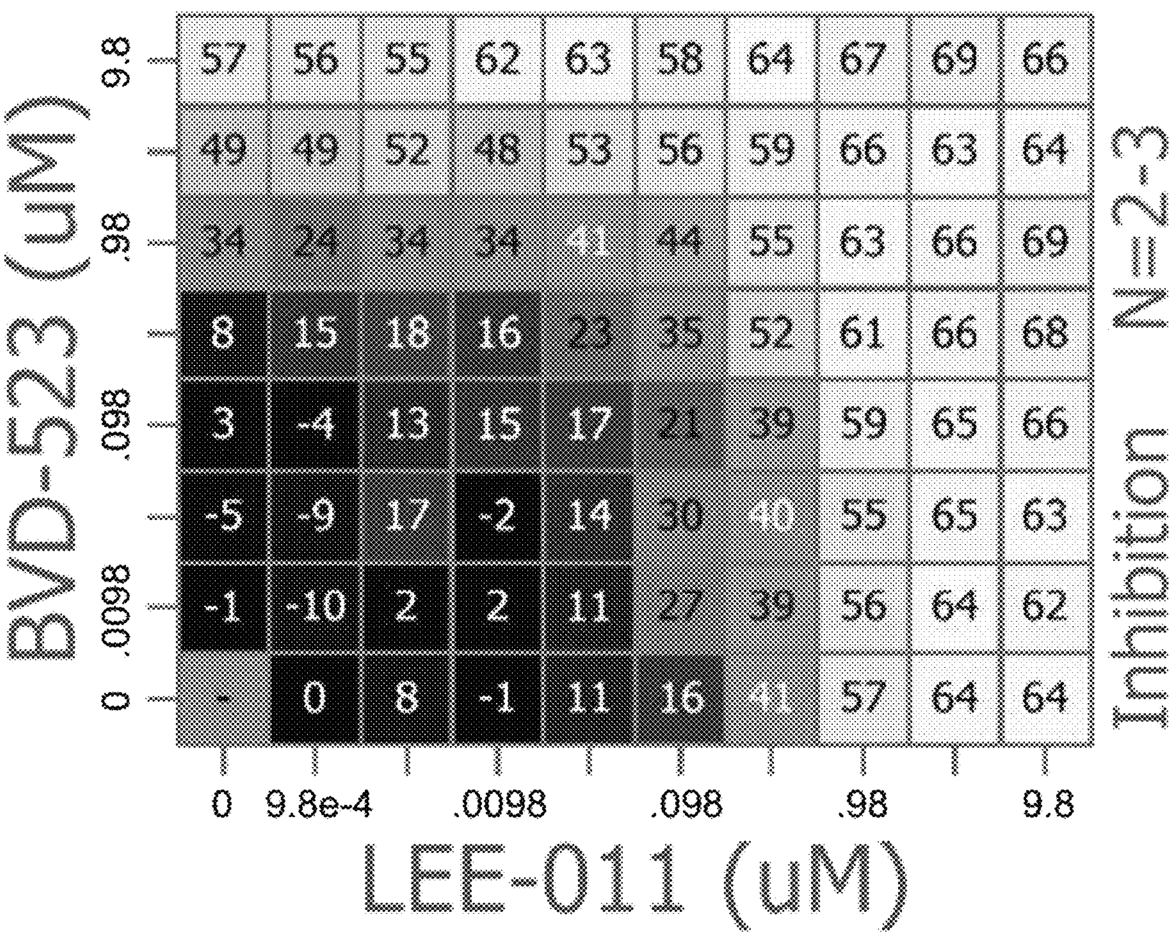
FIG. 4P shows a dose matrix showing inhibition (%) for the combination in H226 cells.
Figure 4Q:
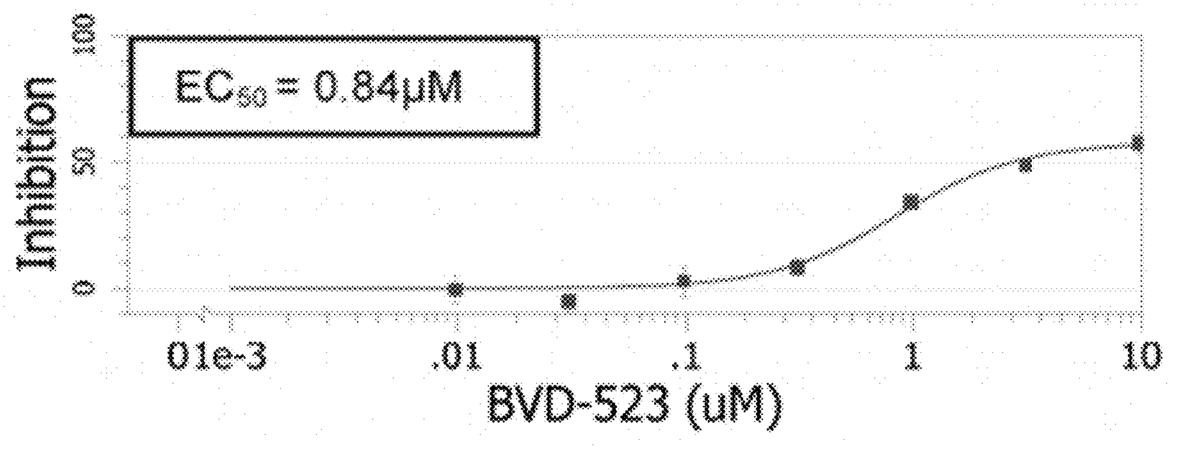
FIG. 4Q-FIG. 4R show the results of single agent proliferation assays for the combination in 4P.
Figure 4R:
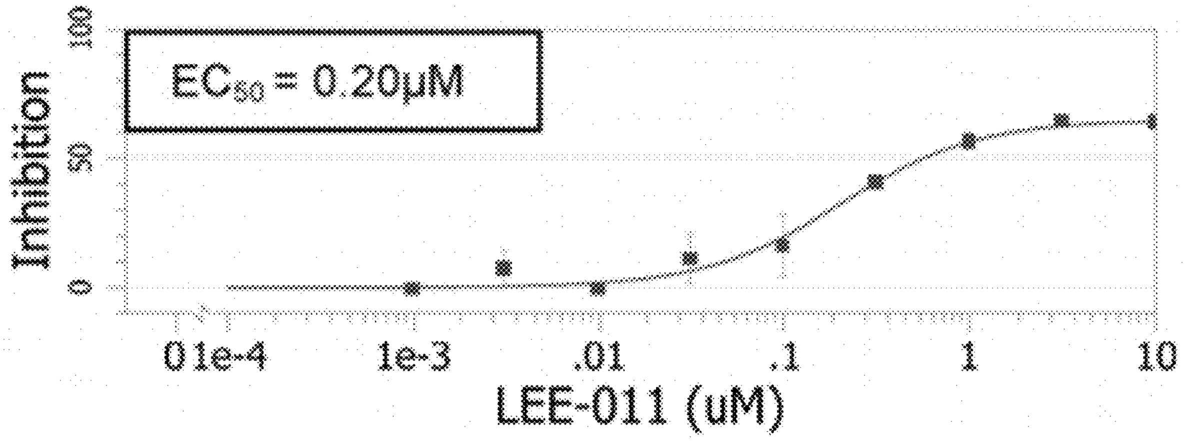
Figure 4S:
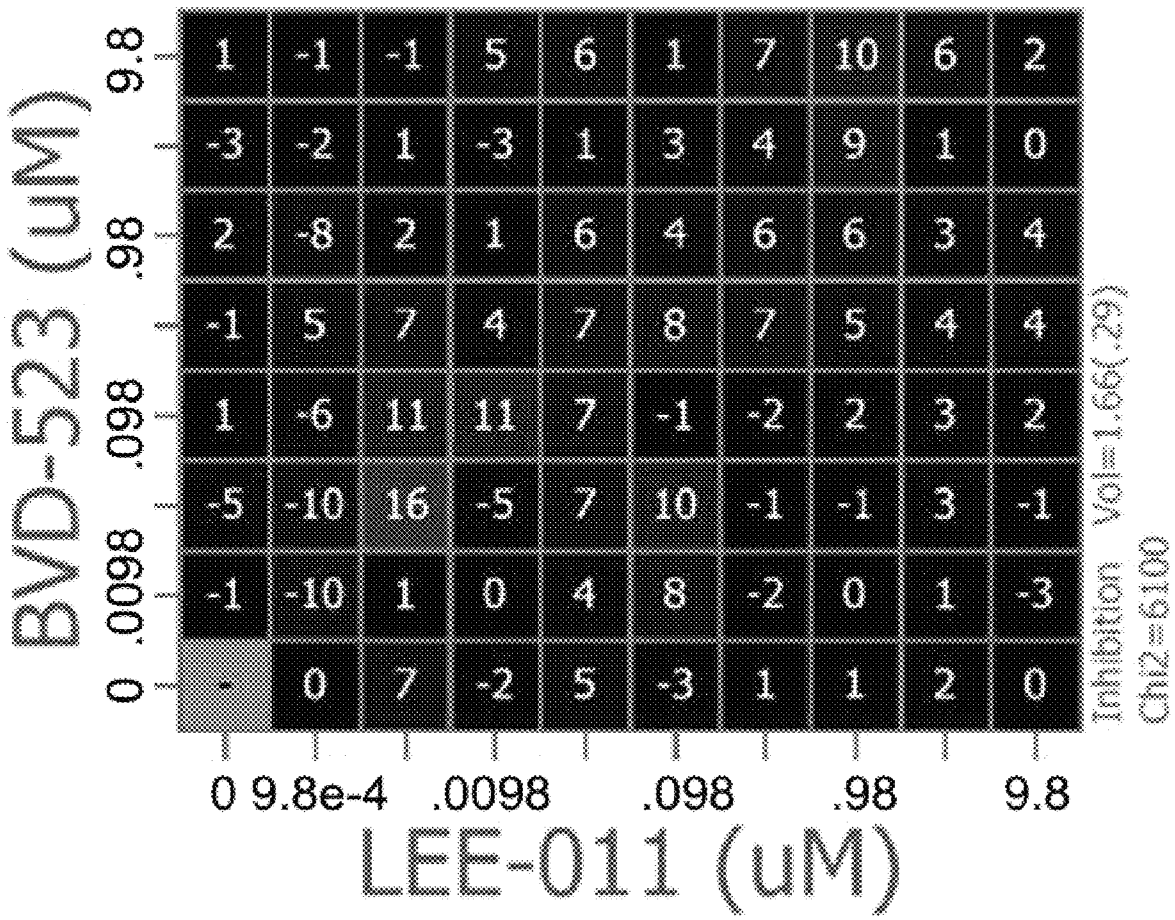
Figure 4T:
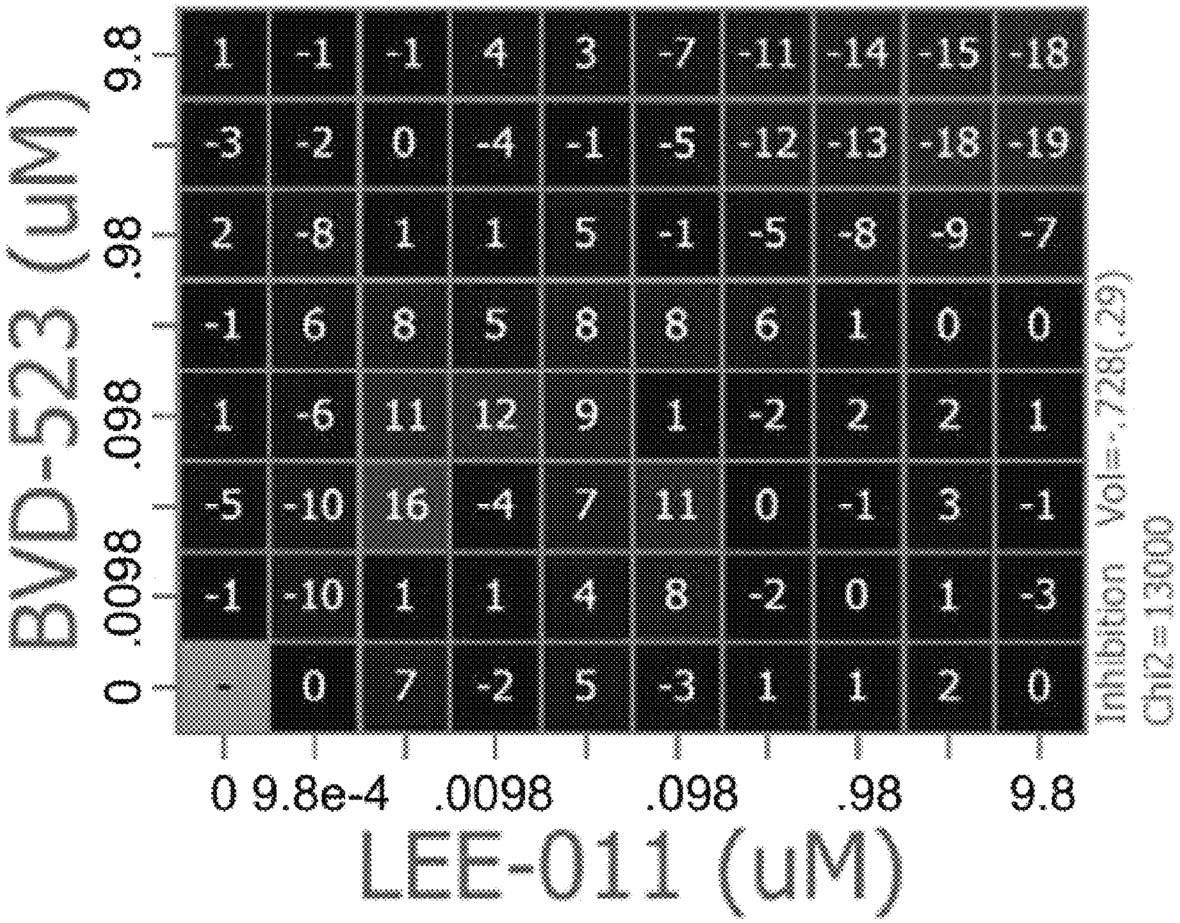
Figure 5A:
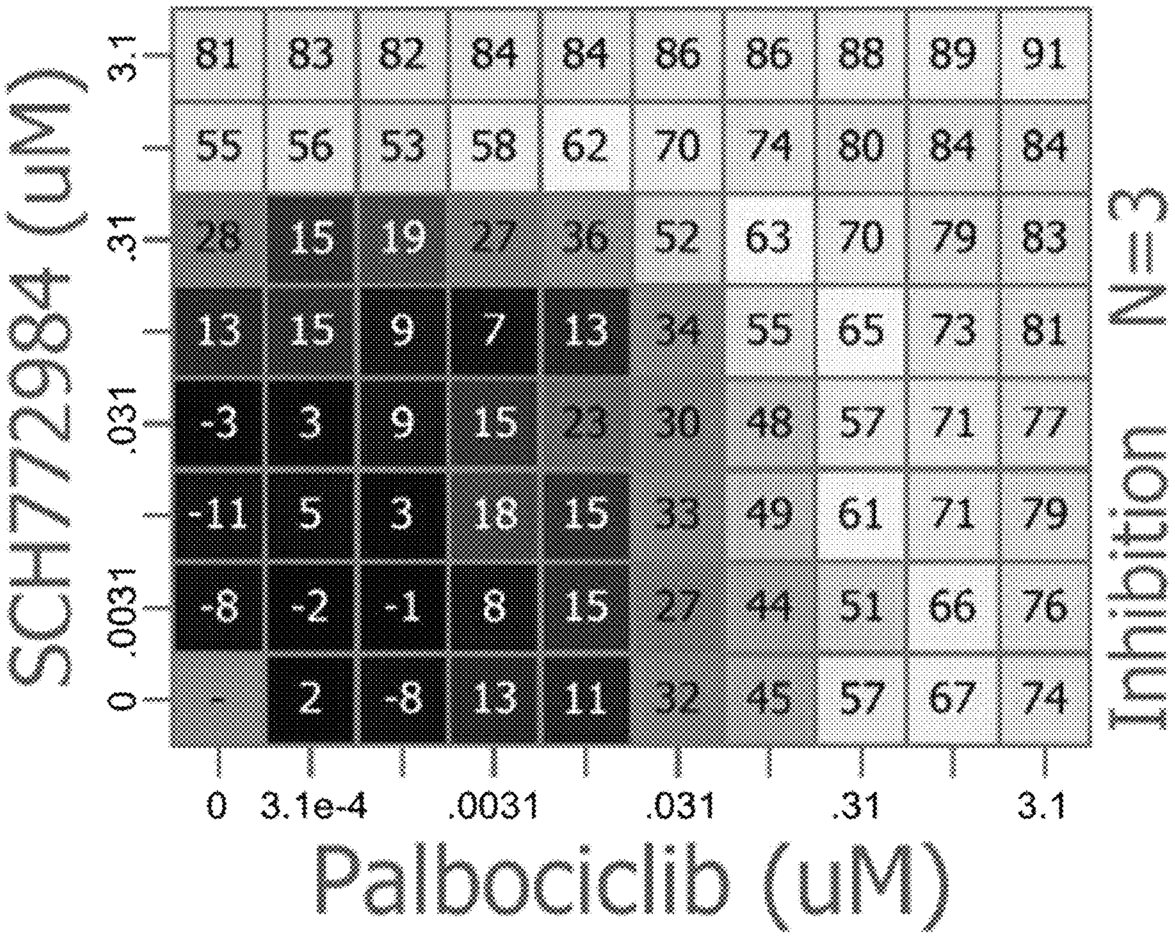
FIGS. 5A-5T show the results of the combination of SCH772984 and Palbociclib.
Figure 5B:
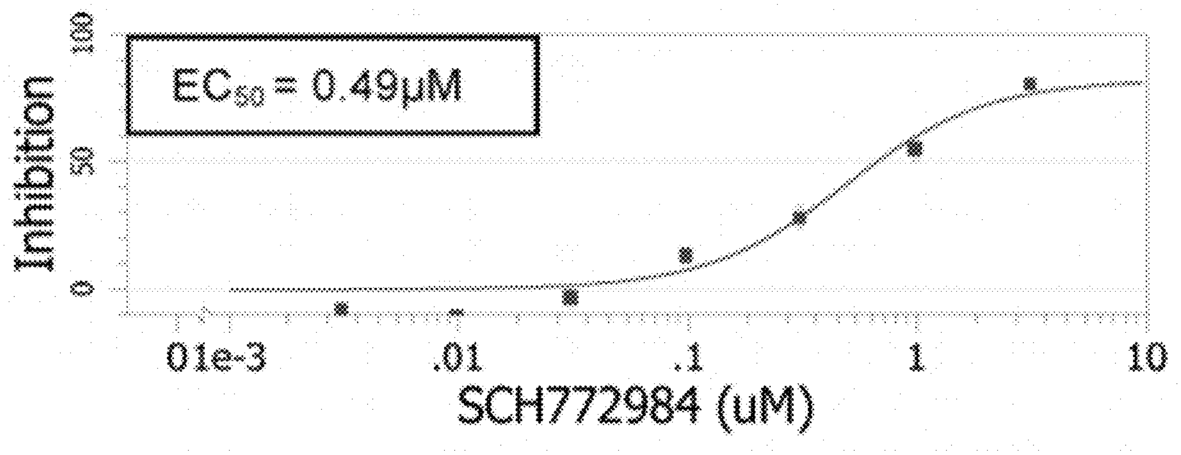
FIG. 5B-FIG. 5C show the results of single agent proliferation assays for the combination in 5A.
Figure 5C:
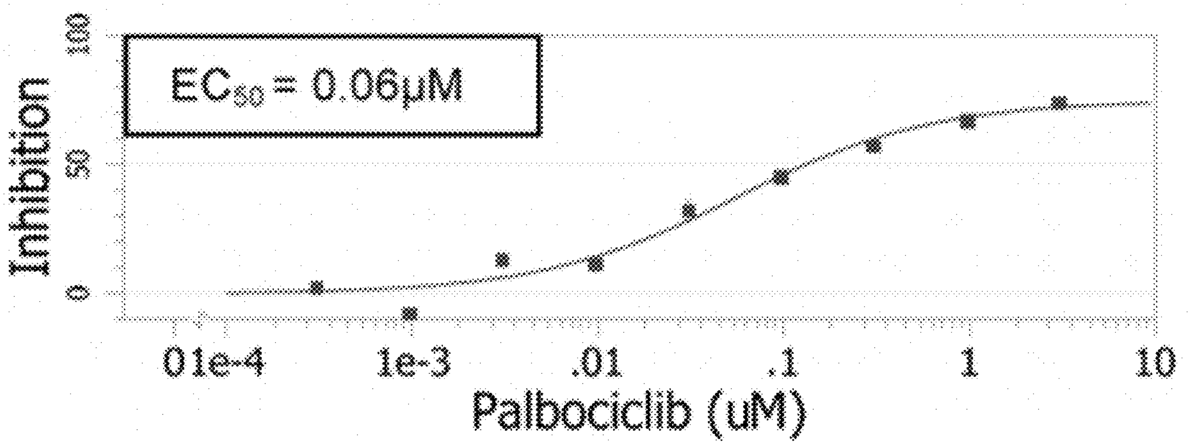
Figure 5D:
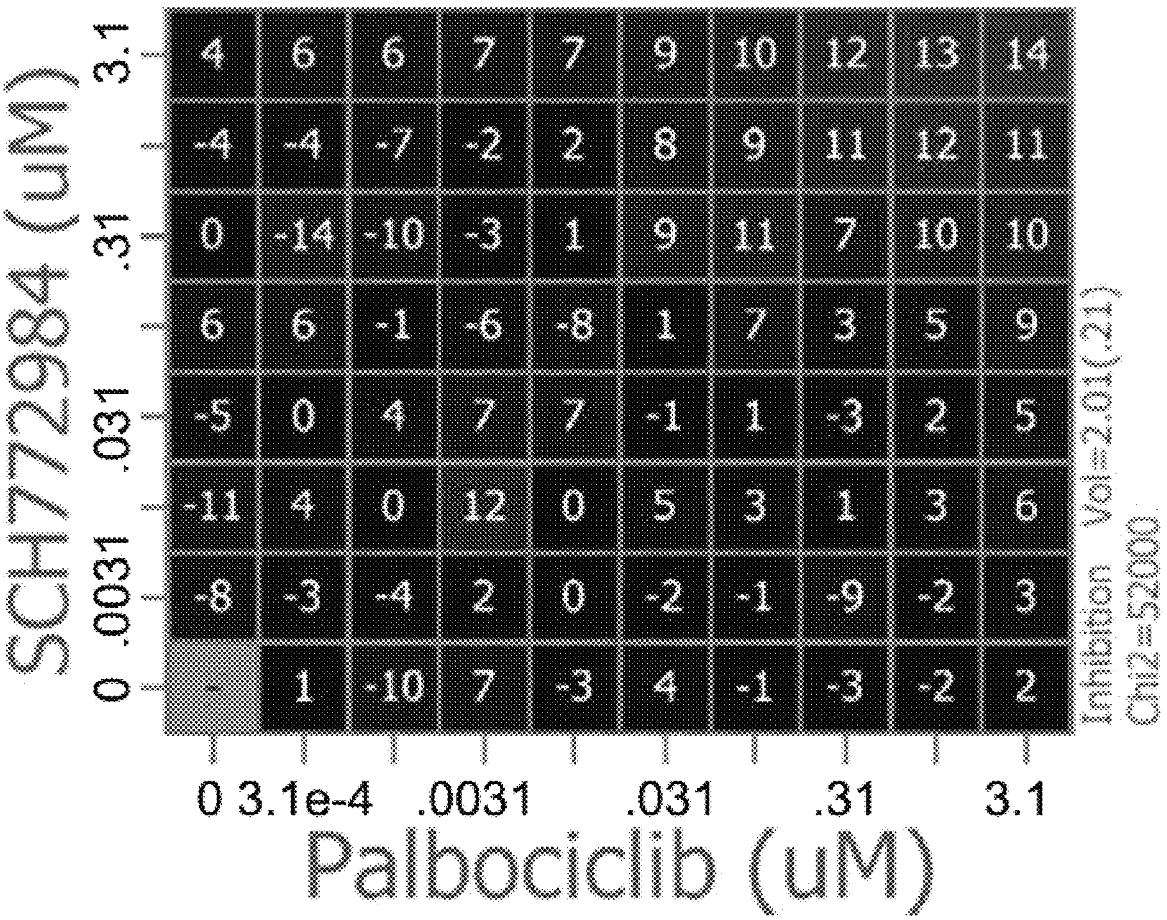
FIG. 5D shows Loewe excess for the combination in 5A and FIG. 5E shows Bliss excess for the combination in 5A.
Figure 5E:
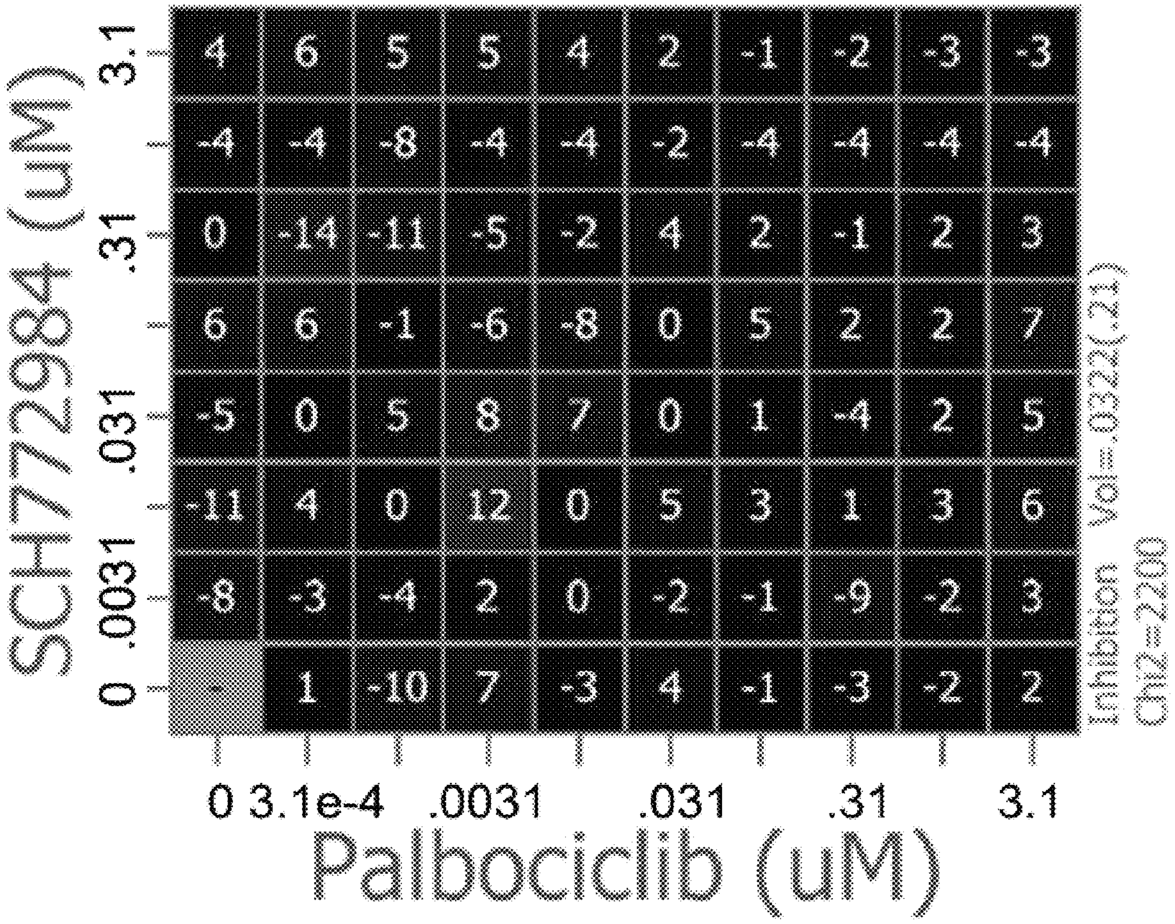
Figure 5F:
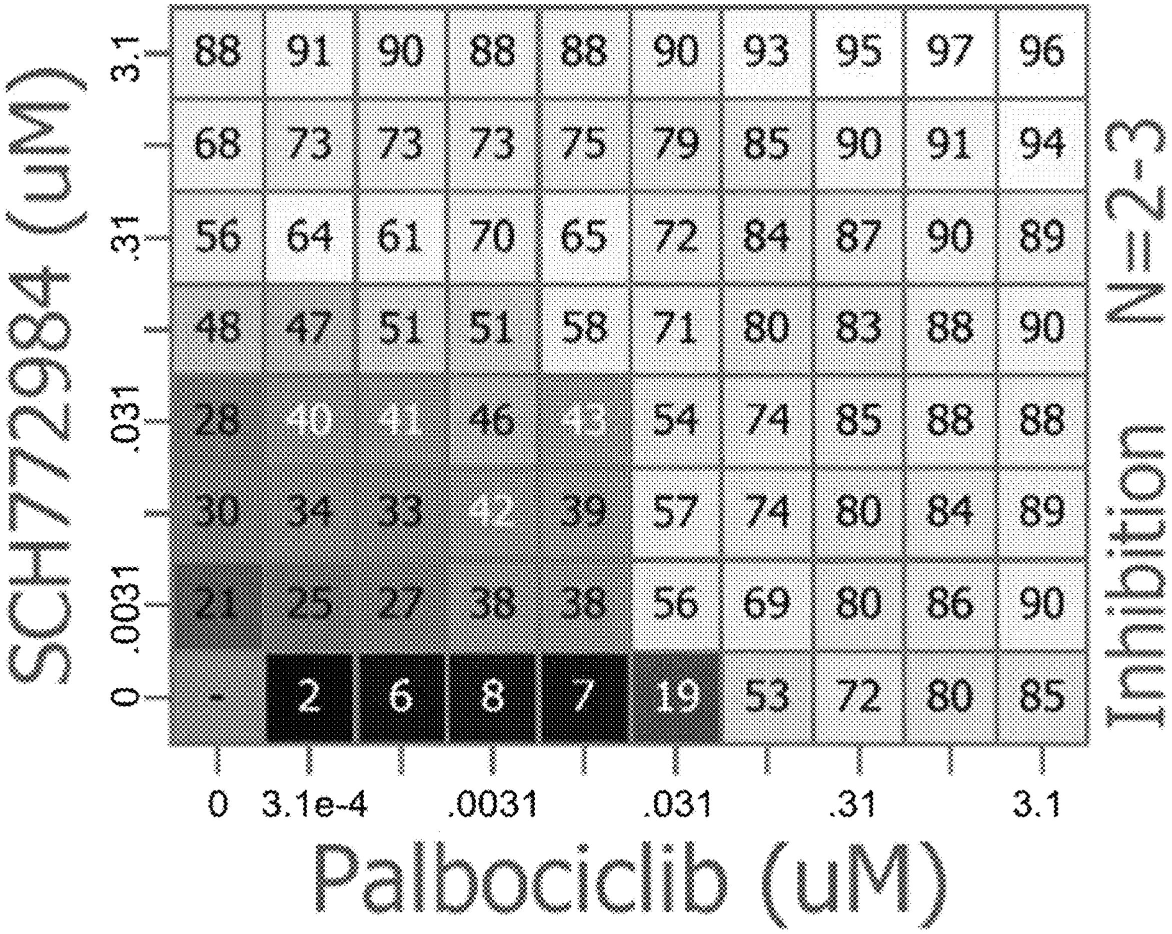
FIG. 5F shows a dose matrix showing inhibition (%) for the combination in H2122 cells.
Figure 5G:
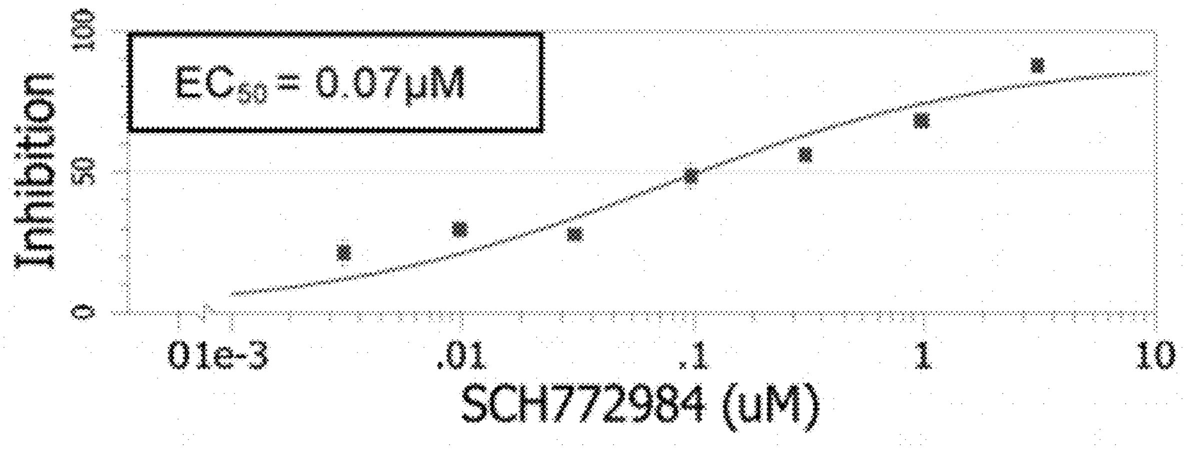
FIG. 5G-FIG. 5H show the results of single agent proliferation assays for the combination in 5F.
Figure 5H:
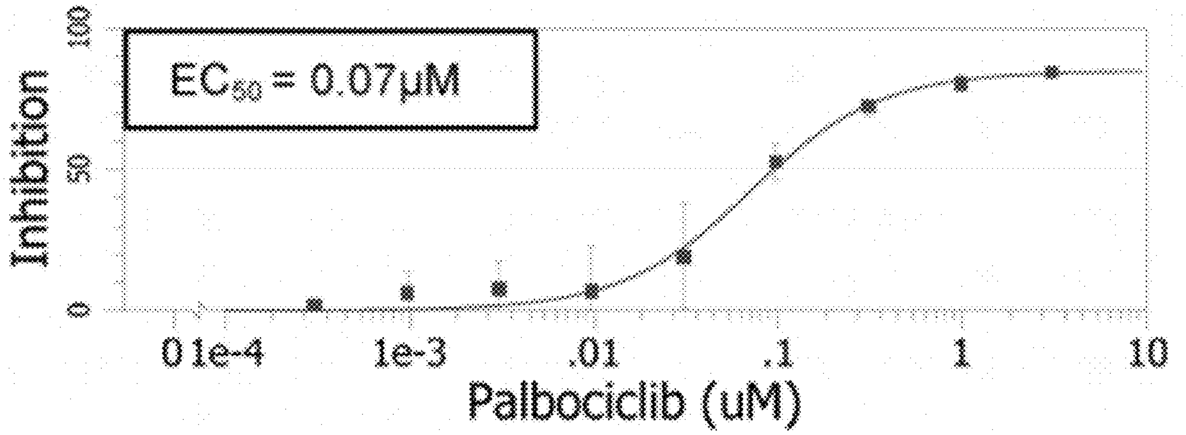
Figure 5I:
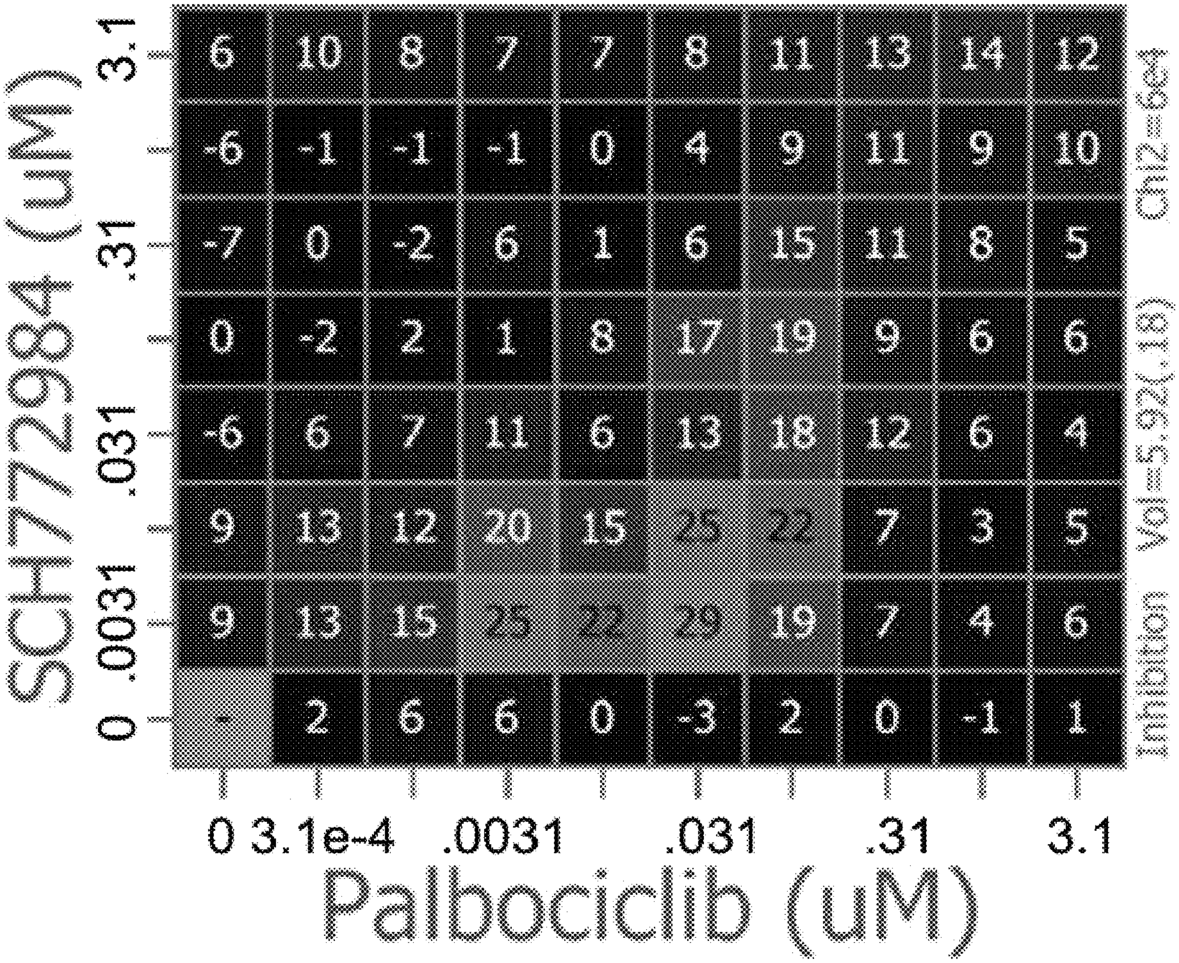
FIG. 5I shows Loewe excess for the combination in 5F and FIG. 5J shows Bliss excess for the combination in 5F.
Figure 5J:
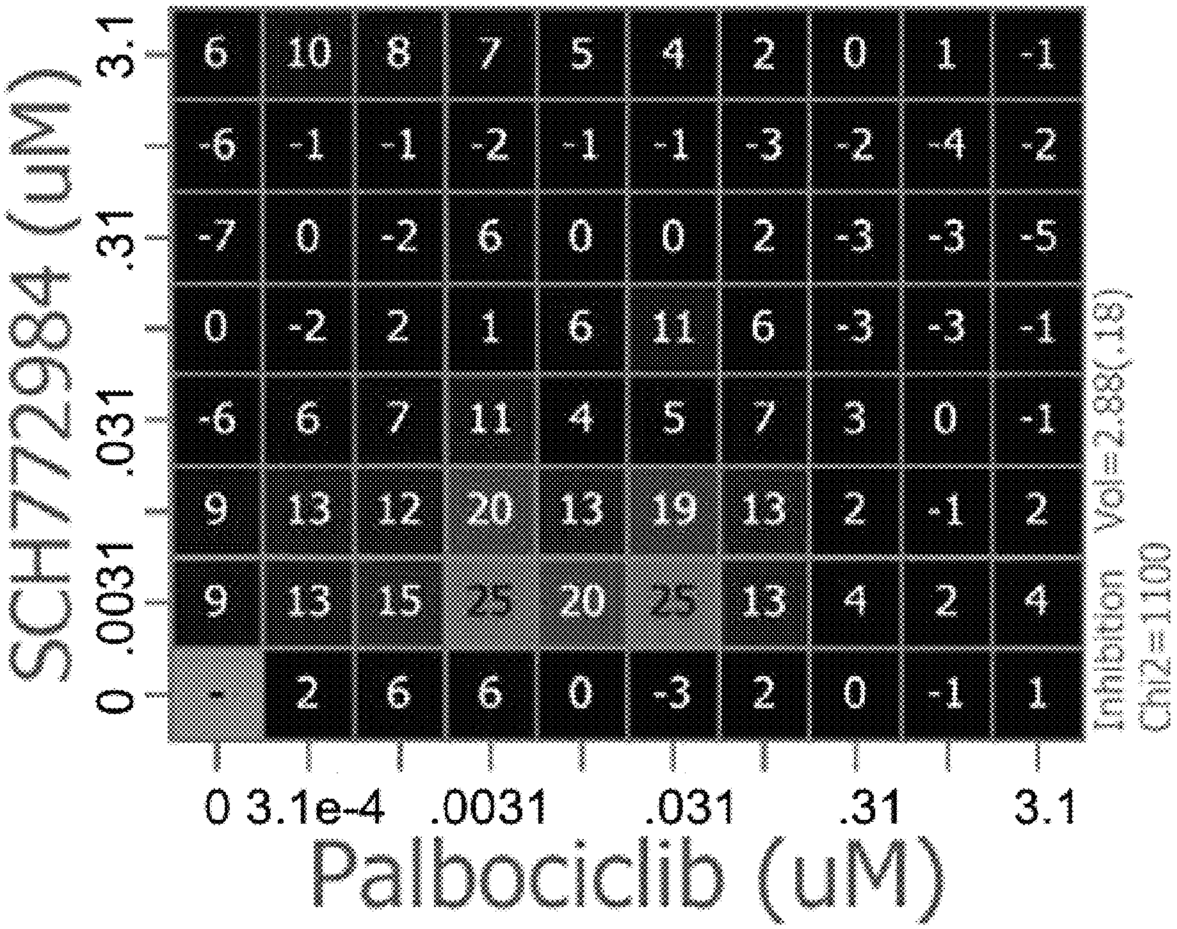
Figure 5K:
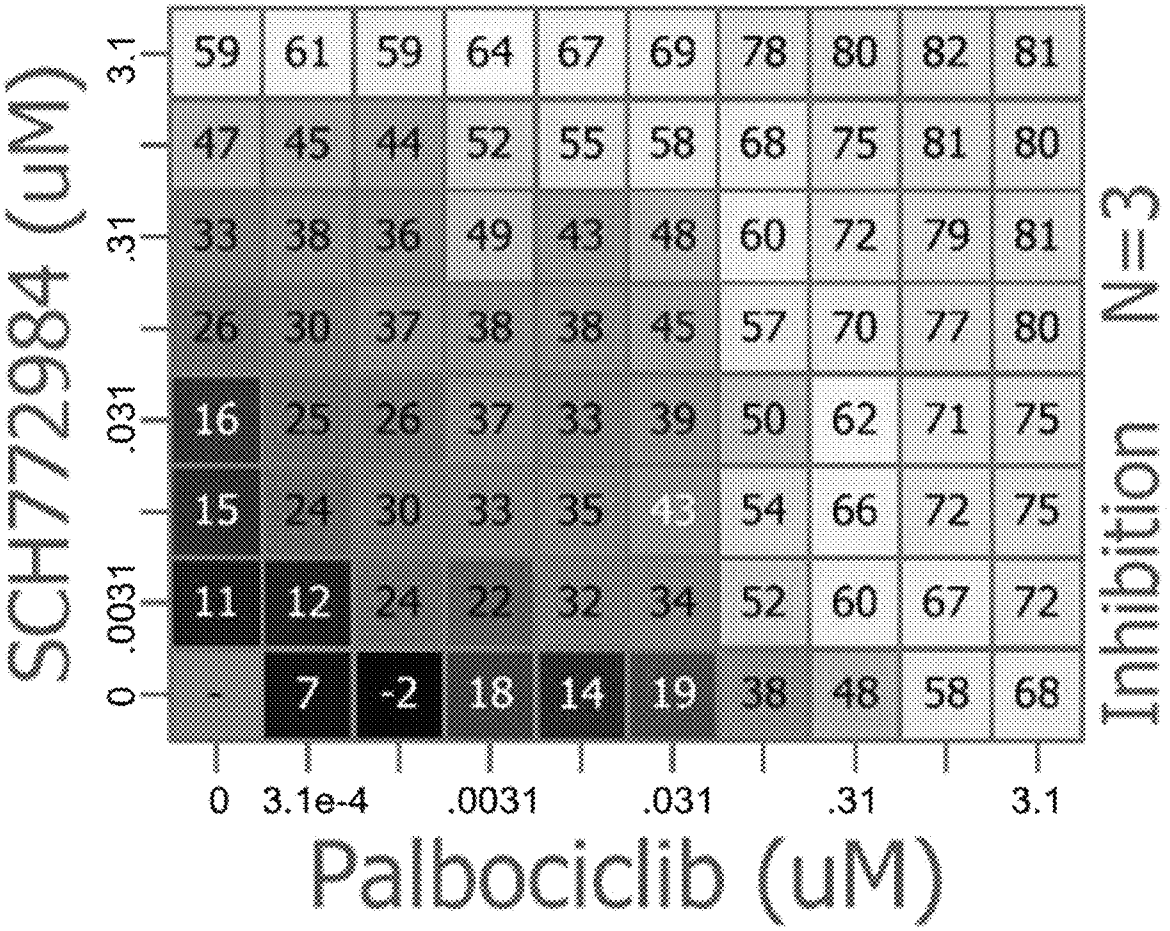
FIG. 5K shows a dose matrix showing inhibition (%) for the combination in H1437 cells.
Figure 5L:
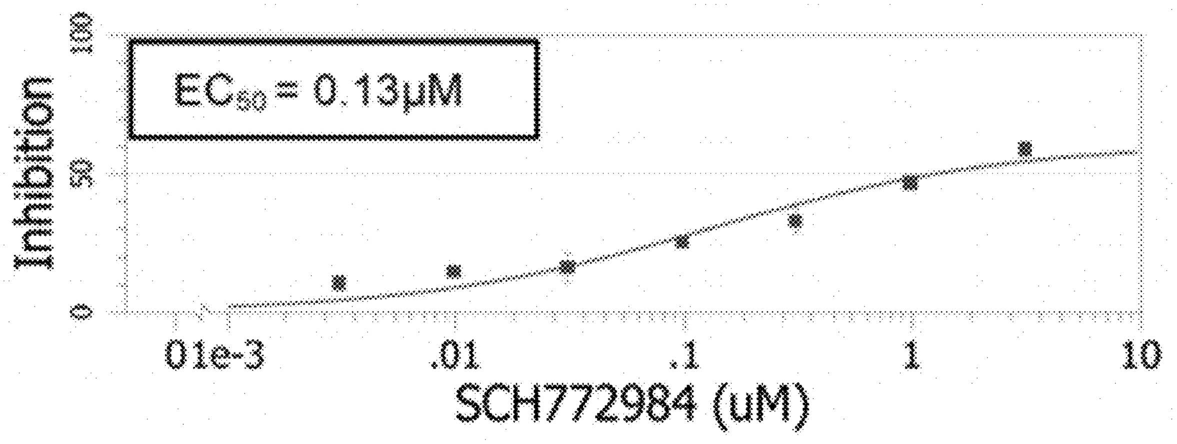
FIG. 5L-FIG. 5M show the results of single agent proliferation assays for the combination in 5K.
Figure 5M:
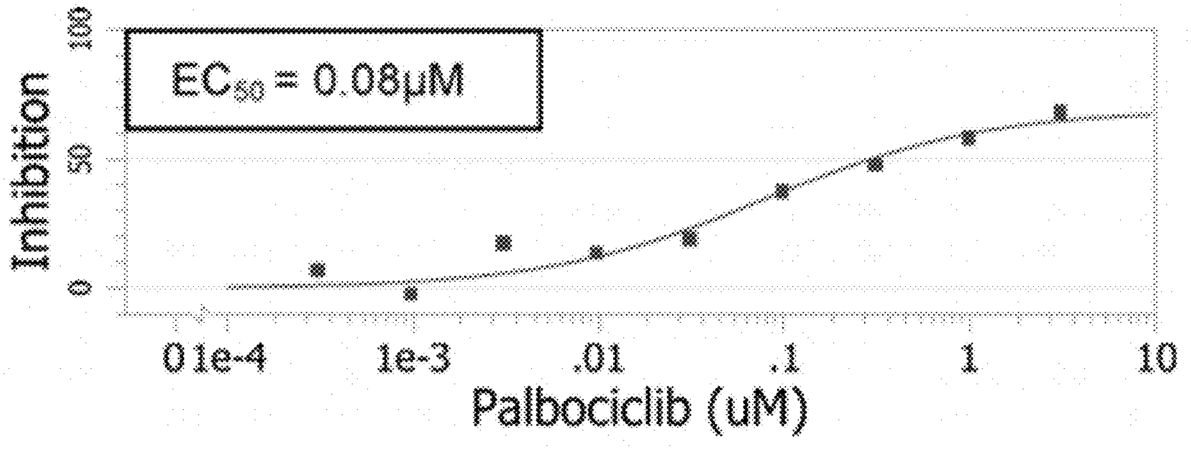
Figure 5N:
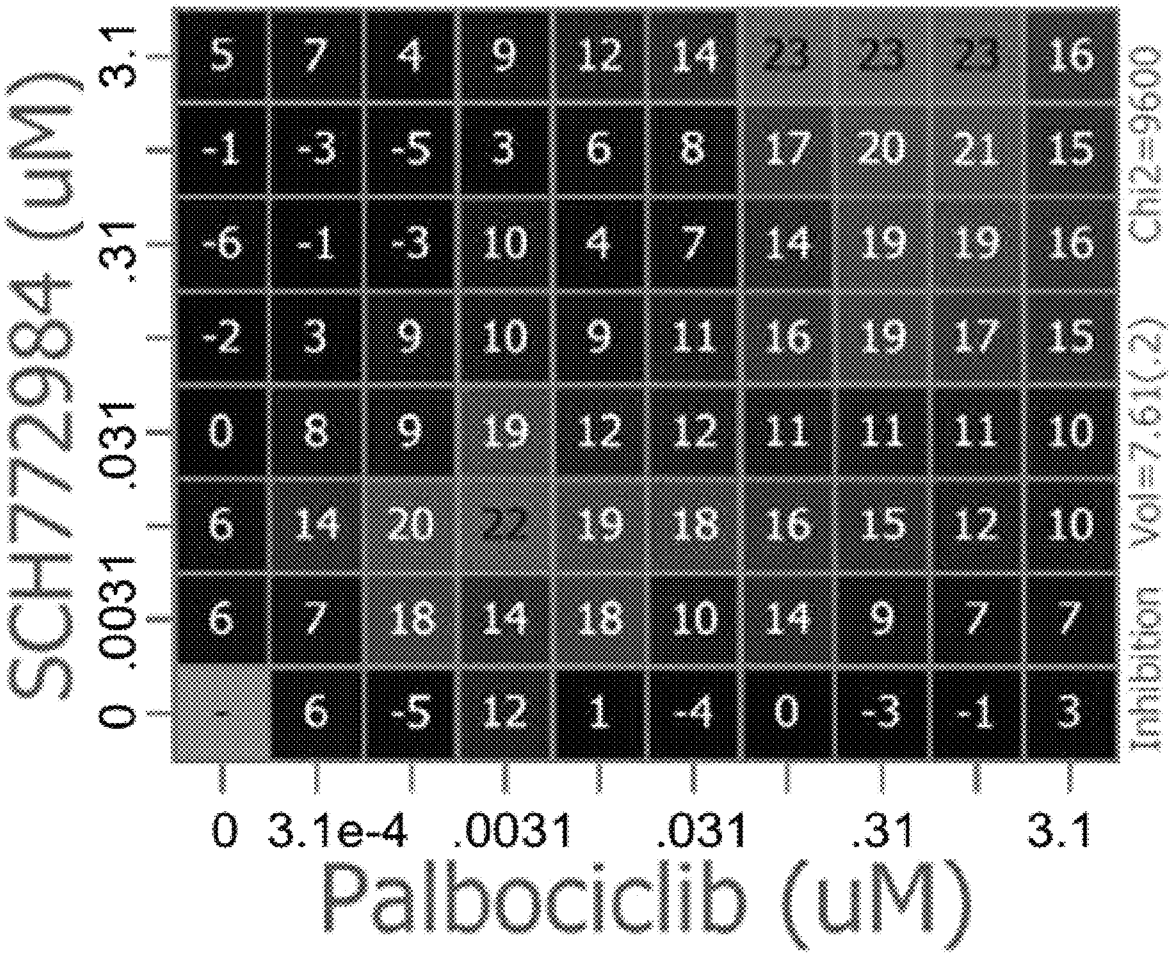
FIG. 5N shows Loewe excess for the combination in 5K and FIG. 5O shows Bliss excess for the combination in 5K.
Figure 5O:
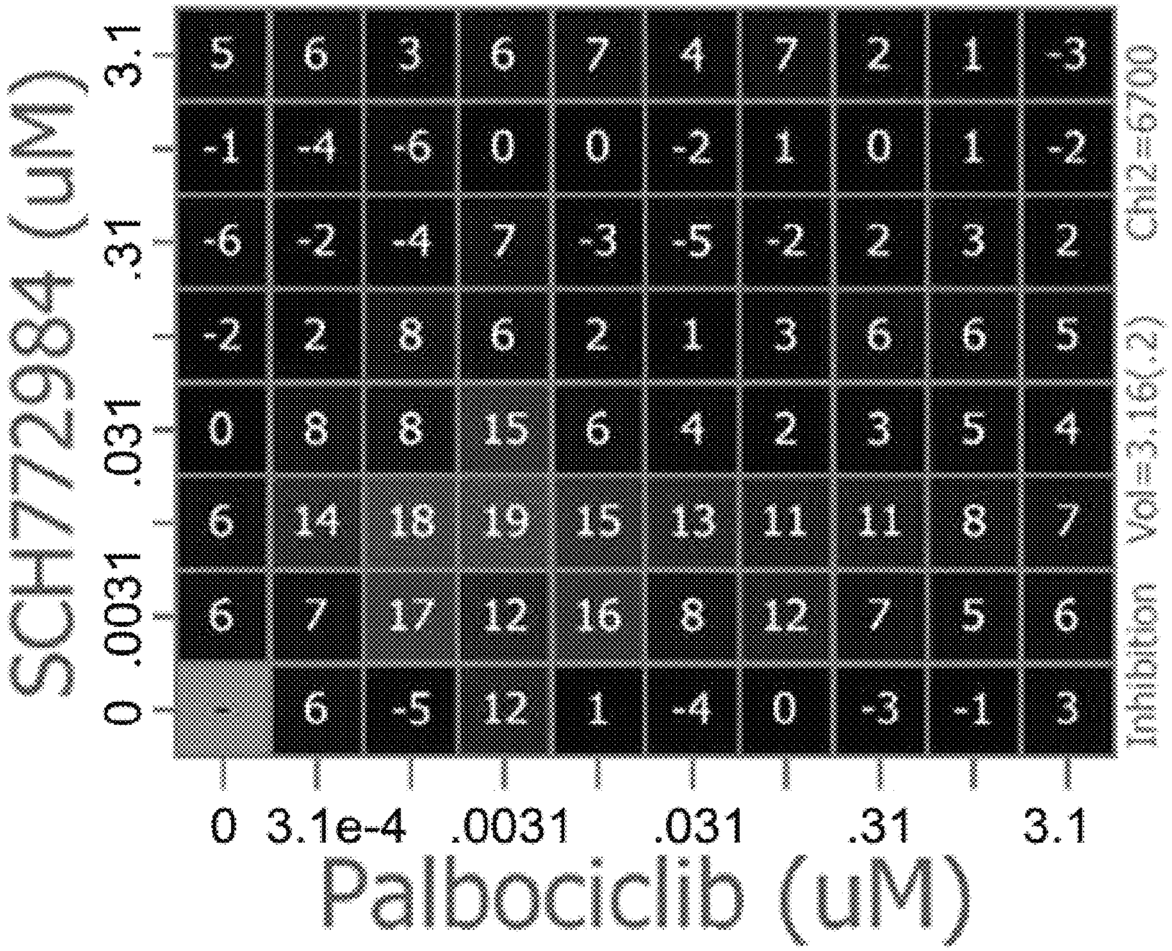
Figure 5P:
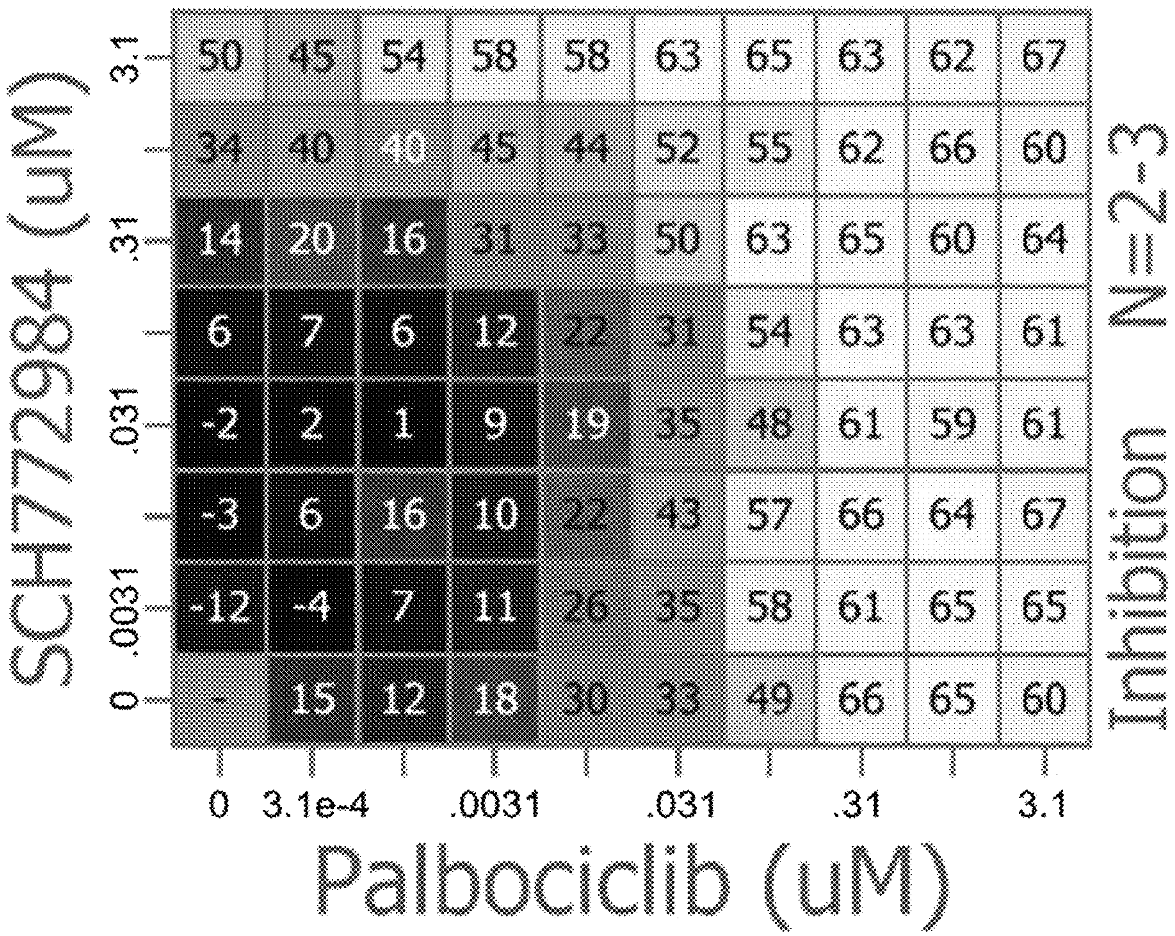
FIG. 5P shows a dose matrix showing inhibition (%) for the combination in H226 cells.
Figure 5Q:
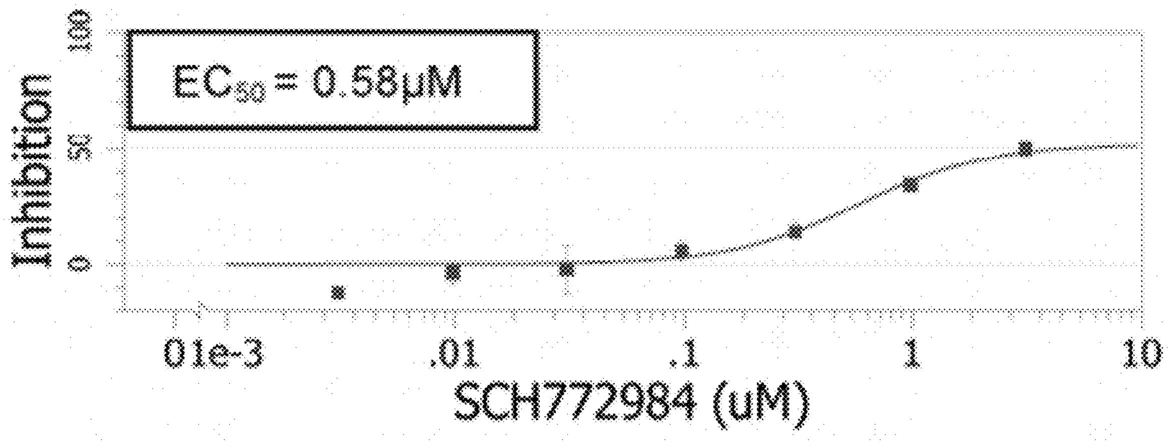
FIG. 5Q-FIG. 5R show the results of single agent proliferation assays for the combination in 5P.
Figure 5R:
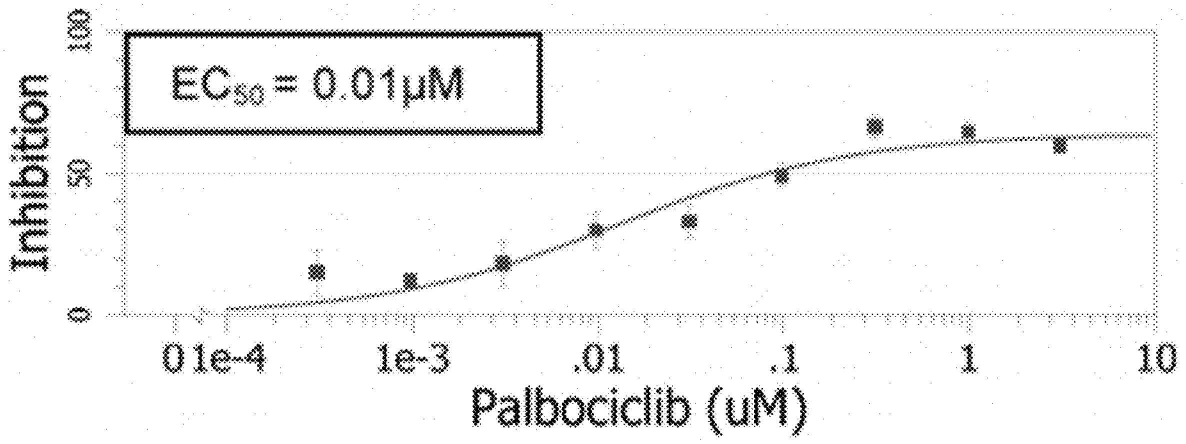
Figure 5S:
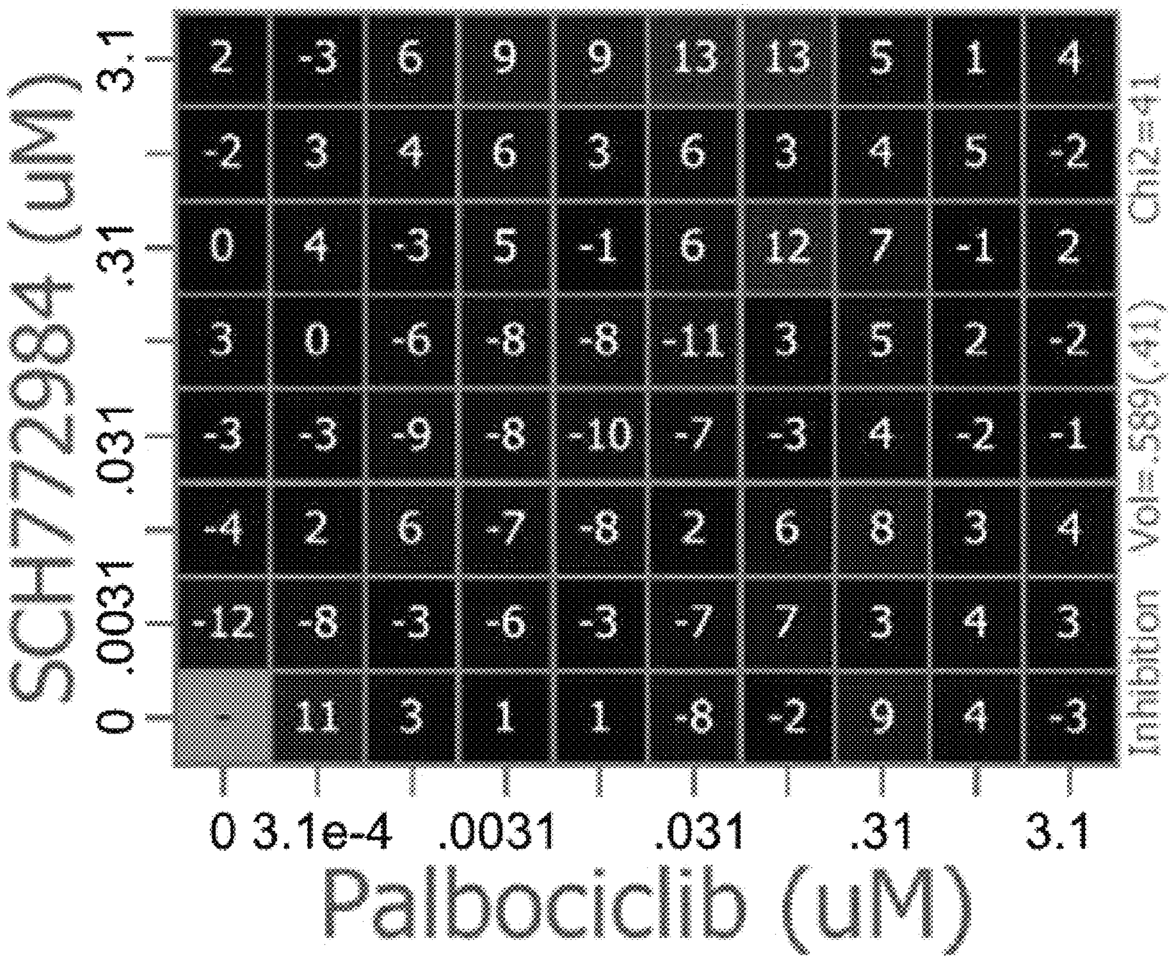
Figure 5T:
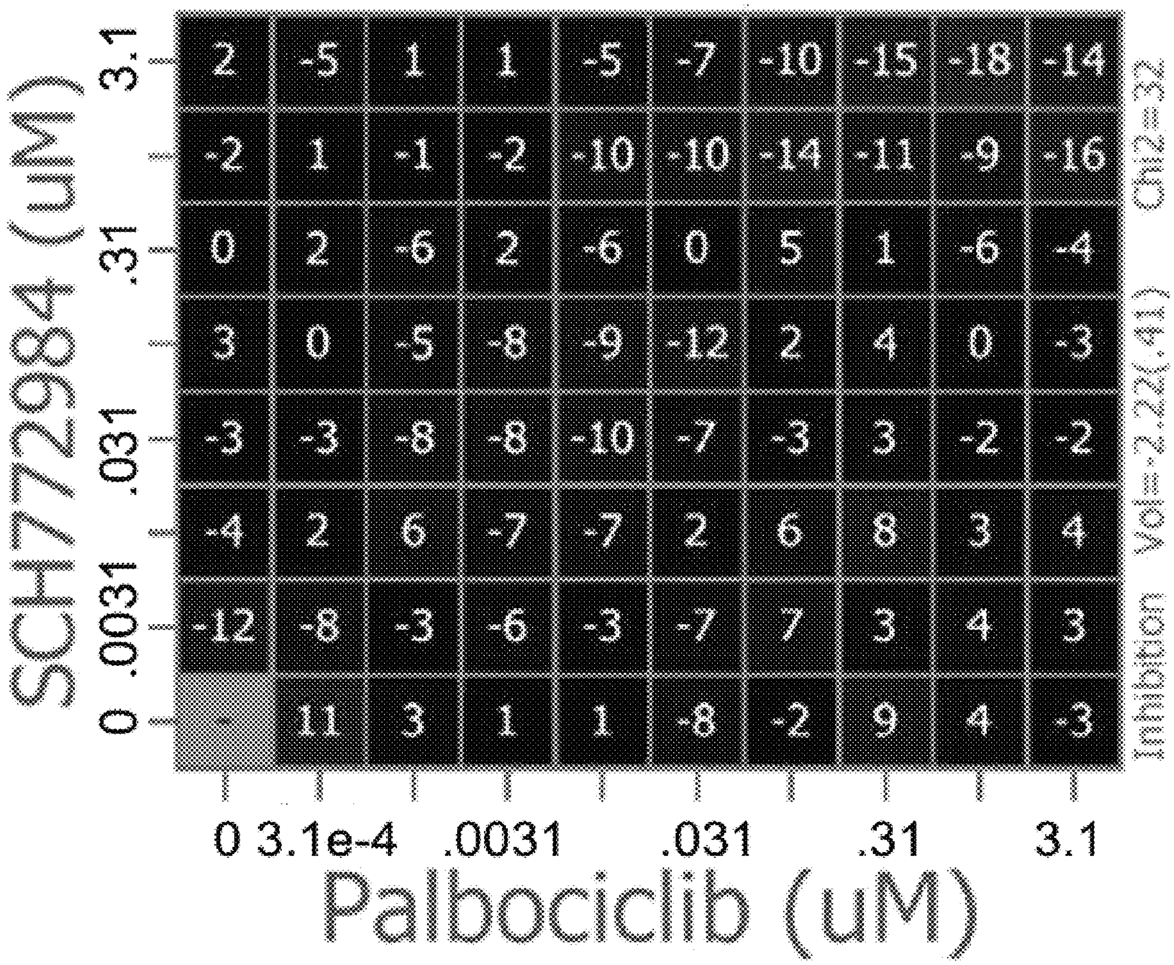
Figure 6A:
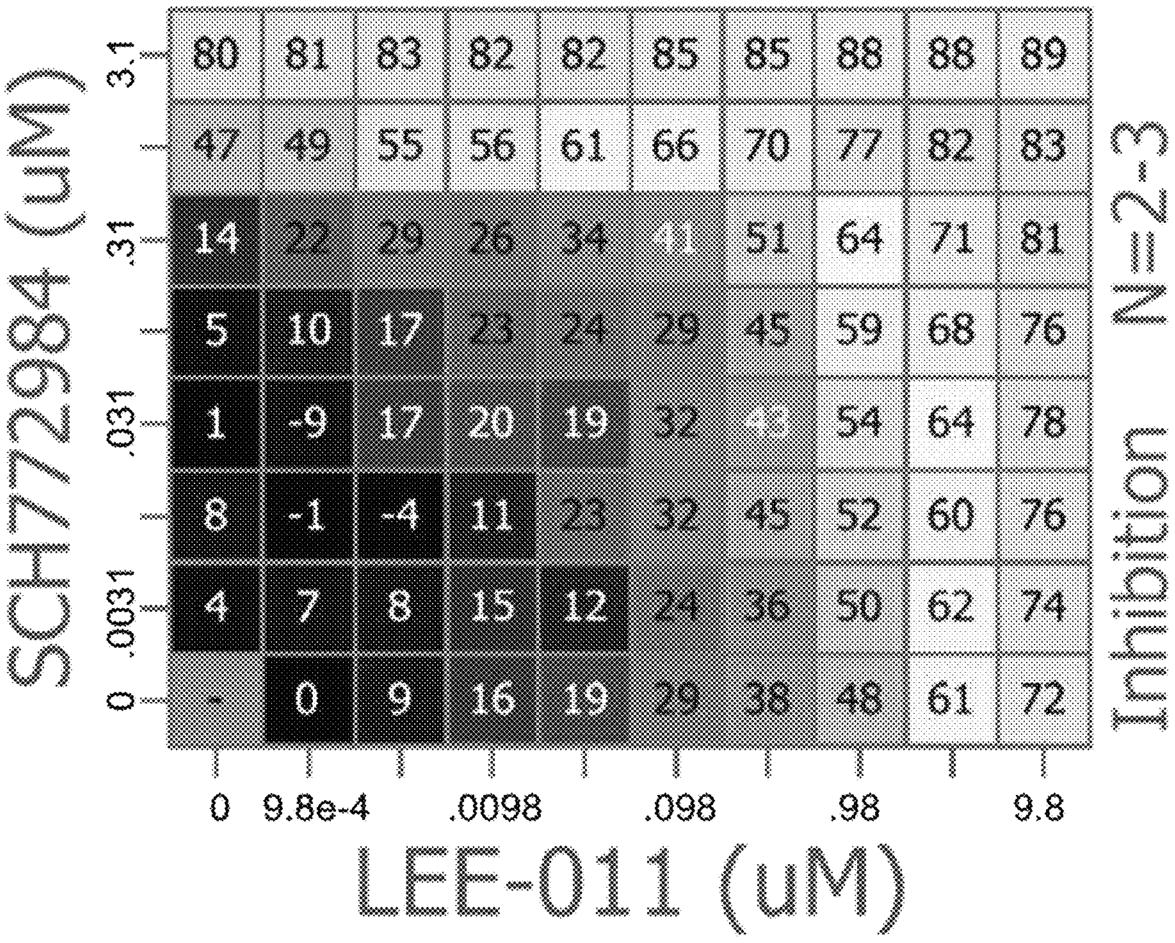
FIGS. 6A-6T show the results of the combination of SCH772984 and LEE-011.
Figure 6B:
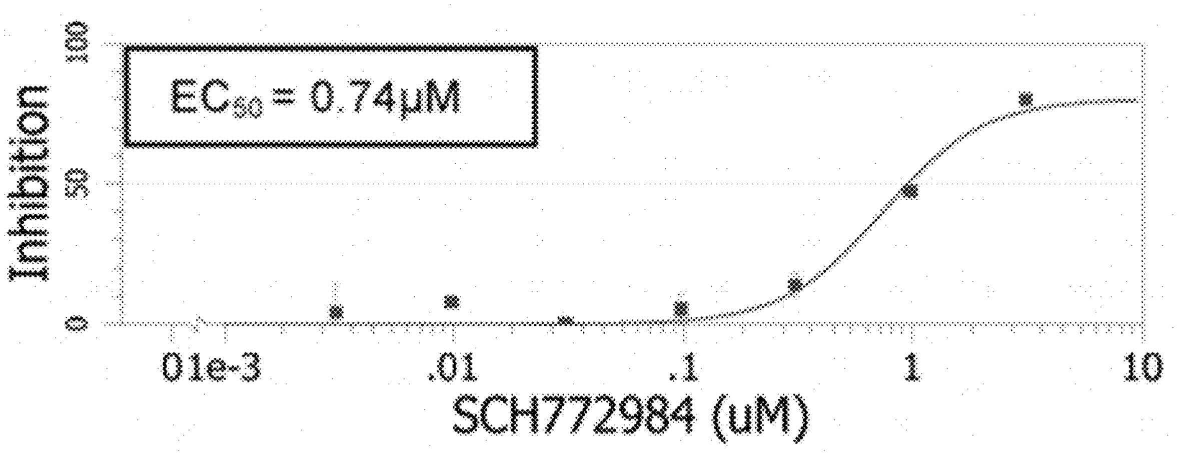
FIG. 6B-FIG. 6C show the results of single agent proliferation assays for the combination in 6A.
Figure 6C:
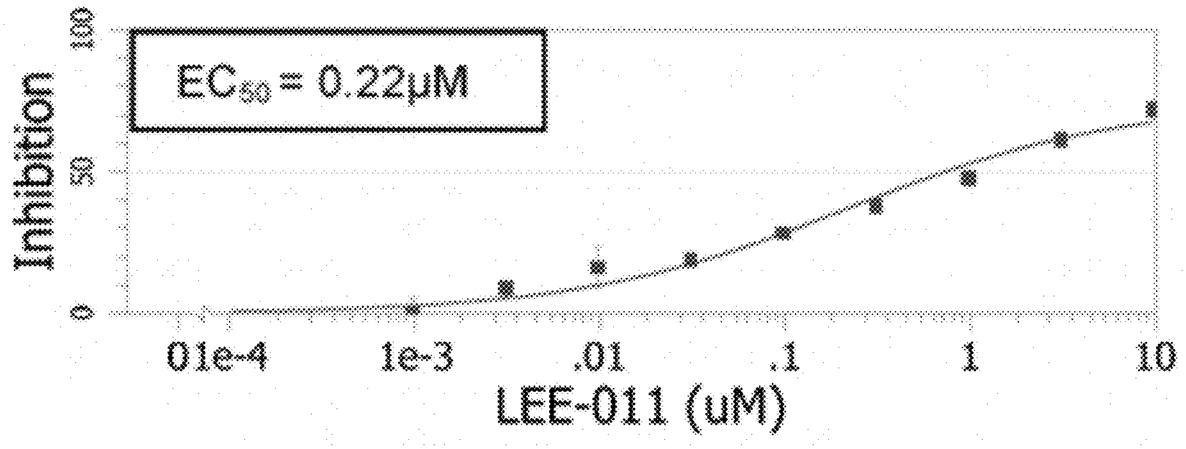
Figure 6D:
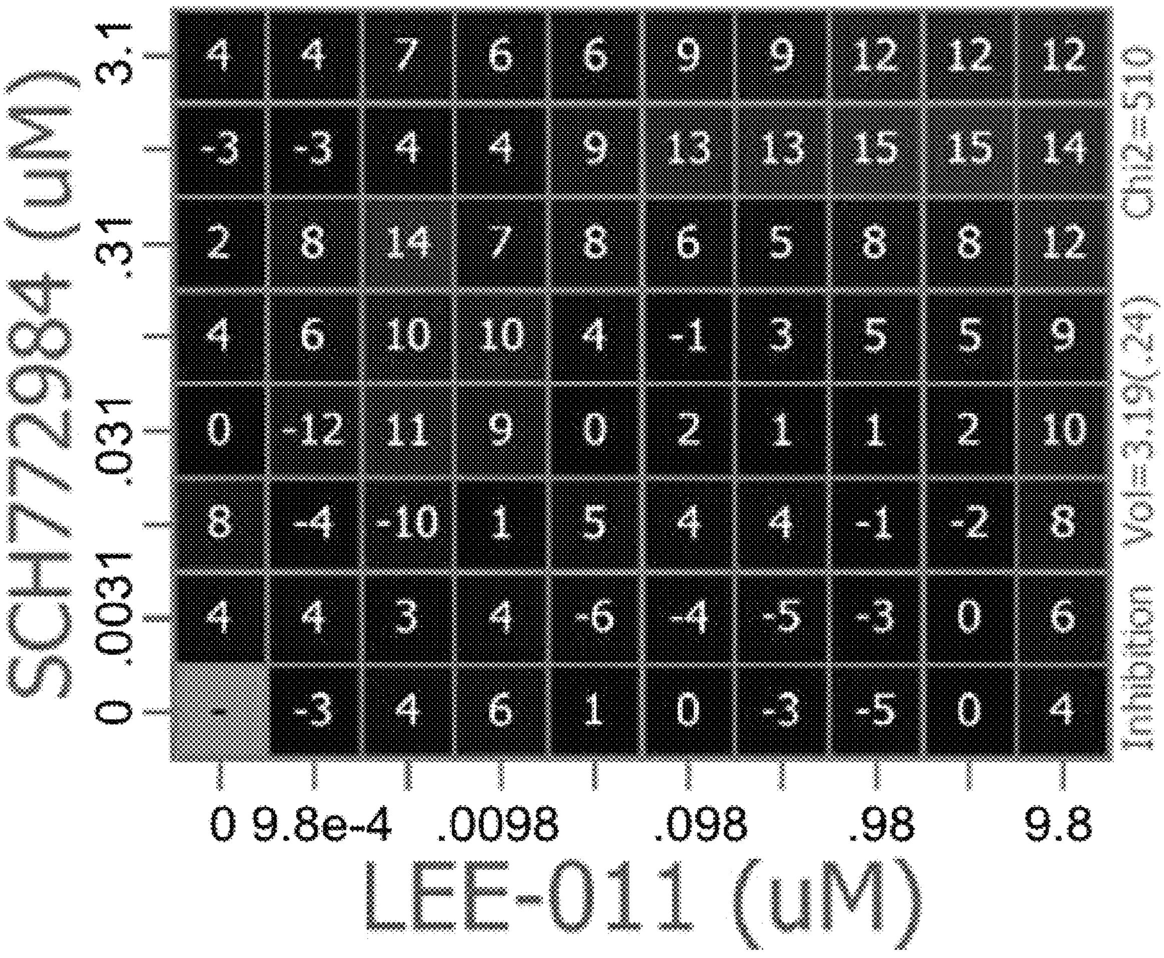
FIG. 6D shows Loewe excess for the combination in 6A and FIG. 6E shows Bliss excess for the combination in 6A.
Figure 6E:
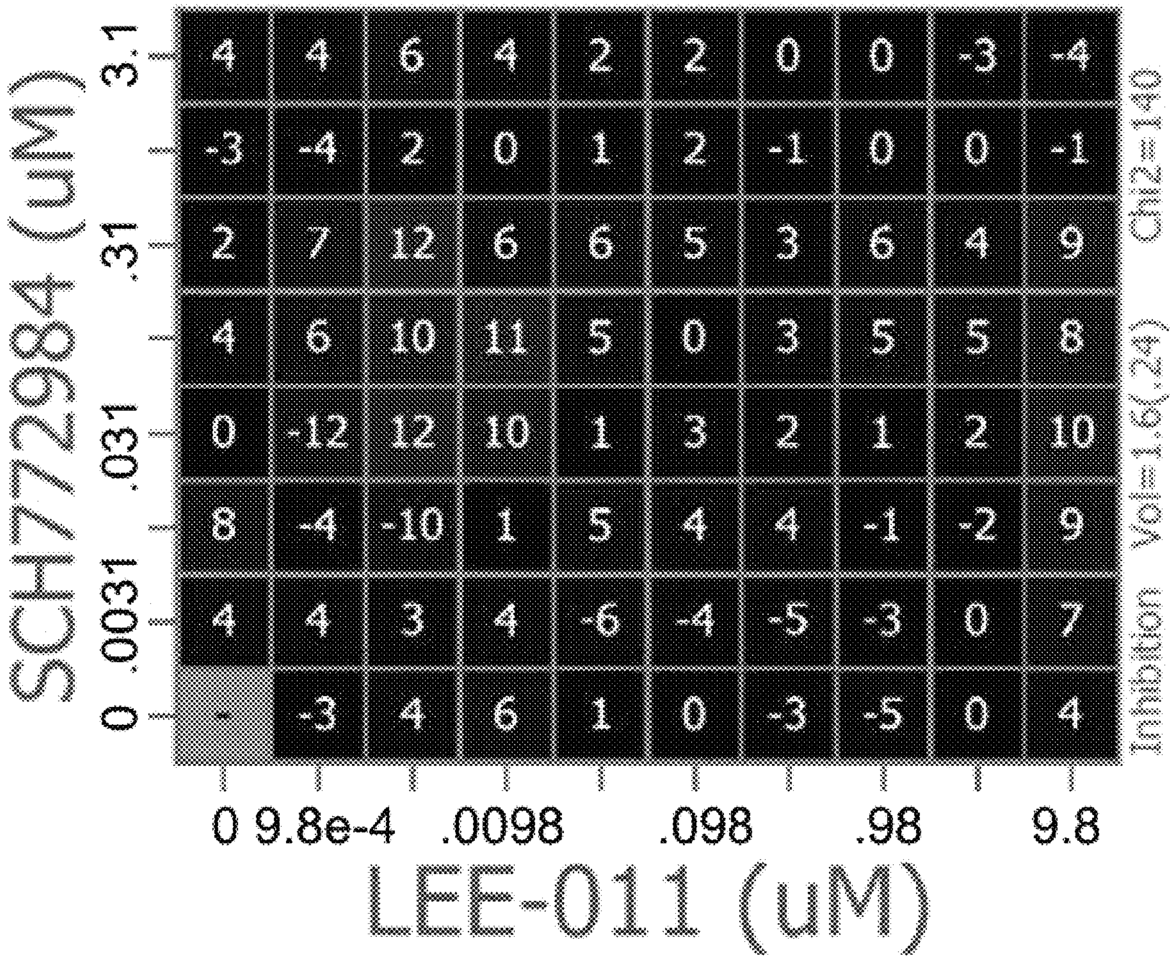
Figure 6F:
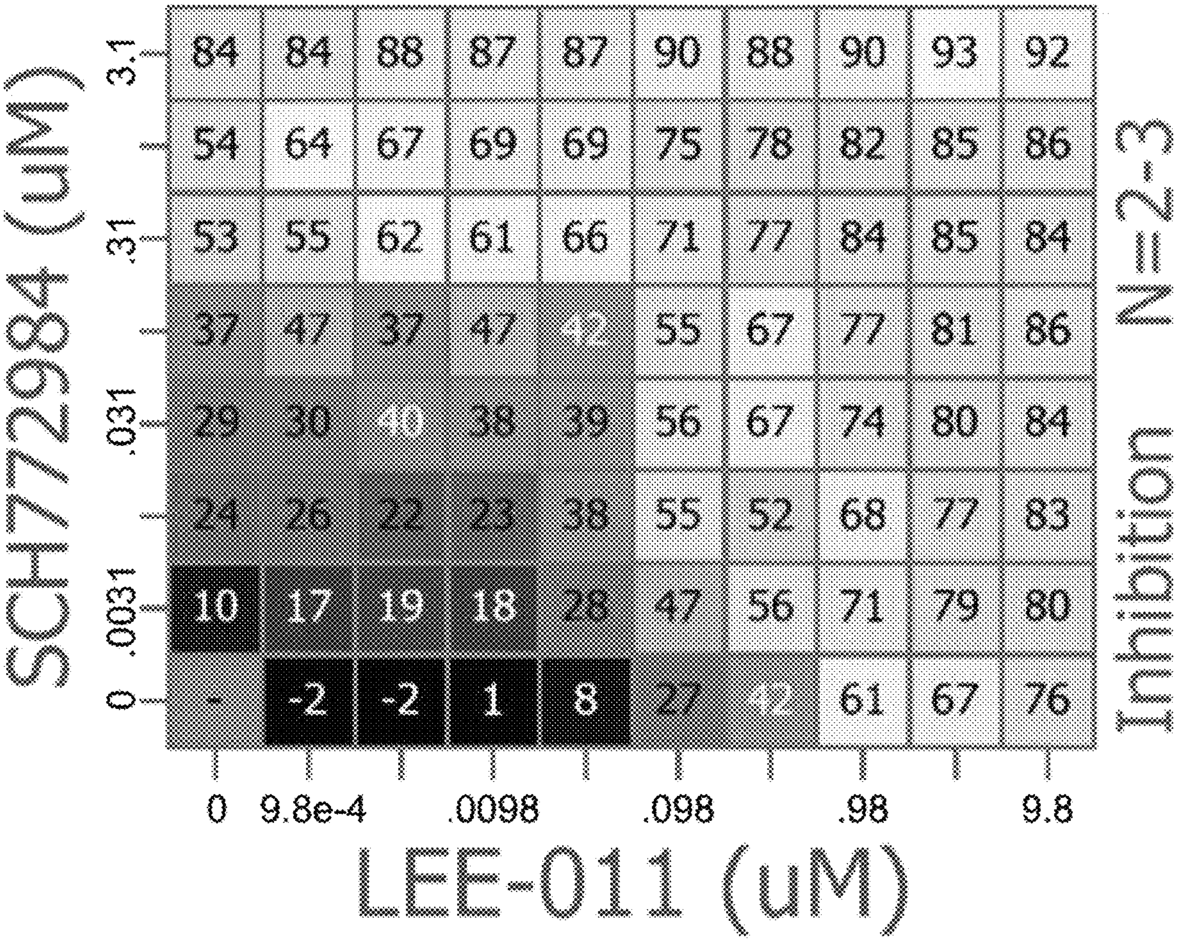
FIG. 6F shows a dose matrix showing inhibition (%) for the combination in H2122 cells.
Figure 6G:
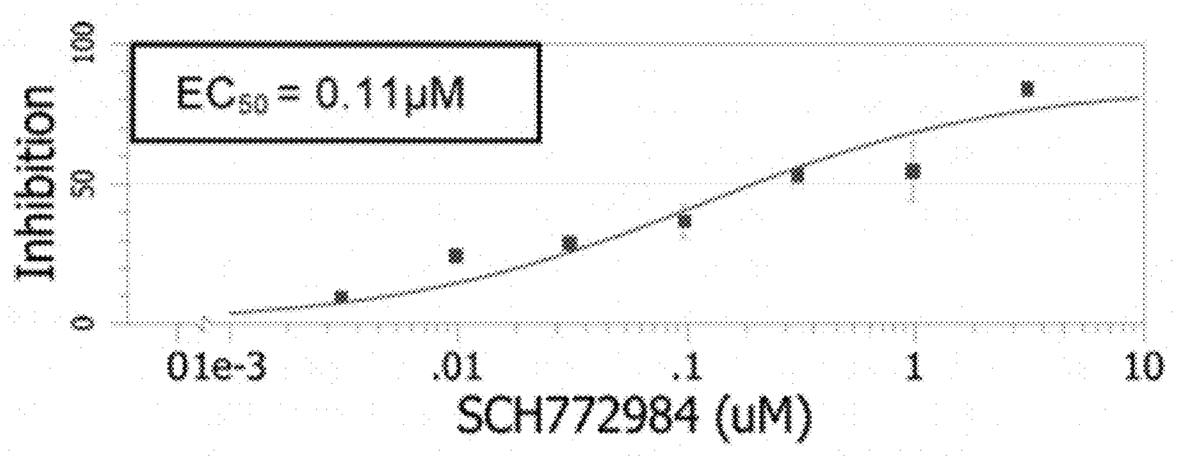
FIG. 6G-FIG. 6H show the results of single agent proliferation assays for the combination in 6F.
Figure 6H:
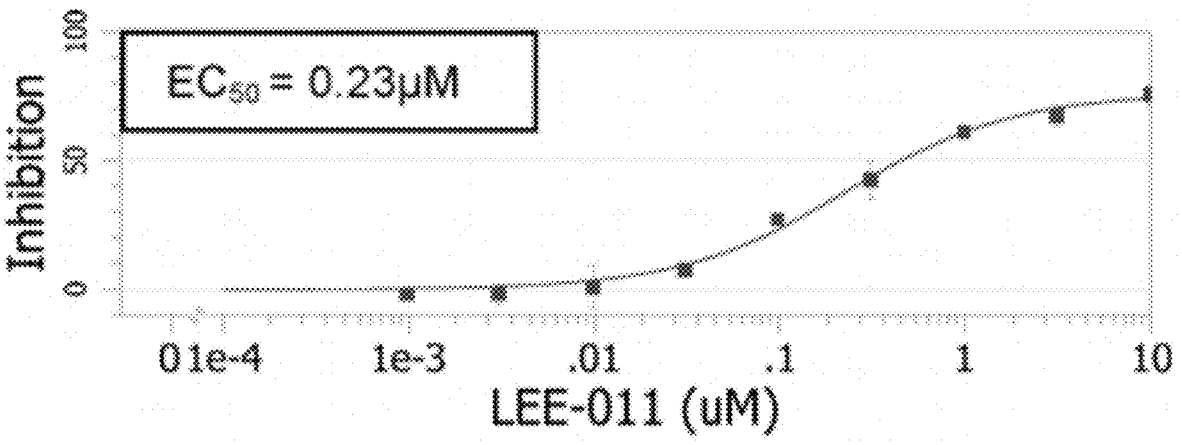
Figure 6I:
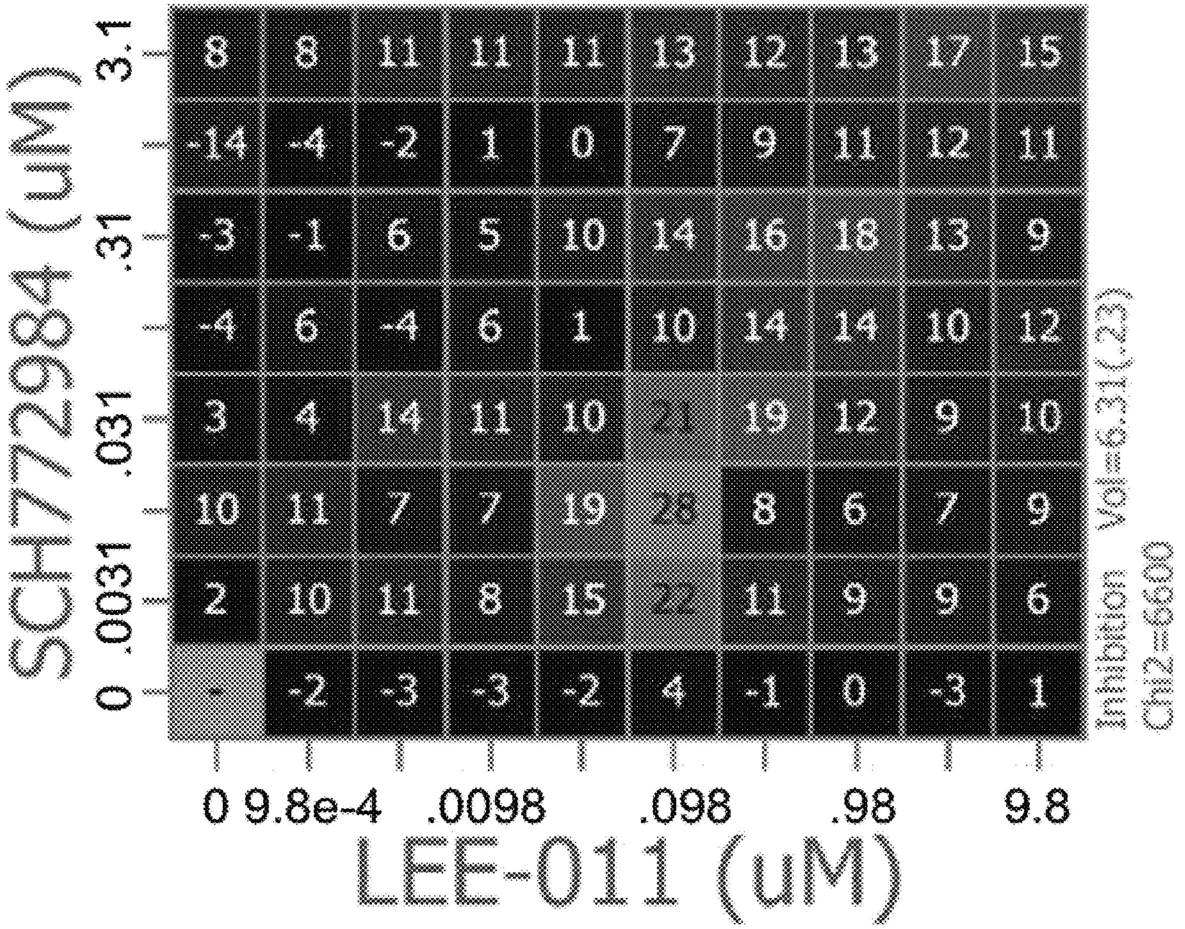
FIG. 6I shows Loewe excess for the combination in 6F and FIG. 6J shows Bliss excess for the combination in 6F.
Figure 6J:
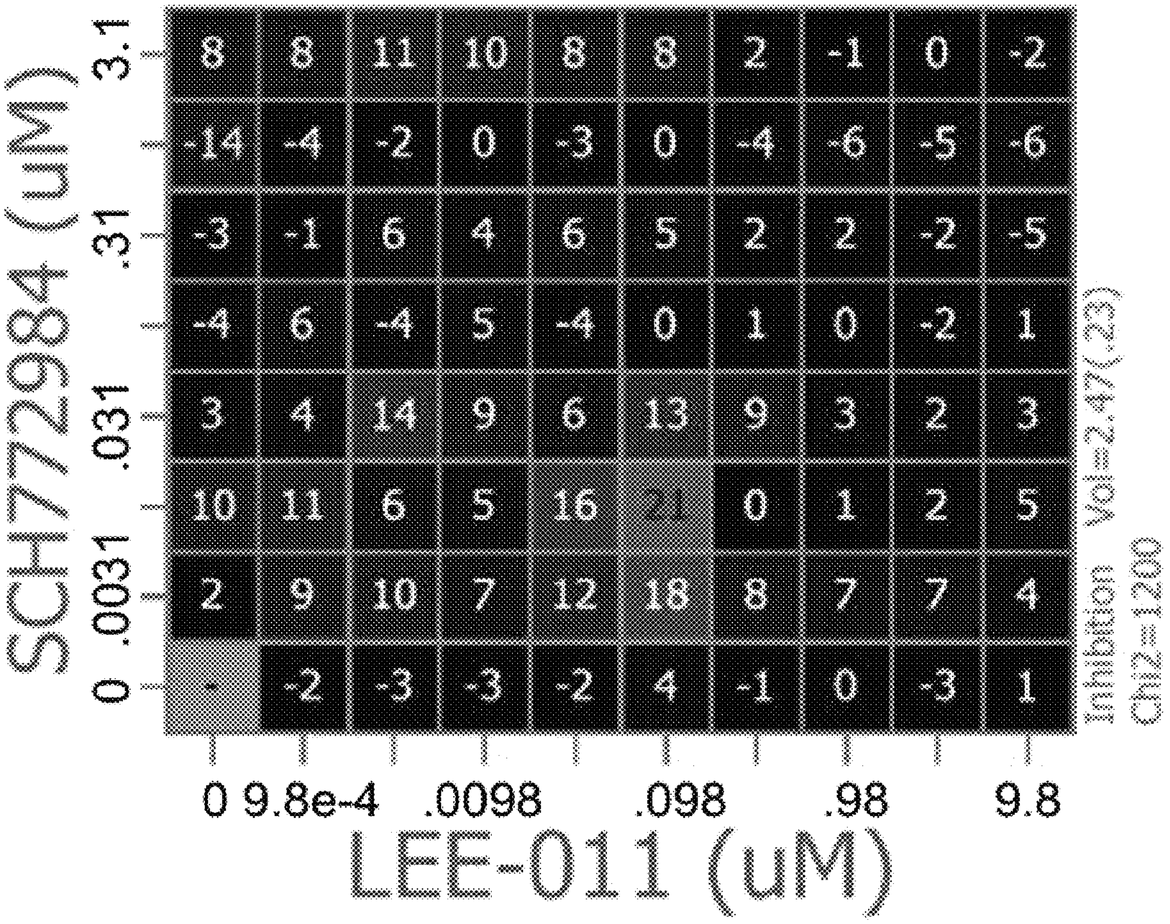
Figure 6K:
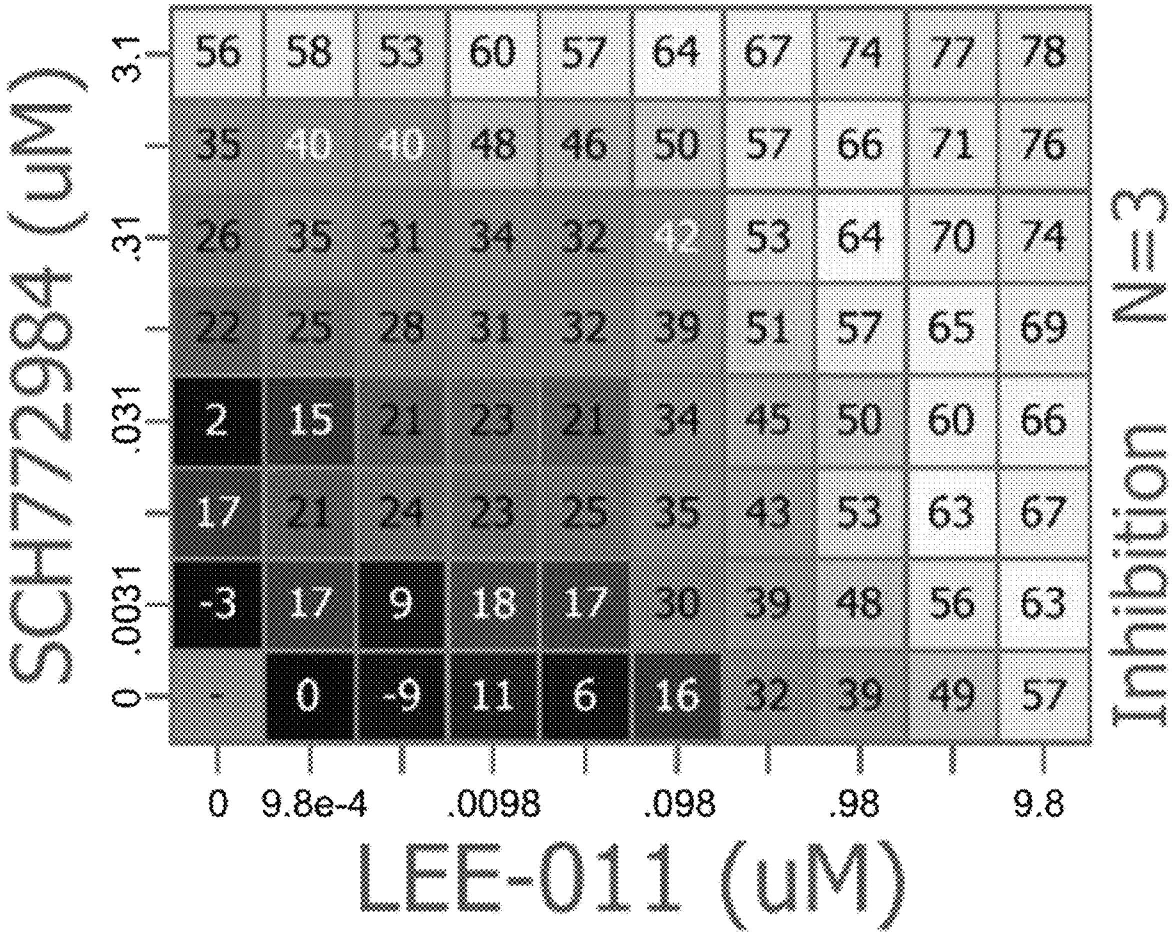
FIG. 6K shows a dose matrix showing inhibition (%) for the combination in H1437 cells.
Figure 6L:
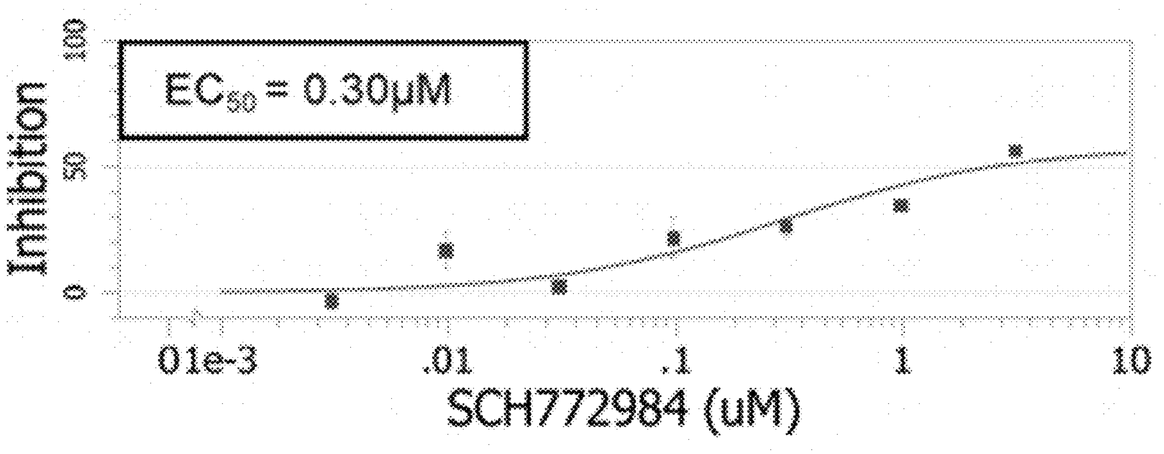
FIG. 6L-FIG. 6M show the results of single agent proliferation assays for the combination in 6K.
Figure 6M:
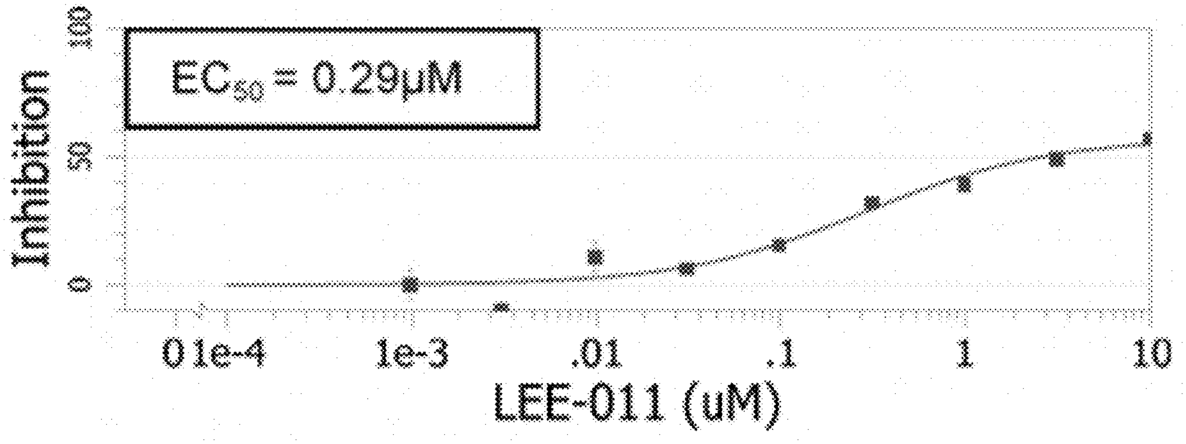
Figure 6N:
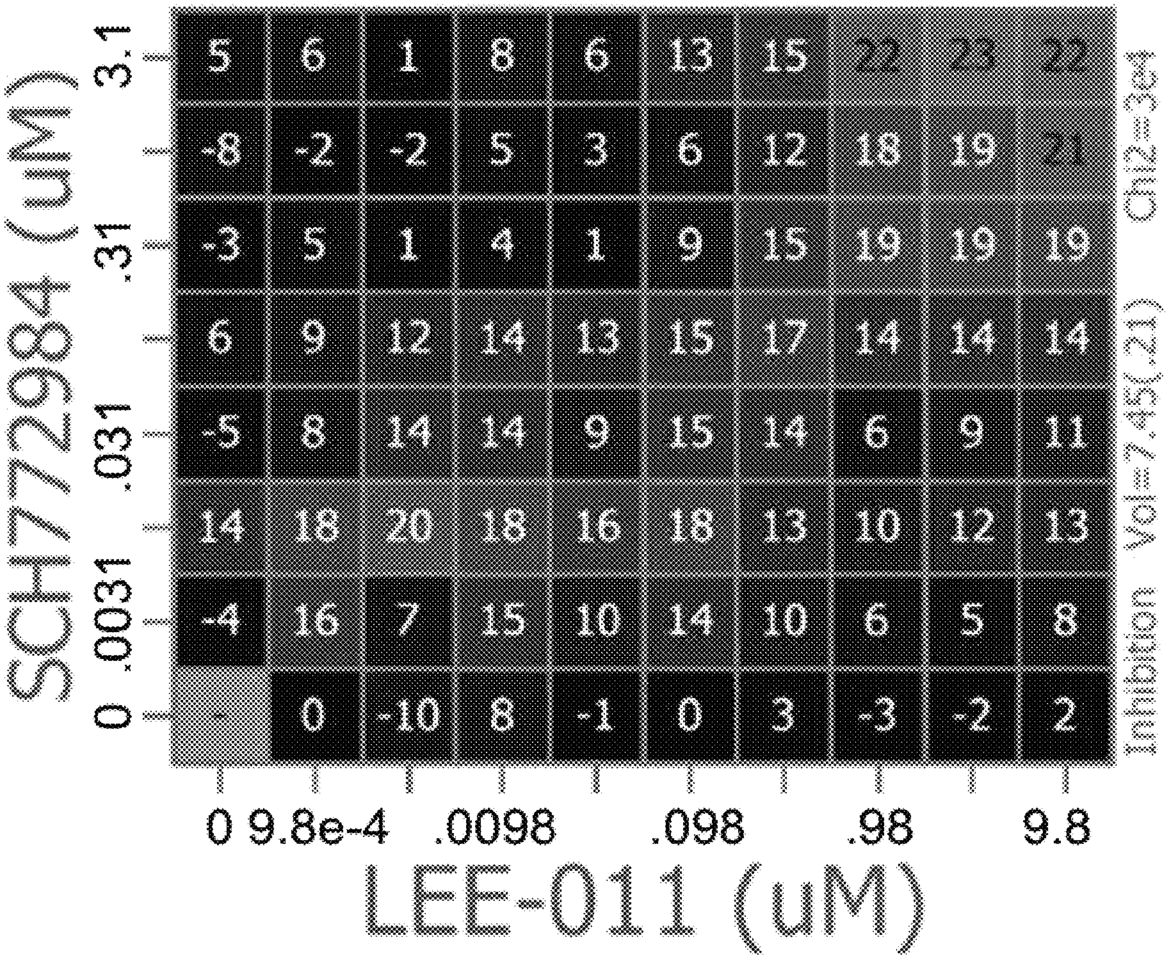
FIG. 6N shows Loewe excess for the combination in 6K and FIG. 6O shows Bliss excess for the combination in 6K.
Figure 6O:
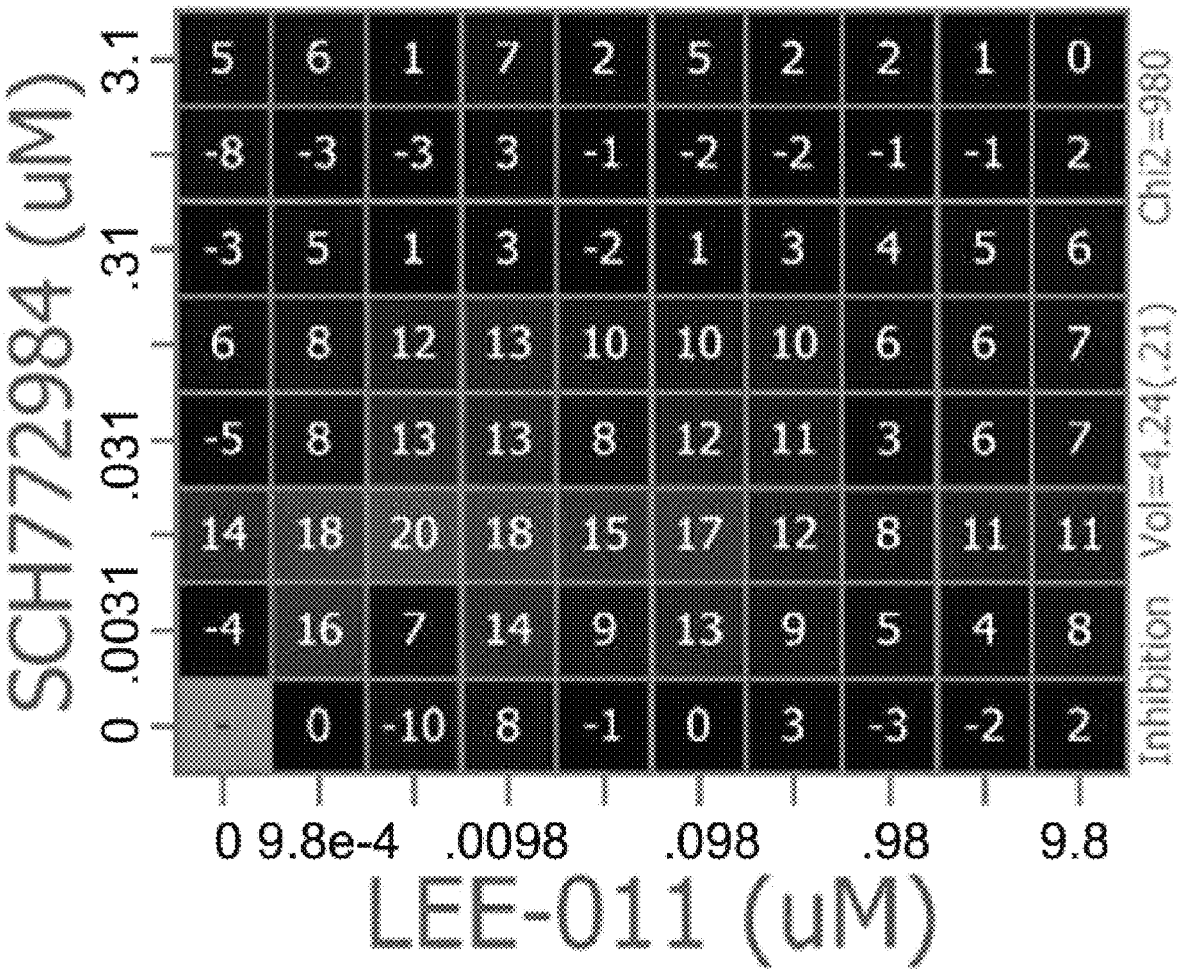
Figure 6P:
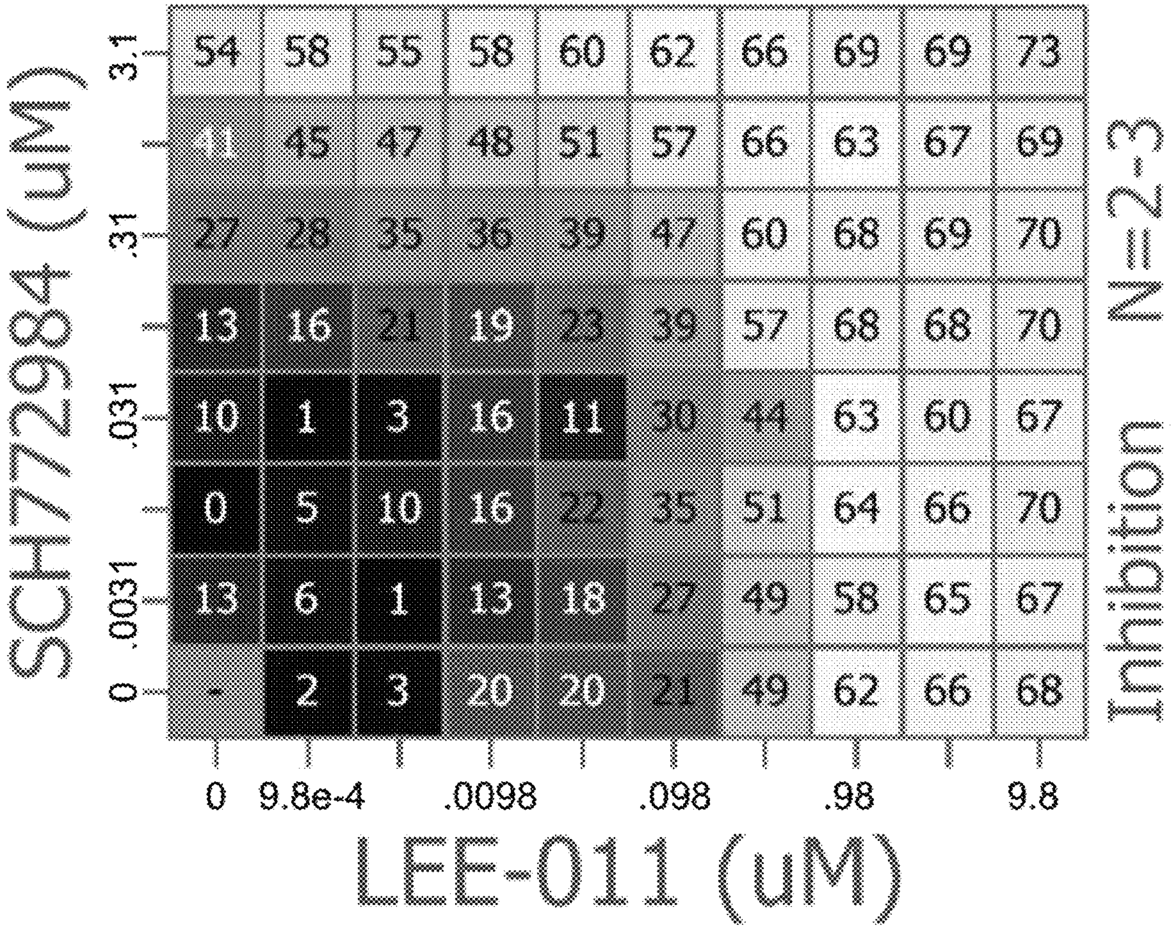
FIG. 6P shows a dose matrix showing inhibition (%) for the combination in H226 cells.
Figure 6Q:
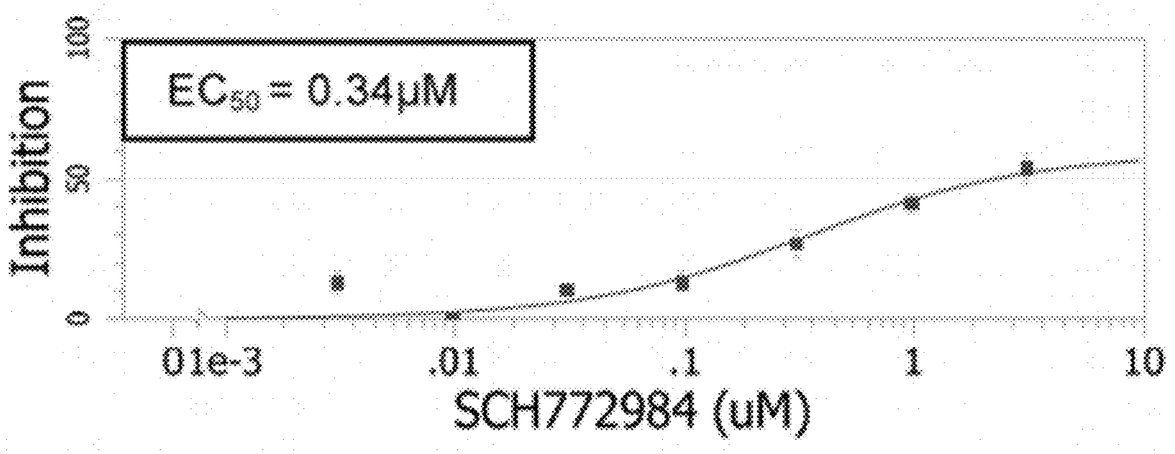
FIG. 6Q-FIG. 6R show the results of single agent proliferation assays for the combination in 6P.
Figure 6R:
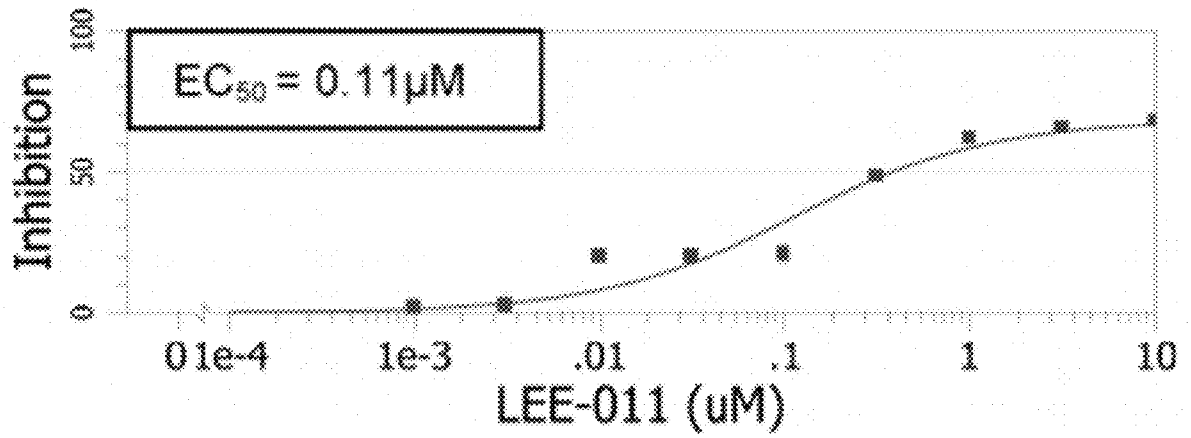
Figure 6S:
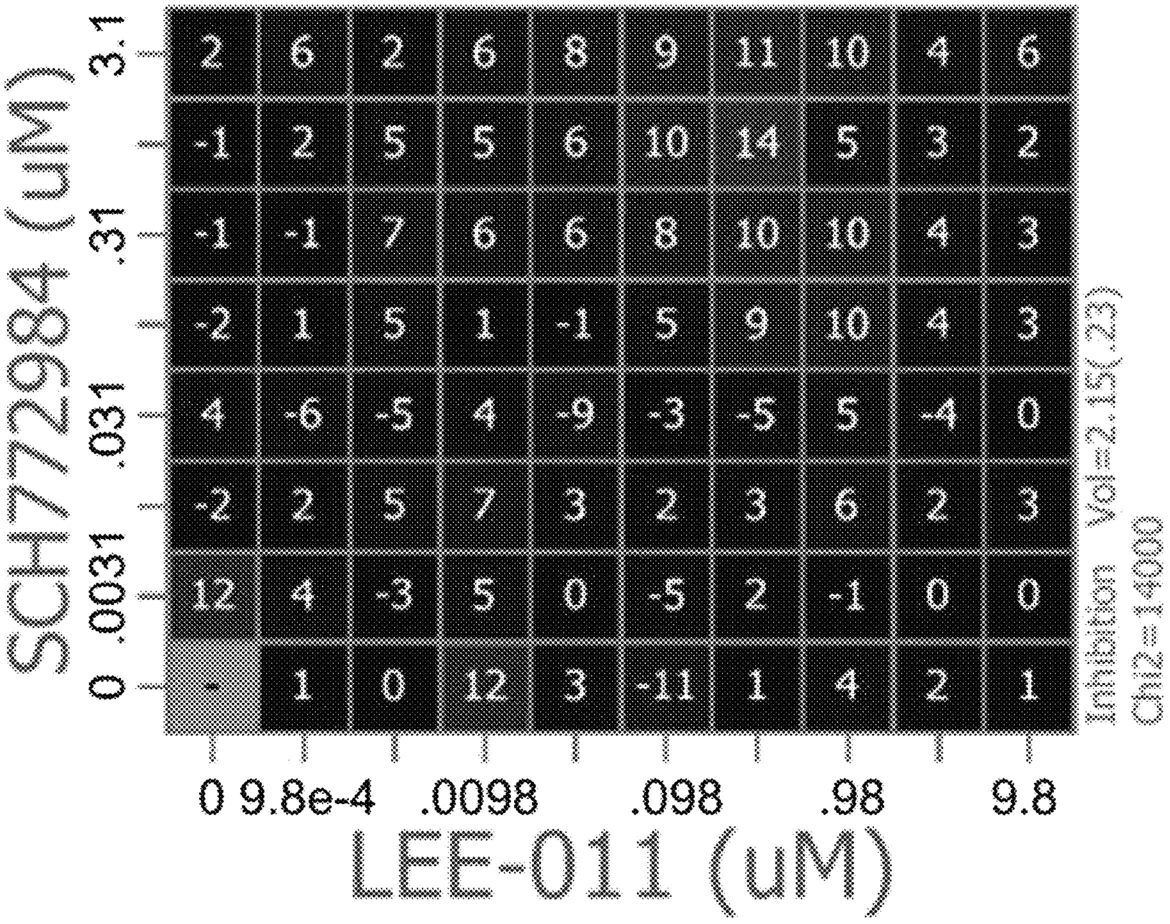
Figure 6T:
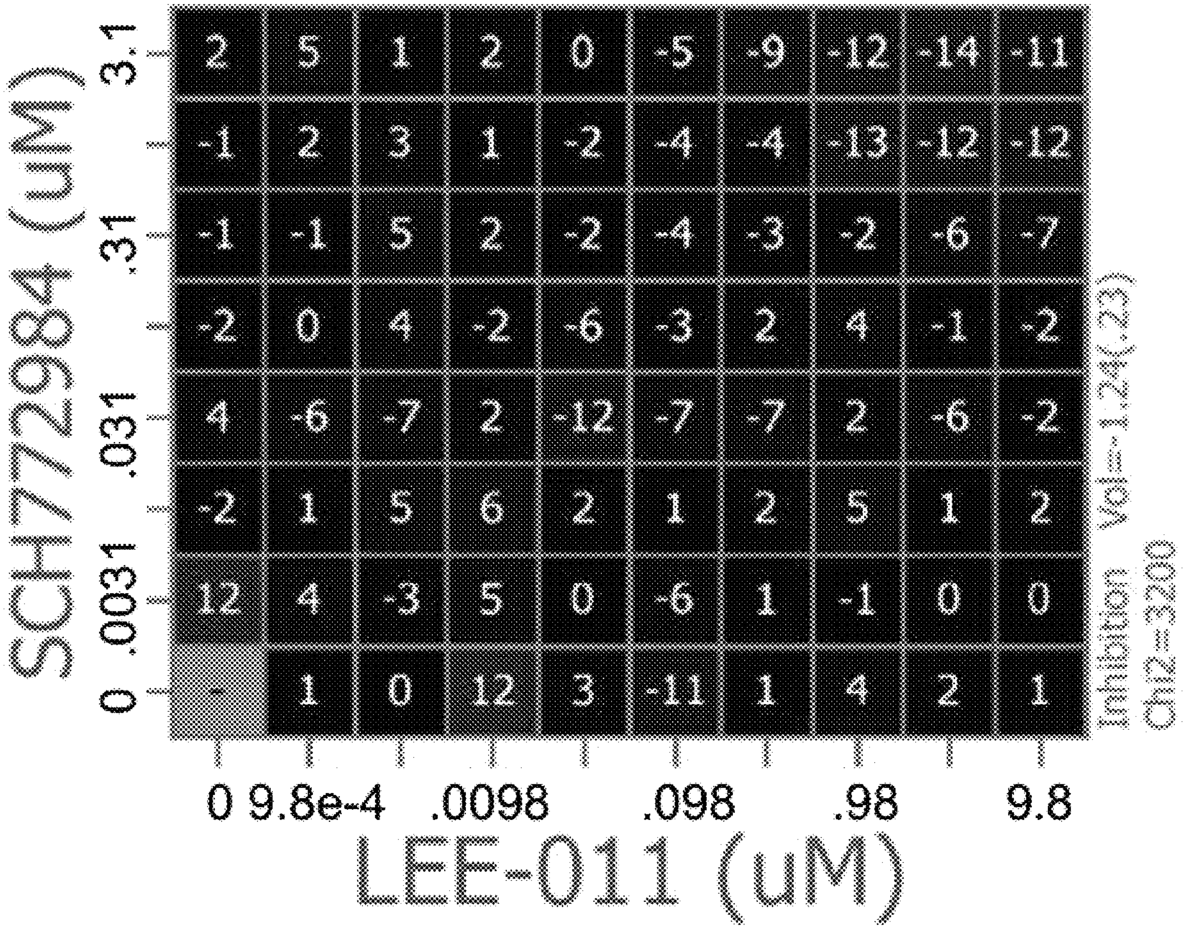
Figure 7A:
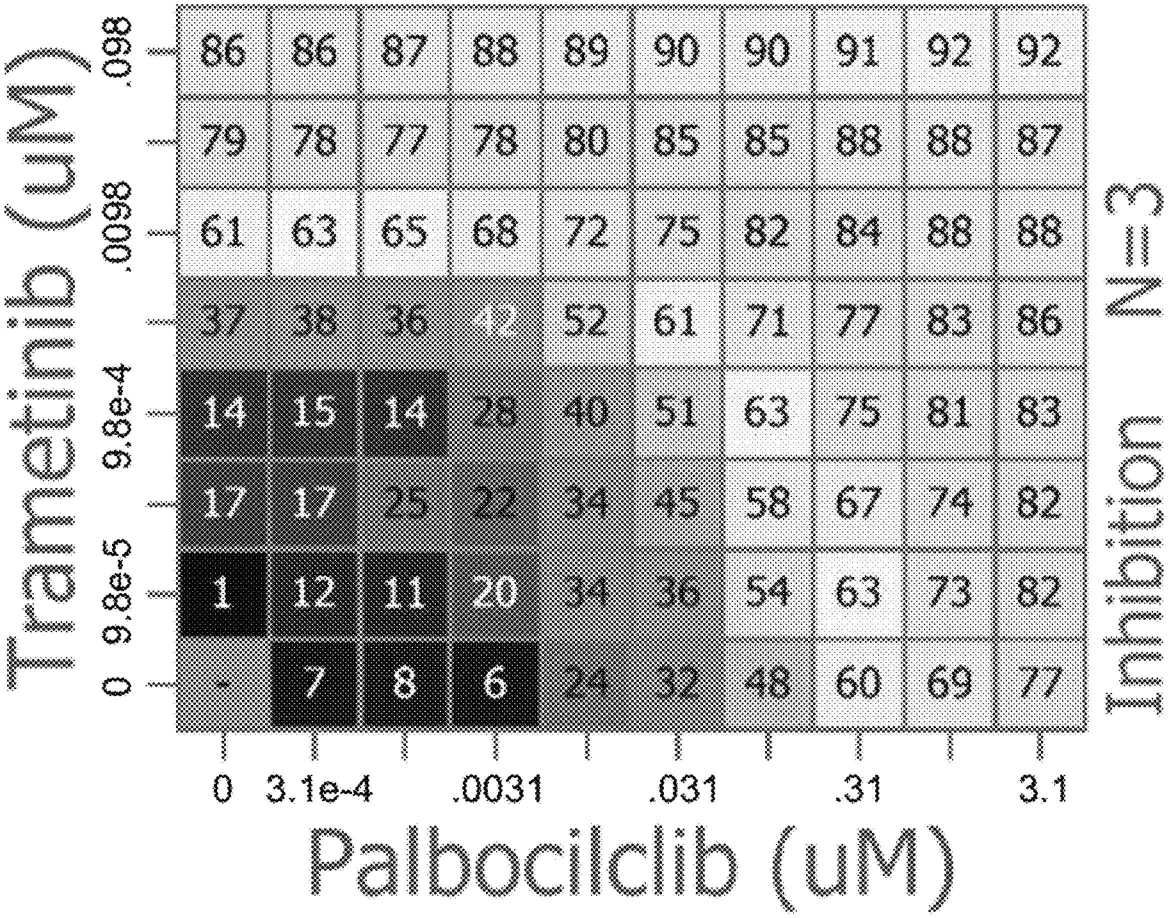
FIGS. 7A-7T show the results of the combination of Trametinib and Palbociclib.
Figure 7B:
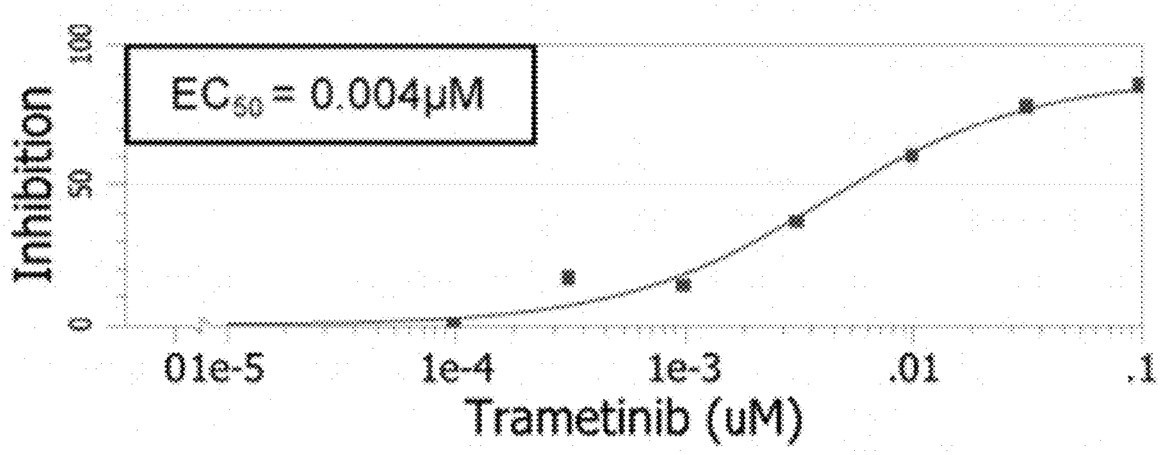
FIG. 7B-FIG. 7C show the results of single agent proliferation assays for the combination in 7A.
Figure 7C:
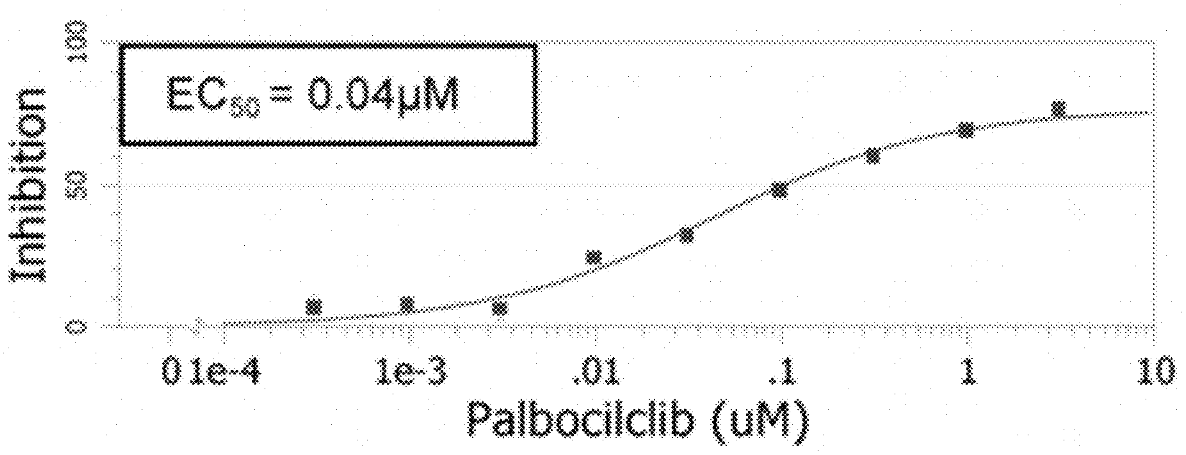
Figure 7D:
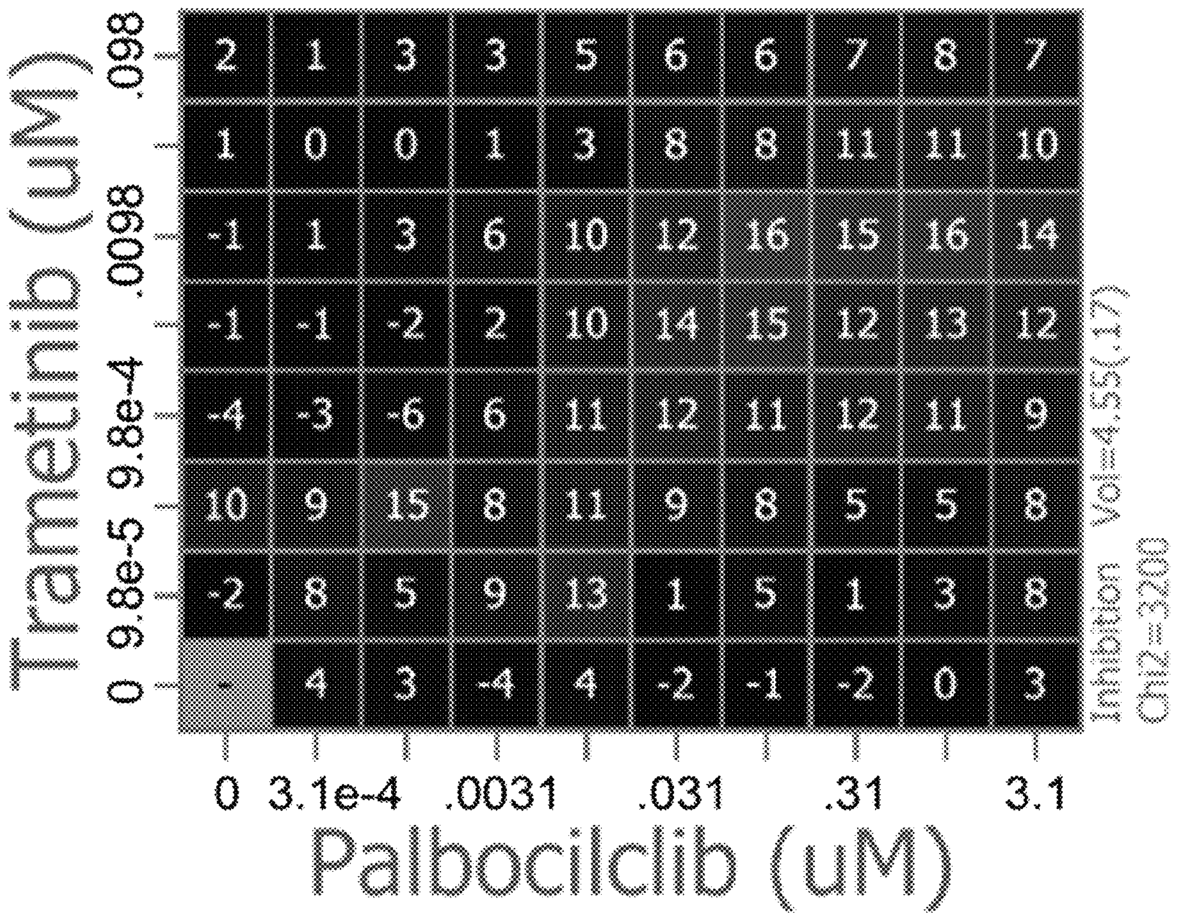
FIG. 7D shows Loewe excess for the combination in 7A and FIG. 7E shows Bliss excess for the combination in 7A.
Figure 7E:
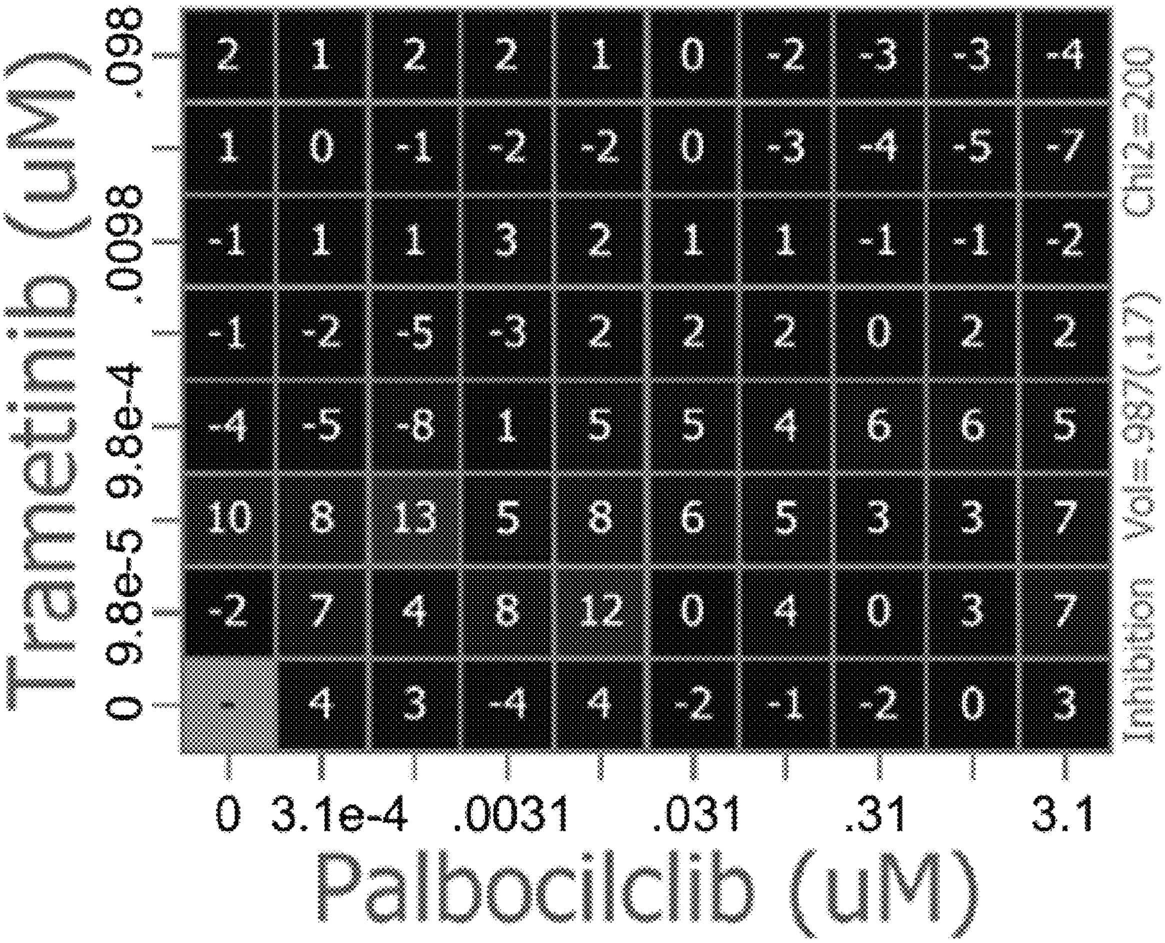
Figure 7F:
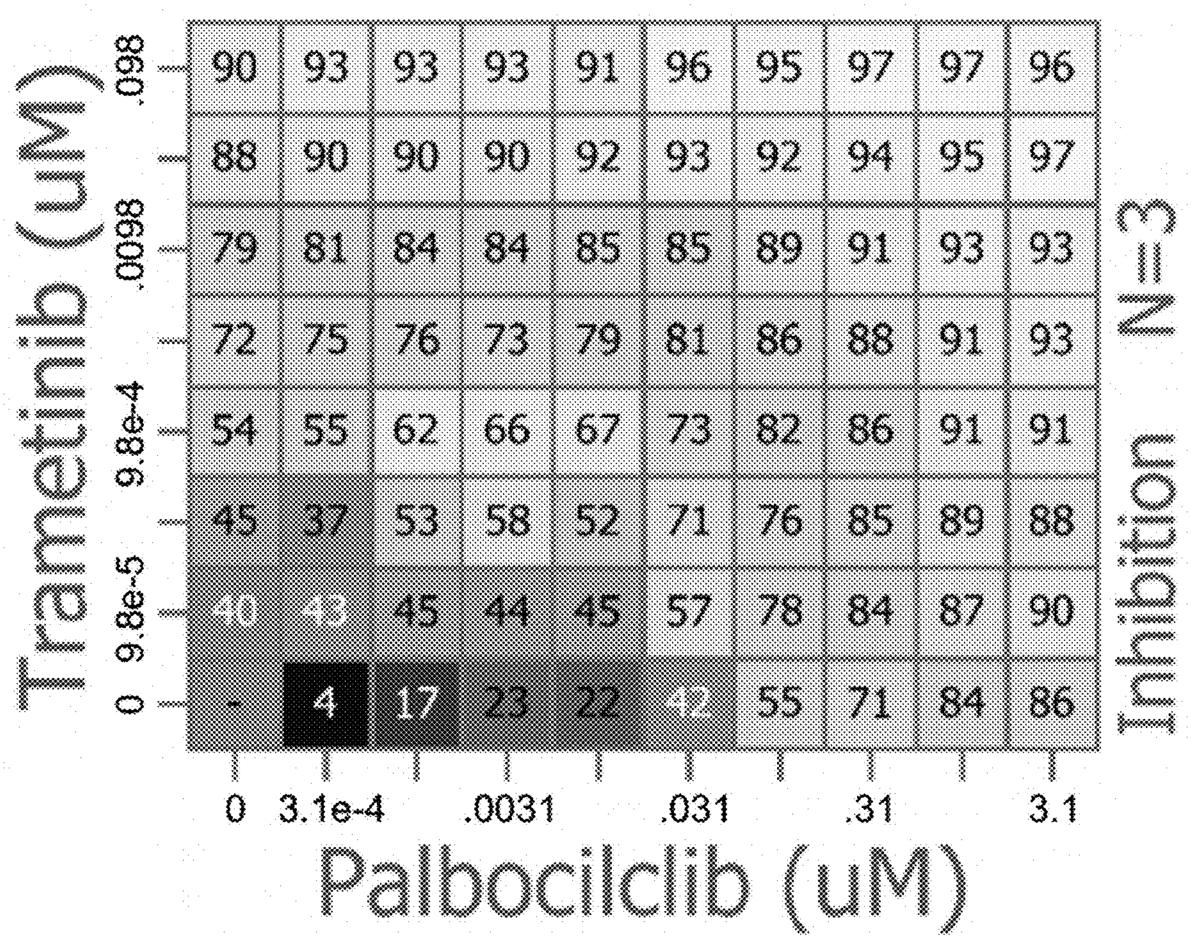
FIG. 7F shows a dose matrix showing inhibition (%) for the combination in H2122 cells.
Figure 7G:
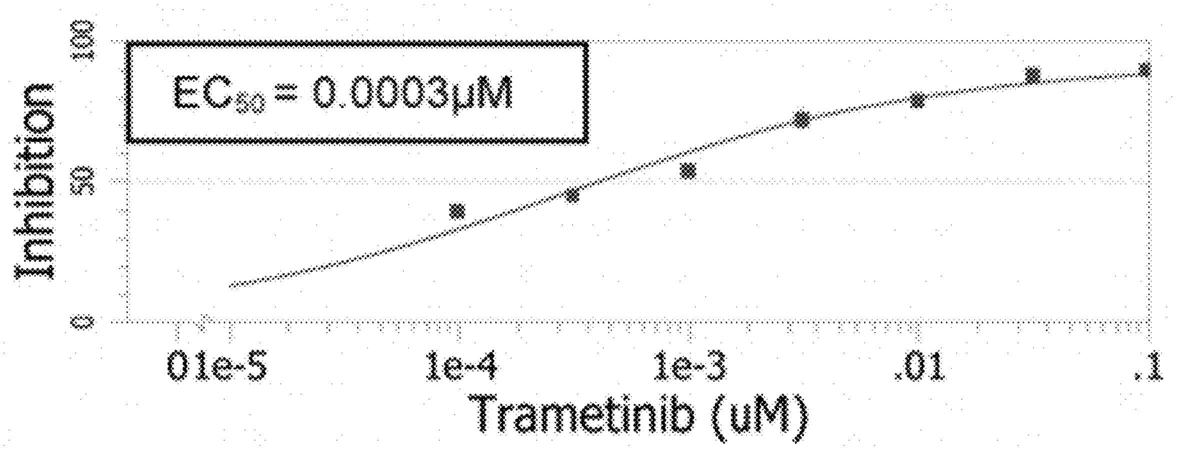
FIG. 7G-FIG. 7H show the results of single agent proliferation assays for the combination in 7F.
Figure 7H:
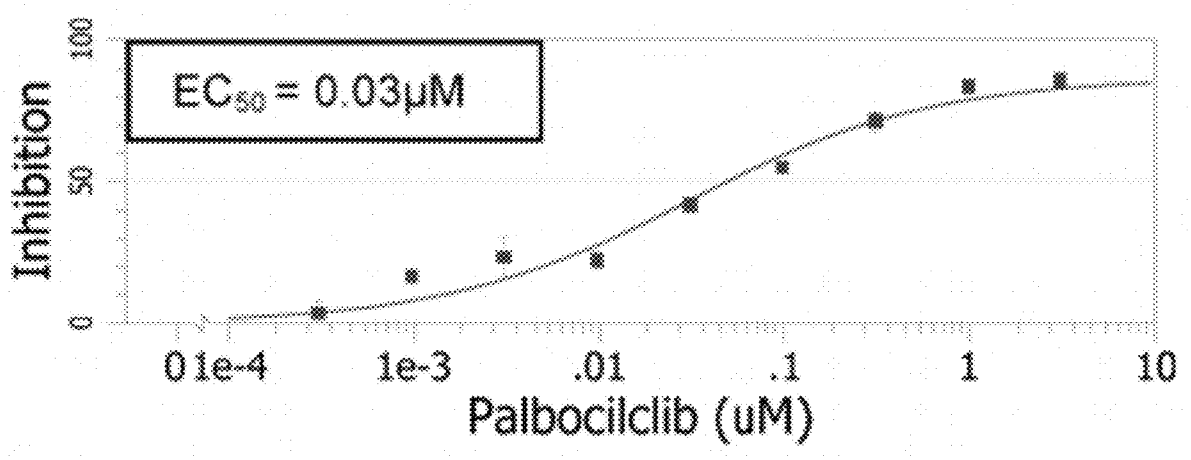
Figure 7I:
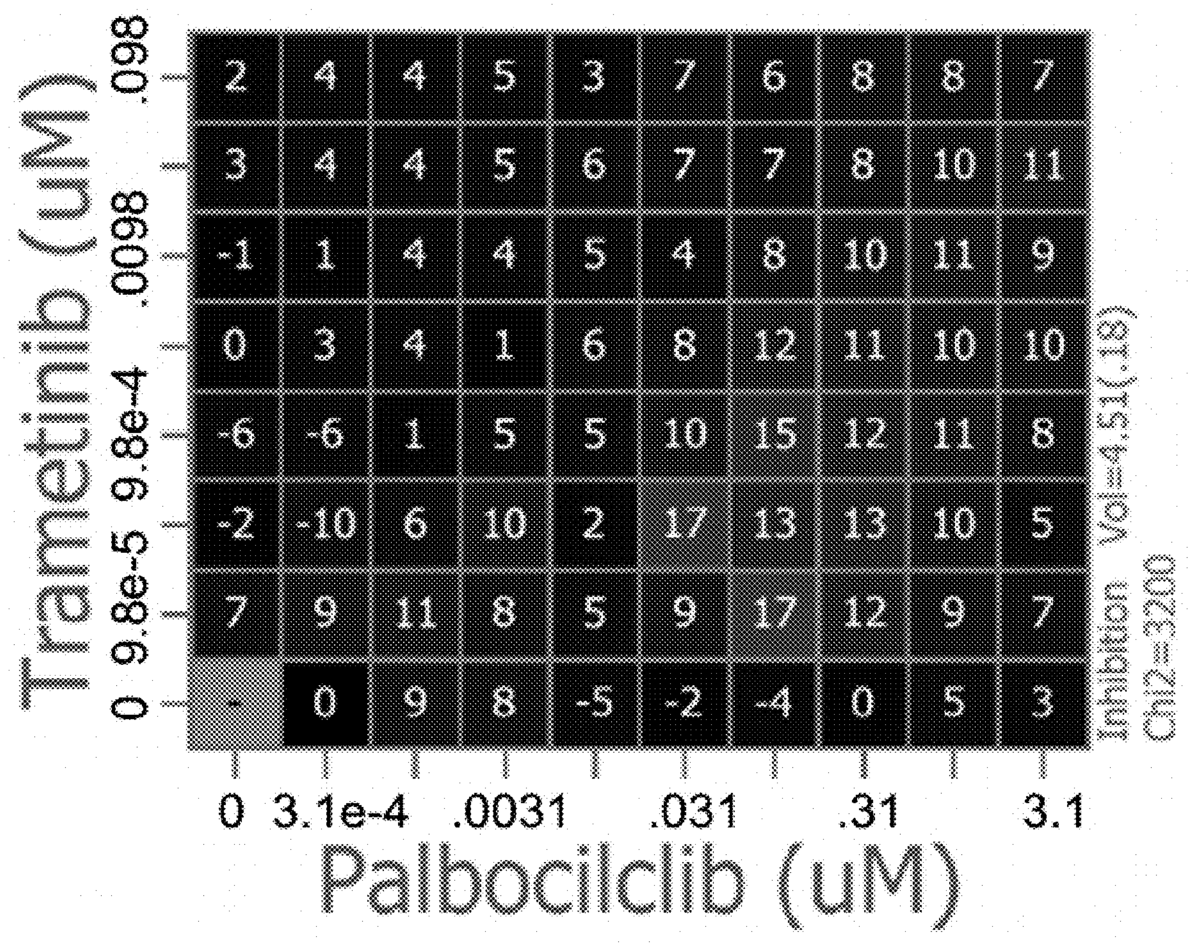
FIG. 7I shows Loewe excess for the combination in 7F and FIG. 7J shows Bliss excess for the combination in 7F.
Figure 7J:
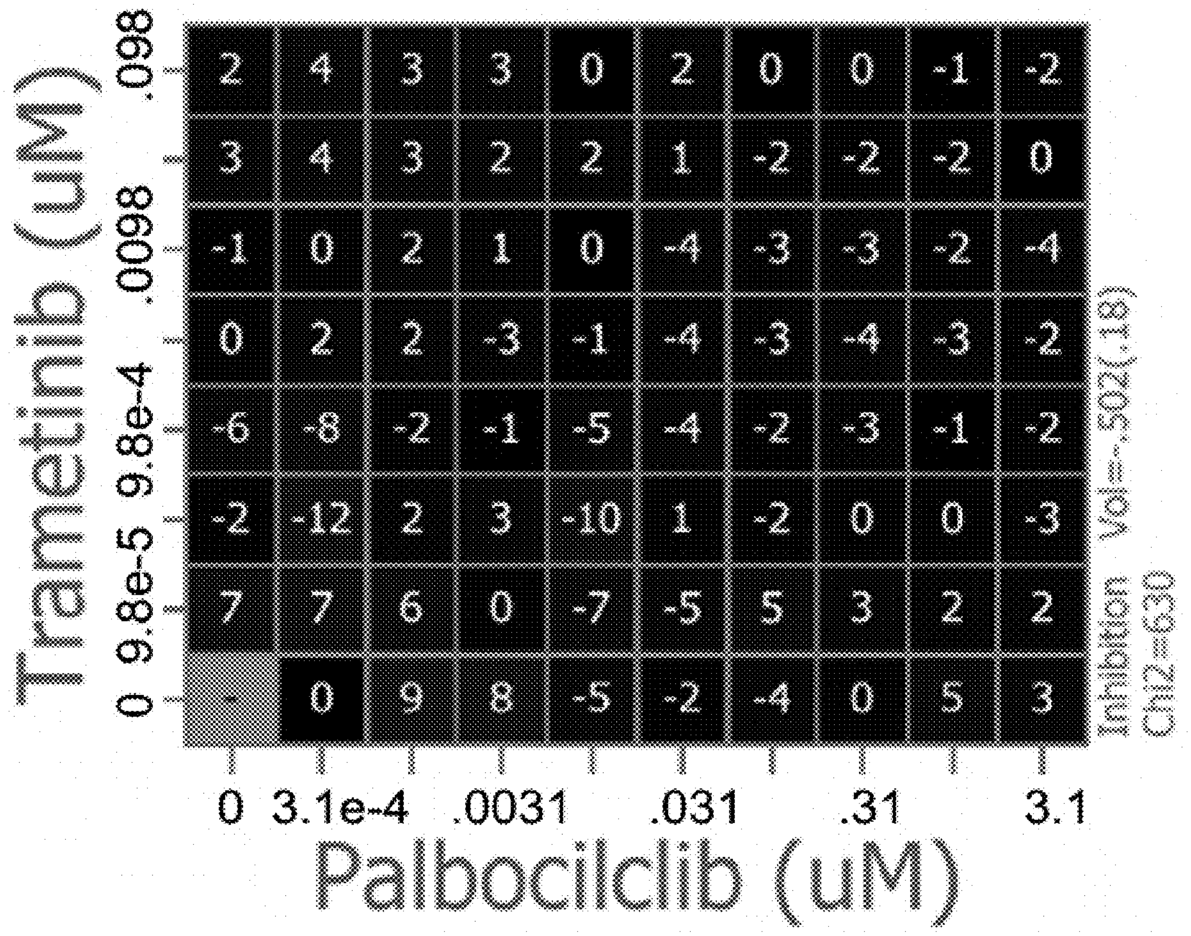
Figure 7K:
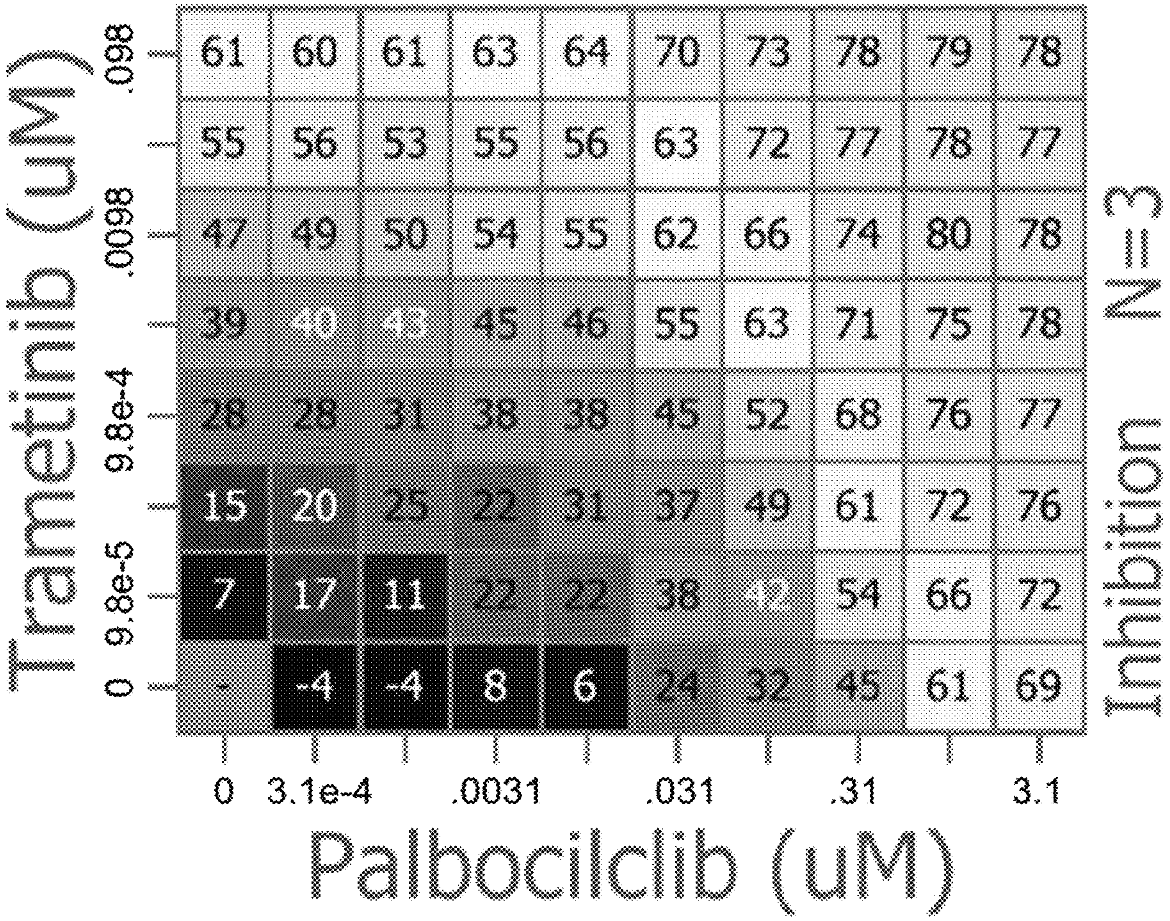
FIG. 7K shows a dose matrix showing inhibition (%) for the combination in H1437 cells.
Figure 7L:
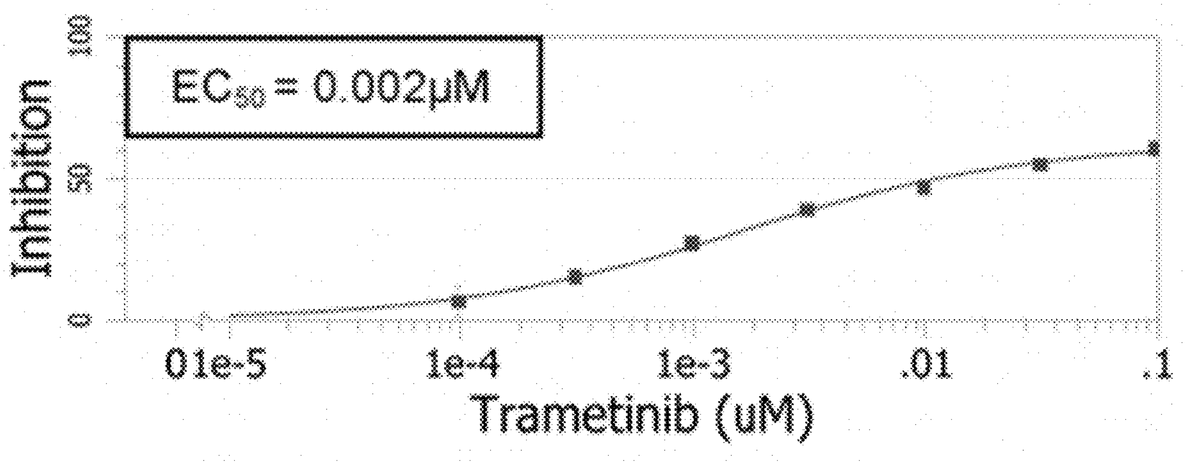
FIG. 7L-FIG. 7M show the results of single agent proliferation assays for the combination in 7K.
Figure 7M:
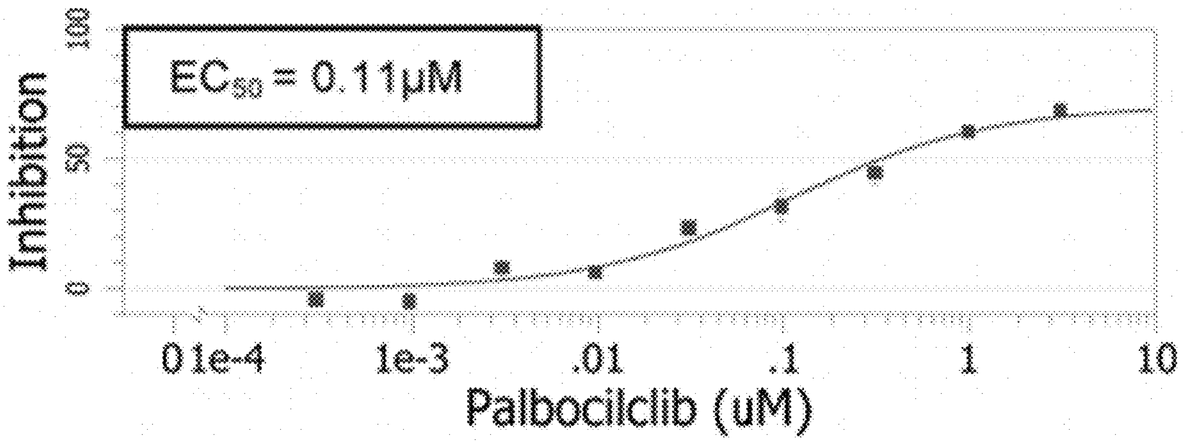
Figure 7N:
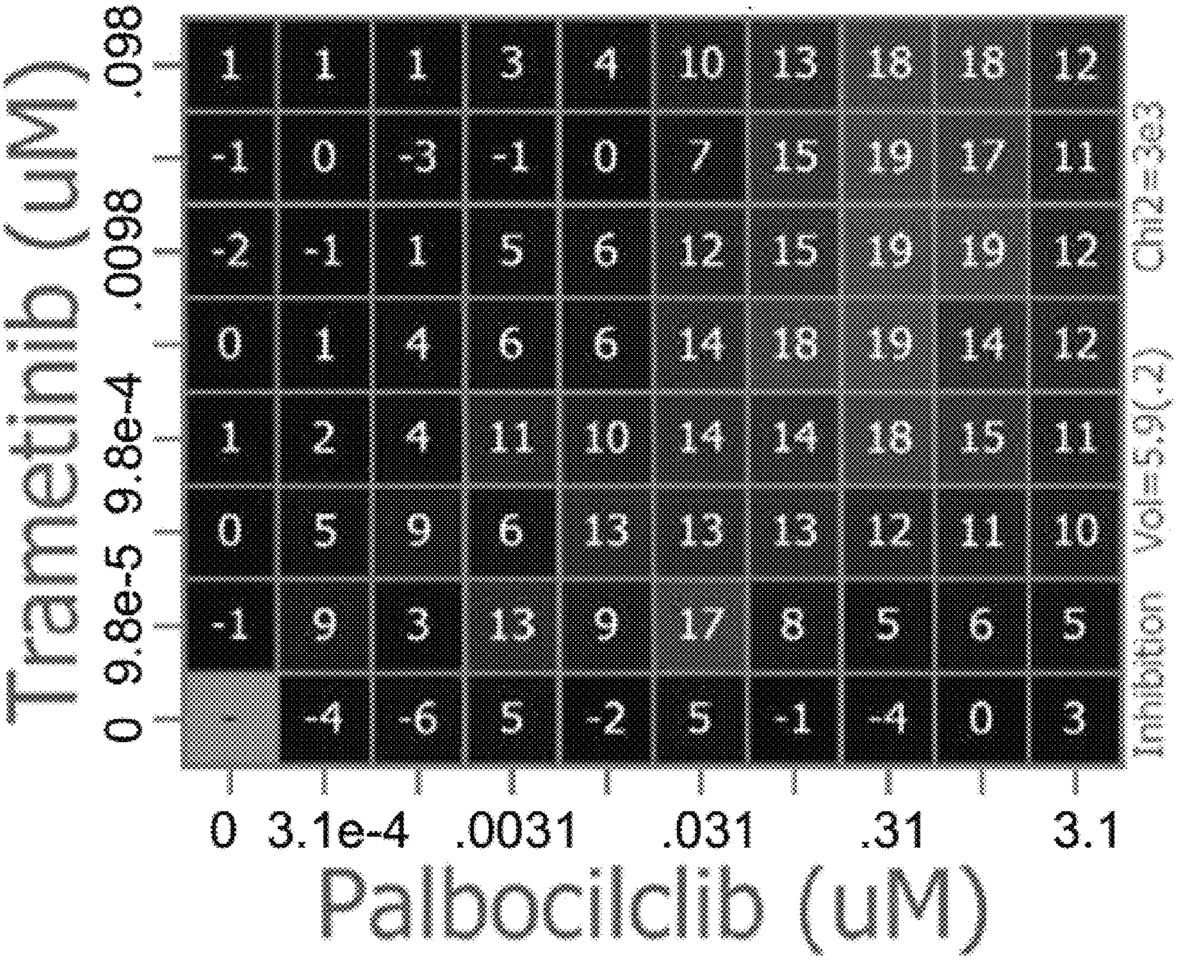
FIG. 7N shows Loewe excess for the combination in 7K and FIG. 7O shows Bliss excess for the combination in 7K.
Figure 7O:
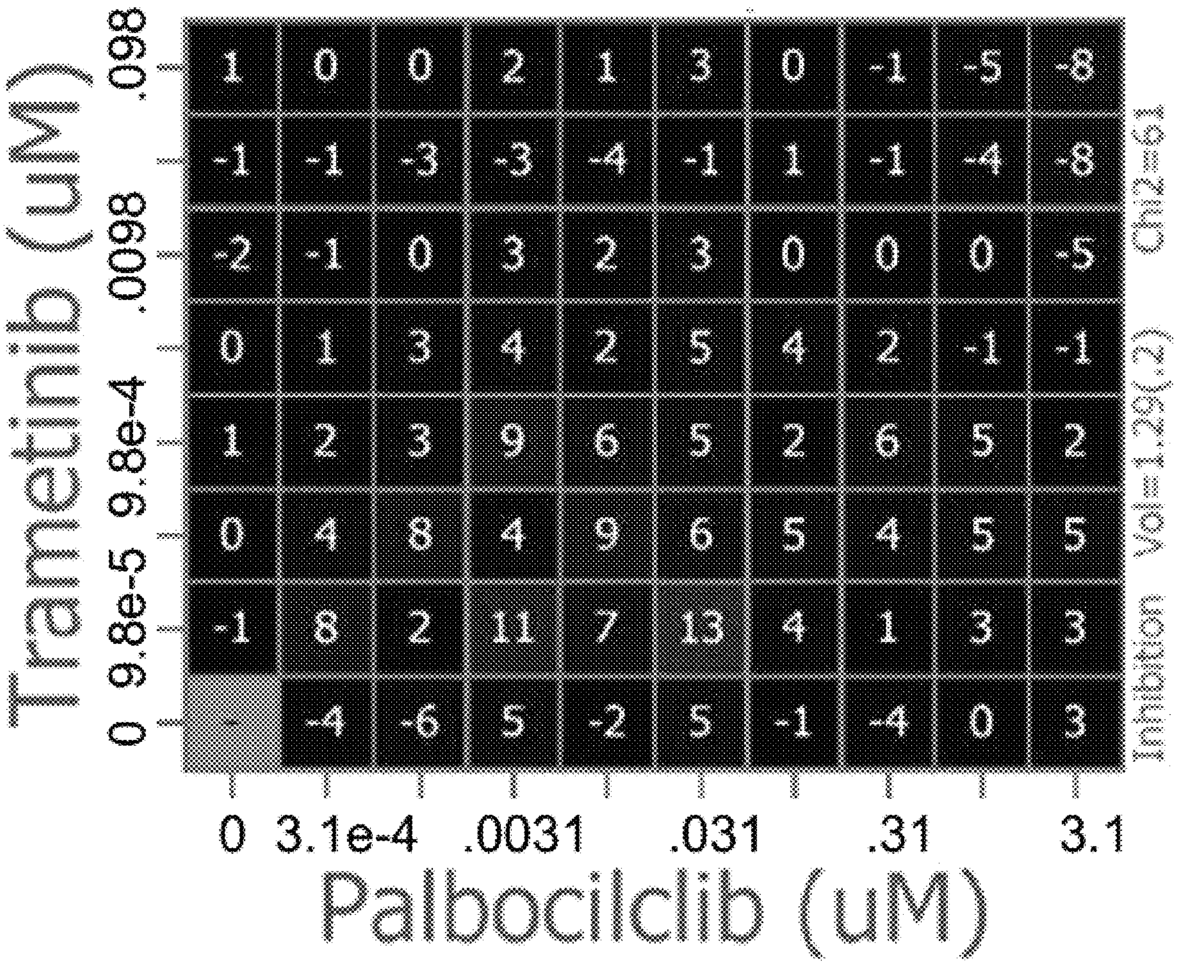
Figure 7P:
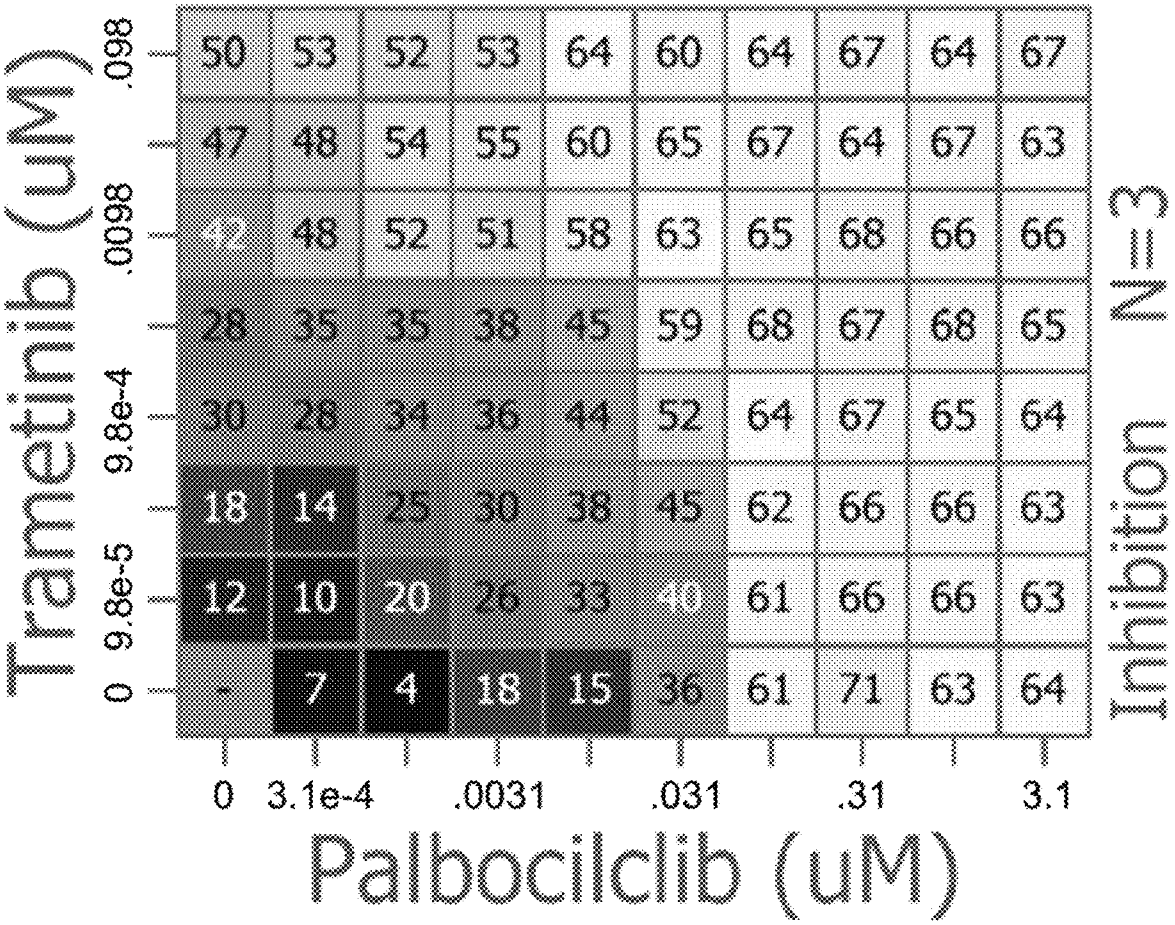
FIG. 7P shows a dose matrix showing inhibition (%) for the combination in H226 cells.
Figure 7Q:
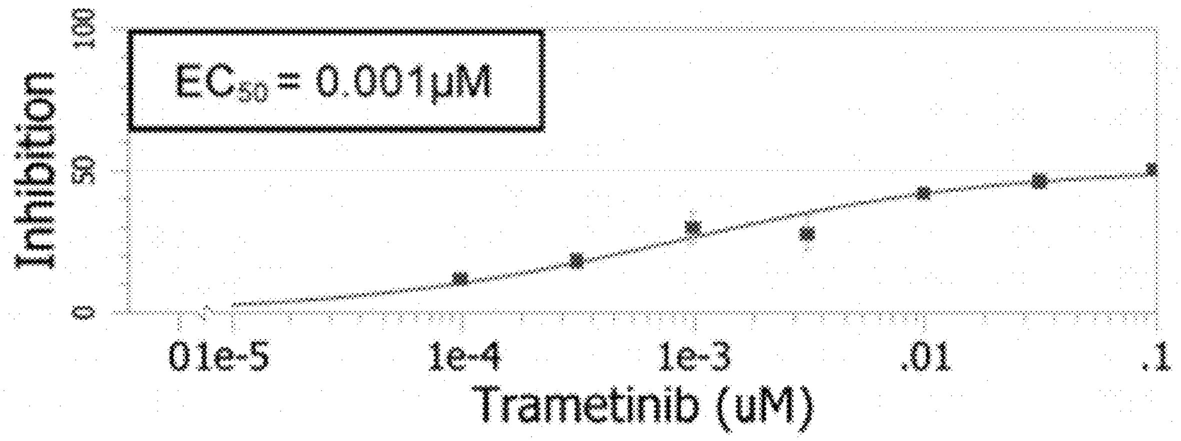
FIG. 7Q-FIG. 7R show the results of single agent proliferation assays for the combination in 7P.
Figure 7R:
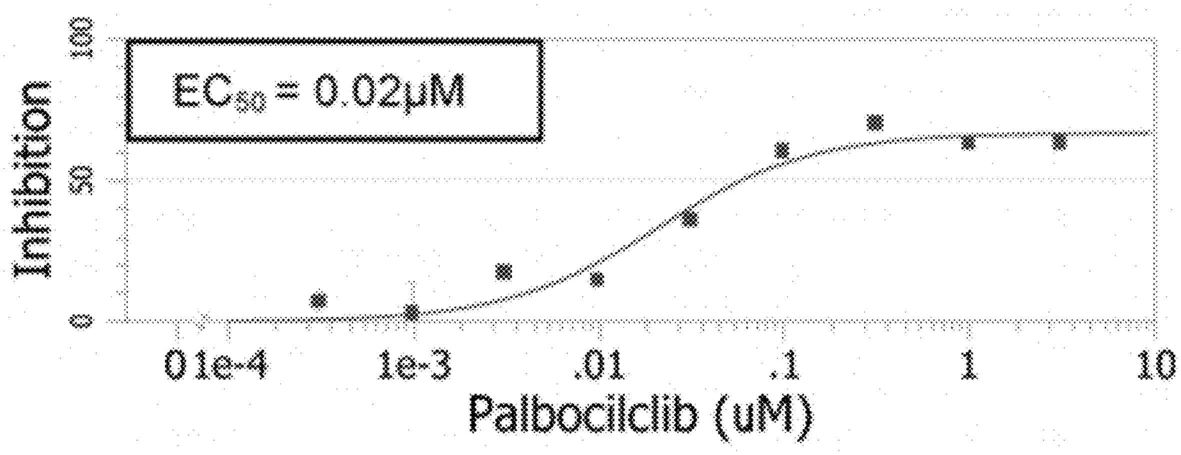
Figure 7S:
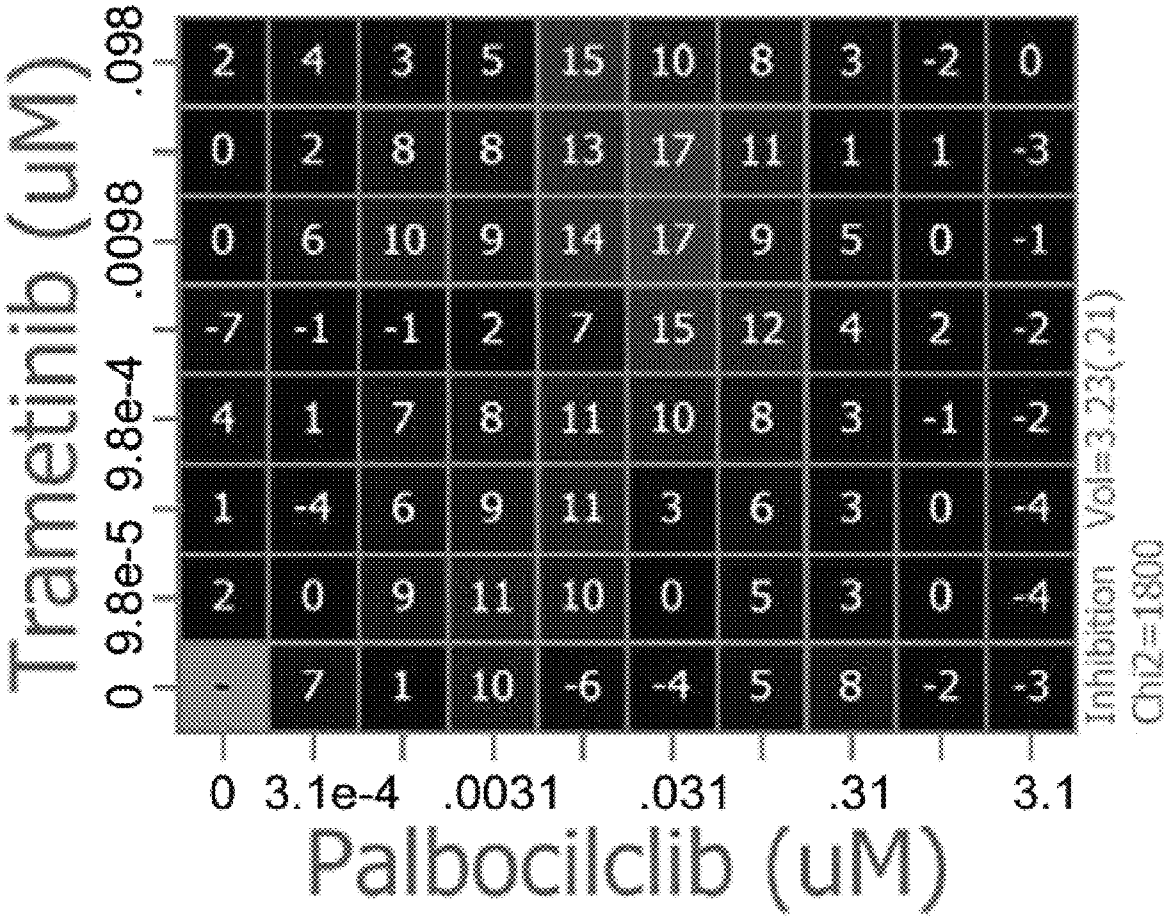
Figure 7T:
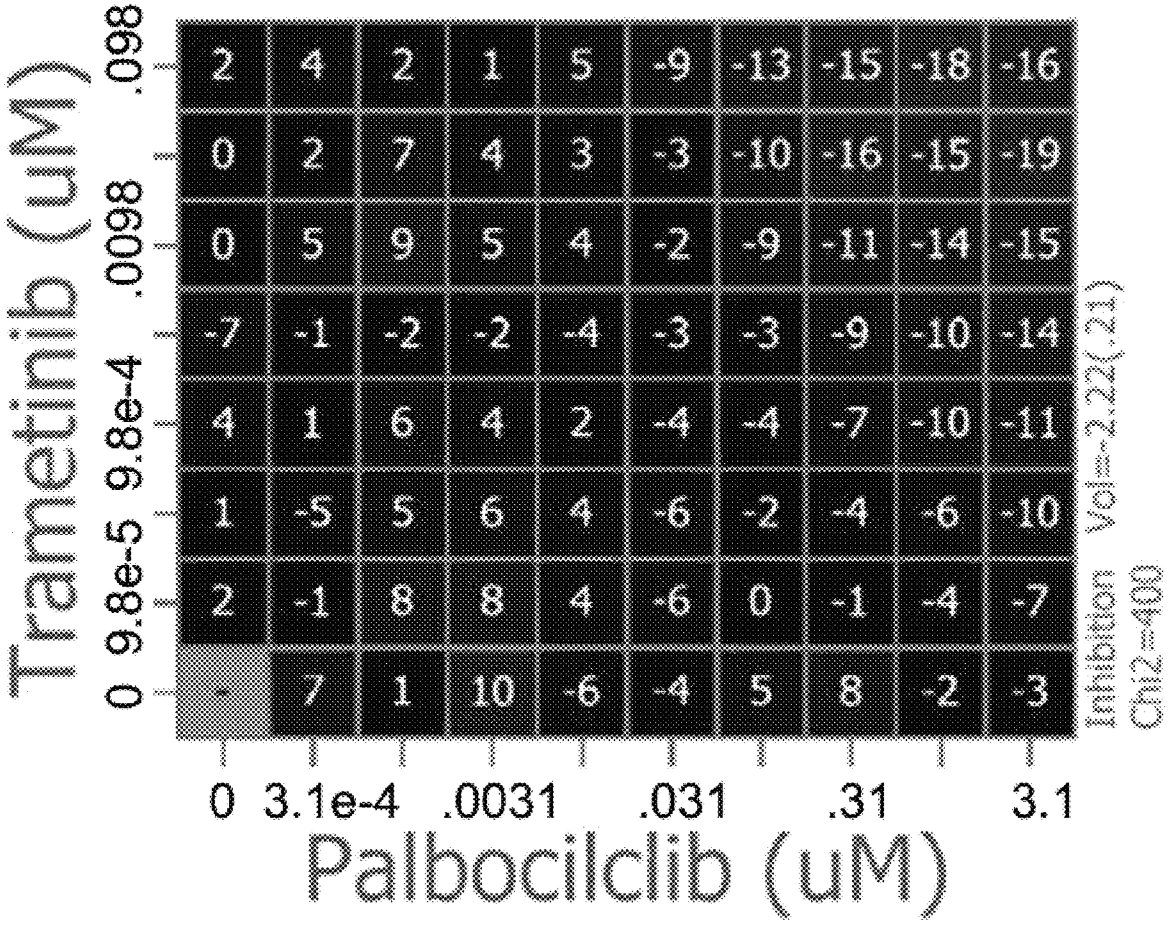
Figure 8A:
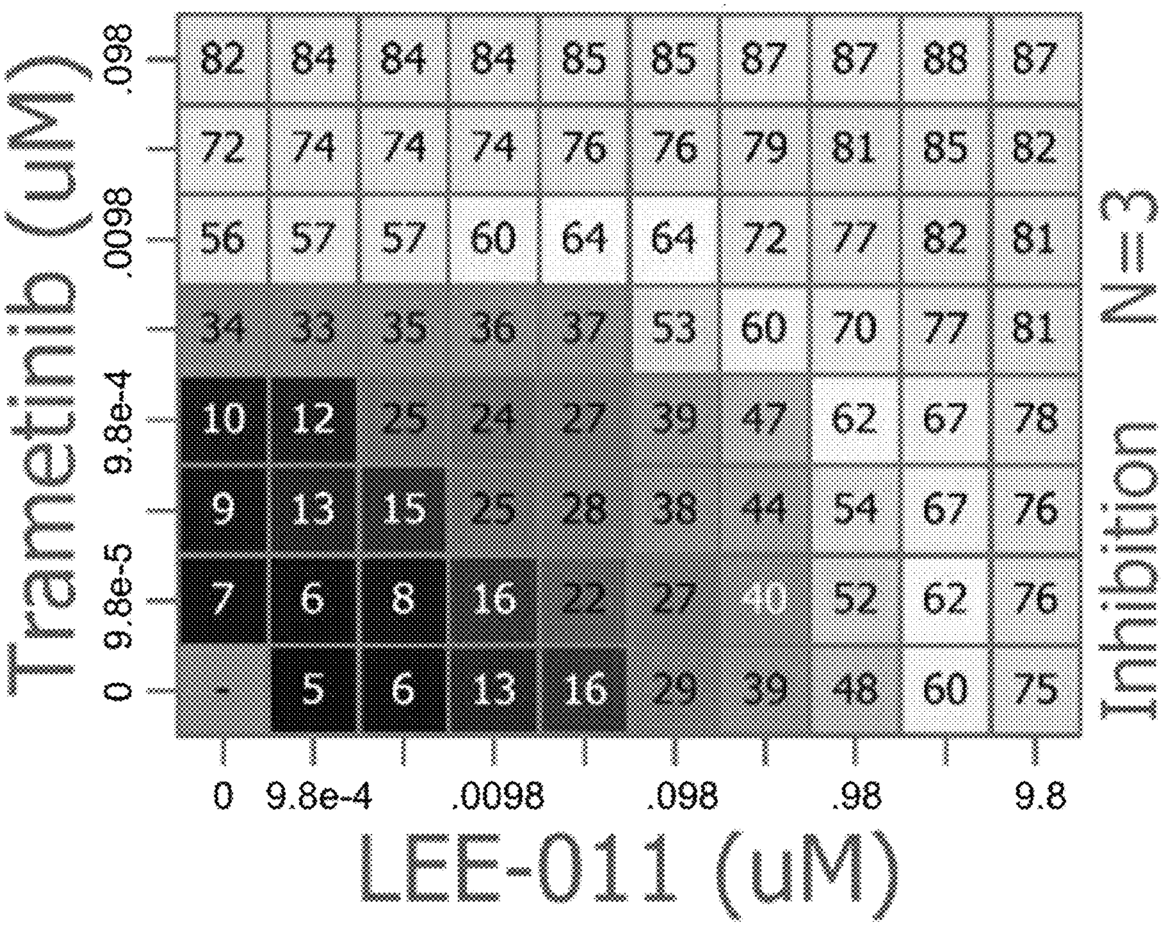
FIGS. 8A-8T show the results of the combination of Trametinib and LEE-011.
Figure 8B:
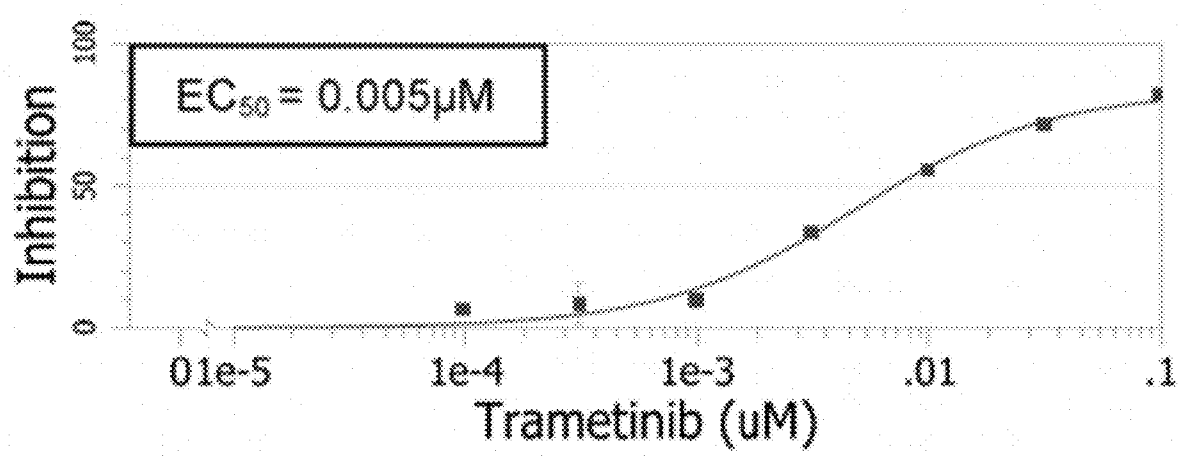
FIG. 8B-FIG. 8C show the results of single agent proliferation assays for the combination in 8A.
Figure 8C:
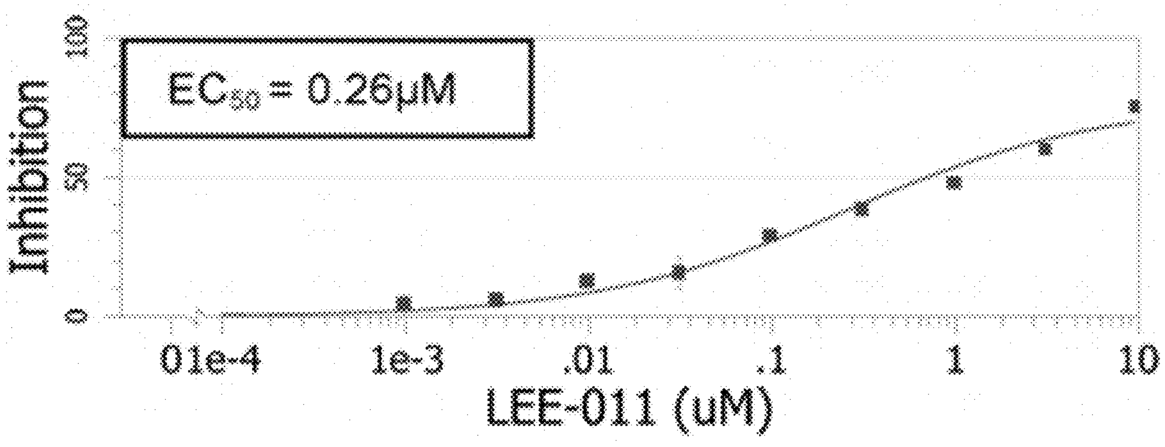
Figure 8D:
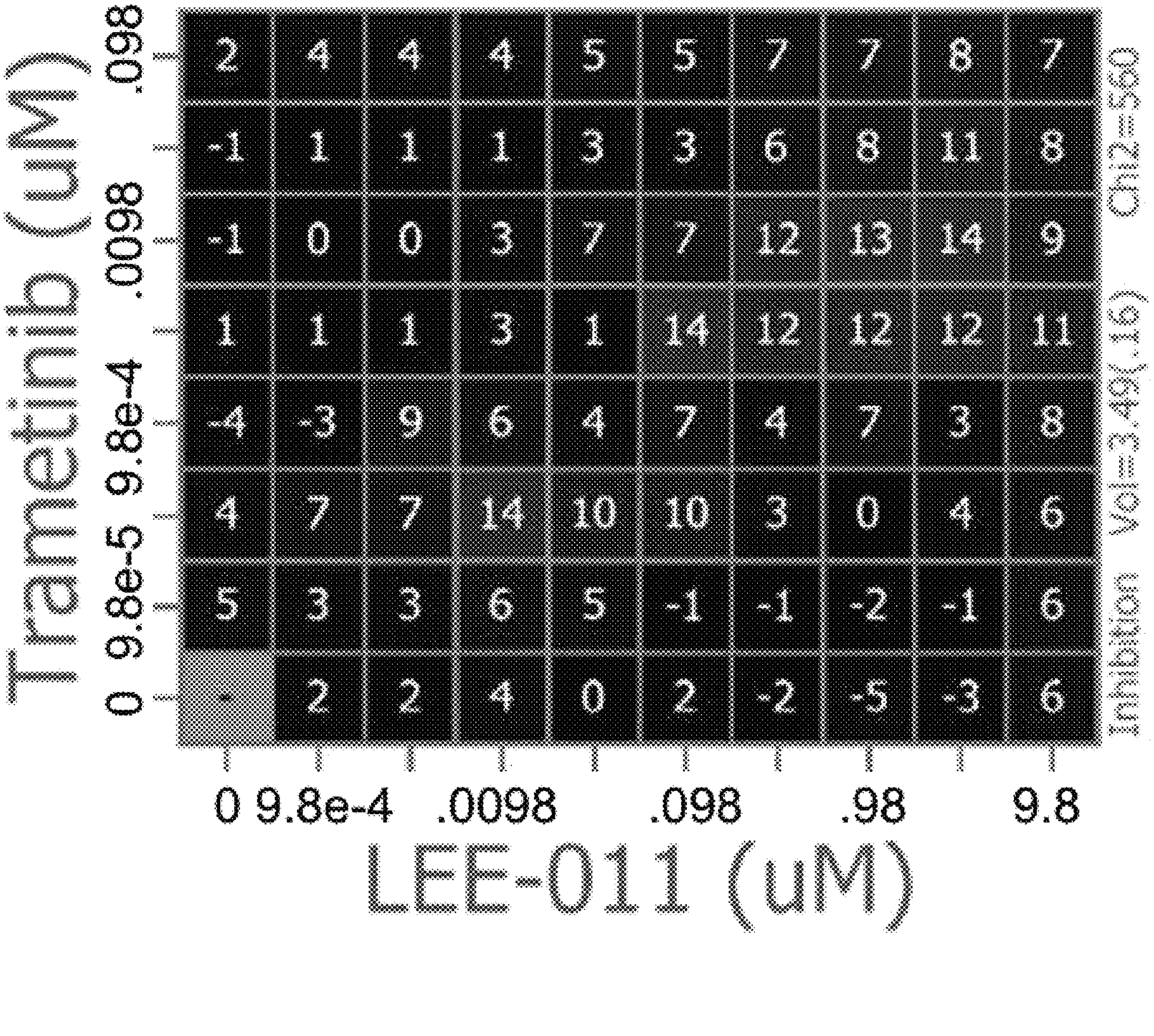
FIG. 8D shows Loewe excess for the combination in 8A and FIG. 8E shows Bliss excess for the combination in 8A.
Figure 8E:
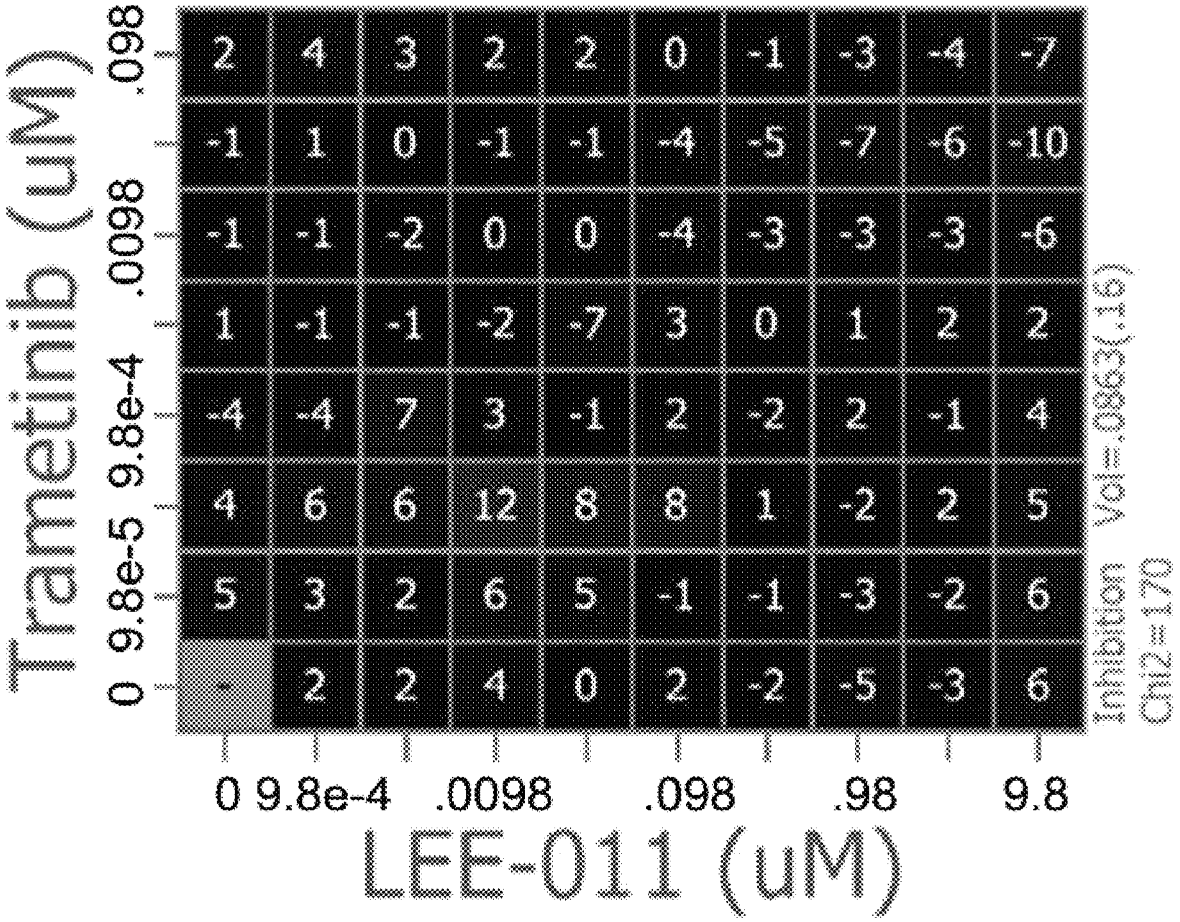
Figure 8F:
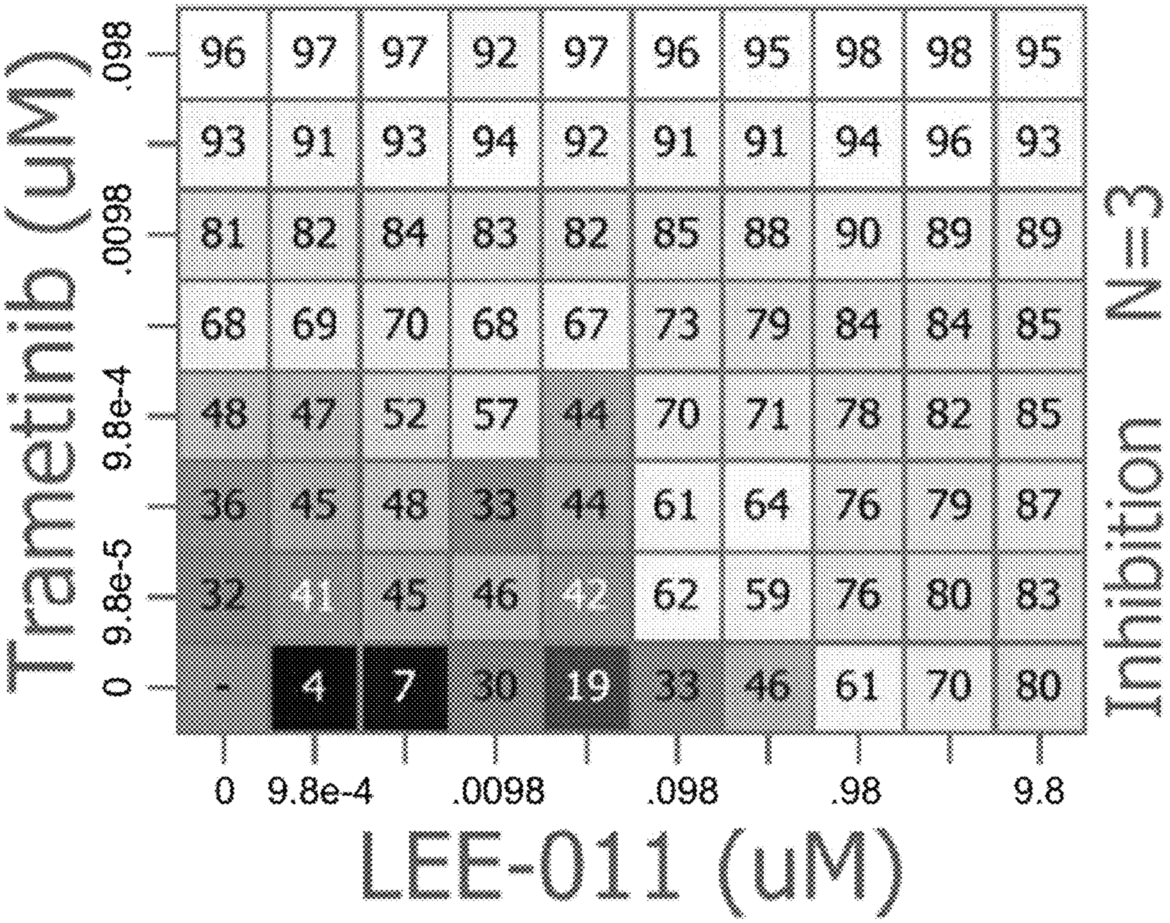
FIG. 8F shows a dose matrix showing inhibition (%) for the combination in H2122 cells.
Figure 8G:
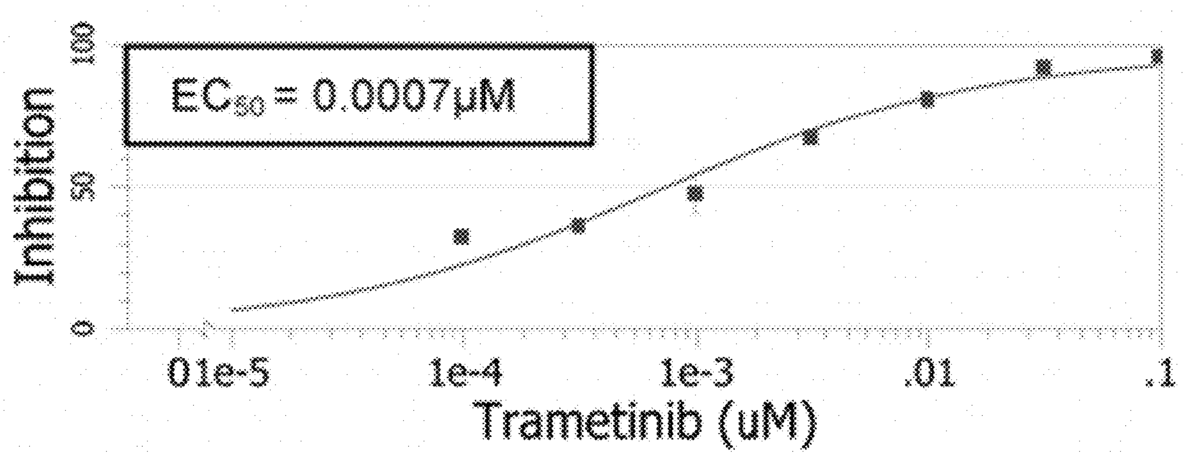
FIG. 8G-FIG. 8H show the results of single agent proliferation assays for the combination in 8F.
Figure 8H:
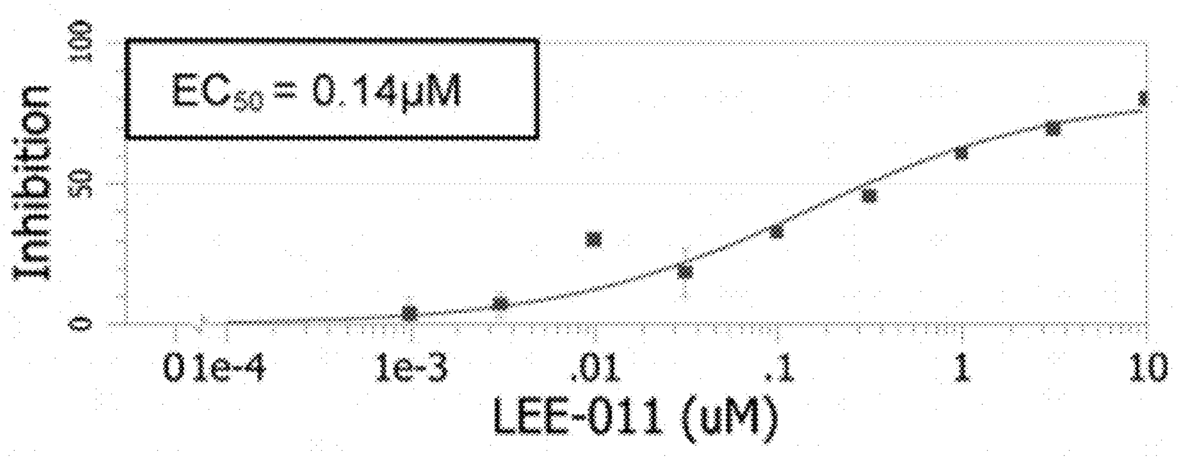
Figure 8I:
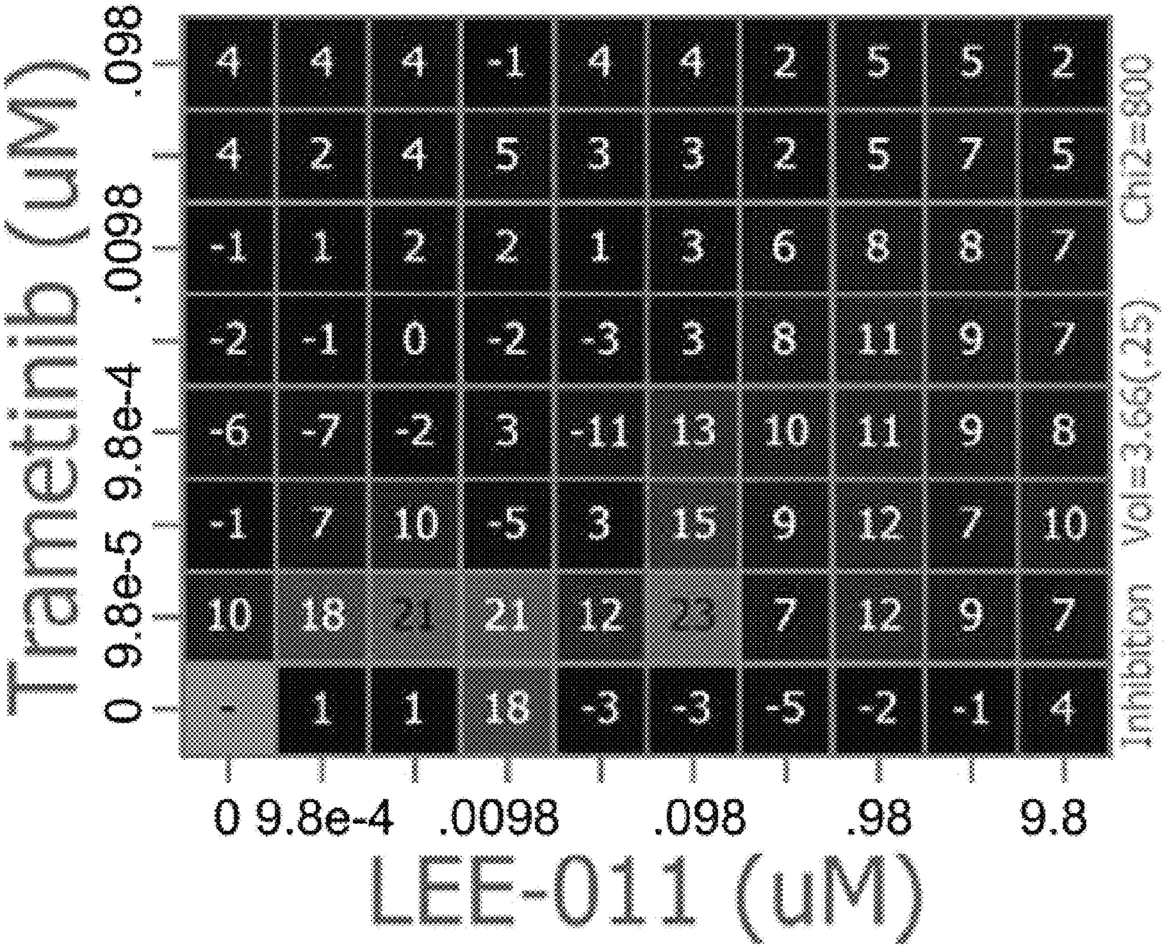
FIG. 8I shows Loewe excess for the combination in 8F and FIG. 8J shows Bliss excess for the combination in 8F.
Figure 8J:
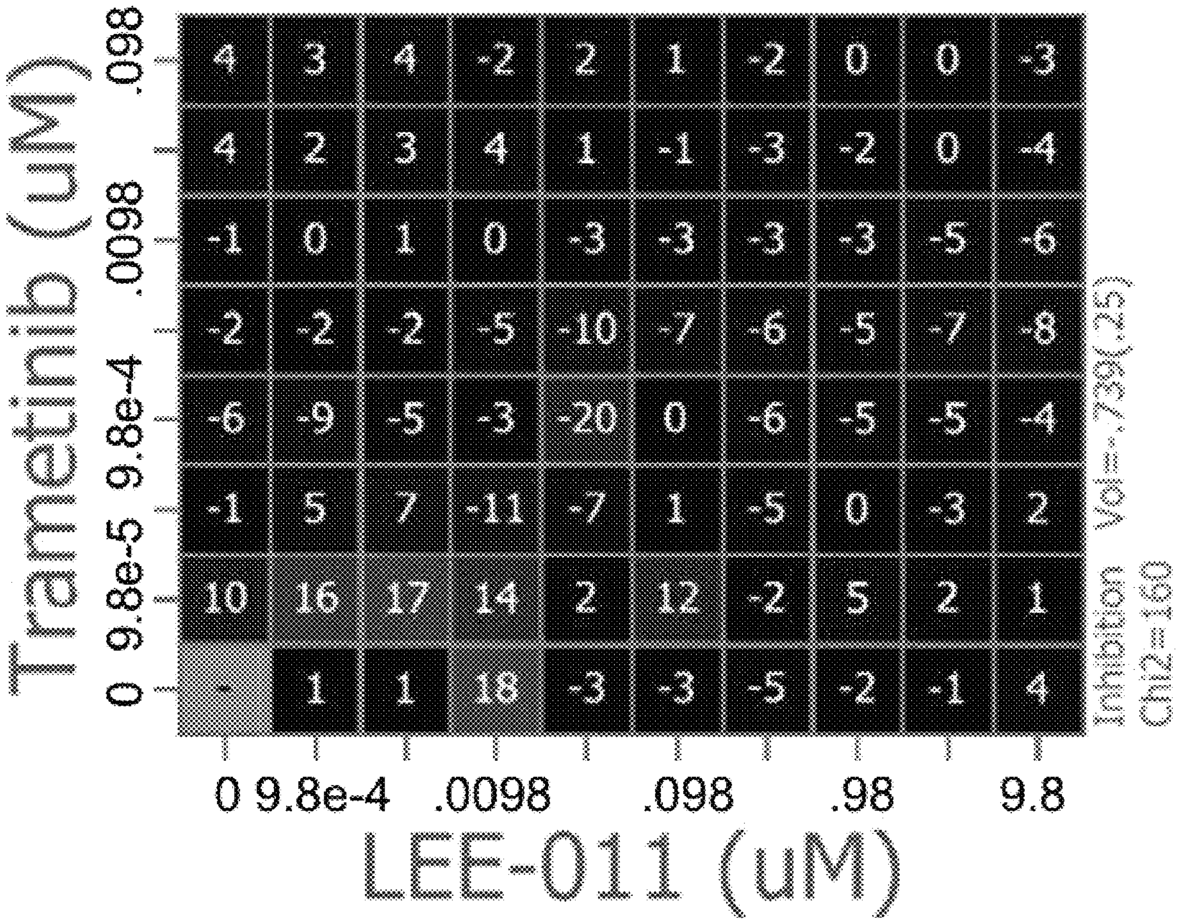
Figure 8K:
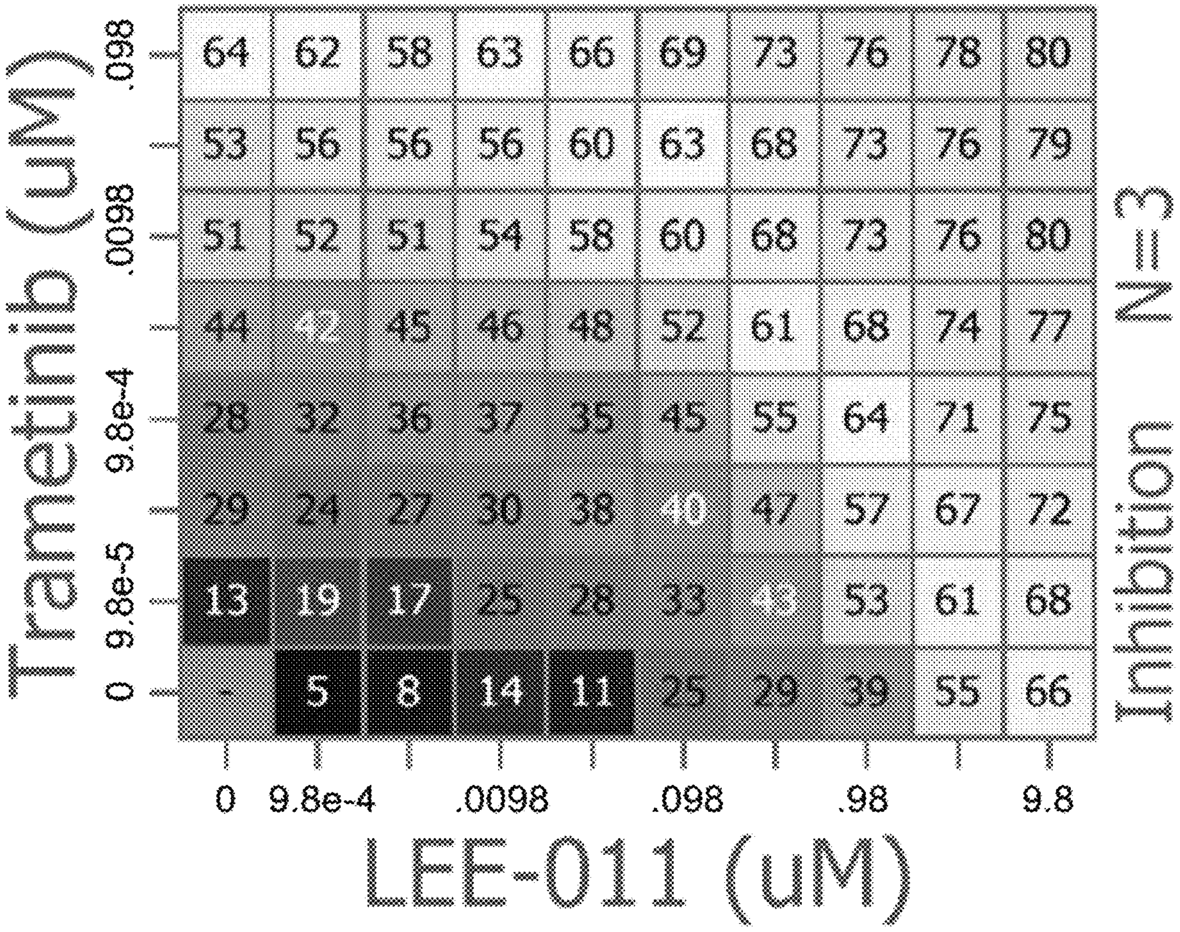
FIG. 8K shows a dose matrix showing inhibition (%) for the combination in H1437 cells.
Figure 8L:
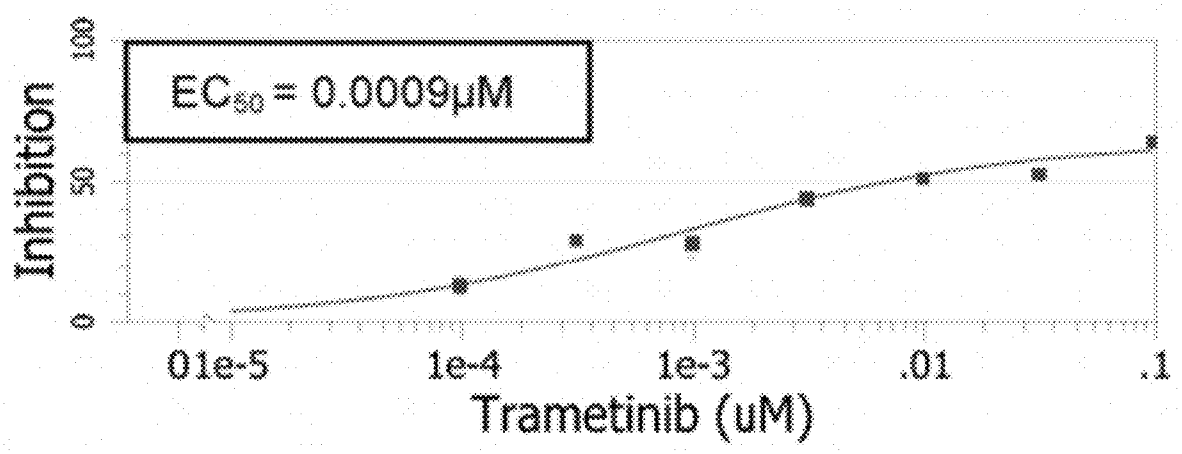
FIG. 8L-FIG. 8M show the results of single agent proliferation assays for the combination in 8K.
Figure 8M:
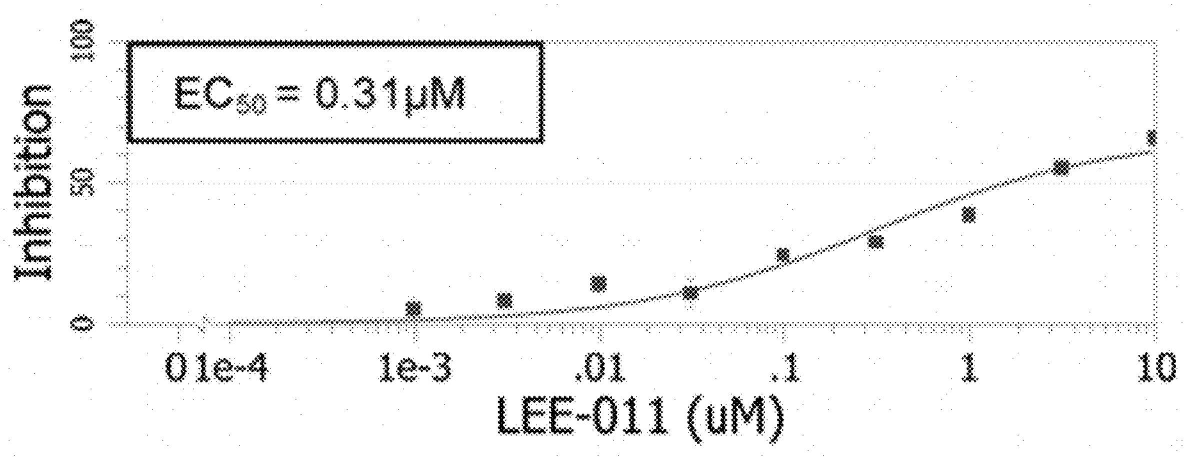
Figure 8N:
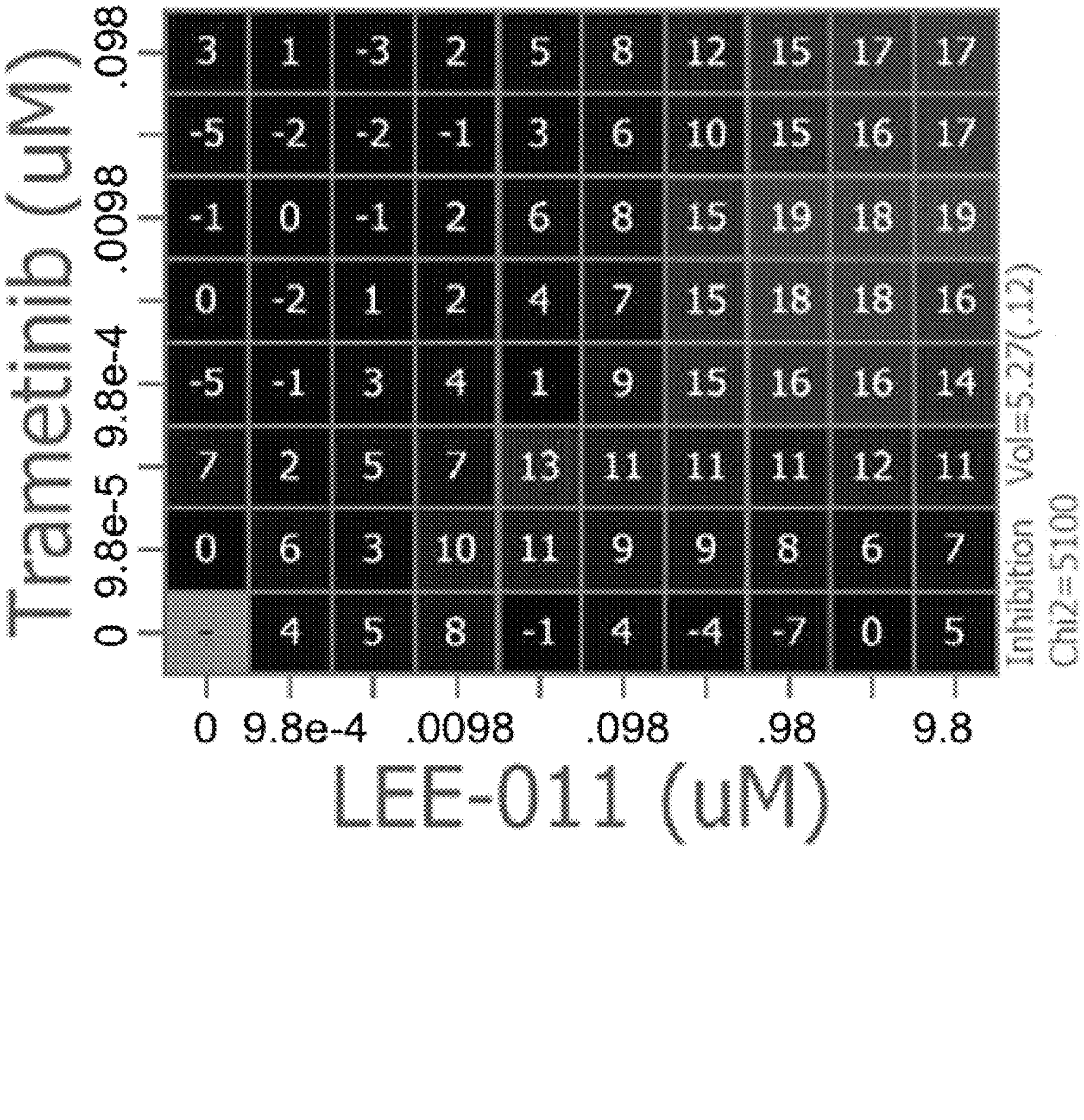
FIG. 8N shows Loewe excess for the combination in 8K and FIG. 8O shows Bliss excess for the combination in 8K.
Figure 8O:
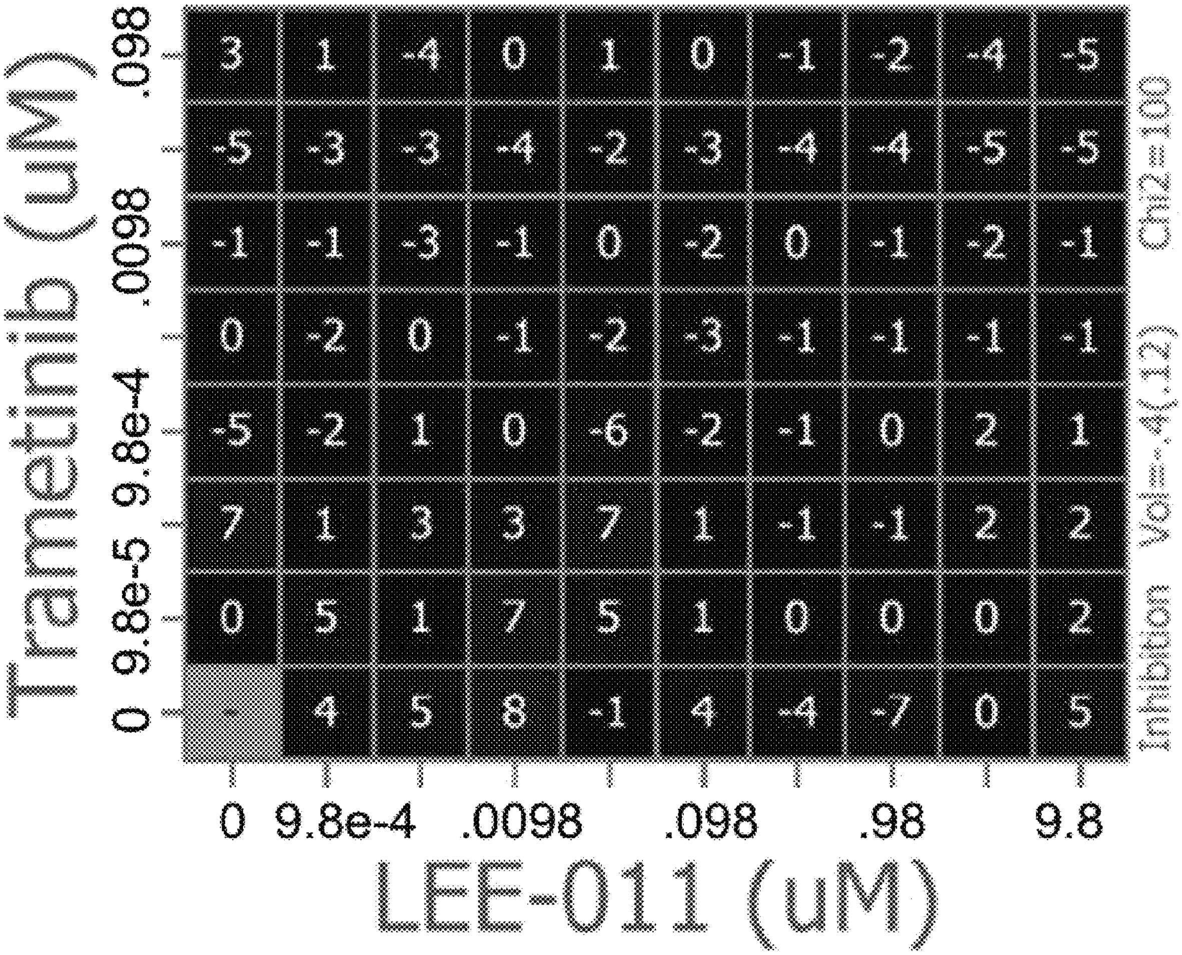
Figure 8P:
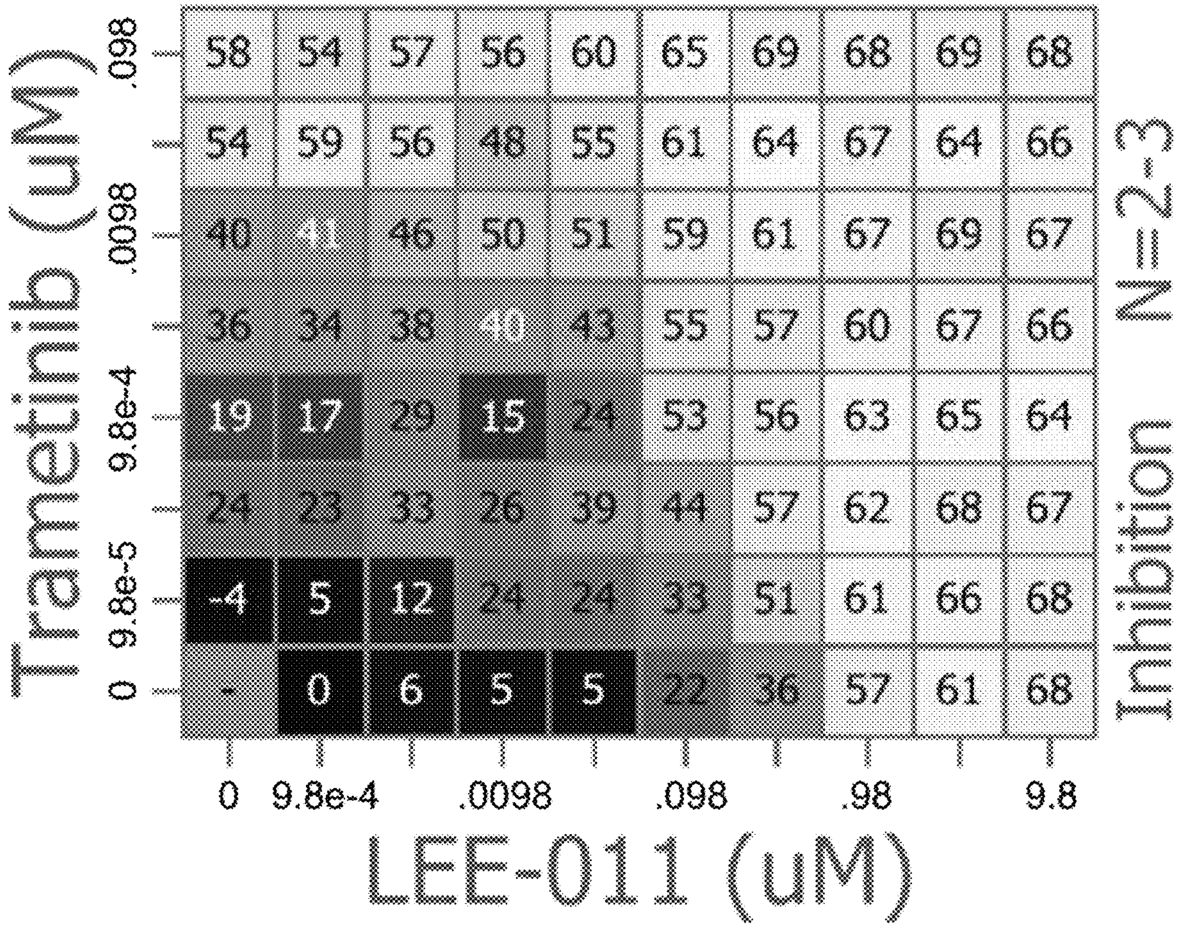
FIG. 8P shows a dose matrix showing inhibition (%) for the combination in H226 cells.
Figure 8Q:
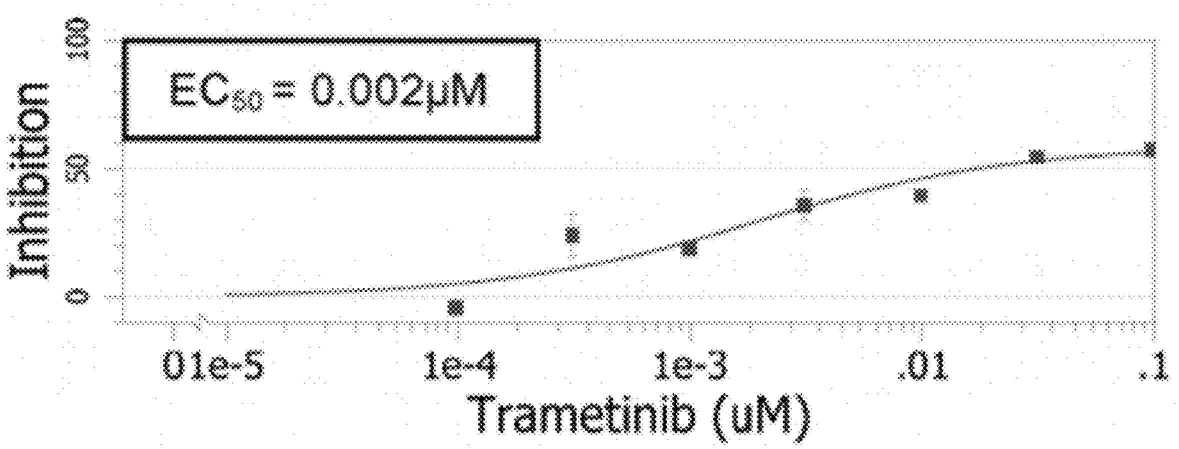
FIG. 8Q-FIG. 8R show the results of single agent proliferation assays for the combination in 8P.
Figure 8R:
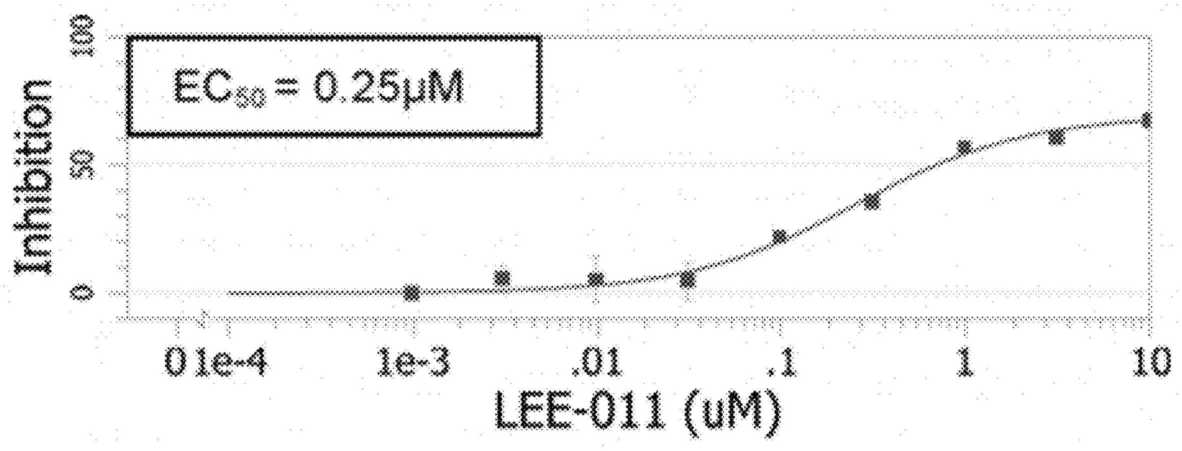
Figure 8S:
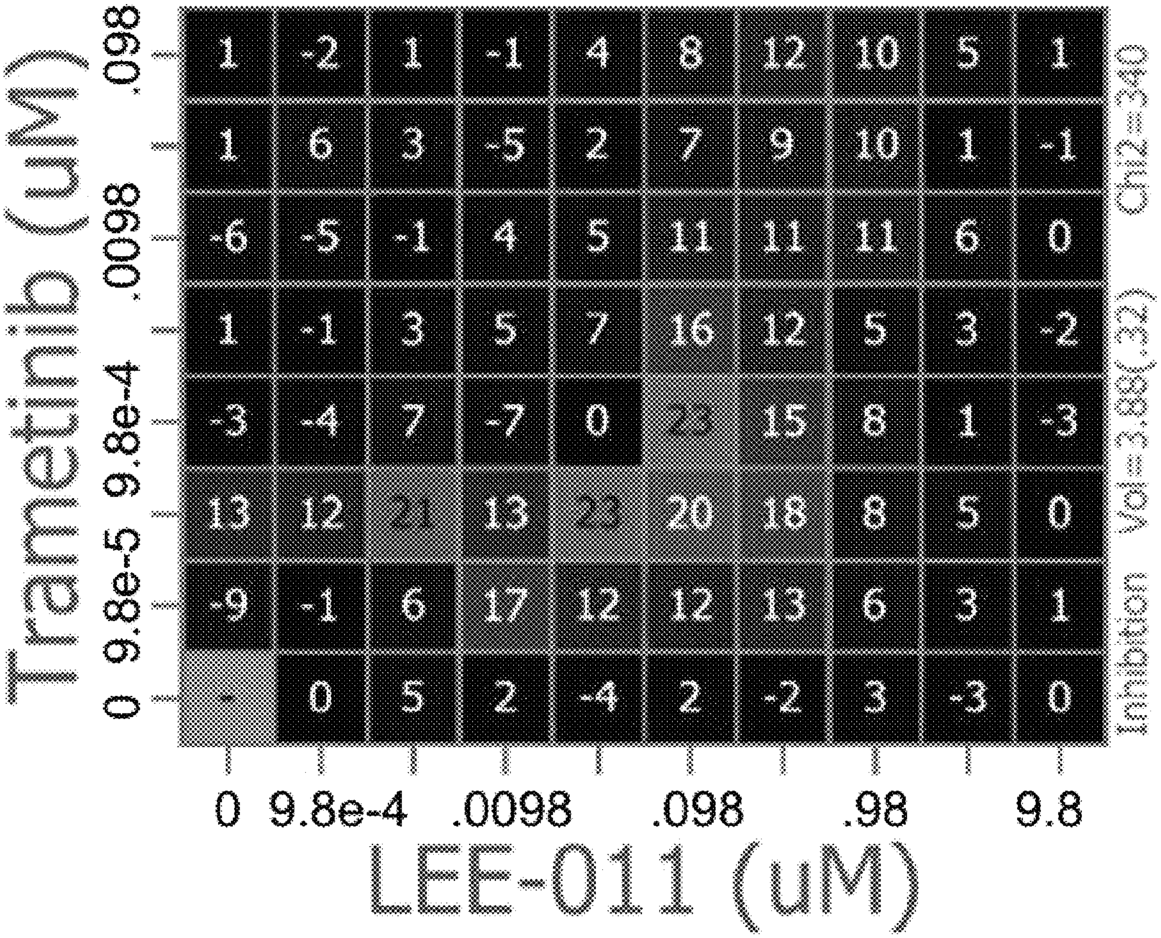
Figure 8T:
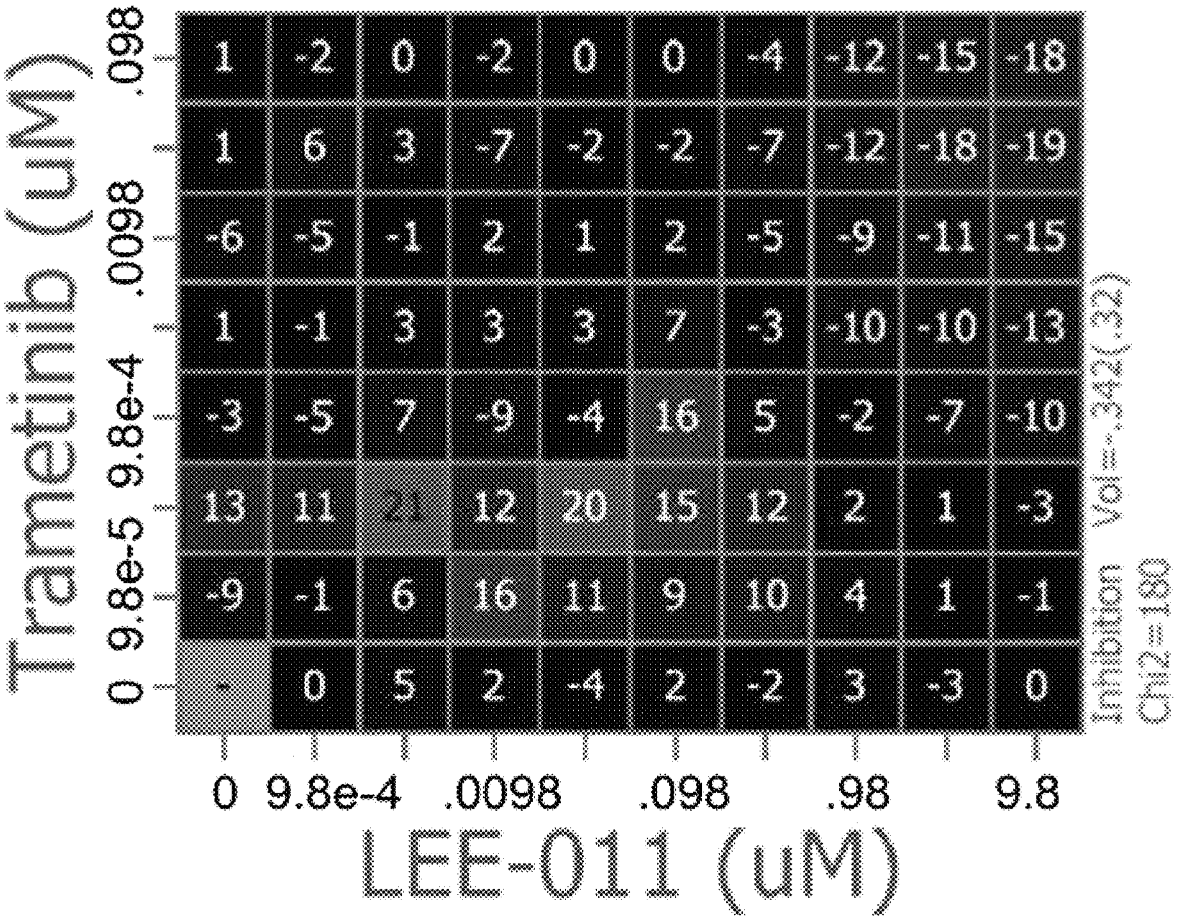

One embodiment of the present invention is a method of treating or ameliorating the effects of a cancer in a subject in need thereof. The method comprises administering to the subject an effective amount of (i) a first anti-cancer agent, which is BVD-523 or a pharmaceutically acceptable salt thereof and (ii) a second anti-cancer agent, which is a CDK inhibitor or a pharmaceutically acceptable salt thereof, to treat or ameliorate the effects of the cancer.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

As used herein, the terms "ameliorate", "ameliorating" and grammatical variations thereof mean to decrease the severity of the symptoms of a disease in a subject.

As used herein, a "subject" is a mammal, preferably, a human. In addition to humans, categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc.

Cancers include both solid and hemotologic cancers. Non-limiting examples of solid cancers include adrenocortical carcinoma, anal cancer, bladder cancer, bone cancer (such as osteosarcoma), brain cancer, breast cancer, carcinoid cancer, carcinoma, cervical cancer, colon cancer, endometrial cancer, esophageal cancer, extrahepatic bile duct cancer, Ewing family of cancers, extracranial germ cell cancer, eye cancer, gallbladder cancer, gastric cancer, germ cell tumor, gestational trophoblastic tumor, head and neck cancer, hypopharyngeal cancer, islet cell carcinoma, kidney cancer, large intestine cancer, laryngeal cancer, leukemia, lip and oral cavity cancer, liver cancer, lung cancer, lymphoma, malignant mesothelioma, Merkel cell carcinoma, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell cancer, pancreatic cancer, paranasal sinus and nasal cavity cancer, parathyroid cancer, penile cancer, pituitary cancer, plasma cell neoplasm, prostate cancer, rhabdomyosarcoma, rectal cancer, renal cell cancer, transitional cell cancer of the renal pelvis and ureter, salivary gland cancer, Sezary syndrome, skin cancers (such as cutaneous t-cell lymphoma, Kaposi's sarcoma, mast cell tumor, and melanoma), small intestine cancer, soft tissue sarcoma, stomach cancer, testicular cancer, thymoma, thyroid cancer, urethral cancer, uterine cancer, vaginal cancer, vulvar cancer, and Wilms' tumor.

Examples of hematologic cancers include, but are not limited to, leukemias, such as adult/childhood acute lymphoblastic leukemia, adult/childhood acute myeloid leukemia, chronic lymphocytic leukemia, chronic myelogenous leukemia, and hairy cell leukemia, lymphomas, such as AIDS-related lymphoma, cutaneous T-cell lymphoma, adult/childhood Hodgkin lymphoma, mycosis fungoides, adult/childhood non-Hodgkin lymphoma, primary central nervous system lymphoma, Sezary syndrome, cutaneous T-cell lymphoma, and Waldenstrom macroglobulinemia, as well as other proliferative disorders such as chronic myeloproliferative disorders, Langerhans cell histiocytosis, multiple myeloma/plasma cell neoplasm, myelodysplastic syndromes, and myelodysplastic/myeloproliferative neoplasms. A preferred set of cancers that may be treated according to the present invention include neuroblastoma, leukemia, lymphoma, liver cancer, lung cancer, skin cancer, testicular cancer, and thyroid cancer. Preferably, the cancer is melanoma.

In the present invention, BVD-523 is an ERK1/2 inhibitor. BVD-523 is a compound according to formula (I):

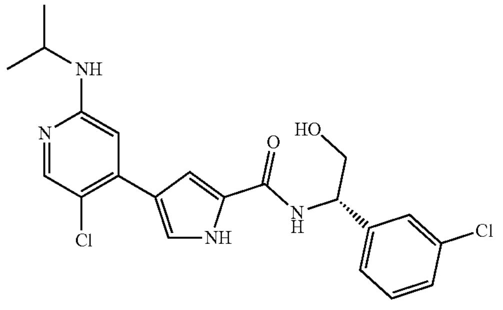 [SMILES: CC(C)Nc1cc(-c2c[nH]c(C(=O)N[C@H](CO)c3cccc(Cl)c3)c2)c(Cl)cn1]

and pharmaceutically acceptable salts thereof. BVD-523 may be synthesized according to the methods disclosed in, e.g., U.S. Pat. No. 7,354,939. BVD-523's mechanism of action is believed to be, inter alia, unique and distinct from certain other ERK1/2 inhibitors, such as SCH772984. For example, SCH772984 inhibits autophosphorylation of ERK (Morris et al., 2013), whereas BVD-523 allows for the autophosphorylation of ERK while still inhibiting ERK. (See, e.g., FIG. 1). This is important, inter alia, because it is believed that the properties of BVD-523 allows for dissociation of multiple signaling pathways, for example, by controlling cell proliferation without substantially affecting cell death.

As used herein, "CDK" means a family of protein kinases that regulate the cell cycle. Known CDKs include cdk1, cdk2, ckd3, ckd4, cdk5, cdk6, cdk7, cdk8, cdk9, cdk10, and cdk11. A "CDK inhibitor" means those substances that (i) directly interact with CDK, e.g. by binding to CDK and (ii) decrease the expression or the activity of CDK.

Non-limiting examples of CDK inhibitors according to the present invention include 2-Hydroxybohemine, 3-ATA, 5-Iodo-Indirubin-3'-monoxime, 9-Cyanopaullone, Aloisine A, Alsterpaullone 2-Cyanoethyl, alvocidib (Sanofi), AM-5992 (Amgen), Aminopurvalanol A, Arcyriaflavin A, AT-7519 (Astex Pharmaceuticals), AZD 5438 (CAS #602306-29-6), BMS-265246 (CAS #582315-72-8), BS-181 (CAS #1092443-52-1), Butyrolactone I (CAS #87414-49-1), Cdk/Crk Inhibitor (CAS #784211-09-2), Cdk1/5 Inhibitor (CAS #40254-90-8), Cdk2 Inhibitor II (CAS #222035-13-4), Cdk2 Inhibitor IV, NU6140 (CAS #444723-13-1), Cdk4 Inhibitor (CAS #546102-60-7), Cdk4 Inhibitor III (CAS #265312-55-8), Cdk4/6 Inhibitor IV (CAS #359886-84-3), Cdk9 Inhibitor II (CAS #140651-18-9), CGP 74514A, CR8, CYC-065 (Cyclacel), dinaciclib (Ligand), (R)-DRF053 dihydrochloride (CAS #1056016-06-8), Fascaplysin, Flavopiridol, Hygrolidin, Indirubin, LEE-011 (Astex Pharmaceuticals), LY-2835219 (Eli Lilly), milciclib maleate (Nerviano Medical Sciences), MM-D37K (Maxwell Biotech), N9-Isopropyl-olomoucine, NSC 625987 (CAS #141992-47-4), NU2058 (CAS #161058-83-9), NU6102 (CAS #444722-95-6), Olomoucine, ON-108600 (Onconova), ON-123300 (Onconova), Oxindole I, P-1446-05 (Piramal), P-276-00 (Piramal), palbociclib (Pfizer), PHA-767491 (CAS #845714-00-3), PHA-793887 (CAS #718630-59-2), PHA-848125 (CAS #802539-81-7), Purvalanol A, Purvalanol B, R547 (CAS #741713-40-6), RO-3306 (CAS #872573-93-8), Roscovitine, SB-1317 (SBIO), SCH 900776 (CAS #891494-63-6), SEL-120 (Selvita), seliciclib (Cyclacel), SNS-032 (CAS #345627-80-7), SU9516 (CAS #377090-84-1), WHI-P180 (CAS #211555-08-7), pharmaceutically acceptable salts thereof, and combinations thereof. Preferably, the CDK inhibitor is selected from the group consisting of dinaciclib, palbociclib, pharmaceutically acceptable salts thereof, and combinations thereof.

In another aspect of this embodiment, the subject with cancer has a somatic mutation in a MAPK pathway node, including RAS, RAF, MEK and ERK. As used herein, "somatic mutation" means a change occurring in any cell that is not destined to become a germ cell. The mutation may be a substitution, deletion, insertion, or a fusion. Preferably, the somatic mutation is a mutation in H-RAS, N-RAS, or K-RAS. More preferably, the cancer has a somatic N-RAS mutation. Table 1 shows the SEQ ID Nos. of representative nucleic acid and amino acid sequences of wild type N-RAS from various animals. These sequences may be used in methods for identifying subjects with a mutant N-RAS genotype (such as in the methods set forth below).

TABLE 1

| N-RAS sequences | | | |
|---|---|---|---|
| SEQ ID No. | polypeptide or nucleic acid sequence | Organism | Other Information |
| 1 | nucleic acid | human | |
| 2 | Polypeptide | human | |
| 3 | nucleic acid | rat (*Rattus norvegicus*) | |
| 4 | Polypeptide | rat (*Rattus norvegicus*) | |
| 5 | nucleic acid | mouse, *Mus musculus* | |
| 6 | Polypeptide | mouse, *Mus musculus* | |
| 7 | nucleic acid | guinea pig, *Cavia porcellus* | |
| 8 | Polypeptide | guinea pig, *Cavia porcellus* | |
| 9 | nucleic acid | guinea pig, *Cavia porcellus* | variant X1 |
| 10 | Polypeptide | guinea pig, *Cavia porcellus* | variant X1 |
| 11 | nucleic acid | dog, *Canis lupus familiaris* | |
| 12 | Polypeptide | dog, *Canis lupus familiaris* | |
| 13 | nucleic acid | cat, *Felis catus* | |
| 14 | Polypeptide | cat, *Felis catus* | |
| 15 | nucleic acid | cow, *Bos taurus* | |
| 16 | Polypeptide | cow, *Bos taurus* | |
| 17 | nucleic acid | chicken, *Gallus gallus* | |
| 18 | Polypeptide | chicken, *Gallus gallus* | |

Methods for identifying mutations in nucleic acids, such as the above identified RAS genes, are known in the art. Nucleic acids may be obtained from biological samples. In the present invention, biological samples include, but are not limited to, blood, plasma, urine, skin, saliva, and biopsies. Biological samples are obtained from a subject by routine procedures and methods which are known in the art.

Non-limiting examples of methods for identifying mutations include PCR, sequencing, hybrid capture, in-solution capture, molecular inversion probes, fluorescent in situ hybridization (FISH) assays, and combinations thereof.

Various sequencing methods are known in the art. These include, but are not limited to, Sanger sequencing (also referred to as dideoxy sequencing) and various sequencing-by-synthesis (SBS) methods as disclosed in, e.g., Metzker 2005, sequencing by hybridization, by ligation (for example, WO 2005021786), by degradation (for example, U.S. Pat. Nos. 5,622,824 and 6,140,053) and nanopore sequencing (which is commercially available from Oxford Nanopore Technologies, UK). In deep sequencing techniques, a given nucleotide in the sequence is read more than once during the sequencing process. Deep sequencing techniques are disclosed in e.g., U.S. Patent Publication No. 20120264632 and International Patent Publication No. WO2012125848.

PCR-based methods for detecting mutations are known in the art and employ PCR amplification, where each target sequence in the sample has a corresponding pair of unique, sequence-specific primers. For example, the polymerase chain reaction-restriction fragment length polymorphism (PCR-RFLP) method allows for rapid detection of mutations after the genomic sequences are amplified by PCR. The mutation is discriminated by digestion with specific restriction endonucleases and is identified by electrophoresis. See, e.g., Ota et al., 2007. Mutations may also be detected using real time PCR. See, e.g., International Application publication No. WO2012046981.

Hybrid capture methods are known in the art and are disclosed in e.g., U.S. Patent Publication No. 20130203632 and U.S. Pat. Nos. 8,389,219 and 8,288,520. These methods are based on the selective hybridization of the target genomic regions to user-designed oligonucleotides. The hybridization can be to oligonucleotides immobilized on high or low density microarrays (on-array capture), or solution-phase hybridization to oligonucleotides modified with a ligand (e.g. biotin) which can subsequently be immobilized to a solid surface, such as a bead (in-solution capture).

Molecular Inversion Probe (MIP) techniques are known in the art and are disclosed in e.g., Absalan et al., 2008. This method uses MIP molecules, which are special "padlock" probes (Nilsson et al, 1994) for genotyping. A MIP molecule is a linear oligonucleotide that contains specific regions, universal sequences, restriction sites and a Tag (index) sequence (16-22 bp). A MIP hybridizes directly around the genetic marker/SNP of interest. The MIP method may also use a number of "padlock" probe sets that hybridize to genomic DNA in parallel (Hardenbol et al., 2003). In case of a perfect match, genomic homology regions are ligated by undergoing an inversion in configuration (as suggested by the name of the technique) and creating a circular molecule. After the first restriction, all molecules are amplified with universal primers. Amplicons are restricted again to ensure short fragments for hybridization on a microarray. Generated short fragments are labeled and, through a Tag sequence, hybridized to a cTag (complementary strand for index) on an array. After the formation of Tag-cTag duplex, a signal is detected.

In another aspect of this embodiment, the method further comprises administering to the subject at least one additional therapeutic agent effective for treating or ameliorating the effects of the cancer. The additional therapeutic agent may be selected from the group consisting of an antibody or fragment thereof, a cytotoxic agent, a toxin, a radionuclide, an immunomodulator, a photoactive therapeutic agent, a radiosensitizing agent, a hormone, an anti-angiogenesis agent, and combinations thereof.

As used herein, an "antibody" encompasses naturally occurring immunoglobulins as well as non-naturally occurring immunoglobulins, including, for example, single chain antibodies, chimeric antibodies (e.g., humanized murine antibodies), and heteroconjugate antibodies (e.g., bispecific antibodies). Fragments of antibodies include those that bind antigen, (e.g., Fab', F $(ab')_2$, Fab, Fv, and rIgG). See also, e.g., Pierce Catalog and Handbook, 1994-1995 (Pierce Chemical Co., Rockford, Ill.); Kuby, J., Immunology, 3rd Ed., W.H. Freeman & Co., New York (1998). The term antibody also includes bivalent or bispecific molecules, diabodies, triabodies, and tetrabodies. The term "antibody" further includes both polyclonal and monoclonal antibodies.

Examples of therapeutic antibodies that may be used in the present invention include rituximab (Rituxan), Cetuximab (Erbitux), bevacizumab (Avastin), and Ibritumomab (Zevalin).

Cytotoxic agents according to the present invention include DNA damaging agents, antimetabolites, anti-microtubule agents, antibiotic agents, etc. DNA damaging agents include alkylating agents, platinum-based agents, intercalating agents, and inhibitors of DNA replication. Non-limiting examples of DNA alkylating agents include cyclophosphamide, mechlorethamine, uramustine, melphalan, chlorambucil, ifosfamide, carmustine, lomustine, streptozocin, busulfan, temozolomide, pharmaceutically acceptable salts thereof, prodrugs, and combinations thereof. Non-limiting examples of platinum-based agents include cisplatin, carboplatin, oxaliplatin, nedaplatin, satraplatin, triplatin tetranitrate, pharmaceutically acceptable salts thereof, prodrugs, and combinations thereof. Non-limiting examples of intercalating agents include doxorubicin, daunorubicin, idarubicin, mitoxantrone, pharmaceutically acceptable salts thereof, prodrugs, and combinations thereof. Non-limiting examples of inhibitors of DNA replication include irinotecan, topotecan, amsacrine, etoposide, etoposide phosphate, teniposide, pharmaceutically acceptable salts thereof, prodrugs, and combinations thereof. Antimetabolites include folate antagonists such as methotrexate and premetrexed, purine antagonists such as 6-mercaptopurine, dacarbazine, and fludarabine, and pyrimidine antagonists such as 5-fluorouracil, arabinosylcytosine, capecitabine, gemcitabine, decitabine, pharmaceutically acceptable salts thereof, prodrugs, and combinations thereof. Anti-microtubule agents include without limitation *vinca* alkaloids, paclitaxel (Taxol®), docetaxel (Taxotere®), and ixabepilone (Ixempra®). Antibiotic agents include without limitation actinomycin, anthracyclines, valrubicin, epirubicin, bleomycin, plicamycin, mitomycin, pharmaceutically acceptable salts thereof, prodrugs, and combinations thereof.

Cytotoxic agents according to the present invention also include an inhibitor of the PI3K/Akt pathway. Non-limiting examples of an inhibitor of the PI3K/Akt pathway include A-674563 (CAS #552325-73-2), AGL 2263, AMG-319 (Amgen, Thousand Oaks, CA), AS-041164 (5-benzo[1,3] dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, Genentech (Roche Holdings Inc., South San Francisco, CA), BML-257 (CAS #32387-96-5), CAL-120 (Gilead Sciences, Foster City, CA), CAL-129 (Gilead Sciences), CAL-130 (Gilead Sciences), CAL-253 (Gilead Sciences), CAL-263 (Gilead Sciences), CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432 (Chroma Therapeutics, Ltd., Abingdon, UK), FPA 124 (CAS #902779-59-3), GS-1101 (CAL-101) (Gilead Sciences), GSK 690693 (CAS #937174-76-0), H-89 (CAS #127243-85-0), Honokiol, IC87114 (Gilead Science), IPI-145 (Intellikine Inc.), KAR-4139 (Karus Therapeutics, Chilworth, UK), KAR-4141 (Karus Therapeutics), KIN-1 (Karus Therapeutics), KT 5720 (CAS ##108068-98-0), Miltefosine, MK-2206 dihydrochloride (CAS #1032350-13-2), ML-9 (CAS #105637-50-1), Naltrindole Hydrochloride, OXY-111A (NormOxys Inc., Brighton, MA), perifosine, PHT-427 (CAS #1191951-57-1), PI3 kinase delta inhibitor, Merck KGaA (Merck & Co., Whitehouse Station, NJ), PI3 kinase delta inhibitors, Genentech (Roche Holdings Inc.), PI3 kinase delta inhibitors, Incozen (Incozen Therapeutics, Pvt. Ltd., Hydrabad, India), PI3 kinase delta inhibitors-2, Incozen (Incozen Therapeutics), PI3 kinase inhibitor, Roche-4 (Roche Holdings Inc.), PI3 kinase inhibitors, Roche (Roche Holdings Inc.), PI3 kinase inhibitors, Roche-5 (Roche Holdings Inc.), PI3-alpha/delta inhibitors, Pathway Therapeutics (Pathway Therapeutics Ltd., South San Francisco, CA), PI3-delta inhibitors, Cellzome (Cellzome AG, Heidelberg, Germany), PI3-delta inhibitors, Intellikine (Intellikine Inc., La Jolla, CA), PI3-delta inhibitors, Pathway Therapeutics-1 (Pathway Therapeutics Ltd.), PI3-delta inhibitors, Pathway Therapeutics-2 (Pathway Therapeutics Ltd.), PI3-delta/gamma inhibitors, Cellzome (Cellzome AG), PI3-delta/gamma inhibitors, Cellzome (Cellzome AG), PI3-delta/gamma inhibitors, Intellikine (Intellikine Inc.), PI3-delta/gamma inhibitors, Intellikine (Intellikine Inc.), PI3-delta/gamma inhibitors, Pathway Therapeutics (Pathway Therapeutics Ltd.), PI3-delta/gamma inhibitors, Pathway Therapeutics (Pathway Therapeutics Ltd.), PI3-gamma inhibitor Evotec (Evotec), PI3-gamma inhibitor, Cellzome (Cellzome AG), PI3-gamma inhibitors, Pathway Therapeutics (Pathway Therapeutics Ltd.), PI3K delta/gamma inhibitors, Intellikine-1 (Intellikine Inc.), PI3K delta/gamma inhibitors, Intellikine-1 (Intellikine Inc.), pictilisib (Roche Holdings Inc.), PIK-90 (CAS #677338-12-4), SC-103980 (Pfizer, New York, NY), SF-1126 (Semafore Pharmaceuticals, Indianapolis, IN), SH-5, SH-6, Tetrahydro Curcumin, TG100-115 (Targegen Inc., San Diego, CA), Triciribine, X-339 (Xcovery, West Palm Beach, FL), XL-499 (Evotech, Hamburg, Germany), pharmaceutically acceptable salts thereof, and combinations thereof.

In the present invention, the term "toxin" means an antigenic poison or venom of plant or animal origin. An example is diphtheria toxin or portions thereof.

In the present invention, the term "radionuclide" means a radioactive substance administered to the patient, e.g., intravenously or orally, after which it penetrates via the patient's normal metabolism into the target organ or tissue, where it delivers local radiation for a short time. Examples of radionuclides include, but are not limited to, I-125, At-211, Lu-177, Cu-67, I-131, Sm-153, Re-186, P-32, Re-188, In-114m, and Y-90.

In the present invention, the term "immunomodulator" means a substance that alters the immune response by augmenting or reducing the ability of the immune system to produce antibodies or sensitized cells that recognize and react with the antigen that initiated their production. Immunomodulators may be recombinant, synthetic, or natural preparations and include cytokines, corticosteroids, cytotoxic agents, thymosin, and immunoglobulins. Some immunomodulators are naturally present in the body, and certain of these are available in pharmacologic preparations. Examples of immunomodulators include, but are not limited to, granulocyte colony-stimulating factor (G-CSF), interferons, imiquimod and cellular membrane fractions from bacteria, IL-2, IL-7, IL-12, CCL3, CCL26, CXCL7, and synthetic cytosine phosphate-guanosine (CpG).

In the present invention, the term "photoactive therapeutic agent" means compounds and compositions that become active upon exposure to light. Certain examples of photoactive therapeutic agents are disclosed, e.g., in U.S. Patent Application Ser. No. 2011/0152230 A1, "Photoactive Metal Nitrosyls For Blood Pressure Regulation And Cancer Therapy."

In the present invention, the term "radiosensitizing agent" means a compound that makes tumor cells more sensitive to radiation therapy. Examples of radiosensitizing agents include misonidazole, metronidazole, tirapazamine, and trans sodium crocetinate.

In the present invention, the term "hormone" means a substance released by cells in one part of a body that affects cells in another part of the body. Examples of hormones include, but are not limited to, prostaglandins, leukotrienes, prostacyclin, thromboxane, amylin, antimullerianormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, and calcidiol.

Some compounds interfere with the activity of certain hormones or stop the production of certain hormones. These hormone-interfering compounds include, but are not limited to, tamoxifen (Nolvadex®), anastrozole (Arimidex®), letrozole (Femara®), and fulvestrant (Faslodex®). Such compounds are also within the meaning of hormone in the present invention.

As used herein, an "anti-angiogenesis" agent means a substance that reduces or inhibits the growth of new blood vessels, such as, e.g., an inhibitor of vascular endothelial growth factor (VEGF) and an inhibitor of endothelial cell migration. Anti-angiogenesis agents include without limitation 2-methoxyestradiol, angiostatin, bevacizumab, cartilage-derived angiogenesis inhibitory factor, endostatin, IFN-α, IL-12, itraconazole, linomide, platelet factor-4, prolactin, SU5416, suramin, tasquinimod, tecogalan, tetrathiomolybdate, thalidomide, thrombospondin, thrombospondin, TNP-470, ziv-aflibercept, pharmaceutically acceptable salts thereof, prodrugs, and combinations thereof.

In an additional aspect of this embodiment, administration of the first and second anti-cancer agents provides a synergistic effect compared to administration of either anti-cancer agent alone. As used herein, "synergistic" means more than additive. Synergistic effects may be measured by various assays known in the art, including but not limited to those disclosed herein, such as the excess over bliss assay.

Another embodiment of the present invention is a method of treating or ameliorating the effects of a cancer in a subject in need thereof. The method comprises administering to the subject an effective amount of (i) a first anti-cancer agent, which is BVD-523 or a pharmaceutically acceptable salt thereof and (ii) a second anti-cancer agent, which is selected from the group consisting of dinaciclib, palbociclib, and pharmaceutically acceptable salts thereof, to treat or ameliorate the effects of the cancer.

Suitable and preferred subjects are as disclosed herein. In this embodiment, the methods may be used to treat the cancers disclosed above, including those cancers with the mutational backgrounds identified above. Methods of identifying such mutations are also as set forth above.

In one aspect of this embodiment, the BVD-523 or a pharmaceutically acceptable salt thereof is administered in the form of a pharmaceutical composition further comprising a pharmaceutically acceptable carrier or diluent.

In an additional aspect of this embodiment, the dinaciclib, palbociclib or a pharmaceutically acceptable salt thereof is administered in the form of a pharmaceutical composition further comprising a pharmaceutically acceptable carrier or diluent.

In another aspect of this embodiment, the method further comprises administering to the subject at least one additional therapeutic agent, preferably an inhibitor of the PI3K/Akt pathway, as disclosed herein.

In another aspect of this embodiment, administration of the first and second anti-cancer agents provides a synergistic effect compared to administration of either anti-cancer agent alone.

An additional embodiment of the present invention is a method of effecting cancer cell death. The method comprises contacting the cancer cell with an effective amount of (i) a first anti-cancer agent, which is BVD-523 or a pharmaceutically acceptable salt thereof and (ii) a second anti-cancer agent, which is a CDK inhibitor or a pharmaceutically acceptable salt thereof. In this embodiment, "contacting" means bringing BVD-523, the CDK inhibitors, and optionally one or more additional therapeutic agents into close proximity to the cancer cells. This may be accomplished using conventional techniques of drug delivery to mammals or in the in vitro situation by, e.g., providing BVD-523, the CDK inhibitors, and optionally other therapeutic agents to a culture media in which the cancer cells are located.

Suitable and preferred CDK inhibitors are as disclosed herein. In this embodiment, effecting cancer cell death may be accomplished in cancer cells having various mutational backgrounds and/or that are characterized as disclosed above. Methods of identifying such mutations are also as set forth above.

The methods of this embodiment, which may be carried out in vitro or in vivo, may be used to effect cancer cell death, by e.g., killing cancer cells, in cells of the types of cancer disclosed herein.

In one aspect of this embodiment, the cancer cell is a mammalian cancer cell. Preferably, the mammalian cancer cell is obtained from a mammal selected from the group consisting of humans, primates, farm animals, and domestic animals. More preferably, the mammalian cancer cell is a human cancer cell.

In another aspect of this embodiment, the method further comprises contacting the cancer cell with at least one additional therapeutic agent, preferably an inhibitor of the PI3K/Akt pathway, as disclosed herein.

In a further aspect of this embodiment, contacting the cancer cell with the first and second anti-cancer agents provides a synergistic effect compared to contacting the cancer cell with either anti-cancer agent alone.

Another embodiment of the present invention is a kit for treating or ameliorating the effects of a cancer in a subject in need thereof. The kit comprises an effective amount of (i) a first anti-cancer agent, which is BVD-523 or a pharmaceutically acceptable salt thereof and (ii) a second anti-cancer agent, which is a CDK inhibitor or a pharmaceutically acceptable salt thereof, packaged together with instructions for their use.

The kits may also include suitable storage containers, e.g., ampules, vials, tubes, etc., for each pharmaceutical composition and other reagents, e.g., buffers, balanced salt solutions, etc., for use in administering the pharmaceutical compositions to subjects. The pharmaceutical compositions and other reagents may be present in the kits in any convenient form, such as, e.g., in a solution or in a powder form. The kits may further include instructions for use of the pharmaceutical compositions. The kits may further include a packaging container, optionally having one or more partitions for housing the pharmaceutical composition and other optional reagents.

For use in the kits of the invention, suitable and preferred CDK inhibitors and subjects are as disclosed herein. In this embodiment, the kit may be used to treat the cancers disclosed above, including those cancers with the mutational backgrounds identified herein. Methods of identifying such mutations are as set forth above.

In an additional aspect of this embodiment, the kit further comprises at least one additional therapeutic agent, preferably an inhibitor of the PI3K/Akt pathway, as disclosed herein.

In another aspect of this embodiment, administration of the first and second anti-cancer agents provides a synergistic effect compared to administration of either anti-cancer agent alone.

An additional embodiment of the present invention is a pharmaceutical composition for treating or ameliorating the effects of a cancer in a subject in need thereof. The pharmaceutical composition comprises a pharmaceutically acceptable diluent or carrier and an effective amount of (i) a first anti-cancer agent, which is BVD-523 or a pharmaceutically acceptable salt thereof and (ii) a second anti-cancer agent, which is a CDK inhibitor or a pharmaceutically acceptable salt thereof, wherein administration of the first and second anti-cancer agents provides a synergistic effect compared to administration of either anti-cancer agent alone.

Suitable and preferred CDK inhibitors and subjects are as disclosed herein. The pharmaceutical compositions of the invention may be used to treat the cancers disclosed above, including those cancers with the mutational backgrounds identified herein. Methods of identifying such mutations are also as set forth above.

In another aspect of this embodiment, the pharmaceutical composition further comprises at least one additional therapeutic agent, preferably an inhibitor of the PI3K/Akt pathway, as disclosed herein.

The pharmaceutical compositions according to the present invention may be in a unit dosage form comprising both anti-cancer agents. In another aspect of this embodiment, the first anti-cancer agent is in a first unit dosage form and the second anti-cancer agent is in a second unit dosage form, separate from the first.

The first and second anti-cancer agents may be co-administered to the subject, either simultaneously or at different times, as deemed most appropriate by a physician. If the first and second anti-cancer agents are administered at different times, for example, by serial administration, the first anti-cancer agent may be administered to the subject before the second anti-cancer agent. Alternatively, the second anti-cancer agent may be administered to the subject before the first anti-cancer agent.

In the present invention, an "effective amount" or a "therapeutically effective amount" of an anti-cancer agent of the invention, including the pharmaceutical compositions containing same, is an amount of such agent or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of an agent or composition according to the invention will be that amount of the agent or composition, which is the lowest dose effective to produce the desired effect. The effective dose of an agent or composition of the present invention may be administered as two, three, four, five, six or more sub-doses, administered separately at appropriate intervals throughout the day.

A suitable, non-limiting example of a dosage of an anti-cancer agent disclosed herein is from about 1 mg/kg to about 2400 mg/kg per day, such as from about 1 mg/kg to about 1200 mg/kg per day, 75 mg/kg per day to about 300 mg/kg per day, including from about 1 mg/kg to about 100 mg/kg per day. Other representative dosages of such agents include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. The effective dose of anti-cancer agents disclosed herein, e.g., BVD-523 and CDK inhibitors, may be administered as two, three, four, five, six or more sub-doses, administered separately at appropriate intervals throughout the day.

The anti-cancer agents or pharmaceutical compositions containing same of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, the anti-cancer agents or pharmaceutical compositions containing same of the present invention may be administered in conjunction with other treatments. The anti-cancer agents or the pharmaceutical compositions of the present invention may be encapsulated or otherwise protected against gastric or other secretions, if desired.

The pharmaceutical compositions of the invention may comprise one or more active ingredients, e.g. anti-cancer agents, in admixture with one or more pharmaceutically-acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21st Edition, Lippincott Williams and Wilkins, Philadelphia, PA).

Pharmaceutically acceptable diluents or carriers are well known in the art (see, e.g., Remington, The Science and Practice of Pharmacy (21st Edition, Lippincott Williams and Wilkins, Philadelphia, PA) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

The pharmaceutical compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable diluents or carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

The pharmaceutical compositions of the present invention for rectal or vaginal administration may be presented as a suppository, which may be prepared by mixing one or more active ingredient(s) with one or more suitable nonirritating diluents or carriers which are solid at room temperature, but liquid at body temperature and, therefore, will melt in the rectum or vaginal cavity and release the active compound. The pharmaceutical compositions of the present invention which are suitable for vaginal administration also include pessaries, tampons, creams, gels, pastes, foams or spray formulations containing such pharmaceutically-acceptable diluents or carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

The pharmaceutical compositions of the present invention suitable for parenteral administrations may comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be present in unit-dose or multi-dose sealed containers, for example, ampules and vials, and may be stored in a lyophilized condition requiring only the addition of the sterile liquid diluent or carrier, for example water for injection, immediately prior to use. Extemporaneous injection solutions and suspensions may be prepared from sterile powders, granules and tablets of the type described above.

The present invention provides combinations shown to enhance the effects of ERK inhibitors. Herein, applicants have also shown that the combination of different ERK inhibitors is likewise synergistic. Therefore, it is contemplated that the effects of the combinations described herein can be further improved by the use of one or more additional ERK inhibitors. Accordingly, some embodiments of the present invention include one or more additional ERK inhibitors.

The following examples are provided to further illustrate the methods of the present invention. These examples are illustrative only and are not intended to limit the scope of the invention in any way.

EXAMPLES

Example 1

BVD-523 Altered Markers of MAPK Kinase Activity and Effector Function

For Western blot studies, HCT116 cells ($5\times10^6$) were seeded into 10 cm dishes in McCoy's 5A plus 10% FBS. A375 cells ($2.5\times10^6$) were seeded into 10 cm dishes in DMEM plus 10% FBS. Cells were allowed to adhere overnight prior to addition of the indicated amount of test compound (BVD-523) or vehicle control. Cells were treated for either 4 or 24 hours before isolation of whole-cell protein lysates, as specified below. Cells were harvested by trypsinisation, pelleted and snap frozen. Lysates were prepared with RIPA (Radio-Immunoprecipitation Assay) buffer, clarified by centrifugation and quantitated by bicinchoninic acid assay (BCA) assay. 20-50 μg of protein was resolved by SDS-PAGE electrophoresis, blotted onto PVDF membrane and probed using the antibodies detailed in Table 2 (for the 4-hour treatment) and Table 3 (for the 24-hour treatment) below.

TABLE 2

| Antigen | Size (kDa) | Supplier | Cat No | Dilution | Incubation/ Block Conditions | Secondary |
|---|---|---|---|---|---|---|
| Antibody Details | | | | | | |
| pRSK1/2 pS380 | 90 | Cell Signaling | 9335 | 1:1000 | o/n 4° C. 5% BSA | anti-rabbit |
| pRSK1/2 pS380 | 90 | Cell Signaling | 11989 | 1:2000 | o/n 4° C. 5% BSA | anti-rabbit |
| pRSK-T359/S363 | 90 | Millipore | 04-419 | 1:40000 | o/n 4° C. 5% BSA | anti-rabbit |
| Total RSK | 90 | Cell Signaling | 9333 | 1:1000 | o/n 4° C. 5% BSA | anti-rabbit |
| pErk 1/2 | 42/44 | Cell Signaling | 9106S | 1:500 | o/n 4° C. 5% milk | anti-mouse |
| Total ERK | 42/44 | Cell Signaling | 9102 | 1:2000 | o/n 4° C. 5% milk | anti-rabbit |
| pMEK1/2 | 45 | Cell Signaling | 9154 | 1:1000 | o/n 4° C. 5% BSA | anti-rabbit |
| Total MEK | 45 | Cell Signaling | 9126 | 1:1000 | o/n 4° C. 5% BSA | anti-rabbit |
| pS6-pS235 | 32 | Cell Signaling | 2211S | 1:3000 | o/n 4° C. 5% milk | anti-rabbit |
| Total S6 | 32 | Cell Signaling | 2217 | 1:2000 | o/n 4° C. 5% milk | anti-rabbit |
| DUSP6 | 48 | Cell Signaling | 3058S | 1:1000 | o/n 4° C. 5% BSA | anti-rabbit |
| Total CRAF | 73 | BD Bio-sciences | 610152 | 1:2000 | o/n 4° C. 5% milk | anti-mouse |
| pCRAF-Ser338 | 73 | Cell Signaling | 9427 | 1:1000 | o/n 4° C. 5% BSA | anti-rabbit |
| pRB (Ser780) | 105 | Cell Signaling | 9307 | 1:2000 | o/n 4° C. 5% BSA | anti-rabbit |
| β-Actin | 42 | Sigma | A5441 | 1:500,000 | o/n 4° C. 5% milk | anti-mouse |

TABLE 3

| Antigen | Size (kDa) | Supplier | Cat No | Dilution | Incubation/ Block Conditions | Secondary |
|---|---|---|---|---|---|---|
| Antibody details | | | | | | |
| pRB (Ser780) | 105 | Cell Signaling | 9307 | 1:2000 | o/n 4° C. 5% BSA | anti-rabbit |
| CCND1 | 34 | Abcam | ab6152 | 1:500 | o/n 4° C. 5% milk | anti-mouse |
| Bim-EL | 23 | Millipore | AB17003 | 1:1000 | o/n 4° C. 5% BSA | anti-rabbit |
| Bim-EL | 23 | Cell Signaling | 2933 | 1:1000 | o/n 4° C. 5% BSA | anti-rabbit |
| BCL-xL | 30 | Cell Signaling | 2762 | 1:2000 | o/n 4° C. 5% BSA | anti-rabbit |
| PARP | 116/89 | Cell Signaling | 9542 | 1:1000 | o/n 4° C. 5% milk | anti-rabbit |
| Cleaved Caspase 3 | 17, 19 | Cell Signaling | 9664X | 1:1000 | o/n 4° C. 5% milk | anti-rabbit |
| DUSP6 | 48 | Cell Signaling | 3058S | 1:1000 | o/n 4° C. 5% BSA | anti-rabbit |
| pRSK1/2 pS380 | 90 | Cell Signaling | 9335 | 1:1000 | o/n 4° C. 5% BSA | anti-rabbit |
| pRSK1/2 pS380 | 90 | Cell Signaling | 11989 | 1:2000 | o/n 4° C. 5% BSA | anti-rabbit |
| pRSK-T359/S363 | 90 | Millipore | 04-419 | 1:40000 | o/n 4° C. 5% BSA | anti-rabbit |
| Total RSK | 90 | Cell Signaling | 9333 | 1:1000 | o/n 4° C. 5% BSA | anti-rabbit |
| pErk 1/2 | 42/44 | Cell Signaling | 9106S | 1:500 | o/n 4° C. 5% milk | anti-mouse |
| Total ERK | 42/44 | Cell Signaling | 9102 | 1:2000 | o/n 4° C. 5% milk | anti-rabbit |
| B-Actin | 42 | Sigma | A5441 | 1:500,000 | o/n 4° C. 5% milk | anti-mouse |

FIG. 1 shows Western blot analyses of cells treated with BVD-523 at various concentrations for the following: 1) MAPK signaling components in A375 cells after 4 hours; 2) cell cycle and apoptosis signaling in A375 24 hours treatment with various amounts of BVD-523; and 3) MAPK signaling in HCT-116 cells treated for 4 hours. The results show that acute and prolonged treatment with BVD-523 in RAF and RAS mutant cancer cells in-vitro affects both substrate phosphorylation and effector targets of ERK kinases. The concentrations of BVD-523 required to induce these changes is typically in the low micromolar range.

Changes in several specific activity markers are noteworthy. First, the abundance of slowly migrating isoforms of ERK kinase increase following BVD-523 treatment; modest changes can be observed acutely, and increase following prolonged treatment. While this could indicate an increase in enzymatically active, phosphorylated forms of ERK, it remains noteworthy that multiple proteins subject to both direct and indirect regulation by ERK remain "off" following BVD-523 treatment. First, RSK1/2 proteins exhibit reduced phosphorylation at residues that are strictly dependent on ERK for protein modification (T359/S363). Second, BVD-523 treatment induces complex changes in the MAPK feedback phosphatase, DUSP6: slowly migrating protein isoforms are reduced following acute treatment, while total protein levels are greatly reduced following prolonged BVD-523 treatment. Both of these findings are consistent with reduced activity of ERK kinases, which control DUSP6 function through both post-translational and transcriptional mechanisms. Overall, despite increases in cellular forms of ERK that are typically thought to be active, it appears likely that cellular ERK enzyme activity is fully inhibited following either acute or prolonged treatment with BVD-523.

Consistent with these observations, effector genes that require MAPK pathway signaling are altered following treatment with BVD-523. The G1/S cell-cycle apparatus is regulated at both post-translational and transcriptional levels by MAPK signaling, and cyclin-D1 protein levels are greatly reduced following prolonged BVD-523 treatment. Similarly, gene expression and protein abundance of apoptosis effectors often require intact MAPK signaling, and total levels of Bim-EL increase following prolonged BVD-523 treatment. As noted above, however, PARP protein cleavage and increased apoptosis were not noted in the A375 cell background; this suggests that additional factors may influence whether changes in BVD-523/ERK-dependent effector signaling are translated into definitive events such as cell death and cell cycle arrest.

Consistent with the cellular activity of BVD-523, marker analysis suggests that ERK inhibition alters a variety of molecular signaling events in cancer cells, making them susceptible to both decreased cell proliferation and survival.

In sum, FIG. 1 shows that BVD-523 inhibits the MAPK signaling pathway and may be more favorable compared to RAF or MEK inhibition in this setting.

Finally, properties of BVD-523 may make this a preferred agent for use as an ERK inhibitor, compared to other agents with a similar activity. It is known that kinase inhibitor drugs display unique and specific interactions with their enzyme targets, and that drug efficacy is strongly influenced by both the mode of direct inhibition, as well as susceptibility to adaptive changes that occur following treatment. For example, inhibitors of ABL, KIT, EGFR and ALK kinases are effective only when their cognate target is found in active or inactive configurations. Likewise, certain of these inhibitors are uniquely sensitive to either secondary genetic mutation, or post-translational adaptive changes, of the protein target. Finally, RAF inhibitors show differential potency to RAF kinases present in certain protein complexes and/or subcellular localizations. In summary, as ERK kinases are similarly known to exist in diverse, variable, and complex biochemical states, it appears likely that BVD-523 may interact with and inhibit these targets in a fashion that is distinct and highly preferable to other agents.

Example 2

BVD-523/CDK Inhibitor Combinations are Effective to Inhibit the Growth of Cancer Cell Lines In Vitro Cancer cell lines are maintained in cell culture under standard media and serum conditions.

For all combination studies, MM415 cells (N-RAS mutant human melanoma cells) are seeded into triplicate 96-well plates at a cell density of 1500 cells/well in RPMI 1640 media supplemented with 10% (vol/vol) fetal bovine serum (FBS). HCT 116 cells (K-RAS mutant human colorectal carcinoma cells) are seeded into triplicate 96-well plates at a cell density of 1500 cells/well in McCoy's 5A medium plus 10% FBS. A375 cells (BRAF V600 E human malignant melanoma) are seeded at a density of 3000 cells/well in Dulbecco's Modified Eagle Medium (DMEM) plus 10% FBS. Cells are allowed to adhere overnight prior to addition of test compound or vehicle control.

For dinaciclib studies, the following combinations are tested using a 10×8 dose matrix: dinaciclib (ranging from 1-50 nM) with BVD-0523 (ranging from 0 to 10 μM), dinaciclib (ranging from 1-50 nM) with dabrafenib (ranging from 0 to 1 μM), and dinaciclib (ranging from 1-50 nM) with trametinib (ranging from 0 to 0.010 UM). The final concentration of DMSO is 0.2%. The compounds are incubated with the cells for 96 hours.

For palbociclib studies, the following combinations are tested using a 10×8 dose matrix: palbociclib (ranging from 10 nM-500 nM) with BVD-0523 (0 to 10 μM), palbociclib (ranging from 10 nM-500 nM) with dabrafenib (ranging from 0 to 1 μM), and palbociclib (ranging from 10 nM-500 nM) with trametinib (ranging from 0 to 0.1 μM). The final concentration of DMSO is 0.2%. The compounds are incubated with the cells for 96 hours.

Next, ALAMAR BLUE™ (a ready-to-use resazurin-based solution that functions as a cell health indicator) 10% (v/v) is added and incubated with the cells for 4 hours prior to reading on a fluorescent plate reader. After reading ALAMAR BLUE™, the medium/ALAMAR BLUE™ mix is flicked off, 100 μl of CELLTITER-GLO®/PBS (1:1) is added, and the plates are processed as per the manufacturer's instructions (Promega, Madison, WI). Media only background values are subtracted before the data is analyzed.

CASPASE-GLO® 3/7 Assays (a Homogeneous, Luminescent Assay that Measures Caspase-3 and -7 Activities)

In brief, MM415 cells are seeded in triplicate in white 96-well plates at a cell density of 5000 cells/well in RPMI 1640 plus 10% FBS. A375 cells are seeded at a density of 5000 cells/well in DMEM plus 10% FBS. HCT 116 cells are seeded at a cell density of 5000 cells/well in McCoy's 5A medium plus 10% FBS. Cells are allowed to adhere overnight prior to addition of test compound or vehicle control. The final concentration of DMSO is 0.2%, and 800 nM staurosporine is included as a positive control. 24 and 48 hour assay incubation periods are used. Then, CASPASE-GLO® 3/7 50% (v/v) is added, plates are mixed for 5 minutes on an orbital shaker and incubated for 1 hour at room temperature prior to reading on a luminescent plate reader. Media only background values are subtracted before the data is analysed.

Data Analysis

The combination data may be presented as dose-response curves generated in GraphPad Prism (plotted using % viability relative to DMSO only treated controls).

Predicted fractional inhibition values for combined inhibition are calculated using the equation $C_{bliss}$=A+B−(A×B) where A and B are the fractional inhibitions obtained by drug A alone or drug B alone at specific concentrations. $C_{bliss}$ is the fractional inhibition that would be expected if the combination of the two drugs is exactly additive. $C_{bliss}$ values are subtracted from the experimentally observed fractional inhibition values to give an 'excess over Bliss' value. Excess over Bliss values greater than 0 indicate synergy, whereas values less than 0 indicate antagonism. Excess over Bliss values may be plotted as heat maps±SD.

It is expected that the combinations of dinaciclib or palbociclib with BVD-523 will be effective in inhibiting the growth of A375, MM415, and HCT116 cells. Dose response curves will be obtained. It is expected that the $IC_{50}$ of BVD-523 in these cell lines will be approximately 150 nM. It is also expected that the $IC_{50}$ of dinaciclib and palbociclib in these cell lines will be approximately 13 nM (Parry et al., 2010) and 130 nM (Fry et al., 2004), respectively.

Example 3

BVD-523/CDK Inhibitor Combinations are Effective to Inhibit the Growth of Cancer Cell Lines In Vivo Mice Female athymic nude mice (Crl:NU(Ncr)-Foxn/nu, Charles River) are nine weeks old with a body weight (BW) range of about 15 to about 30 grams on Day 1 of the study. The animals are fed ad libitum water (reverse osmosis, 1 ppm CI), and NIH 31 Modified and Irradiated LAB DIET® (a laboratory animal diet consisting of feed products used in biomedical research) consisting of 18.0% crude protein, 5.0% crude fat, and 5.0% crude fiber. The mice are housed on irradiated ENRICH-O'COBS® (a three-in-one bedding-enrichment-nesting system that promotes animal enrichment and nesting activity) Laboratory Animal Bedding in static microisolators on a 12-hour light cycle at 20-22° C. (68-72° F.) and 40-60% humidity. The recommendations of the Guide for Care and Use of Laboratory Animals with respect to restraint, husbandry, surgical procedures, feed and fluid regulation, and veterinary care are complied with.

In Vivo Implantation and Tumor Growth

MM415 N-RAS mutant human melanoma cells are cultured in RPMI-1640 medium supplemented with 10% fetal bovine serum, 2 mM glutamine, 100 units/mL penicillin G sodium, 100 μg/mL streptomycin sulfate, and 25 μg/mL gentamicin. The tumor cells are grown in tissue culture flasks in a humidified incubator at 37° C., in an atmosphere of 5% $CO_2$ and 95% air.

The MM415 cells used for implantation are harvested during exponential growth and resuspended in 50% Matrigel (BD Biosciences): 50% phosphate buffered saline at a concentration of $2.5\times10^7$ cells/mL. On the day of tumor implant, each test mouse is injected subcutaneously in the right flank with $5\times10^6$ cells (0.2 mL cell suspension), and tumor growth is monitored as the average size approaches the target range of 100 to 150 $mm^3$. Tumors are measured in two dimensions using calipers, and volume is calculated using the formula:

$$\text{Tumor Volume } (mm^3) = (w^2 \times l)/2$$

where w=width and l=length, in mm, of the tumor. Tumor weight may be estimated with the assumption that 1 mg is equivalent to 1 $mm^3$ of tumor volume.

Ten days after tumor implantation, designated as Day 1 of the study, the animals are sorted into sixteen groups, each described below.

Treatment

On Day 1 of the study, mice are sorted into groups each consisting of fifteen mice and one group consisting of ten mice, and dosing is initiated. All doses are given by oral gavage (p.o.) except dacarbazine (DTIC), which is given intravenously (i.v.). For each agent, the dosing volume of 10 ml/kg (0.2 mL per 20 grams of BW) is scaled to the BW of the individual animal. The dinaciclib/palbociclib doses are to be given once daily (qd) until study end (qd to end), whereas the vehicle and BVD-523 doses are to be given twice daily (bid) until study end (bid to end). For bid dosing, dosing is initiated in the afternoon of Day 1, so that one dose is given on the first day ("first day 1 dose").

Controls

One group receives 1% CMC vehicle p.o. bid to end, and serves as the control group for calculation of % TGD. Another group receives DTIC i.v. at 80 mg/kg once every other day (qod) for five doses (qod×5), and serves as the positive control for the model.

Monotherapy Treatments

Four groups receive either dinaciclib at 5 or 60 mg/kg or palbociclib at 100 or 150 mg/kg. Two groups receive 50 or 100 mg/kg BVD-523 p.o. bid to end.

Combination Treatments

Each one of two groups receives a combination of 50 mg/kg BVD-523 with 5 or 60 mg/kg of dinaciclib. Two other groups receive 100 mg/kg BVD-523 with 5 or 60 mg/kg of dinaciclib. Two additional groups will receive 50 mg/kg BVD-523 with 100 or 150 mg/kg palbociclib, and another two groups will receive 100 mg/kg BVD-523 with 100 or 150 mg/kg palbociclib.

Endpoint and Tumor Growth Delay (TGD) Analysis

Tumors are measured using calipers twice per week, and each animal is euthanized when its tumor reaches the pre-determined tumor volume endpoint of 2000 $mm^3$ or on the final day, whichever comes first. Animals that exit the study for tumor volume endpoint are documented as euthanized for tumor progression (TP), with the date of euthanasia. The time to endpoint (TTE) for analysis is calculated for each mouse by the following equation:

$$TTE = [\log_{10}(\text{endpoint volume}) - b]/m$$

where TTE is expressed in days, endpoint volume is expressed in $mm^3$, b is the intercept, and m is the slope of the line obtained by linear regression of a log-transformed tumor growth data set. The data set consists of the first observation that exceeds the endpoint volume used in analysis and the three consecutive observations that immediately precede the attainment of this endpoint volume. The calculated TTE is usually less than the TP date, the day on which the animal is euthanized for tumor size. Animals with tumors that do not reach the endpoint volume are assigned a TTE value equal to the last day of the study. Any animal classified as having died from NTR (non-treatment-related) causes due to accident (NTRa) or due to unknown etiology (NTRu) are excluded from TTE calculations (and all further analyses). Animals classified as TR (treatment-related) deaths or NTRm (non-treatment-related death due to metastasis) are assigned a TTE value equal to the day of death.

Treatment outcome is evaluated from TGD, defined as the increase in the median TTE in a treatment group compared to the control group:

$$TGD = T - C,$$

expressed in days, or as a percentage of the median TTE of the control group:

$$\%\ TGD = [(T - C)/C] \times 100$$

where:

T=median TTE for a treatment group, and

C=median TTE for the designated control group.

Criteria for Regression Responses

Treatment efficacy may be determined from the incidence and magnitude of regression responses observed during the study. Treatment may cause partial regression (PR) or complete regression (CR) of the tumor in an animal. In a PR response, the tumor volume is 50% or less of its Day 1 volume for three consecutive measurements during the course of the study, and equal to or greater than 13.5 $mm^3$ for one or more of these three measurements. In a CR response, the tumor volume is less than 13.5 $mm^3$ for three consecutive measurements during the course of the study. An animal with a CR response at the termination of the study is additionally classified as a tumor-free survivor (TFS). Animals are monitored for regression responses.

Toxicity

Animals are weighed daily on Days 1-5, then twice per week until completion of the study. The mice are observed frequently for overt signs of any adverse, TR side effects, and clinical signs are recorded when observed. Individual BW loss is monitored as per protocol, and any animal whose weight exceeds the limits for acceptable BW loss is euthanized. Group mean BW loss also is monitored as per protocol. Dosing is to be suspended in any group that exceeds the limits for acceptable mean BW loss. If mean BW recovers, then dosing is to be resumed in that group, but at a lower dosage or less frequent dosing schedule. Acceptable toxicity for the maximum tolerated dose (MTD) is defined as a group mean BW loss of less than 20% during the study and not more than 10% TR deaths. A death is classified as TR if attributable to treatment side effects as evidenced by clinical signs and/or necropsy, or may also be classified as TR if due to unknown causes during the dosing period or within 14 days of the last dose. A death is classified as NTR if there is no evidence that death is related to treatment side effects. NTR deaths may be further characterized based on cause of death. A death is classified as NTRa if it results from an accident or human error. A death is classified as NTRm if necropsy indicates that it may result from tumor dissemination by invasion and/or metastasis. A death is classified as NTRu if the cause of death is unknown and there is no available evidence of death related to treatment side effects, metastasis, accident or human error, although death due to treatment side effects cannot be excluded.

Statistical and Graphical Analyses

Prism (GraphPad) for Windows 3.03 is used for graphical presentations and statistical analyses.

The logrank test, which evaluates overall survival experience, is used to analyze the significance of the differences between the TTE values of two groups. Logrank analysis includes the data for all animals in a group except those assessed as NTR deaths. Two-tailed statistical analyses are conducted at significance level P=0.05. The statistical tests are not adjusted for multiple comparisons. Prism summarizes test results as not significant (ns) at $P>0.05$, significant (symbolized by "*") at $0.01<P<0.05$, very significant ("") at $0.001<P\leq0.01$, and extremely significant ("*") at $P\leq0.001$. Groups with regimens above the MTD are not evaluated statistically.

A scatter plot is constructed to show TTE values for individual mice, by group. Group mean tumor volumes are plotted as a function of time. When an animal exits the study due to tumor size, the final tumor volume recorded for the animal is included with the data used to calculate the mean volume at subsequent time points. Error bars (when present) indicate one standard error of the mean (SEM). Tumor growth plots exclude the data for NTR deaths, and are truncated after 50% of the assessable animals in a group exit the study or after the second TR death in a group, whichever comes first. Kaplan-Meier plots show the percentage of animals in each group remaining in the study versus time. The Kaplan-Meier plot and logrank test share the same TTE data sets. Percent mean BW changes from Day 1 are calculated for each group for each day of BW measurement, and are plotted as a function of time. BW plots exclude the data for NTR deaths, and are truncated after 50% of the assessable animals in a group exit the study.

Results

It is expected that the combinations of dinaciclib or palbociclib with BVD-523 will be effective against MM415 cell-derived tumors and that the results will be statistically significant. It is also expected that the side effects associated with the BVD-523/CDK inhibitor treatment will be minimal.

Example 4

Cell Culture Studies of CDK and ERK Inhibitors

Single Agent Proliferation Assay

Cells were seeded in 96-well plates at the densities indicated in Table 4 in RPMI containing 10% FBS and allowed to adhere overnight prior to addition of compound or vehicle control. Compounds were prepared from DMSO stocks to give the desired final concentrations. The final DMSO concentration was constant at 0.1%. Test compounds were incubated with the cells for 72 h at 37° C., 5% $CO_2$ in a humidified atmosphere. CELLTITER-GLO® reagent (Promega, Madison, WI) was added according to manufacturer's instructions and luminescence detected using the BMG FLUOstar plate reader (BMG Labtech, Ortenberg, Germany). A duplicate set of assay plates was incubated with 10 μg/ml Hoechst 33342 stain (Invitrogen, Grant Island, NY) in complete growth medium for 1 h at 37° C., 5% $CO_2$ in a humidified atmosphere. The medium was then removed and replaced with PBS and fluorescence detected using a BMG FLUOstar Omega plate reader (BMG labtech, Ortenberg, Germany). The average media only background value was deducted and the data analysed using a 4-parameter logistic equation in GraphPad Prism (GraphPad Software, La Jolla, CA).

Combination Proliferation Assay

Cells were seeded into triplicate 96-well plates at the densities indicated in Table 4 in RPMI media containing 10% FBS and allowed to adhere overnight prior to addition of test compound or vehicle control. Combinations were tested using a 10×8 dose matrix. The final DMSO concentration was constant at 0.2%.

Test compounds were incubated with the cells for 72 h at 37° C., 5% $CO_2$ in a humidified atmosphere. Cells were stained with Hoechst stain and fluorescence detected as described above. The average media only background value was deducted and the data analysed.

Combination interactions across the dose matrix were determined by the Loewe Additivity and Bliss independence models using CHALICE™ (a computer program that analyzes combination interaction of agents, results of which can be shown in, e.g., a dose matrix) Combination Analysis Software (Horizon Discovery Group, Cambridge, MA) as outlined in the user manual (available at chalice.horizondiscovery.com/chalice-portal/documentation/analyzer/home.jsp). Synergy is determined by comparing the experimentally observed level of inhibition at each combination point with the value expected for additivity, which is derived from the single-agent responses along the edges of the matrix. Potential synergistic interactions were identified by displaying the calculated excess inhibition over that predicted as being additive across the dose matrix as a heat map, and by reporting a quantitative 'Synergy Score' based on the Loewe model. The single agent data derived from the combination assay plates were presented as dose-response curves generated in CHALICE™.

TABLE 4

Cell Line Seeding Density

| Cell Line | Seeding Density (cells/well) |
|---|---|
| A549 | 1000 |
| H2212 | 4000 |
| H1437 | 3000 |
| H226 | 1500 |

This study assessed the effects of combining the ERK inhibitors BVD-523 and SCH772984 with two different CDK4/6 inhibitors (Palbociclib and LEE-011) across a panel of four lung cancer cell lines, two mutant for KRas and two wild type.

The effects of BVD-523, the CDK4/6 inhibitors, another ERK inhibitor (SCH772984), and a reference MEK inhibitor (Trametinib), as single agents on cell viability was assessed after 72 h using two methods (FIGS. 2A-2L). The first method was by quantitating cellular ATP levels using CELLTITER-GLO® (Promega, Madison, WI). The second method was by quantitating total amount of DNA in an assay well after staining the DNA with Hoechst stain.

The single agent $IC_{50}$ values are shown in Table 5. The two cell lines carrying a KRas mutation are more sensitive to BVD-523 relative to the wild type cell lines. This may indicate that the presence of a KRas mutation may be a predictive biomarker for sensitivity to BVD-523 as a single agent. The pattern of response to the ERK inhibitor SCH772984 was broadly similar to that of BVD-523.

TABLE 5

Relative $IC_{50}$ Values

| | Relative IC50 (μM) | | | | | | | |
|---|---|---|---|---|---|---|---|---|
| | A549 (KRas mt) | | H2122 (KRas mt) | | H1437 (KRas mt) | | H226 (KRas mt) | |
| Compound | CellTiter | Hoechst | CellTiter | Hoechst | CellTiter | Hoechst | CellTiter | Hoechst |
| BVD-523 | 0.73 | 0.59 | 0.45 | 0.45 | 1.2 | 1.4 | 34% @ 10 μM | 58% @ 10 μM |
| SCH772984 | 1.1 | 0.74 | 0.63 | 0.53 | 57% @ 3 μM | 63% @ 3 μM | 35% @ 3 μM | 49% @ 3 μM |
| Trametinib | 0.005 | 0.005 | 0.003 | 0.003 | 0.002 | 0.003 | 57% @ 1 μM | 0.002 |
| Palbociclib | 41% @ 3 μM | 0.13 | 48% @ 3 μM | 0.15 | 29% @ 3 μM | 0.22 | 20% @ 3 μM | 0.056 |
| LEE-011 | 49% @ 10 μM | 0.70 | 44% @ 10 μM | 0.45 | 30% @ 10 μM | 2.8 | 32% @ 10 μM | 0.37 |
| Paclitaxcel | 0.003 | 0.002 | 0.003 | 0.002 | 0.007 | 0.003 | 0.003 | 0.003 |

Note:
Maximal percentage inhibitions are reported when a cell line is relatively insensitive to compound resulting in a partial response (defined as ≤~60% inhibition achieved) and/or the bottom of the curve not being defined The single agent results for the CDK4/6 inhibitors were dependent on the readout for cell viability used, with cells appearing to be markedly more sensitive to inhibition when assessed using Hoechst staining. This suggests that measurement of ATP levels is not a suitable proxy for the number of viable cells in response to CDK4/6 inhibition and, therefore, only the Hoechst stain readout was used in the combination assays.

Combination interactions between two compounds were assessed across a matrix of concentrations using the Loewe Additivity and Bliss Independence Models with CHALICE™ Bioinformatics Software (Horizon Discovery Group, Cambridge, MA). CHALICE™ enables potential synergistic interactions to be identified by displaying the calculated excess inhibition over that predicted as being additive across the dose matrix as a heat map, and by reporting a quantitative 'Synergy Score' based on the Loewe model.

Combination interactions between BVD-523 and the two CDK4/6 inhibitors are shown in FIGS. 3A-3T and FIGS. 4A-4T, respectively. Combination interactions between SCH772984 and the two CDK4/6 inhibitors are shown in FIGS. 5A-5T and FIGS. 6A-6T, respectively. Combination interactions between Trametinib and the two CDK4/6 inhibitors are shown in FIGS. 7A-7T and FIGS. 8A-8T, respectively.

Visualization of the Loewe 'excess inhibition' heat maps suggested that the combination of BVD-523 with either of the two CDK4/6 inhibitors was mainly additive in A549 and H226 cells, and additive with windows of potential synergy in H1437 and H2122. These windows of synergy appeared broader and stronger in H1437 relative to H2122 cells. Similar results were obtained with the ERK inhibitor SCH772984.

Figure 9A:
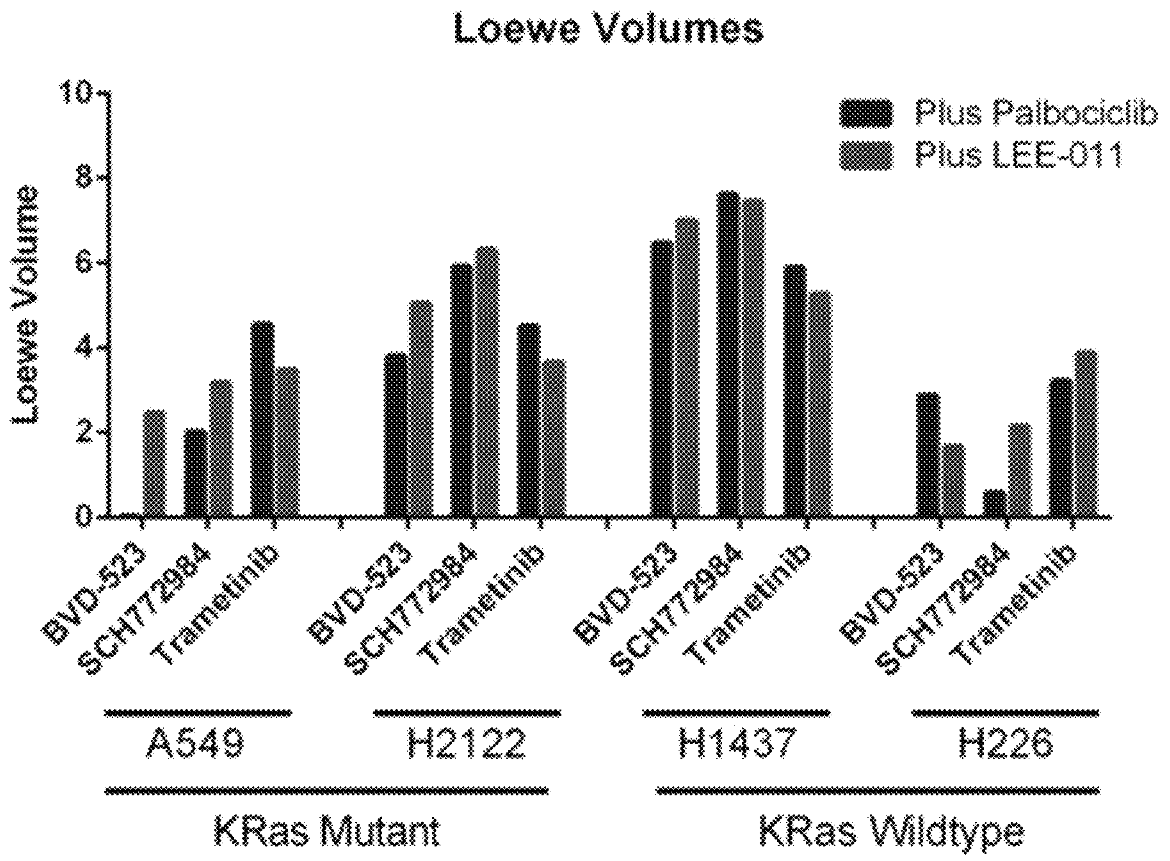
FIG. 9A shows Lowe Volumes for the combinations of CDK and ERK inhibitors.
Figure 9B:
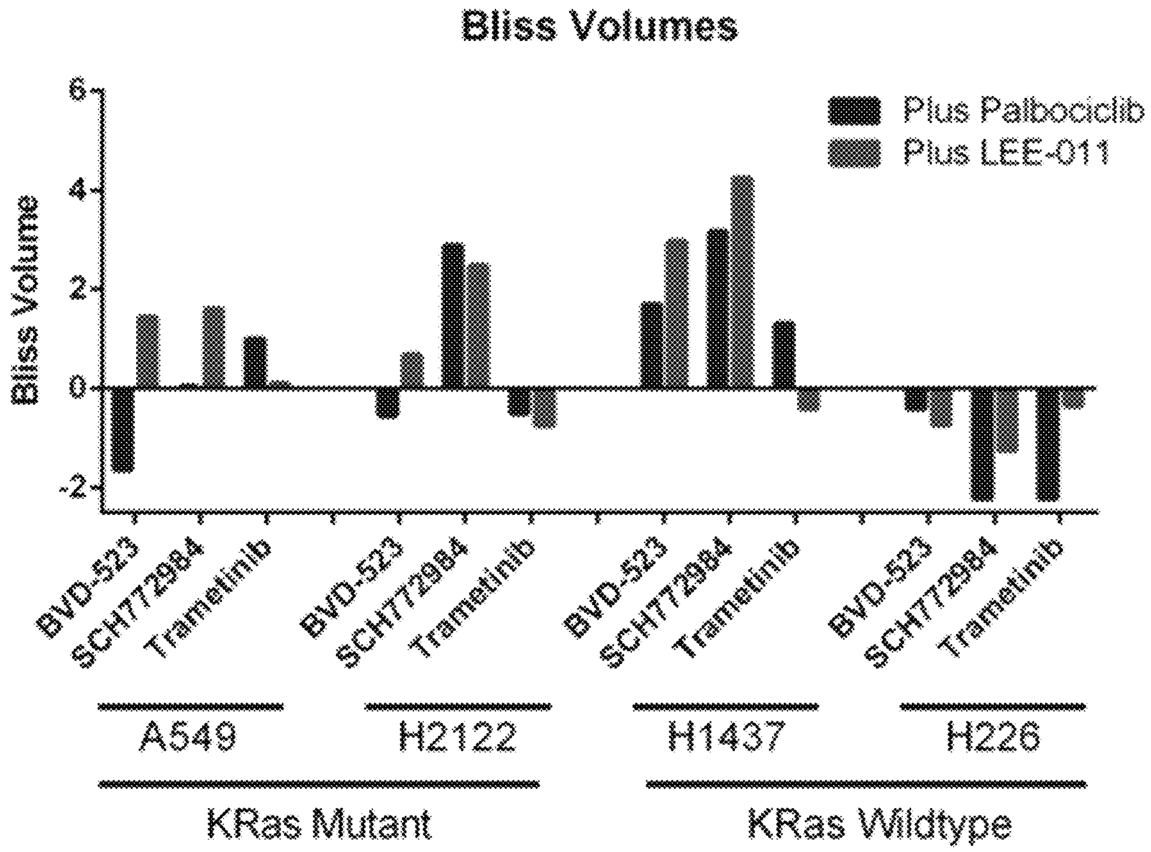
FIG. 9B shows Bliss Volumes for the combinations of CDK and ERK inhibitors.
Figure 9C:
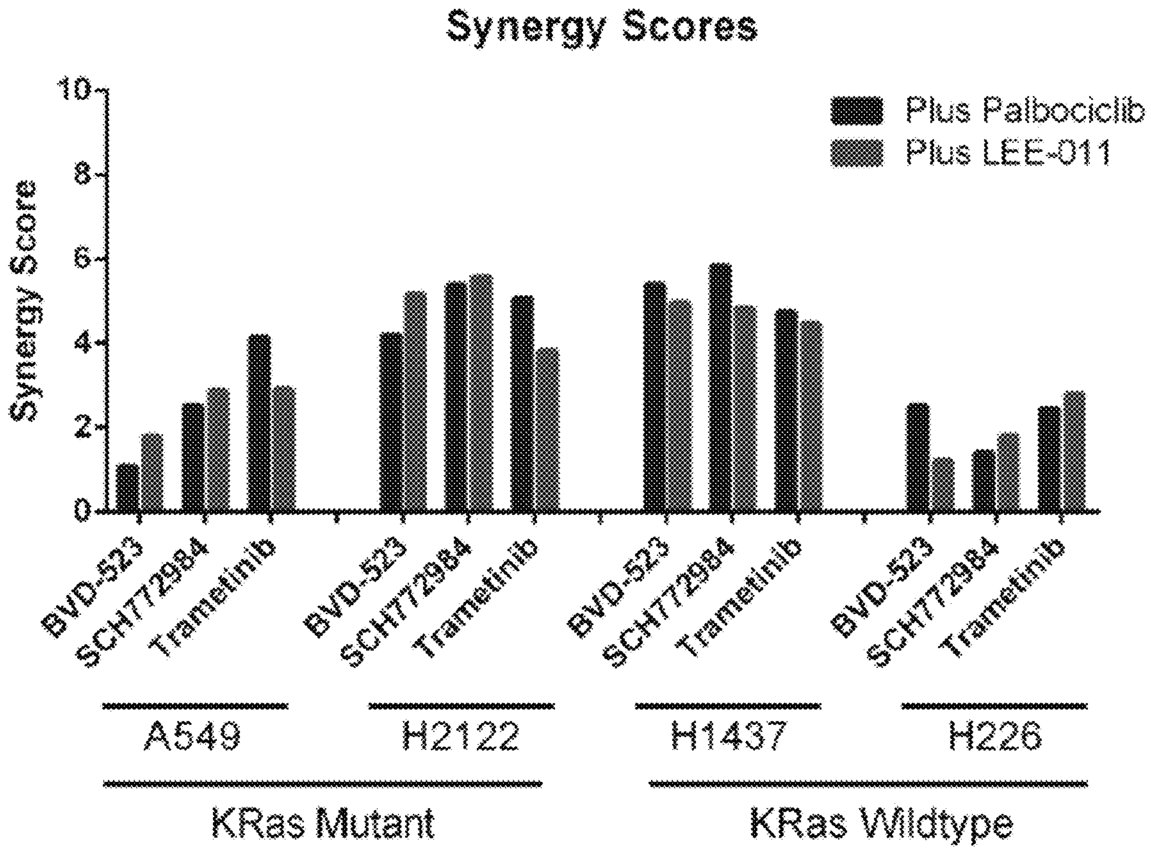
FIG. 9C shows Synergy Scores for the combinations of CDK and ERK inhibitors.
Figure 10A:
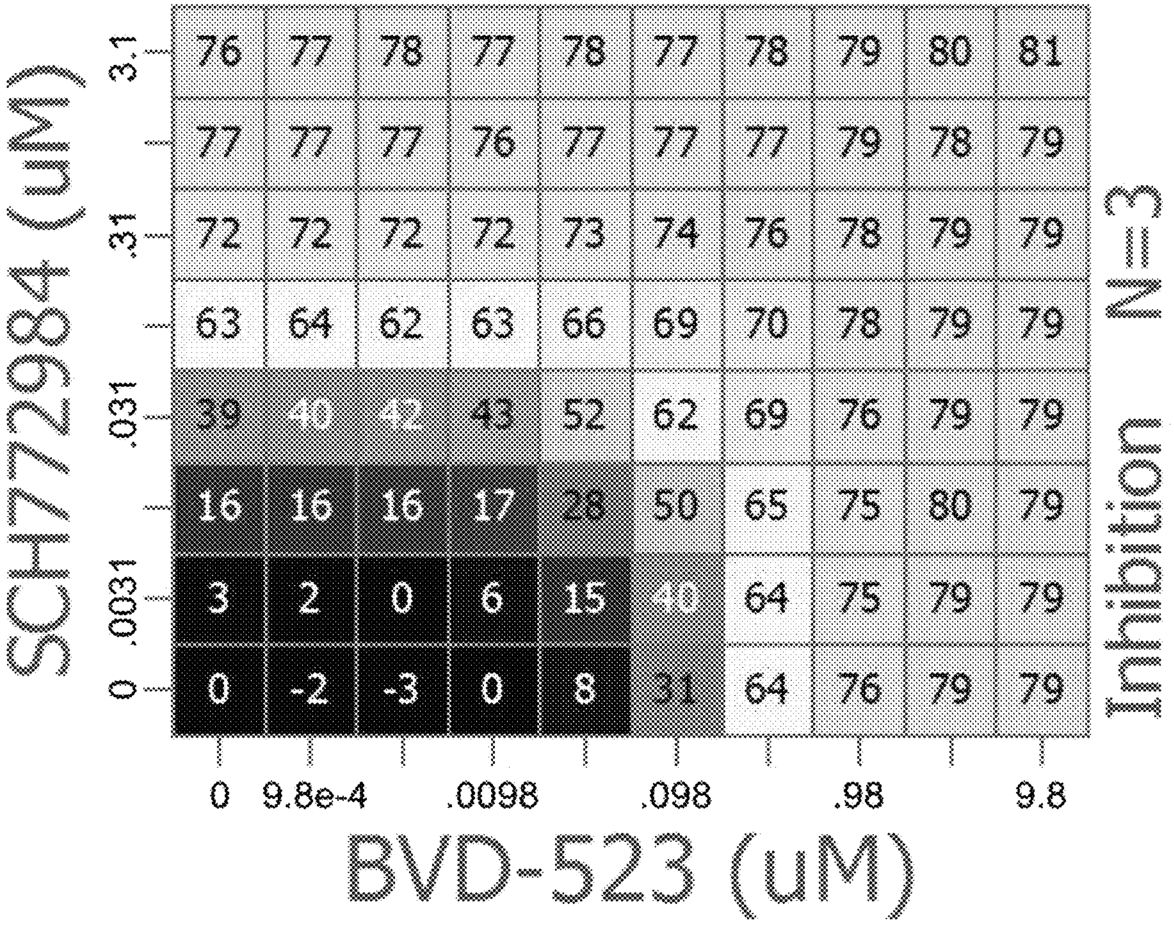
FIGS. 10A-10E show the results of the combination of BVD-523 and SCH772984.
Figure 10B:
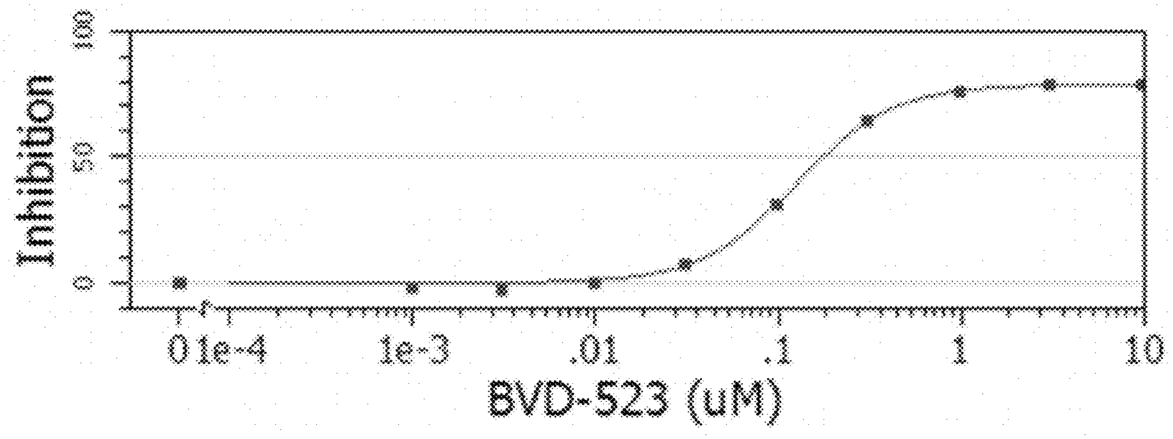
Figure 10C:
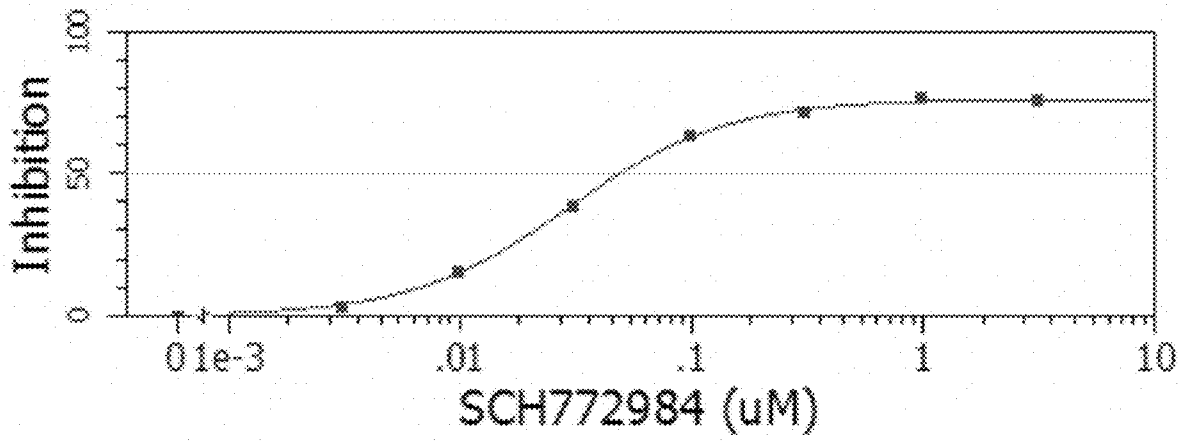
Figure 10D:
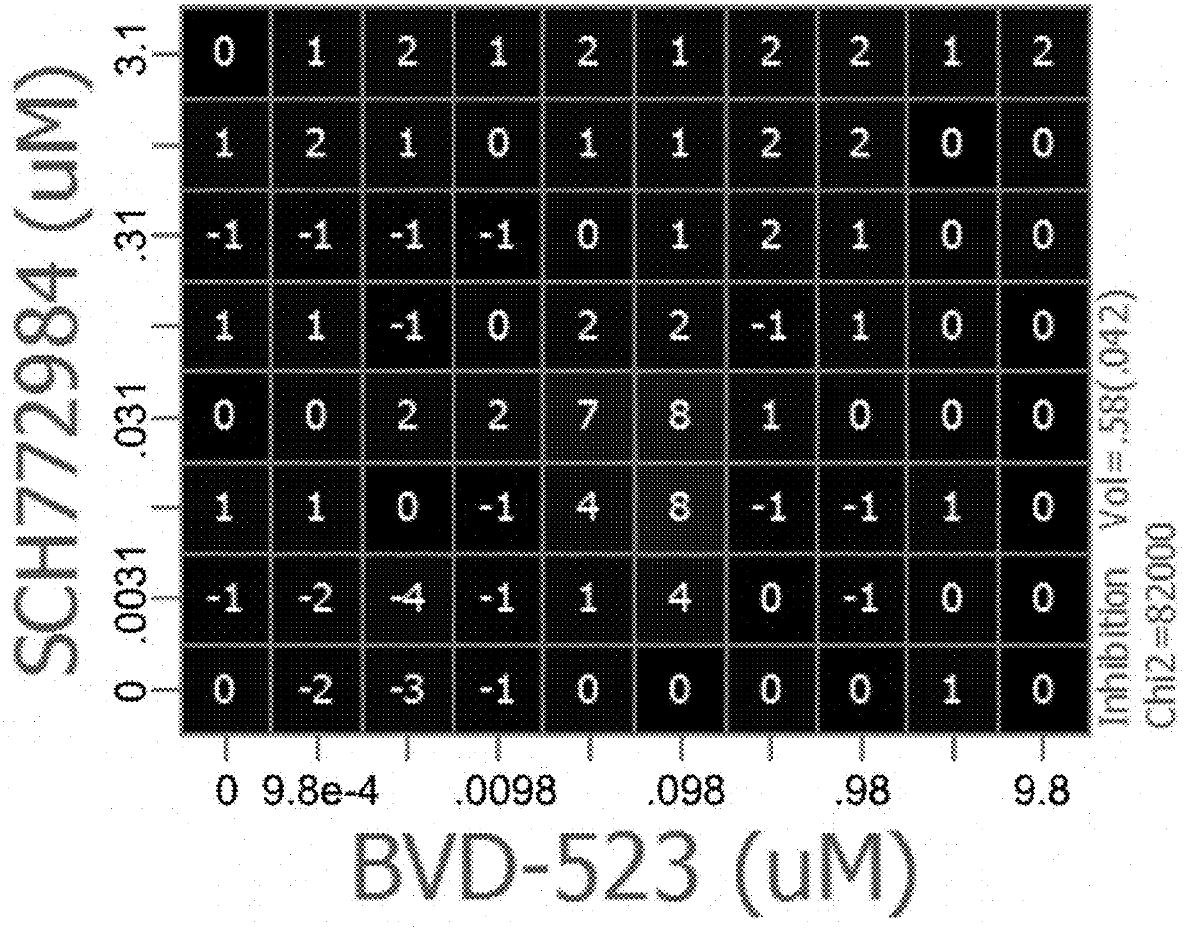
Figure 10E:
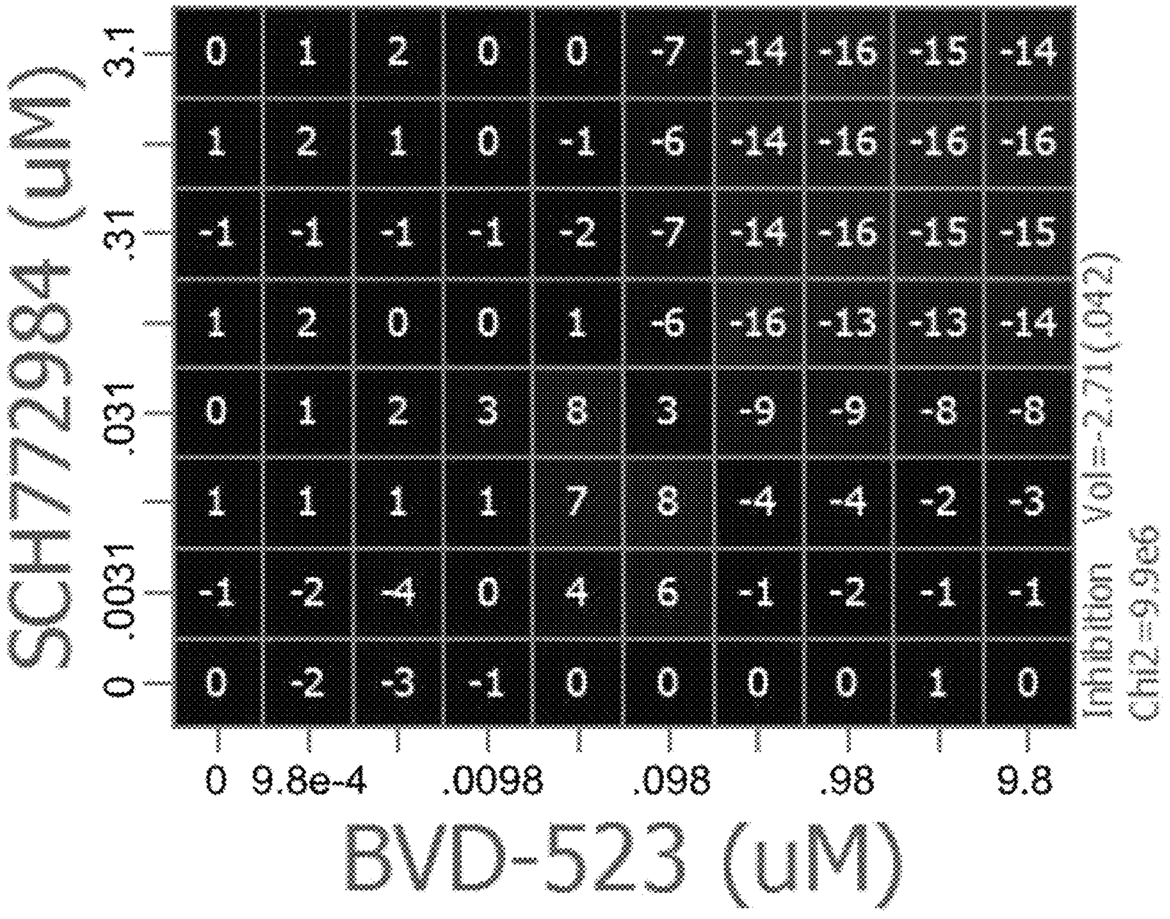

Activity over Loewe additivity can be quantified in CHALICE™ using a simple volume score, which effectively calculates a volume between the measured and Loewe additive response surfaces, and emphasizes the overall synergistic (positive values) or antagonistic (negative values) effect of the combination. Volume scores for the combinations of BVD-523 and SCH772984 with either of the two CDK4/6 inhibitors are shown in FIGS. 9A-9C and Tables 6-8 and are consistent with the conclusions drawn from the heat maps.

TABLE 6

| Loewe Volumes | | | | |
|---|---|---|---|---|
| | A549 | H1437 | H2122 | H226 |
| BVD-523 × Lee-011 | 2.47 | 7 | 5.05 | 1.66 |
| BVD-523 × Palbociclib | 0.0329 | 6.47 | 3.81 | 2.89 |
| SCH772984 × Lee-011 | 3.19 | 7.45 | 6.31 | 2.15 |
| SCH772984 × Palbociclib | 2.01 | 7.61 | 5.92 | 0.589 |
| Trametinib × Lee-011 | 3.49 | 5.27 | 3.66 | 3.88 |
| Trametinib × Palbociclib | 4.55 | 5.9 | 4.51 | 3.23 |

TABLE 7

| Bliss Volumes | | | | |
|---|---|---|---|---|
| | A549 | H1437 | H2122 | H226 |
| BVD-523 × Lee-011 | 1.42 | 2.97 | 0.672 | −0.728 |
| BVD-523 × Palbociclib | −1.63 | 1.68 | −0.543 | −0.398 |
| SCH772984 × Lee-011 | 1.6 | 4.24 | 2.47 | −1.24 |
| SCH772984 × Palbociclib | 0.0322 | 3.16 | 2.88 | −2.22 |
| Trametinib × Lee-011 | 0.0863 | −0.4 | −0.739 | −0.342 |
| Trametinib × Palbociclib | 0.987 | 1.29 | −0.502 | −2.22 |

TABLE 8

| Synergy Scores | | | | |
|---|---|---|---|---|
| | A549 | H1437 | H2122 | H226 |
| BVD-523 × Lee-011 | 1.79 | 4.95 | 5.16 | 1.21 |
| BVD-523 × Palbociclib | 1.08 | 5.38 | 4.19 | 2.51 |
| SCH772984 × Lee-011 | 2.88 | 4.83 | 5.57 | 1.8 |
| SCH772984 × Palbociclib | 2.52 | 5.83 | 5.37 | 1.4 |
| Trametinib × Lee-011 | 2.91 | 4.47 | 3.81 | 2.78 |
| Trametinib × Palbociclib | 4.14 | 4.73 | 5.07 | 2.45 |

In summary, these results suggest that interactions between BVD-523 and CDK4/6 inhibitors are at least additive, and in some cases synergistic, in lung cancer cell lines wild type or mutated for KRas.

Example 5

Combination Interactions Between ERK Inhibitors

RAF mutant melanoma cell line A375 cells were cultured in DMEM with 10% FBS and seeded into triplicate 96-well plates at an initial density of 2000 cells per well. Combination interactions between ERK inhibitors BVD-523 and SCH772984 were analized after 72 hours as described above in Example 4 and viability was determined using CELLTITER-GLO® (Promega) reagent as described above in Example 4.

Visualization of the Loewe and Bliss 'excess inhibition' heat maps suggested that the combination of BVD-523 and SCH772984 was mainly additive with windows of potential synergy in mid-range doses (FIGS. 10A-10E).

In summary, these results suggest that interactions between BVD-523 and SCH772984 are at least additive, and in some cases synergistic.

DOCUMENTS

AVRUCH, J. et al. Ras activation of the Raf kinase: tyrosine kinase recruitment of the MAP kinase cascade. Recent Prog. Horm. Res., 2001, 127-155.

BROSE et al. BRAF and RAS mutations in human lung cancer and melanoma. Cancer Res., 2002, 62, 6997-7000.

DAVIES et al., Mutations of the BRAF gene in human cancer. Nature, 2002, 417, 949-954.

FRANSEN et al., Mutation analysis of the BRAF, ARAF and RAF-1 genes in human colorectal adenocarcinomas. Carcinogenesis, 2004, 25, 527-533.

FRY, D. W. et al. (2004). Specific inhibition of cyclin-dependent kinase 4/6 by PD 0332991 and associated antitumor activity in human tumor xenografts.

GARNETT, M. J. et al. Wildtype and mutant B-RAF activate C-RAF through distinct mechanisms involving heterodimerization. Mol. Cell, 2005, 20, 963-969.

HOCKER et al., Ultraviolet radiation and melanoma: A systematic review and analysis of reported sequence variants. Hum. Mutat., 2007, 28, 578-588.

LI et al., Recent advances in the research and development of B-Raf Inhibitors. *Current Medicinal Chemistry,* 2010, 17:1618-1634.

LONG G V, Menzies A M, Nagrial A M, et al. Prognostic and Clinicopathologic Associations of Oncogenic BRAF in Metastatic Melanoma. J Clin Oncol. 2011

PARRY, D. et al. (2010). Dinaciclib (SCH 727965), a novel and potent cyclin-dependent kinase inhibitor. Mol Cancer Ther 9:2344-2353.

RUSHWORTH, L. K. et al. Regulation and role of Raf-1/B-Raf heterodimerization. Mol. Cell Biol., 2006, 26, 2262-2272.

SETH et al., Concomitant mutations and splice variants in KRAS and BRAF demonstrate complex perturbation of the Ras/Raf signalling pathway in advanced colorectal cancer, Gut 2009; 58:1234-1241.

WAN, et al., Mechanism of activation of the RAF-ERK signaling pathway by oncogenic mutations of B-RAF. Cell, 2004, 116, 855-867.

WEBER, C. K. et al. Active Ras induces heterodimerization of cRaf and BRaf. Cancer Res., 2001, 61, 3595-3598.

WELLBROCK C, Karasarides M, Marais R. The RAF proteins take centre stage. Nat Rev Mol Cell Biol. 2004; 5:875-85.

XU et al., High prevalence of BRAF gene mutation in papillary thyroid carcinomas and thyroid tumor cell lines. Cancer Res., 2003, 63, 4561-4567.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

SEQUENCE LISTING

```
Sequence total quantity: 18
SEQ ID NO: 1            moltype = DNA  length = 4454
FEATURE                 Location/Qualifiers
source                  1..4454
                        mol_type = genomic DNA
                        organism = Homo sapiens
SEQUENCE: 1
gaaacgtccc gtgtgggagg ggcgggtctg ggtgcggcct gccgcatgac tcgtggttcg  60
gaggcccacg tggccggggc ggggactcag gcgcctgggg cgccgactga ttacgtagcg  120
ggcggggccg gaagtgccgc tccttggtgg gggctgttca tggcggttcc ggggtctcca  180
acatttttcc cggctgtggt cctaaatctg tccaaagcag aggcagtgga gcttgaggtt  240
cttgctggtg tgaaatgact gagtacaaac tggtggtggt tggagcaggt ggtgttggga  300
aaagcgcact gacaatccag ctaatccaga accactttgt agatgaatat gatcccacca  360
tagaggattc ttacagaaaa caagtggtta tagatggtga aacctgtttg ttggacatac  420
tggatacagc tggacaagaa gagtacagtg ccatgagaga ccaatacatg aggacaggcg  480
aaggcttcct ctgtgtattt gccatcaata atagcaagtc atttgcggat attaacctct  540
acagggagca gattaagcga gtaaaagact cggatgatgt acctatggtg ctagtgggaa  600
acaagtgtga tttgccaaca aggacagttg atacaaaaca agcccacgaa ctggccaaga  660
gttacgggat tccattcatt gaaacctcag ccaagaccag acagggtgtt gaagatgctt  720
tttacacact ggtaagagaa atacgccagt accgaatgaa aaaactcaac agcagtgatg  780
atgggactca gggttgtatg ggattgccat gtgtggtgat gtaacaagat acttttaaag  840
ttttgtcaga aaagagccac tttcaagctg cactgacacc ctggtcctga cttccctgga  900
ggagaagtat tcctgttgct gtcttcagtc tcacagagaa gctcctgcta cttccccagc  960
tctcagtagt ttagtacaat aatctctatt tgagaagttc tcagaataac tacctcctca  1020
cttggctgtc tgaccagaga atgcacctct tgttactccc tgttattttt ctgccctggg  1080
ttcttccaca gcacaaacac acctctgcca ccccaggttt ttcatctgaa aagcagttca  1140
tgtctgaaac agagaaccaa accgcaaacg tgaaattcta ttgaaaacag tgtcttgagc  1200
tctaaagtag caactgctgg tgattttttt tttcttttta ctgttgaact tagaactatg  1260
ctaatttttg gagaaatgtc ataaattact gttttgccaa gaatatagtt attattgctg  1320
tttggtttgt ttataatgtt atcggctcta ttctctaaac tggcatctgc tctagattca  1380
taaatacaaa aatgaatact gaattttgag tctatcctag tcttcacaac tttgacgtaa  1440
ttaaatccaa ctttcacagt gaagtgcctt tttcctagaa gtggtttgta gacttccttt  1500
ataatatttc agtggaatag atgtctcaaa aatccttatg catgaaatga atgtctgaga  1560
tacgtctgtg acttatctac cattgaagga aagctatatc tatttgagag cagatgccat  1620
tttgtacatg tatgaaattg gttttccaga ggcctgtttt ggggctttcc caggagaaag  1680
atgaaactga aagcacatga ataatttcac ttaataattt ttacctaatc tccacttttt  1740
tcataggtta ctacctatac aatgtatgta atttgtttcc cctagcttac tgataaacct  1800
aatattcaat gaacttccat ttgtattcaa atttgtgtca taccagaaag ctctacattt  1860
gcagatgttc aaatattgta aaactttggt gcattgttat ttaatagctg tgatcagtga  1920
ttttcaaacc tcaaatatag tatattaaca aattacattt tcactgtata tcatggtatc  1980
ttaatgatgt atataattgc cttcaatccc cttctcaccc caccctctac agcttccccc  2040
acagcaatag ggcttgattt atttcagttg agtaaagcat ggtgctaatg gaccagggtc  2100
acagtttcaa aacttgaaca atccagttag catcacagag aaagaaattc ttctgcattt  2160
gctcattgca ccagtaactc cagctagtaa ttttgctagg tagctgcagt tagccctgca  2220
aggaaagaag aggtcagtta gcacaaaccc tttaccatga ctggaaaact cagtatcacg  2280
tatttaaaca tttttttttc ttttagccat gtagaaactc taaattaagc caatattctc  2340
atttgagaat gaggatgtct cagctgagaa acgttttaaa ttctctttat tcataatgtt  2400
ctttgaaggg tttaaaacaa gatgttgata aatctaagct gatgagtttg ctcaaaacag  2460
gaagttgaaa ttgttgagac aggaatggaa aatataatta attgatacct atgaggattt  2520
ggaggcttgg catttttaatt tgcagataat accctggtaa ttctcatgaa aaatagactt  2580
ggataacttt tgataaaaga ctaattccaa aatggccact ttgttcctgt ctttaatatc  2640
taaatactta ctgaggtcct ccatcttcta tattatgaat tttcatttat taagcaaatg  2700
tcatattacc ttgaaattca gaagagaaga aacatatact gtgtccagag tataatgaac  2760
ctgcagagtt gtgcttctta ctgctaattc tgggagcttt cacagtactg tcatcatttg  2820
taaatggaaa ttctgctttt ctgtttctgc tccttctgga gcagtgctac tctgtaattt  2880
tcctgaggct tatcacctca gtcatttctt ttttaaatgt ctgtgactgg cagtgattct  2940
ttttcttaaa aatctattaa atttgatgtc aaattaggga gaaagatagt tactcatctt  3000
gggctcttgt gccaatagcc cttgtatgta tgtacttaga gttttccaag tatgttctaa  3060
gcacagaagt ttctaaatgg ggccaaaatt cagacttgag tatgttcttt gaatacctta  3120
agaagttaca attagccggg catggtggcc cgtgcctgta gtcccagcta cttgagaggc  3180
tgaggcagga gaatcacttc aacccaggag gtggaggtta cagtgagcag agatcgtgcc  3240
actgcactcc agcctgggtg acaagagaga cttgtctcca aaaaaaaagt tacacctagg  3300
tgtgaatttt ggcacaaagg agtgacaaac ttatagttaa aagctgaata acttcagtgt  3360
ggtataaaac gtggttttta ggctatgttt gtgattgctg aaaagaattc tagtttacct  3420
caaaatcctt ctctttcccc aaattaagtg cctggccagc tgtcataaat tacatattcc  3480
ttttggtttt tttaaaggtt acatgttcaa gagtgaaaat aagatgttct gtctgaaggc  3540
taccatgccg gatctgtaaa tgaacctgtt aaatgctgta tttgctccaa cggcttacta  3600
tagaatgtta cttaatacaa tatcatactt attacaattt ttactatagg agtgtaatag  3660
gtaaaattaa tctctatttt agtgggccca tgtttagtct ttcaccatcc tttaaactgc  3720
tgtgaatttt tttgtcatga cttgaaagca aggatagaga aacactttag agatatgtgg  3780
ggttttttta ccattccaga gcttgtgagc ataatcatat ttgctttata tttatagtca  3840
tgaactccta agttggcagc tacaaccaag aaccaaaaaa tggtgcgttc tgcttcttgt  3900
aattcatctc tgctaataaa ttataagaag caaggaaaat tagggaaaat attttatttg  3960
gatggtttct ataaacaagg gactataatt cttgtacatt atttttcatc tttgctgttt  4020
ctttgagcag tctaatgtgc cacacaatta tctaaggtat ttgttttcta taagaattgt  4080
tttaaaagta ttcttgttac cagagtagtt gtattatatt tcaaaacgta agatgatttt  4140
taaaagcctg agtactgacc taagatggaa ttgtatgaac tctgctctgg agggagggga  4200
ggatgtccgt ggaagttgta agacttttat ttttttgtgc catcaaatat aggtaaaaat  4260
```

-continued

```
aattgtgcaa ttctgctgtt taaacaggaa ctattggcct ccttggccct aaatggaagg  4320
gccgatattt taagttgatt attttattgt aaattaatcc aacctagttc tttttaattt  4380
ggttgaatgt tttttcttgt taaatgatgt ttaaaaaata aaaactggaa gttcttggct  4440
tagtcataat tctt                                                    4454

SEQ ID NO: 2           moltype = AA  length = 189
FEATURE                Location/Qualifiers
source                 1..189
                       mol_type = protein
                       organism = Homo sapiens
SEQUENCE: 2
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                          189

SEQ ID NO: 3           moltype = DNA  length = 1326
FEATURE                Location/Qualifiers
source                 1..1326
                       mol_type = genomic DNA
                       organism = Rattus norvegicus
SEQUENCE: 3
gccgttcatg gcggtttcgg ggtctccaac agcttctcag gttgaaatcc aaaagcctcc  60
cgaggcgggg tctgcggagt ttgagatttt tgcaggtgtg aaatgactga gtacaaactg  120
gtggtggttg gagcaggtgg cgttgggaaa agtgctttga caatccagct aatccagaac  180
cactttgtgg atgaatatga tcccaccata gaggattctt accgaaaaca agtggtgatt  240
gacggtgaga cctgtctact ggacatactg gacacagctg gacaagagga gtacagtgcc  300
atgagagacc aatacatgag gacaggcgaa gggttcctct gtgtgtttgc catcaataat  360
agcaaatcct ttgcagatat taacctctac agggagcaaa ttaagcgcgt gaaagactct  420
gatgatgtac ccatggtgct ggtagggaac aagtgtgact tgccaacaag gacagttgac  480
acaaagcaag cccacgagct ggccaagagt tatggaattc cattcattga aacctcagcc  540
aagacccgac agggtgtgga ggatgccttt tacacgcttg taagggagat acgccagtac  600
cggatgaaga agctcaacag cagtgaggat ggcactcaag gctgtatggg gctgccctgt  660
gtggtgatgt agtaagaccc tttaaaagtt ctgtcatcag aaacgagcca ctttcaagcc  720
tcactgatgc cctggttctg acatccctgg aggagacgtg tttctgctgc tctctgcatc  780
tcagagaagc tcctgcttcc tgcttcccca acttagttac tgagcacagc catctaacct  840
gagacctctt cagaataact acctcctcac tcggctgtcc gaccagagaa atgaacctgt  900
ttctccccag tagttctctg ccctgggttt cccctagaaa caaacacacc tgccagctgg  960
ctttgtcctc cgaaaagcag tttacattga tgcagagaac caaactatag acaagcaatt  1020
ctgttgtcaa cagtttctta agctctaagg taacaattgc tggtgatttc cccctttgcc  1080
cccaactgtt gaacttggcc ttgttagttt tgggggaaat gtcaaaaatt aatctcttcc  1140
cgagaataga attagtgttg ctgattgcct gatttgcaat gtgatcagct atattctata  1200
agctggcgtc tgctctgtat tcataaatgc aaacatgagt actgacgtaa gtgcatccct  1260
agtcttctca gctgcatgca attaaatcca acgttcacaa caaaaaaaaa aaaaaaaaaa  1320
aaaaaa                                                             1326

SEQ ID NO: 4           moltype = AA  length = 189
FEATURE                Location/Qualifiers
source                 1..189
                       mol_type = protein
                       organism = Rattus norvegicus
SEQUENCE: 4
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSEDGTQG  180
CMGLPCVVM                                                          189

SEQ ID NO: 5           moltype = DNA  length = 4470
FEATURE                Location/Qualifiers
source                 1..4470
                       mol_type = genomic DNA
                       organism = Mus musculus
SEQUENCE: 5
gggactgggg cgccttgggc gcctagtgat tacgtagcgg gtggggccgg aagtgccgct  60
ccctggcggg ggctgttcat ggcggtttcg gggtctccaa cagcttctca ggttgaagtc  120
caaaagcctc ccgaggcggg gtctgcggag tttgaggttt ttgctggtgt gaaatgactg  180
agtacaaact ggtggtggtt ggagcaggtg gtgttgggaa aagcgccttg acgatccagc  240
taatccagaa ccactttgtg gatgaatatg atcccaccat agaggattct taccgaaagc  300
aagtggtgat tgatggtgag acctgcctgc tggacatact ggacacagct ggacaagagg  360
agtacagtgc catgagagac cagtacatga ggacaggcga agggttcctc tgtgtatttg  420
ccatcaataa tagcaaatca tttgcagata ttaacctcta cagggagcaa attaagcgtg  480
tgaaagattc tgatgatgtc cccatggtgc tggtaggcaa caagtgtgac ttgccaacaa  540
ggacagttga cacaaagcaa gcccacgaac tggccaagag ttacggaatt ccattcattg  600
agacctcagc caagacccga cagggtgtgg aggatgcctt ttacacactg gtaagggaga  660
tacgccagta ccgaatgaaa aagctcaaca gcagtgacga tggcactcaa ggttgtatgg  720
ggctgccctg tgtgctgatg tagtaagaca ctttgaaagt tctgtcatca gaaaagagcc  780
actttgaagc tgcactgatg ccctggttct gacatccctg gaggagacct gttcctgctg  840
ctctctgcat ctcagagaag ctcctgcttc ctgcttcccc gactcagtta ctgagcacag  900
ccatctaacc tgagacctct tcagaataac tacctcctca ctcggctgtc tgaccagaga  960
```

-continued

```
aatagacctg tctctcccgg tcgttctctg ccctgggttc ccctagaaac agacacagcc  1020
tccagctggc tttgtcctct gaaaagcagt ttacattgat gcagagaacc aaactagaca  1080
tgccattctg ttgacaacag tttcttatac tctaaggtaa caactgctgg tgattttccc  1140
ctgcccccaa ctgttgaact tggccttgtt ggtttggggg gaaaatgtca taaattactt  1200
tcttcccaaa atataattag tgttgctgat tgatttgtaa tgtgatcagc tatattccat  1260
aaactggcat ctgctctgta ttcataaatg caaacacgaa tactctcaac tgcatgcaat  1320
taaatccaac attcacaaca aagtgccttt ttcctaaaag tgctctgtag gctccattac  1380
agtttgtaat tggaatagat gtgtcaagaa ccattgtata ggaaagtgac tctgagccat  1440
ctacctttga gggaaaggtg tatgtacctg atggcagatg ctttgtgtat gcacatgaag  1500
atagtttccc tgtctgggat tctcccagga gaaagatgga actgaaacaa ttacaagtaa  1560
tttcatttaa ttctagctaa tctttttttt tttttttttt tttttggta gactatcacc  1620
tataaatatt tggaatatct tctagcttac tgataatcta ataattaatg agcttccatt  1680
ataatgaatt ggttcatacc aggaagccct ccatttatag tatagatact gtaaaaattg  1740
gcatgttgtt actttatagc tgtgattaat gattcctcag accttgctga gatatagtta  1800
ttagcagaca ggttatatct ttgctgcata gtttcttcat ggaatatata tctatctgta  1860
tgtggagaga acgtggccct cagttccctt ctcagcatcc ctcatctctc agcctagaga  1920
agttcgagca tcctagaggg gcttgaacag ttatctcggt taaaccatgg tgctaatgga  1980
ccgggtcatg gtttcaaaac ttgaacaagc cagttagcat cacagagaaa cagtccatcc  2040
atatttgctc cctgcctatt attcctgctt acagactttt gcctgatgcc tgctgttagt  2100
gctacaagga taaagcttgt gtggttctca ccaggactgg aagtacctgg tgagctctgg  2160
ggtaagccta gatatcttta cattttcaga cccttattct tagccacgtg gaaactgaag  2220
ccagagtcca tacctccatc tccttccccc cccaaaaaaa ttagattaat gttctttata  2280
tagcttttttt aaagtattta aaacatgtct ataagttagg ctgccaacta acaaaagctg  2340
atgtgtttgt tcaaataaag aggtatcctt cgctactcga gagaagaatg taaaatgcca  2400
ttgattgttg tcacttggag gcttgatgtt tgccctgata attcattagt gggttttgtt  2460
tgtcacatga tacctaagat gtaactcagc tcagtaattc taatgaaaac ataaattgga  2520
taccttaatt gaaaaaagca aacctaattc caaaatggcc attttctctt ctgatcttgt  2580
aatacctaaa attctgaggt ccttgggatt cttttgttta taacaggatc ttgctgtgta  2640
gtcctagctg gcctcaaact cacaatactc ttcctggatc aatctcccaa gtgctgggat  2700
tacaggcaca ttccaccaca cacacctgac tgagctcgtt cctaatgagt tttcattaag  2760
caaattcccc atcaccttga aactaatcag aagggggaag aaacatttgc tatgctcctg  2820
agtgctaaca ctgggatcat tcacatgggg tttgcattcc taggcaaact aaactgctgc  2880
cttttacaac aaggctcagt catcttcctg aagctgctga gaccagcact tggtcttgtt  2940
ttgttttaat atgtctatat gactggtggt ggatccctaa atagtttatt aattaaactc  3000
cagttaagga gaaagttact caccttgacc cgtttgacca tatcccgtgt gtgtgtgtgt  3060
gtgtgtgtgt gtgtgtgtgt gtgtgtgtgt gtgcacgcgt atgtacgtac gtatgtatgt  3120
aggtatgtag gtggtttcca gtataaacac agaaacaaat ggagccaatt caggtttcag  3180
atgcccttac taacatatat tcccacgggg tgtgggtttt ggcacaacag tgacaaactt  3240
aaaagccaag taagagccgg gcgtggtggc gcacgccttt aatcccagca cttgggaggc  3300
agaggcaggc ggatttctga gttctaggcc atcctggtct acagtgagtt ccaggacagc  3360
cagtgctaca cagagaaacc ctgtctcgaa aagccaaaaa aaaaaaaaaa aaaaaaaaaa  3420
aaaagccaag taggtccagt tggtatagta tcaaagtgtt tttagagtaa ttagtgaagg  3480
tctgctttac ctcaaagttg cagagcctct cttcctgagt ttaagtgcct ggccggcagt  3540
cacaaattaa catgttgctg taaggcagtt agttgaagct ttgttcacac attggagagt  3600
atgaaaataa agtgttctaa gagcgctgat actggatctg tgtaaacctg gtaaatgccg  3660
tttgtccagg acttagcgtg tgtgagttgg tagctcagta cgagtttact agttccgcag  3720
tgtgtacaat ggaggcgggt ttgttttagc tggccacctg tagaatcagc ctttaaactg  3780
ctgtgaactt tgtcatgact tgaatatgaa gatagacaaa aactctgtaa agacaaatgt  3840
ttgttttccc ccttacagaa cgtgtgagct tggttttatc ttcctttgta tttagtcata  3900
acctctcaag ctggcagctc cgaccaagga tcagaagctg tgtgcgttcc acctggtgga  3960
attagctcag ctctatatga gaagtggagt taatggaaaa cgtgttgact gggtggtttc  4020
tatttaaaag agtgatgata attcttgaac agtagttttt attttgctat ttctttaagc  4080
tgactgatgt gccacaaaat tattttaagg tatttgtgtt ttaagagtgt tctcatgaga  4140
ttagttgtag atatttttta aaatacaact ggtttttaaa atctgagtat tgctctaagc  4200
aagtgtttag actcttacgg gaaggtgggt ggaagttgtt tggcttccgt atttccatgc  4260
gtgccgtcag acataggtca gaacgccaac tgtgcatcct gctgtttaaa gacctcttgg  4320
cctctgtgac cctcatgaag gggctgatat tttaagttga ctgtttgatt gtaaattaat  4380
cctttctaat ttttaaagac ttgcttgact gttttccttg ttaaataatt ttaaaaaaat  4440
aaaaaactgg aagttctttg cttaactgta                                   4470
```

```
SEQ ID NO: 6           moltype = AA  length = 189
FEATURE                Location/Qualifiers
source                 1..189
                       mol_type = protein
                       organism = Mus musculus
SEQUENCE: 6
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVLM                                                          189
```

```
SEQ ID NO: 7           moltype = DNA  length = 570
FEATURE                Location/Qualifiers
source                 1..570
                       mol_type = genomic DNA
                       organism = Cavia porcellus
SEQUENCE: 7
atgactgagt ataaactggt ggtggttgga gcaggtggtg tcgggaaaag tgcactgacc  60
atccagctaa ttcagaacca ctttgtcgat gaatatgatc ccaccataga ggattcttac  120
```

-continued

```
cgaaaacagg tggttataga tggtgaaact tgtctgttgg atattctgga tacagctgga  180
caagaggagt acagtgccat gagagaccaa tacatgagga caggcgaagg cttcctctgt  240
gtgtttgcca tcaataatag caaatcattt gcagatatta acctctacag ggagcagatt  300
aaacgagtaa aagactcaga tgatgtacct atggtgctgg tagggaacaa gtgtgatttg  360
ccaacaagga ctgttgacac aaaacaagcc catgaactgg ccaagagtta cgggattcca  420
ttcattgaaa cctcagccaa gaccagacag ggtgttgaag atgcatttta cacactcgta  480
agagaaatac gccagtacag aatgaaaaaa ctcaacagca atgatgatgg gactcaaggt  540
tgtatggggt tgccatgtgt ggtgatgtaa                                  570

SEQ ID NO: 8           moltype = AA  length = 189
FEATURE                Location/Qualifiers
source                 1..189
                       mol_type = protein
                       organism = Cavia porcellus
SEQUENCE: 8
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSNDDGTQG  180
CMGLPCVVM                                                         189

SEQ ID NO: 9           moltype = DNA  length = 1220
FEATURE                Location/Qualifiers
source                 1..1220
                       mol_type = genomic DNA
                       organism = Cavia porcellus
SEQUENCE: 9
gttccggggt cctcaacgtt tctcagggtt gagattctat atccttttga agctggggcg  60
gcagagcttg aggttcttgc tggtgtgaaa tgactgagta taaactggtg gtggttggag  120
caggtggtgt cgggaaaagt gcactgacca tccagctaat tcagaaccac tttgtcgatg  180
aatatgatcc caccatagag gattcttacc gaaaacaggt ggttatagat ggtgaaactt  240
gtctgttgga tattctggat acagctggac aagaggagta cagtgccatg agagaccaat  300
acatgaggac aggcgaaggc ttcctctgtg tgtttgccat caataatagc aaatcatttg  360
cagatattaa cctctacagg gagcagatta aacgagtaaa agactcagat gatgtaccta  420
tggtgctggt agggaacaag tgtgatttgc caacaaggac tgttgacaca aaacaagccc  480
atgaactggc caagagttac gggattccat tcattgaaac ctcagccaag accagacagg  540
gtgttgaaga tgcattttac acactcgtaa gagaaatacg ccagtacaga atgaaaaaac  600
tcaacagcaa tgatgatggg actcaaggtt gtatggggtt gccatgtgtg gtgatgtaac  660
aagatattta acaaagttct atcagaaaag agccactttc aagctgcact gataccctgg  720
tcctgacttc cctggaggag aagtatccct gttgctctct tcatctcaga gaagctcctg  780
ctgtttgtcc acctctcagt gtatgagcac agtctctgct tgagaacttc tcagaataac  840
tacctcctca cttggttgtc tgaccagaga aatgcacctc ttgttaattc cccaataatt  900
ttctgccctg ggctctcccc aacaaaaaac aaacacttct gccatccaaa aagcaacttg  960
gtctgaaaca gaaccaaact gtagattgaa attctcttaa aaagtcttga gctctaaagt  1020
tagcaaccgc tggtgatttt tattttcctt tttattttg aacttggaac tgacctatgt  1080
tagattttgg agaaatgtca taaagtactg ttgtgccaag aagataatta tgttgctgaa  1140
tggttgattt atagtgttat cagctatatt ttacaaactg gcatctgctc tgtattcata  1200
aatacaaaaa tgaagccagg                                             1220

SEQ ID NO: 10          moltype = AA  length = 189
FEATURE                Location/Qualifiers
source                 1..189
                       mol_type = protein
                       organism = Cavia porcellus
SEQUENCE: 10
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSNDDGTQG  180
CMGLPCVVM                                                         189

SEQ ID NO: 11          moltype = DNA  length = 1307
FEATURE                Location/Qualifiers
source                 1..1307
                       mol_type = genomic DNA
                       organism = Canis lupus
SEQUENCE: 11
tgattacgta gcgggcgggg ccggaagtgc cgctccctag tgggggctgt tcatggcggt  60
tccggggtct ccaacctttc tcctagttgt ggtcctaaat acgtcggaag cggaggcggc  120
gaagcttgag gttcttgctg gtgtgaaatg actgagtaca aactggtggt ggttggagca  180
ggtggtgttg ggaaaagcgc actgacaatc cagctaatcc agaaccactt tgtagatgaa  240
tatgatccca ccatagagga ttcttaccga aaacaggtgg ttatagacgg tgaaacctgt  300
ctgttggata tactggatac agctggtcaa gaagagtaca gtgccatgag agaccaatac  360
atgaggacag gcgaaggctt cctctgtgta tttgccatca ataatagcaa atcatttgca  420
gacattaacc tctacaggga acagattaag cgagtaaaag attcagatga tgtacctatg  480
gtgctagtag gaaacaagtg tgatttgcca acaaggacag ttgacacaaa acaagcccat  540
gaactggcca agagttatgg gattccattc attgaaacct cagccaagac cagacagggt  600
gtcgaggatg ccttttacac actggtaaga gaaatacgtc agtaccgaat gaagaaactc  660
aacagcagtg atgatgggac tcaaggttgt atggggttac catgtgtggt gatgtaacaa  720
gacactttta aagttctagc atcagaaaag agccactgtc aagctgcact gacaccctgg  780
tcctgacttc cctggaggag aagtattcct gttgctatct tcagtctcac aaagaagctc  840
```

-continued

```
ctgctacttc cccaactctc agtagatcag tacaatgttc tctatttgag aagttctccg  900
aacaactacc tcctcacttg gttgtctgac cagagaaatg aacctcttgt tccttcccgc  960
tgtttttcca ccctgaattc tcccccaaca cacataaaca aacctctgcc atcccaggtt  1020
tttcatctga aaaataattc atgctctgaa acagagaaca aaactgtaga catgaaattc  1080
tgtaggaaac aaggtcttga gctcaaaagt agcaactgct ggtgaccttt ttttcccccc  1140
tttttactgt tgaacttgga actatgttgg tttttggaga aatgtcataa gttactgttt  1200
tgctgagaat atagttaagt tgacatttgg tttgtttgta atatcattag ctattttcta  1260
taaattggca tctgctctgc attcataaat acacgagtga attctga               1307

SEQ ID NO: 12          moltype = AA  length = 189
FEATURE                Location/Qualifiers
source                 1..189
                       mol_type = protein
                       organism = Canis lupus
SEQUENCE: 12
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                         189

SEQ ID NO: 13          moltype = DNA  length = 3104
FEATURE                Location/Qualifiers
source                 1..3104
                       mol_type = genomic DNA
                       organism = Felis catus
SEQUENCE: 13
aaaaaataaa taaatttaag aaaccatttt aaaattatgc acagttgcag cctggaaaac  60
ttaaggtggc gccttatagt atcaatctta ggagctttat ttggtgcatt taacgcaact  120
ggtaattgca aaatccactt cgcctgtgta agtgaaaaat atagactgtt atcttgttgg  180
ccctatgaaa ttctgcactt ggtatttagc atatactcta ccttcattac tatctggcaa  240
gatgttctgc cttagcactc agttgcattc ttttcctttt ctttcctgtt cattatgctt  300
taattctgag gaccatatga gggtagaata tattaaaaat tacaaaaatt ataaaaattt  360
gtataggcaa accatttcct taagttgatg gccaaatgtt aaaatgttat ttttcatatc  420
atttataatc ttgtcacagt ccacttaacg aagtttggtt agatttcagt gaaaattatc  480
ttccagagta gttttttttt ttttttcctg ggattaggga ggggggtaac tttactgcaa  540
ttagtatgta tggtgcagaa tttcatgcaa atgaggtgtg ccagcagtgt ggtaatttaa  600
tcgtatttaa acaaaaacaa acaaaaaaaa aacgaatgca caaacttgct gctgcttaga  660
tcactgcagc ttctaggacc cagtttcttt tactgatttc aaaacaaaac aaaacaaaaa  720
aataaaaaaa gttgtgcctg aaatgaatct tgtttttttt ataagtagcc gcctggttcc  780
tgtgtcctgt gaaatacagg cacttgaccc ttggtgtagc ttctgttcga ctttatatca  840
cgggaatgga ttggtctgat ttcttggccc tcatcttgaa ttggccacat ccagggtccc  900
tggccagtgg actgaaggct ttgtctaaga ggacaagggc agctcagggg atgtggggga  960
gggcgctttt atcttccccg ttgtcgtttg aggttttgat cttctctggg taaagaggcc  1020
gtttatcttt gtaaacacaa aacatttttg ctttctccag ttttctgtta atggcgaaag  1080
aatggaagcg aataaagttt tactgatttt tgagactcta gcacctagcg ctttcatttt  1140
tgaaacgtcc tgtgtgggag gggcgggtct gggtgcggcc cgccgcgtga ctcctgagtc  1200
gggggcccac gtggctgggg cggggactcg gacgccccgg gcgccgactg attacgtagc  1260
gggcggggcc ggaagtgccg ctccctagtg ggggctgttc atggcggttc cggggtctcc  1320
atcctttttc ccagttgttc taaatcagtc ggaagcggag gcagcgaagt ttgaggttct  1380
cgctggtgtg aaatgactga gtacaaactg gtggtggttg gagcaggtgg tgttgggaaa  1440
agcgcactga caatccagct aatccagaac cactttgtag atgaatatga tcccaccata  1500
gaggattctt accgaaaaca ggtggttata gacggtgaaa cctgtctgtt ggacatactg  1560
gatacagctg gtcaagaaga gtacagtgcc atgagagacc aatacatgag gacaggcgaa  1620
ggcttcctct gtgtatttgc catcaacaat agcaaatcat ttgcagatat taacctttac  1680
agggaacaga ttaagcgagt aaaagactcc gatgatgtac ctatggtgct agtaggaaac  1740
aagtgtgatt tgccaacaag gaccgtcgac acaaaacaag cccacgaact ggccaagagt  1800
tatgggattc cattcattga aacctcagcc aagaccagac agggtgttga agatgccttt  1860
tacacactgg taagagaaat acgtcagtac cgaatgaaga aactcaacag cagtgatgac  1920
gggactcaag gttgtatggg gttaccgtgt gtggtgatgt aacaagatac ttttaaagtt  1980
ctagcatcag aaaagagcca ctgtcaagct gcactgacac cctggtcctg acttccctgg  2040
aggagaagcg ttcctgttgc tattttcagt ttcacaaaga agctcctgct atttccccaa  2100
ctctccgtag atcagtacat tattctctgt ttgagaagtt ctccgaataa ctacctcctc  2160
acttggttgt ctgaccagag aaatgaacct cttgttactc cccactgttt ttccaccctg  2220
gttctccccc agcacatata aacaaacctc ccaggttttt catctgaaaa gtaattcatg  2280
ctctgaaaca gagaaccaaa ctgtagacat gaaattctgt aggaaacaat gtcttgagct  2340
ctaaagtagc aactgctggt gacttttttt ttttttttt ccttttact gttgaacttg  2400
gaactatgtt ggtttttgga gaaatgtcgt aagttactgt tttgctgagt atatagttaa  2460
gtttaccatt cggtttgttt gtaatgtcat tggctatact ctgtacctgg catctgctct  2520
gcattcataa atacaaaagt gaattctgac ttttgagtct atcctagtgt tctcaacttc  2580
cacataatta aatctaactt ttgcagcaaa gtgccttttt cctagaagtg gtttgtagat  2640
ttgctttata atactttggt ggaatagatg tctcaaaaac cattatacat gaaaatgaat  2700
gtctgagata cgtctatgat ctgtctacct ttgagggaaa aatataccga cataatagca  2760
gatgccatgt cttacgtgta tgaagttgga tttccagaga cctgatttgg gtctcttcca  2820
agagaaagat gaaactggaa acaattatga ataacttcac ttaattttta cctaatctct  2880
acttcggggt gggagggcag ggagtaggtt accacttaca aaatatatgc aatttgtttc  2940
ttctagctta ctgataatga acttccattc ttatttaaat ttaggtcata tcctaaagct  3000
ttacatttgc aggtgttcga aattgtaagt ttaatgcagt tttatttaat agctatgatc  3060
aatgatttc aagcctcaga tgtattaacg gacacatttt cact                    3104
```

-continued

```
SEQ ID NO: 14          moltype = AA  length = 189
FEATURE                Location/Qualifiers
source                 1..189
                       mol_type = protein
                       organism = Felis catus
SEQUENCE: 14
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                         189

SEQ ID NO: 15          moltype = DNA  length = 4283
FEATURE                Location/Qualifiers
source                 1..4283
                       mol_type = genomic DNA
                       organism = Bos taurus
SEQUENCE: 15
ggccgctccc tagtgggggc tgttcatggc ggttccgggg tctcccaaca attttcccgg  60
ttgtggtcgt aatctatccg aagtggaggc agtggagcta gaggttcttg ctggtgtgaa  120
atgactgagt acaaactggt ggtggttgga gcaggtggtg ttgggaaaag tgcactgaca  180
atccagctaa tccagaacca ctttgtagat gaatatgatc ccaccataga ggattcctac  240
cgaaaacagg tggttataga tggtgaaacc tgtctgttgg acatactgga tacagctgga  300
caagaggagt acagtgccat gagagaccaa tacatgagga caggcgaagg cttcctttgt  360
gtgtttgcca tcaataatag caaatcattt gcagatatta acctctacag ggaacagata  420
aagcgtgtaa aggactcgga tgatgtacct atggtgctag taggaaacaa gtgtgatttg  480
ccaacaagga cagttgacac aaaacaagcc catgaactgg ccaaaagtta tgggattcca  540
ttcattgaaa cctcagccaa gaccagacag ggtgttgaag atgcctttta cacactggta  600
agagaaatac gtcagtaccg aatgaaaaag ctcaacagca gtgatgatgg cactcaaggc  660
tgtatggggt tgccgtgtgt ggtgatgtaa caagatactt ttaaagttct cacatcagaa  720
aagagccact gtcaagctgc actgacaccc tggtcctgac ttccctggag gagaagtatt  780
cctgttgcta tcttcagttt caaaaagaag ctcctgctat ttccccaact ctcagtagat  840
caatataata ttctctattt gagaagttct caagaataac tacctcctca cttggttgtc  900
tgaccagaga attgaacctc ttgttactcc cagtattttt ccaccctggg ttctccccca  960
gcacacacaa acgcacctct gccacccagg tttttcatct gaaaagcaat taatactctg  1020
aaacagagaa ccaaactgta gaaacatgaa attctgtaga aaacaatgtc ttgagctcta  1080
aagtagcaac tgctggtgat tttttttttt tttttttcct ttttattgtt gaacttggaa  1140
ctatgttggt ttgtggagaa atgtcataaa ttactgtttt gctgagaata tagttaatgt  1200
tgctctctgg tttgtttgta atgttatcag ctatattcta taaactggca tctactctgt  1260
atttagaaat acaaaaatga atactgacct tttgagtcta ccctcatctt ctcgactttc  1320
ttgtaattaa atgtaacttt cacgatgaag tgccttttgc ctgggagtga ctcgtagact  1380
tcctttaaaa tacttcagtg gaatagatgt ctcagaaact gttatacata agaataaatg  1440
tctgagatat gtctatgacc catctagctt tgagggaaag atataccaat atgatagcag  1500
atgccatttc ttacatctat aacgttgatt ttctggagac ctattttggg gctctccgag  1560
agaaagatga gactataaat gattaggaat aatttcactt aatttttaca taacctccac  1620
tttttgtttt gtagtttact acctgcaaaa catataattt gattcctttt agcttacaga  1680
taatctaatg ttaaatgaac ttccattcat attttaattt ggatcatatc aggaagtcta  1740
catttgcagg tgttcaaaaa ttgtaaaagt gtgatgcagt tttatttaat agctgtgatc  1800
aatgattttc aagcctcaaa tatgttaata gacacatttt cactgtatat catggtatta  1860
ataattattg atgtatataa ttgtccttgg tccccttctc tgttcatcac ctcatggcaa  1920
tggcttgatt aattatttca gctgagtaaa gcatggtgct aatagaccag ggtcacagtg  1980
tcaaaacttc agtgagccag taagcatcac agagaaagaa attctttcac atttgctcac  2040
cattaactcc agctaatagt tttgccagat gtgtgtggtt agtcctgcaa ggaaaggaga  2100
agtcagttaa tacaaattct taaccaggac tggaaaaact tgttttcctg agaagggtca  2160
gcttagaagt ctttatctgg actctatttt tagccacatg gaaatcaaat taagctgatc  2220
tttttctcca agtttttgag agtgaggatg cctcagatca acatttttaa aatattcttt  2280
attcttacgt tcttttaagg gtttaaaaca acgttgagta attagtctgg gcataccagg  2340
taacaagctg ataagtttgt gctgaacaag aagtagcctt tggattgaaa ttgctgtttt  2400
gagaagggat agaaaatata attaataatt atgagacttg acttttctat ttgcagataa  2460
tatcctgata attctgatga aaatagactt ggataatttt tgataaaaga atcgttccaa  2520
aatggccact tgctgttctt gtcttctaat gtgtaaatac ttactgaggt cctcttctaa  2580
tatgagttgt catttattaa gcaaattcca cattgccttg aaatgaattc ggaagagaag  2640
aaaaagtcat agtataccca gagaatgaaa aatccagaga attgtgctcc ttagtgttaa  2700
ttctgaagcc ttcgtagtcc acacccatag acagaaactc tctgccactt tgcttctgct  2760
cctcttggag cattgcgctg tcatttcctt gaggatagat tgaggcttgt caactcagtt  2820
gtattgtctt cctcctcttc ctcttgtctg tgtgactgac agtgtgactc ttactaatgt  2880
cagatgcggg gatgcgggga ggtggggggg agtagctcat tttaggctct tgcacccttt  2940
accgttgtat gtgtgtgtct tttagttttc tcaagaatgt tctaagcaca gaagtatcta  3000
aatggggcca aaattcagac ttgaaaatgt tcttttaata gcttcttaaa aagttacact  3060
ttggtgtgaa ttttggcagg atagagtgac aaactcttaa acgctgaata acttcagtta  3120
gtgtgttata gtttttagaa tatgtttgtg attgctgaaa acaattatag tttacctcaa  3180
aatctgaaag tctctttccc caagttaagt gcctggccag ctgtcaaaga ttacatatta  3240
ctttatgttt gtttgttttt taaaggttgc acattcaaga ttgtgaaaat aaggtgttct  3300
gtctgaaagc taccatgcct gtctgtaaat gaatccactg agtgctgtac ttgttccaac  3360
agcttactac agaatgctac ttggtaatat catactcgtt acagttttca cttcaggagt  3420
gtactaggta gaatgatcct gtgtgtattg tagtgggctc catgtttagt cttttcagca  3480
tcctttaaac tgctgtgaat ttttgtcttg acttgaaagc aaggatagag aaacacttta  3540
aagagatact ttgggttttt ttccattcca gaattggtga gcatagttag attttgcttt  3600
acatttacag tcatgaactc ttaagctggc agctacaacc aagaaccaaa agagggtgca  3660
ttctgcttct tgtaattcat ctttgctaat aaattatgag aagcaaagat aattaattag  3720
```

```
agaaactatt ttatttgggt ggtttctata aacaagggac tataattctt aaacattatt  3780
tttcattttt gctgtttctt taagaaacct aatgtgccac aacattattt taaggtgttt  3840
cttaaaagaa ttgtttttaa aagtgttctc attttcagag taattgtaga tatatttcaa  3900
aatataactg ataattttta aaggcctgag tactgaccta agaagcagtt gtatgaattc  3960
tctgggggga agggaggagc tcagtgaaag ttgtatgact tttatatttc tgtgccatca  4020
aataaaggta aaaatgtctt ttgtgcagtt ttgctgttca aacagaaact attggcctcc  4080
ttggccctaa atgaaagggc tggtatttta agttgactat tttattgtaa attaatccat  4140
cttaattttt ttaaatttgg ttgaatgttc tcttgttaaa tgtttaaaaa ataaaaactg  4200
gaagttcttt gcttagtcat aaaaaaaaaa aaaaaaaaaa aaaaaaaaaa aaaaaaaaaa  4260
aaaaaaataa aaaaaaaaaa aaa                                          4283

SEQ ID NO: 16          moltype = AA  length = 189
FEATURE                Location/Qualifiers
source                 1..189
                       mol_type = protein
                       organism = Bos taurus
SEQUENCE: 16
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                          189

SEQ ID NO: 17          moltype = DNA  length = 4825
FEATURE                Location/Qualifiers
source                 1..4825
                       mol_type = genomic DNA
                       organism = Gallus gallus
SEQUENCE: 17
gcgccgggac cggaagccgg aagctttgca gaagggtgtt ccgcgttcgc ggtgcgggag  60
cggtcagccg gggtggcggg gctggggccg gccggggcag gcggctccgc gctccgcact  120
gggccgctgg gagggcgatg actgaataca agctggtggt ggtgggagct ggcggcgtcg  180
ggaagagcgc gttgaccatc cagctcatcc agaaccactt cgtggacgag tacgacccca  240
ccatcgagga ttcgtacaga aagcaggttg tcatcgatgg agagacgtgc ttgttggaca  300
ttctggacac tgcaggacag gaagaataca gtgctatgcg tgatcagtac atgagaactg  360
gggaaggatt cctttgtgtg tttgccatta acaacagtaa atcattcgct gatattaacc  420
tttacagaga gcaaatcaag agagtgaaag attcagacga tgtgccaatg gtgctggtgg  480
ggaataagtg cgatttgcca acaaggacag tagacaccaa acaggctcaa gagttagcaa  540
aaagctacgg cattcccttc atagagacat cagccaaaac gagacagggt gtggaagatg  600
cgttttacac actggtgagg gagattcggc agtaccggat gaaaaagctc aacagcaacg  660
aagatgggaa tcagggctgt atggggttgt cctgcattgt gatgtgataa gatgccaggt  720
tcagatgtag ctgctggaca agtctcgatg ctactgtatt gtgtctcatg ctgatgccct  780
gcagtatttt ggtgccagcg accagactct tggtaccagt taattagctc aggatccttt  840
cctgtgctcc atctgaagaa aacatctctg gtatctacct ccttgctcag ctcacagagc  900
agtcatatct cttggtgtac tgggattctt ttctagctgt gttgtctggg tttgttcaag  960
aagaaaacca gtcacaagaa aagtgaatta cagagactaa atgctgtgaa aaagatcaca  1020
ctttacctcc agagtaaaag ctagaaagtgg cgtttgaccc ctttgcattg gattcagatt  1080
tgcggtgttg tcagaggagt ggcagaagta attttgccat tacaaaggtt tctgtcacca  1140
gtcggattgg tatctgctgt ctgtgcaccc acacagtgta tctgcaacat ctgcattgtg  1200
ccagaagtat cacttaactg atgaactgat cctttatttt tctgtaataa aaaggagata  1260
tctttgctaa cttaagtgcc tgtttgctca gaaggttgga ggttgtatgc tgttcccttg  1320
ggctgaggag aaccccaagg atgaatttct tgggtgctca ttgtcttgag caggcaagtt  1380
ttgtgtgggt gatctctttt catggcagga tattaaaatg ggaatttgta gtctggaaga  1440
tggagcagct gtttgtgaga ctcttgagtt agggagagaa atgtatacca cgtctgttct  1500
cgatccatca gaatggatcc atccacctct ttgtgtgtgg aactgtgtat agtctgtatt  1560
ggttttctac agcacttgga tctctttgga ccaaattagc gagctgttca ttttaacata  1620
actgccagta tttatagaca atttcttacg gacagataat gaatttagaa actggaggtt  1680
actttgggca gctgttcctc agctctgtct gtaacttgca aattattctg agttattttc  1740
tgcagaacct ccttccttat cacgggagga gcctgggagt tgaggttgac tgtaattggg  1800
tcaatggttg tcacagactt aaggtgtcca ggctgattgg aggaggcact gagccctaac  1860
agagcactga gctgacttct aattgcagca tccttgcaaa atgaggaagg gagttcagtg  1920
atgtctgcac tgaagatgta tgatacactg atagcagttc tgggtatgtt gtaacagctt  1980
caaagtagaa ccgcagtact gcgtgagctg tgtgacttct tcctagaaca cagcactgtc  2040
accccatatg gttgggacgt gcaggtgaga ccaacaccta ccaggttccc tggcgtaccg  2100
tggccttctc agttcttgtg ccagtgatac tgggttctgt tctgtggtgt cagacagcgt  2160
cctgtagcaa agctgaattc ccacttagtc tggtgagaga ataaagagcc atcagccaac  2220
agagggagcg ttcattctgc tggagcagtg cgagctgtaa gcattacgag aggcgtagtt  2280
tcagtttgtt gcagtcaggt tcctatattt tcaaagctga aatcagaaat aagtaaatac  2340
ggagaaaata agctgttgct tttaatgctc tttcctccac taattgtact cttaattttc  2400
ttcttgggag gccgaggatc catctgcata actttagctg tgatgctcca gataagtgtt  2460
tagaattcat tttatctttg actgatggga ctgataagaa gttaacgcac aatattttta  2520
catacaacat cgttttccag tgacctcctg agcggtggga agcattatgg gatagcaccg  2580
gctgtgactc gagttcattt gaaggcgatc tcttgcctgc aggttaaatg ggacggagtc  2640
agaatcactg tgagccgtct gtaatcagca aacagtctgt gggcttttct tactgtgttc  2700
tctctgtttg ccttagtttg gtgcaggaag agttccttgt gacagcgtcc tttgaggtgt  2760
gttgcaggag ctgaccattt gctccttgag ctgtgtgatg aactgttgtc cacttaatgg  2820
agttacagaa gcagcttctg ggagtcgcat ctggtcgcat acattcagtg ttttgggaag  2880
ctgtcagtgt ggtgtttgca ctgtgtttga atggtgttca tggtgggtct gttatgctcc  2940
tggatgattt ggggagatgt ggggctgctt ccgtggcaga caggatcagc tcagggcgct  3000
gctgcctatg gctgtgggaa acctcacagt tggtgtttga atagtggcca agtatgtcaa  3060
```

-continued

```
ttaaaaatac attttgaagg gaggtttgtc atagctctgt actttggcat gctctgctta  3120
ctgaaaacat actagctgta gctcaaaaaa agttgtgaat cctcagaata atacaggagc  3180
tggcaattgt ggctgctttc tctttgtgtt ccttttctct tgggttggat gaagctttaa  3240
aaaggaagga gccctggtga gggttggtca gtgtgcattt cattcttgga accagagagg  3300
aagttgcatc aactttcagg acgctgcaga gctcacttgc acaggtggtg ctccagtcta  3360
tgtgattttt ggggtcaaat cttgagatga tcttacaaaa tcagattttg tacccatcat  3420
gagcatgagg tgagtggttg tgctcggttt ctagctgcat gtatgtatac agacacgtgt  3480
atgcagacat gtctatgtgt gagtagttcg agtcagtcaa ggttactggc agcacctaaa  3540
gcgtatgcac cacataatgc atgcaggcaa aagtcctatc ttaggagcca tctcttcatg  3600
ggtttgggtt tatataggca gtatttttaa acagaatatc cgaagcactt tctggagttc  3660
tgtggtaatg cagtgacacc tatttggatg aaggaagatg tgtctgagga gcacgtaagc  3720
agatttgctg ccctaacaga gaggttttgg taaccgtgga aaaggttttc tcctggatct  3780
gtgtgtgctc ttggtgagct gcaatccatg acagggcaca accagatgag aaggaaaccc  3840
ggccatccca tgcttgagca cagctctgac tcagtagttc caccagatgt gccctttcag  3900
tcaaagtgtt ctgatctctt agagctttct gtagttcaag ttaccactca ctctccagct  3960
tgctcggtta atgtctgttg gcggcgttga gttggacttg ggaaaggtgt gtgtggtagg  4020
aacaagcaga gtgtgatgtg cttctgttat caggacttaa gctagagtgg ttggcagata  4080
ggaaatgcag ctattccttg aaagcaagca gatcatggat ggtcagccaa actgccctgg  4140
ctttggtggg agctgcactg cagaaggacc aaaccccaac aagatttggc acatttgttt  4200
agaagataag cacagatggt tttgcacaag gcagctcctc ataatggtgg ctttgtagat  4260
ttagtccaaa tgttcttatt tagatctagc agcacatcac tgtgtccgtg cccatctaac  4320
ctcgctatcc taagtagagc agaccccaaa caaccttgtt caaaaactac cagtgcaaat  4380
aactgaacta aatatttgtt actgctgact gagaacagct gttcgagtgt agcattgtgg  4440
cttgttaatg tgagtgcccc aactctatgg tcttattaaa gaaacccaaa cattgctcag  4500
attttgttct tattgtcatc ataagacttg aatagtgatg gtaatgctta cgtagacgtg  4560
tcttgtgagt gcacttcagt gatttagaaa gaactggatt tcaagcaact ttggacctgt  4620
ggggggaggg agattaatga aggtttgaat cacattctaa ttctatgtac agtccttcat  4680
tactccacaa gcctaaatcc tatacagcct ccaggatagc tggaaactgt tgagatctgg  4740
acttttttttt tttaatccaa gggctaactt gttgtaactt ggtataatta tctgctttcg  4800
gaaatgcatc tctgttggtt tgaaa                                         4825

SEQ ID NO: 18          moltype = AA  length = 189
FEATURE                Location/Qualifiers
source                 1..189
                       mol_type = protein
                       organism = Gallus gallus
SEQUENCE: 18
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA QELAKSYGIP FIETSAKTRQ GVEDAFYTLV REIRQYRMKK LNSNEDGNQG  180
CMGLSCIVM                                                         189
```

What is claimed is:

1. A kit for treating or ameliorating the effects of melanoma in a subject having a somatic NRAS mutation, comprising an effective amount of (i) a first anti-cancer agent, which is BVD-523 or a pharmaceutically acceptable salt thereof and (ii) a second anti-cancer agent, which is LEE-011 or a pharmaceutically acceptable salt thereof, packaged together with instructions for their use, wherein administration of the first and second anti-cancer agents provides a synergistic effect compared to administration of either anti-cancer agent alone.

2. The kit of claim 1, wherein the subject is a mammal.

3. The kit of claim 2, wherein the mammal is selected from the group consisting of humans, primates, farm animals, and domestic animals.

4. The kit of claim 2, wherein the mammal is a human.

5. The kit of claim 1, further comprising at least one additional therapeutic agent selected from the group consisting of an antibody or fragment thereof, a toxin, a radionuclide, an immunomodulator, a radiosensitizing agent, a hormone, an anti-angiogenesis agent, and combinations thereof.

6. The kit of claim 5, wherein the at least one additional therapeutic agent is an antibody or fragment thereof selected from the group consisting of rituximab, Cetuximab, bevacizumab, and Ibritumomab.

7. The kit of claim 5, wherein the at least one additional therapeutic agent is a toxin, which is diphtheria toxin or portions thereof.

8. The kit of claim 5, wherein the at least one additional therapeutic agent is a radionuclide selected from the group consisting of I-125, At-211, Lu-177, Cu-67, I-131, Sm-153, Re-186, P-32, Re-188, In-114m, and Y-90.

9. The kit of claim 5, wherein the at least one additional therapeutic agent is an immunomodulator selected from the group consisting of granulocyte colony-stimulating factor (G-CSF), interferons, imiquimod and cellular membrane fractions from bacteria, IL-2, IL-7, IL-12, CCL3, CCL26, CXCL7, and synthetic cytosine phosphate-guanosine (CpG).

10. The kit of claim 5, wherein the at least one additional therapeutic agent is a radiosensitizing agent selected from the group consisting of misonidazole, metronidazole, tirapazamine, and trans sodium crocetinate.

11. The kit of claim 5, wherein the at least one additional therapeutic agent is a hormone selected from the group consisting of prostaglandins, leukotrienes, prostacyclin, thromboxane, amylin, antimullerianormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, calcidiol, tamoxifen, anastrozole, letrozole, and fulvestrant.

12. The kit of claim 5, wherein the at least one additional therapeutic agent is an anti-angiogenesis agent selected from the group consisting of 2-methoxyestradiol, angiostatin, bevacizumab, cartilage-derived angiogenesis inhibitory factor, endostatin, IFN-α, IL-12, itraconazole, linomide, platelet factor-4, prolactin, SU5416, suramin, tasquinimod, tecogalan, tetrathiomolybdate, thalidomide, thrombospondin, thrombospondin, TNP-470, ziv-aflibercept, pharmaceutically acceptable salts thereof, prodrugs, and combinations thereof.

13. A pharmaceutical composition for treating or ameliorating the effects of melanoma in a subject having a somatic NRAS mutation, the pharmaceutical composition comprising a pharmaceutically acceptable diluent or carrier and an effective amount of (i) a first anti-cancer agent, which is BVD-523 or a pharmaceutically acceptable salt thereof and (ii) a second anti-cancer agent, which is LEE-011 or a pharmaceutically acceptable salt thereof, wherein administration of the first and second anti-cancer agents provides a synergistic effect compared to administration of either anti-cancer agent alone.

14. The pharmaceutical composition of claim 13, wherein the subject is a mammal.

15. The pharmaceutical composition of claim 14, wherein the mammal is selected from the group consisting of humans, primates, farm animals, and domestic animals.

16. The pharmaceutical composition of claim 14, wherein the mammal is a human.

17. The pharmaceutical composition of claim 13, further comprising at least one additional therapeutic agent selected from the group consisting of an antibody or fragment thereof, a toxin, a radionuclide, an immunomodulator, a radiosensitizing agent, a hormone, an anti-angiogenesis agent, and combinations thereof.

18. The pharmaceutical composition of claim 17, wherein the at least one additional therapeutic agent is an antibody or fragment thereof selected from the group consisting of rituximab, Cetuximab, bevacizumab, and Ibritumomab.

19. The pharmaceutical composition of claim 17, wherein the at least one additional therapeutic agent is a toxin, which is diphtheria toxin or portions thereof.

20. The pharmaceutical composition of claim 17, wherein the at least one additional therapeutic agent is a radionuclide selected from the group consisting of I-125, At-211, Lu-177, Cu-67, I-131, Sm-153, Re-186, P-32, Re-188, In-114m, and Y-90.

21. The pharmaceutical composition of claim 17, wherein the at least one additional therapeutic agent is an immunomodulator selected from the group consisting of granulocyte colony-stimulating factor (G-CSF), interferons, imiquimod and cellular membrane fractions from bacteria, IL-2, IL-7, IL-12, CCL3, CCL26, CXCL7, and synthetic cytosine phosphate-guanosine (CpG).

22. The pharmaceutical composition of claim 17, wherein the at least one additional therapeutic agent is a radiosensitizing agent selected from the group consisting of misonidazole, metronidazole, tirapazamine, and trans sodium crocetinate.

23. The pharmaceutical composition of claim 17, wherein the at least one additional therapeutic agent is a hormone selected from the group consisting of prostaglandins, leukotrienes, prostacyclin, thromboxane, amylin, antimulleri-anormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, calcidiol, tamoxifen, anastrozole, letrozole, and fulvestrant.

24. The pharmaceutical composition of claim 17, wherein the at least one additional therapeutic agent is an anti-angiogenesis agent selected from the group consisting of 2-methoxyestradiol, angiostatin, bevacizumab, cartilage-derived angiogenesis inhibitory factor, endostatin, IFN-α, IL-12, itraconazole, linomide, platelet factor-4, prolactin, SU5416, suramin, tasquinimod, tecogalan, tetrathiomolybdate, thalidomide, thrombospondin, thrombospondin, TNP-470, ziv-aflibercept, pharmaceutically acceptable salts thereof, prodrugs, and combinations thereof.

25. The pharmaceutical composition of claim 13, which is in a unit dosage form comprising both anti-cancer agents.

26. The pharmaceutical composition of claim 13, in which the first anti-cancer agent is in a first unit dosage form and the second anti-cancer agent is in a second unit dosage form, separate from the first.

* * * * *